US012715859B2

(12) United States Patent
Zhang et al.

(10) Patent No.: US 12,715,859 B2
(45) **Date of Patent: *Aug. 25, 2026**

(54) PYRAZOLE-SUBSTITUTED CYCLOPENTANOL ESTER DERIVATIVE AND USE THEREOF

(71) Applicant: CHIA TAI TIANQING PHARMACEUTICAL GROUP CO., LTD., Lianyungang (CN)

(72) Inventors: Yinsheng Zhang, Lianyungang (CN); Yong Gao, Lianyungang (CN); Bin Cao, Shanghai (CN); Jinan Wang, Lianyungang (CN); Damin Zhao, Lianyungang (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 19/197,391

(22) Filed: May 2, 2025

(65) Prior Publication Data

US 2025/0270194 A1 Aug. 28, 2025

Related U.S. Application Data

(63) Continuation of application No. 18/860,069, filed as application No. PCT/CN2023/091330 on Apr. 27, 2023.

(30) Foreign Application Priority Data

| | | |
|---|---|---|
| Apr. 28, 2022 | (CN) | 202210469621.9 |
| Jul. 15, 2022 | (CN) | 202210836180.1 |
| Aug. 19, 2022 | (CN) | 202210999975.4 |
| Dec. 13, 2022 | (CN) | 202211603669.0 |
| Mar. 15, 2023 | (CN) | 202310250462.8 |
| Apr. 17, 2023 | (CN) | 202310411874.5 |

(51) Int. Cl.

| | |
|---|---|
| ***C07D 403/12*** | (2006.01) |
| ***A61K 31/4155*** | (2006.01) |
| ***A61K 31/427*** | (2006.01) |
| ***A61K 31/4355*** | (2006.01) |
| ***A61K 31/4439*** | (2006.01) |
| ***A61K 31/444*** | (2006.01) |
| ***A61K 31/506*** | (2006.01) |
| ***C07D 231/38*** | (2006.01) |
| ***C07D 401/12*** | (2006.01) |
| ***C07D 401/14*** | (2006.01) |
| ***C07D 405/12*** | (2006.01) |
| ***C07D 409/12*** | (2006.01) |
| ***C07D 413/14*** | (2006.01) |
| ***C07D 417/12*** | (2006.01) |
| ***C07D 417/14*** | (2006.01) |
| ***C07D 491/048*** | (2006.01) |

(52) U.S. Cl.

CPC ........ *C07D 403/12* (2013.01); *A61K 31/4155* (2013.01); *A61K 31/427* (2013.01); *A61K 31/4355* (2013.01); *A61K 31/4439* (2013.01); *A61K 31/444* (2013.01); *A61K 31/506* (2013.01); *C07D 231/38* (2013.01); *C07D 401/12* (2013.01); *C07D 401/14* (2013.01); *C07D 405/12* (2013.01); *C07D 409/12* (2013.01); *C07D 413/14* (2013.01); *C07D 417/12* (2013.01); *C07D 417/14* (2013.01); *C07D 491/048* (2013.01)

(58) Field of Classification Search

None

See application file for complete search history.

(56) References Cited

U.S. PATENT DOCUMENTS

2024/0246950 A1 * 7/2024 Liu ...................... C07D 405/12

FOREIGN PATENT DOCUMENTS

WO WO-2023116884 A1 * 6/2023 ........... C07D 487/04

OTHER PUBLICATIONS

PubChem CID 2084944, create date Jul. 14, 2005, retrieved from the internet Aug. 19, 2025 (Year: 2005).*

* cited by examiner

*Primary Examiner* — Clinton A Brooks
*Assistant Examiner* — Jed A Kucharczk
(74) *Attorney, Agent, or Firm* — Oliff PLC

(57) ABSTRACT

The present application relates to a pyrazole-substituted cyclopentanol ester derivative and use thereof, and in particular to a compound represented by formula (I), an isomer thereof, or a pharmaceutically acceptable salt thereof.

(I)

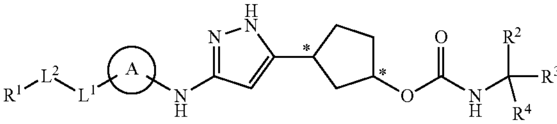

18 Claims, No Drawings

PYRAZOLE-SUBSTITUTED CYCLOPENTANOL ESTER DERIVATIVE AND USE THEREOF

CROSS-REFERENCE TO RELATED APPLICATIONS

The present application is a continuation of U.S. patent application Ser. No. 18/860,069, filed Oct. 25, 2024, which is a national phase application filed under 35 U.S.C. 371 of PCT/CN2023/091330 filed on Apr. 27, 2023, which claims the priority and benefit to the Chinese Patent Application No. 202210469621.9 filed with China National Intellectual Property Administration on Apr. 28, 2022, the priority and benefit to the Chinese Patent Application No. 202210836180.1 filed with China National Intellectual Property Administration on Jul. 15, 2022, the priority and benefit to the Chinese Patent Application No. 202210999975.4 filed with China National Intellectual Property Administration on Aug. 19, 2022, the priority and benefit to the Chinese Patent Application No. 202211603669.0 filed with China National Intellectual Property Administration on Dec. 13, 2022, the priority and benefit to the Chinese Patent Application No. 202310250462.8 filed with China National Intellectual Property Administration on Mar. 15, 2023, and the priority and benefit to the Chinese Patent Application No. 202310411874.5 filed with China National Intellectual Property Administration on Apr. 17, 2023, the contents of which are incorporated herein by reference in their entireties.

TECHNICAL FIELD

The present application relates to a pyrazole-substituted cyclopentanol ester derivative and use thereof, and in particular to a compound represented by formula (I), an isomer thereof, or a pharmaceutically acceptable salt thereof.

BACKGROUND

Cyclin-dependent kinases (CDKs) belong to the serine/threonine protein kinase family, and are directly involved in the regulation of the cell cycle to promote the ordered growth, the proliferation and the apoptosis of cells. The cell division cycle is divided into 4 phases: G1, S, G2, and M phases, with the G1-S regulatory point being the most important, and its regulation being closely related to CDKs. CDKs form protein kinase complexes through binding to cyclins, and the complexes catalyze substrate phosphorylation, control cell cycle progression, and complete DNA replication and mitosis in sequence, leading to cell division and proliferation. The cell division cycle is regulated by two modes: inhibition and promotion, both of which are normally in a dynamic balance. However, when the signal for promoting cell proliferation is enhanced or the signal for inhibiting cell proliferation is weakened, the balance is lost, and cell proliferation is out of control, resulting in the development of tumors. Studies have shown that overexpression of CDKs occurs in many malignancies.

Studies have shown that the CDKs directly involved in the cell cycle regulation mainly comprise CDK1, CDK2, CDK4, and CDK6, and play a key role in regulating the cell cycle. CDK2 is a member of the CDK family. It is a cyclin-dependent kinase essential for the completion of the G1 phase and the transition from the G1 phase to the S phase in cell mitosis. In the late G1 phase, CDK2 binds to Cyclin E and becomes activated, promoting the continuous phosphorylation of pRb, and ensuring that cells smoothly pass through the G1 phase and enter the S phase. The inactivation of E2F is a primary condition for the completion of the S phase. At the early stage of the S phase, CDK2 binds to Cyclin A to inactivate the E2F transcription factor, thereby facilitating the smooth completion of the S phase by cells. However, the sustained activity of E2F will lead to cell apoptosis. Therefore, selectively inhibiting the activity of CDK2/Cyclin A to increase the concentration of E2F can cause the cell cycle to stall in the S phase or trigger apoptosis, thereby achieving the purpose of treating tumor cells.

SUMMARY

The present application provides a compound of formula (I), an isomer thereof, or a pharmaceutically acceptable salt thereof, (I)

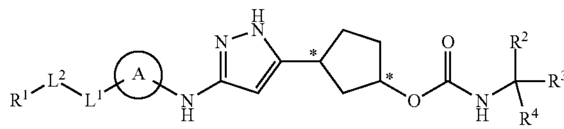

wherein, ring A is selected from the group consisting of a $C_{3-10}$ alkyl ring, a 5-10 membered heteroalkyl ring, a benzene ring, a naphthyl ring, a benzene ring fused to a $C_{5-6}$ alkyl ring, a benzene ring fused to a 5-6 membered heteroalkyl ring, a 5-10 membered heteroaromatic ring, a 5-6 membered heteroaromatic ring fused to a $C_{5-6}$ alkyl ring, or a 5-6 membered heteroaromatic ring fused to a 5-6 membered heteroalkyl ring, and the $C_{3-10}$ alkyl ring, the 5-10 membered heteroalkyl ring, the benzene ring, the naphthyl ring, the benzene ring fused to a $C_{5-6}$ alkyl ring, the benzene ring fused to a 5-6 membered heteroalkyl ring, the 5-10 membered heteroaromatic ring, the 5-6 membered heteroaromatic ring fused to a $C_{5-6}$ alkyl ring, or the 5-6 membered heteroaromatic ring fused to a 5-6 membered heteroalkyl ring is optionally independently substituted with 1 or more $R^a$;

$L^1$ and $L^2$ are each independently selected from the group consisting of a single bond, —N($R^b$)—, —N═, —O—, —S—, —$(CH_2)_m$—, —$(CD_2)_m$-, —$(CHD)_m$-, —C(═O)—, —S(═O)—, —S(═O)$_2$—, —S(═O)(═N($R^b$))—, —S(═O)($R^c$)—, —P(═O)($R^c$)—, or —P(═O)(N$R^bR^b$)—;

$R^1$ is selected from the group consisting of H, deuterium, $C_{1-3}$ alkyl, $C_{1-3}$ alkoxy, —$NH_2$, —NH($C_{1-3}$ alkyl), —N($C_{1-3}$ alkyl)$_2$, $C_{3-6}$ cycloalkyl, 3-6 membered heterocycloalkyl, phenyl, or 5-6 membered heteroaryl; the $C_{1-3}$ alkyl or the $C_{1-3}$ alkoxy is optionally independently substituted with 1, 2 or 3 $R^d$, and the $C_{3-6}$ cycloalkyl, the 3-6 membered heterocycloalkyl, the phenyl, or the 5-6 membered heteroaryl is optionally independently substituted with 1 or more $R^e$;

$R^2$, $R^3$, and $R^4$ are each independently selected from the group consisting of H, deuterium, halogen, OH, CN, $NH_2$, $C_{1-3}$ alkyl, or $C_{1-3}$ alkoxy, and the $C_{1-3}$ alkyl or the $C_{1-3}$ alkoxy is optionally independently substituted with 1 or more $R^z$;

or $R^2$ and $R^3$, together with the carbon atom linked thereto, form $C_{3-6}$ cycloalkyl or 3-6 membered heterocycloalkyl, and $R^4$ is selected from the group consisting of H, deuterium, halogen, OH, CN, $NH_2$, $C_{1-3}$ alkyl, or $C_{1-3}$ alkoxy; the $C_{1-3}$ alkyl, the $C_{1-3}$ alkoxy, the $C_{3-6}$ cycloalkyl, or the 3-6 membered heterocycloalkyl is optionally independently substituted with 1 or more $R^z$;

$R^a$ is each independently selected from the group consisting of deuterium, halogen, OH, CN, $NH_2$, =O, $C_{1-3}$ alkyl, or $C_{1-3}$ alkoxy, and the $C_{1-3}$ alkyl or the $C_{1-3}$ alkoxy is optionally independently substituted with 1 or more $R^x$;

$R^b$ is each independently selected from the group consisting of H, $C_{1-3}$ alkyl, $C_{1-3}$ alkoxy, —C(=O)H, —S(=O)$_2$$C_{1-3}$ alkyl, $C_{3-6}$ cycloalkyl, or 3-6 membered heterocycloalkyl; the $C_{1-3}$ alkyl or the $C_{1-3}$ alkoxy is optionally independently substituted with 1, 2 or 3 $R^x$, and the $C_{3-6}$ cycloalkyl or the 3-6 membered heterocycloalkyl is optionally independently substituted with 1 or more $R^y$;

$R^c$ is selected from the group consisting of halogen, OH, CN, or $C_{1-3}$ alkyl, and the $C_{1-3}$ alkyl is optionally independently substituted with 1 or more $R^x$;

$R^d$ is each independently selected from the group consisting of deuterium, halogen, OH, CN, or $NH_2$;

$R^e$ is each independently selected from the group consisting of deuterium, halogen, OH, CN, $NH_2$, =O, $C_{1-3}$ alkyl, or $C_{1-3}$ alkoxy, and the $C_{1-3}$ alkyl or the $C_{1-3}$ alkoxy is optionally independently substituted with 1 or more $R^x$;

$R^x$ is each independently selected from the group consisting of deuterium, halogen, OH, CN, or $NH_2$;

$R^y$ is each independently selected from the group consisting of deuterium, halogen, OH, CN, $NH_2$, =O, $C_{1-3}$ alkyl, or $C_{1-3}$ alkoxy, and the $C_{1-3}$ alkyl or the $C_{1-3}$ alkoxy is optionally independently substituted with 1 or more substituents selected from the group consisting of deuterium, halogen, OH, CN, or $NH_2$;

$R^z$ is each independently selected from the group consisting of deuterium, halogen, OH, CN, or $NH_2$; m is selected from the group consisting of 1, 2, or 3;

the carbon atom with "*" is a chiral carbon atom present in a form of a single (R) or (S) enantiomer or in a form enriched with one enantiomer;

or, $L^1$, $L^2$, $R^1$, $R^2$, $R^3$, $R^4$, $R^a$, $R^b$, $R^c$, $R^d$, $R^e$, $R^x$, $R^y$, or $R^z$ is each independently optionally substituted with one or more substituents.

In some embodiments of the present application, $R^a$, $R^b$, $R^c$, $R^d$, $R^e$, $R^x$, $R^y$, or $R^z$ is each independently optionally substituted with one or more substituents.

In some embodiments of the present application, $R^d$, $R^x$, $R^y$, or $R^z$ is each independently optionally substituted with one or more substituents.

In other embodiments of the present application, $R^1$, $R^2$, $R^3$, $R^4$, $R^a$, $R^d$, $R^e$, $R^x$, $R^y$, or $R^z$ is each independently optionally substituted with one or more deuterium.

In other embodiments of the present application, $R^1$, $R^2$, $R^3$, $R^4$, $R^a$, $R^d$, $R^e$, $R^x$, $R^y$, or $R^z$ is each independently optionally substituted with 1, 2, 3, 4 or 5 deuterium, or is each independently optionally substituted with 3 or 5 deuterium.

In some embodiments of the present application, at least one of $R^1$, $R^2$, $R^3$, $R^4$, $R^a$, $R^d$, $R^e$, $R^x$, $R^y$, and $R^z$ is a deuterium atom-containing group.

In some embodiments of the present application, the "substituted with 1 or more" is each independently selected from the group consisting of substitution with 1, 2, 3, 4, 5 or 6.

In some embodiments of the present application, the "substituted with 1 or more" is each independently selected from the group consisting of substitution with 1, 2, 3, 4 or 5.

In some embodiments of the present application, the "substituted with 1 or more" is each independently selected from the group consisting of substitution with 1, 2, 3 or 4.

In some embodiments of the present application, the "substituted with 1 or more" is each independently selected from the group consisting of substitution with 1, 2 or 3.

In some embodiments of the present application, the "hetero" mentioned in ring A is each independently selected from the group consisting of heteroatoms of oxygen, sulfur, and nitrogen, wherein the nitrogen atom is optionally quaternized or oxidized to N(O), and the sulfur atom is optionally oxidized to S(O) or S(O)$_2$; and the other variables are as defined herein.

In some embodiments of the present application, the "hetero" mentioned in ring A is each independently selected from the group consisting of heteroatoms of oxygen, sulfur, and nitrogen, wherein the sulfur heteroatom is optionally oxidized to S(O) or S(O)$_2$; and the other variables are as defined herein.

In some embodiments of the present application, ring A is selected from the group consisting of a $C_{3-6}$ alkyl ring, a 5-6 membered heteroalkyl ring, a benzene ring, a naphthyl ring, a benzene ring fused to a $C_{5-6}$ alkyl ring, a benzene ring fused to a 5-6 membered heteroalkyl ring, a 5-10 membered heteroaromatic ring, a 5-6 membered heteroaromatic ring fused to a $C_{5-6}$ alkyl ring, or a 5-6 membered heteroaromatic ring fused to a 5-6 membered heteroalkyl ring, and the $C_{3-6}$ alkyl ring, the 5-6 membered heteroalkyl ring, the benzene ring, the naphthyl ring, the benzene ring fused to a $C_{5-6}$ alkyl ring, the benzene ring fused to a 5-6 membered heteroalkyl ring, the 5-10 membered heteroaromatic ring, the 5-6 membered heteroaromatic ring fused to a $C_{5-6}$ alkyl ring, or the 5-6 membered heteroaromatic ring fused to a 5-6 membered heteroalkyl ring is optionally independently substituted with 1, 2, 3 or 4 $R^a$; and the other variables are as defined herein.

In some embodiments of the present application, ring A is selected from the group consisting of a $C_{3-6}$ alkyl ring, a 5-6 membered heteroalkyl ring, a benzene ring, a naphthyl ring, a benzene ring fused to a $C_{5-6}$ alkyl ring, a benzene ring fused to a 5-6 membered heteroalkyl ring, a 5-6 membered heteroaromatic ring, a 5-6 membered heteroaromatic ring fused to a $C_{5-6}$ alkyl ring, or a 5-6 membered heteroaromatic ring fused to a 5-6 membered heteroalkyl ring, and the $C_{3-6}$ alkyl ring, the 5-6 membered heteroalkyl ring, the benzene ring, the naphthyl ring, the benzene ring fused to a $C_{5-6}$ alkyl ring, the benzene ring fused to a 5-6 membered heteroalkyl ring, the 5-6 membered heteroaromatic ring, the 5-6 membered heteroaromatic ring fused to a $C_{5-6}$ alkyl ring, or the 5-6 membered heteroaromatic ring fused to a 5-6 membered heteroalkyl ring is optionally independently substituted with 1, 2 or 3 $R^a$; and the other variables are as defined herein.

In some embodiments of the present application, ring A is selected from the group consisting of a 5-6 membered heteroalkyl ring, a benzene ring, a benzene ring fused to a 5-6 membered heteroalkyl ring, a 5-6 membered heteroaromatic ring, or a 5-6 membered heteroaromatic ring fused to a 5-6 membered heteroalkyl ring, and the 5-6 membered heteroalkyl ring, the benzene ring, the benzene ring fused to a 5-6 membered heteroalkyl ring, the 5-6 membered heteroaromatic ring, or the 5-6 membered heteroaromatic ring fused to a 5-6 membered heteroalkyl ring is optionally independently substituted with 1, 2 or 3 $R^a$; and the other variables are as defined herein.

In some embodiments of the present application, ring A is selected from the group consisting of a 6 membered heteroalkyl ring, a benzene ring, a benzene ring fused to a 5 membered heteroalkyl ring, a 5-6 membered heteroaromatic ring, or a 6 membered heteroaromatic ring fused to a 5-6 membered heteroalkyl ring, and the 6 membered heteroalkyl ring, the benzene ring, the benzene ring fused to a 5 membered heteroalkyl ring, the 5-6 membered heteroaromatic ring, or the 6 membered heteroaromatic ring fused to a 5-6 membered heteroalkyl ring is optionally independently substituted with 1, 2 or 3 $R^a$; and the other variables are as defined herein.

In some embodiments of the present application, ring A is selected from the group consisting of a 6 membered heteroalkyl ring, a benzene ring, a benzene ring fused to a 5 membered heteroalkyl ring, a 5-9 membered heteroaromatic ring, or a 6 membered heteroaromatic ring fused to a 5-6 membered heteroalkyl ring, and the 6 membered heteroalkyl ring, the benzene ring, the benzene ring fused to a 5 membered heteroalkyl ring, the 5-9 membered heteroaromatic ring, or the 6 membered heteroaromatic ring fused to a 5-6 membered heteroalkyl ring is optionally independently substituted with 1, 2 or 3 $R^a$; and the other variables are as defined herein.

In further embodiments of the present application, ring A is selected from the group consisting of a 6 membered heteroalkyl ring, a benzene ring, a benzene ring fused to a 5 membered heteroalkyl ring, or a 6 membered heteroaromatic ring fused to a 5-6 membered heteroalkyl ring, and the 6 membered heteroalkyl ring, the benzene ring, the benzene ring fused to a 5 membered heteroalkyl ring, or the 6 membered heteroaromatic ring fused to a 5-6 membered heteroalkyl ring is optionally independently substituted with 1, 2 or 3 $R^a$; and the other variables are as defined herein.

In some embodiments of the present application, the ring atoms of the 5-10 membered heteroaromatic ring or the 5-9 membered heteroaromatic ring in the definition of ring A contain only 1 or 2 N atoms, and the other variables are as defined herein.

In other embodiments of the present application, the ring atoms of the 5-10 membered heteroaromatic ring or the 5-9 membered heteroaromatic ring in the definition of ring A contain only 1 N atom, and the other variables are as defined herein.

In some embodiments of the present application, the 5-10 membered heteroaromatic ring or the 5-9 membered heteroaromatic ring in the definition of ring A is selected from the group consisting of a 5 membered heteroaromatic ring or 6 membered heteroaromatic ring, and the other variables are as defined herein.

In other embodiments of the present application, the ring atoms of the 5 membered heteroaromatic ring or the 6 membered heteroaromatic ring in the definition of ring A contain only 1 N atom, and the other variables are as defined herein.

In some embodiments of the present application, ring A is selected from the group consisting of a 6 membered heteroalkyl ring, a benzene ring, a benzene ring fused to a 5 membered heteroalkyl ring, a 5 membered heteroaromatic ring, a 6 membered heteroaromatic ring, a 9 membered heteroaromatic ring, a 6 membered heteroaromatic ring fused to a 5 membered heteroalkyl ring, or a 6 membered heteroaromatic ring fused to a 6 membered heteroalkyl ring, and the 6 membered heteroalkyl ring, the benzene ring, the benzene ring fused to a 5 membered heteroalkyl ring, the 5 membered heteroaromatic ring, the 6 membered heteroaromatic ring, the 9 membered heteroaromatic ring, the 6 membered heteroaromatic ring fused to a 5 membered heteroalkyl ring, or the 6 membered heteroaromatic ring fused to a 6 membered heteroalkyl ring is optionally independently substituted with 1, 2 or 3 $R^a$; and the other variables are as defined herein.

In some embodiments of the present application, ring A is selected from the group consisting of a 6 membered heteroalkyl ring, a benzene ring, a benzene ring fused to a 5 membered heteroalkyl ring, a 5 membered heteroaromatic ring, a 6 membered heteroaromatic ring, a 6 membered heteroaromatic ring fused to a 5 membered heteroalkyl ring, or a 6 membered heteroaromatic ring fused to a 6 membered heteroalkyl ring, and the 6 membered heteroalkyl ring, the benzene ring, the benzene ring fused to a 5 membered heteroalkyl ring, the 5 membered heteroaromatic ring, the 6 membered heteroaromatic ring, the 6 membered heteroaromatic ring fused to a 5 membered heteroalkyl ring, or the 6 membered heteroaromatic ring fused to a 6 membered heteroalkyl ring is optionally independently substituted with 1, 2 or 3 $R^a$; and the other variables are as defined herein.

In further embodiments of the present application, ring A is selected from the group consisting of a 6 membered heteroalkyl ring, a benzene ring, a benzene ring fused to a 5 membered heteroalkyl ring, a 6 membered heteroaromatic ring fused to a 5 membered heteroalkyl ring, or a 6 membered heteroaromatic ring fused to a 6 membered heteroalkyl ring, and the 6 membered heteroalkyl ring, the benzene ring, the benzene ring fused to a 5 membered heteroalkyl ring, the 6 membered heteroaromatic ring fused to a 5 membered heteroalkyl ring, or the 6 membered heteroaromatic ring fused to a 6 membered heteroalkyl ring is optionally independently substituted with 1, 2 or 3 $R^a$; and the other variables are as defined herein.

In other embodiments of the present application, ring A is selected from the group consisting of a benzene ring fused to a 5 membered heteroalkyl ring, a 6 membered heteroaromatic ring fused to a 5 membered heteroalkyl ring, or a 6 membered heteroaromatic ring fused to a 6 membered heteroalkyl ring, and the benzene ring fused to a 5 membered heteroalkyl ring, the 6 membered heteroaromatic ring fused to a 5 membered heteroalkyl ring, or the 6 membered heteroaromatic ring fused to a 6 membered heteroalkyl ring is optionally independently substituted with 1, 2 or 3 $R^a$; the "hetero" mentioned in the 5 membered heteroalkyl ring or the 6 membered heteroalkyl ring is each independently selected from the group consisting of heteroatoms of oxygen, sulfur, and nitrogen, wherein the nitrogen atom is optionally quaternized or oxidized to N(O), and the sulfur atom is optionally oxidized to S(O) or $S(O)_2$; and the other variables are as defined herein.

In other embodiments of the present application, ring A is selected from the group consisting of a 6 membered heteroalkyl ring containing 1-3 N atoms, a benzene ring, a benzene ring fused to a 5 membered heteroalkyl ring containing 1-3 N atoms, a 5 membered heteroaromatic ring containing 1-3 N atoms, a 6 membered heteroaromatic ring containing only 1 N atom, a 6 membered heteroaromatic ring containing 1-3 N atoms fused to a 5 membered heteroalkyl ring containing 1-3 N atoms, or a 6 membered heteroaromatic ring containing 1-3 N atoms fused to a 6 membered heteroalkyl ring containing 1-3 N atoms, and the 6 membered heteroalkyl ring containing 1-3 N atoms, the benzene ring, the benzene ring fused to a 5 membered heteroalkyl ring containing 1-3 N atoms, the 5 membered heteroaromatic ring containing 1-3 N atoms, the 6 membered heteroaromatic ring containing only 1 N atom, the 6 membered heteroaromatic ring containing 1-3 N atoms fused to a 5 membered heteroalkyl ring containing 1-3 N atoms, or the 6 membered heteroaromatic ring containing 1-3 N atoms fused to a 6 membered heteroalkyl ring containing 1-3 N atoms is optionally independently substituted with 1, 2 or 3 $R^a$; and the other variables are as defined herein.

In some embodiments of the present application, ring A is selected from the group consisting of a 6 membered heteroalkyl ring containing 1-3 N atoms, a benzene ring, a benzene ring fused to a 5 membered heteroalkyl ring containing 1-3 N atoms, a 5 membered heteroaromatic ring containing 1-3 N atoms, a 6 membered heteroaromatic ring containing 1-3 N atoms, a 9 membered heteroaromatic ring containing 1-3 N atoms, a 6 membered heteroaromatic ring containing 1-3 N atoms fused to a 5 membered heteroalkyl ring containing 1-3 N atoms, or a 6 membered heteroaromatic ring containing 1-3 N atoms fused to a 6 membered heteroalkyl ring containing 1-3 N atoms, and the 6 membered heteroalkyl ring containing 1-3 N atoms, the benzene ring, the benzene ring fused to a 5 membered heteroalkyl ring containing 1-3 N atoms, the 5 membered heteroaromatic ring containing 1-3 N atoms, the 6 membered heteroaromatic ring containing 1-3 N atoms, the 9 membered heteroaromatic ring containing 1-3 N atoms, the 6 membered heteroaromatic ring containing 1-3 N atoms fused to a 5 membered heteroalkyl ring containing 1-3 N atoms, or the 6 membered heteroaromatic ring containing 1-3 N atoms fused to a 6 membered heteroalkyl ring containing 1-3 N atoms is optionally independently substituted with 1, 2 or 3 $R^a$; and the other variables are as defined herein.

In some embodiments of the present application, ring A is selected from the group consisting of a 6 membered heteroalkyl ring containing 1 or 2 N atoms, a benzene ring, a benzene ring fused to a 5 membered heteroalkyl ring containing 1 or 2 N atoms, a 5 membered heteroaromatic ring containing 1 or 2 N atoms, a 6 membered heteroaromatic ring containing 1 or 2 N atoms, a 6 membered heteroaromatic ring containing 1 or 2 N atoms fused to a 5 membered heteroalkyl ring containing 1 or 2 N atoms, or a 6 membered heteroaromatic ring containing 1 or 2 N atoms fused to a 6 membered heteroalkyl ring containing 1 or 2 N atoms, and the 6 membered heteroalkyl ring containing 1 or 2 N atoms, the benzene ring, a benzene ring fused to a 5 membered heteroalkyl ring containing 1 or 2 N atoms, the 5 membered heteroaromatic ring containing 1 or 2 N atoms, the 6 membered heteroaromatic ring containing 1 or 2 N atoms, the 6 membered heteroaromatic ring containing 1 or 2 N atoms fused to a 5 membered heteroalkyl ring containing 1 or 2 N atoms, or the 6 membered heteroaromatic ring containing 1 or 2 N atoms fused to a 6 membered heteroalkyl ring containing 1 or 2 N atoms is optionally independently substituted with 1, 2 or 3 $R^a$; and the other variables are as defined herein.

In some embodiments of the present application, ring A is selected from the group consisting of a 6 membered heteroalkyl ring containing 1 N atom, a benzene ring, a benzene ring fused to a 5 membered heteroalkyl ring containing 1 N atom, a 5 membered heteroaromatic ring containing 1 or 2 N atoms, a 6 membered heteroaromatic ring containing 1 or 2 N atoms, a 6 membered heteroaromatic ring containing 1 N atom fused to a 5 membered heteroalkyl ring containing 1 N atom, or a 6 membered heteroaromatic ring containing 1 N atom fused to a 6 membered heteroalkyl ring containing 1 N atom, and the 6 membered heteroalkyl ring containing 1 N atom, the benzene ring, the benzene ring fused to a 5 membered heteroalkyl ring containing 1 N atom, the 5 membered heteroaromatic ring containing 1 or 2 N atoms, the 6 membered heteroaromatic ring containing 1 or 2 N atoms, the 6 membered heteroaromatic ring containing 1 N atom fused to a 5 membered heteroalkyl ring containing 1 N atom, or the 6 membered heteroaromatic ring containing 1 N atom fused to a 6 membered heteroalkyl ring containing 1 N atom is optionally independently substituted with 1, 2 or 3 $R^a$; and the other variables are as defined herein.

In other embodiments of the present application, ring A is selected from the group consisting of a 6 membered heteroalkyl ring containing 1 N atom, a benzene ring, a benzene ring fused to a 5 membered heteroalkyl ring containing 1 N atom, a 5 membered heteroaromatic ring containing 1 or 2 N atoms, a 6 membered heteroaromatic ring containing only 1 N atom, a 6 membered heteroaromatic ring containing 1 N atom fused to a 5 membered heteroalkyl ring containing 1 N atom, or a 6 membered heteroaromatic ring containing 1 N atom fused to a 6 membered heteroalkyl ring containing 1 N atom, and the 6 membered heteroalkyl ring containing 1 N atom, the benzene ring, the benzene ring fused to a 5 membered heteroalkyl ring containing 1 N atom, the 5 membered heteroaromatic ring containing 1 or 2 N atoms, the 6 membered heteroaromatic ring containing only 1 N atom, the 6 membered heteroaromatic ring containing 1 N atom fused to a 5 membered heteroalkyl ring containing 1 N atom, or the 6 membered heteroaromatic ring containing 1 N atom fused to a 6 membered heteroalkyl ring containing 1 N atom is optionally independently substituted with 1, 2 or 3 $R^a$; and the other variables are as defined herein.

In some embodiments of the present application, ring A is selected from the group consisting of a 6 membered heteroalkyl ring containing 1 N atom, a benzene ring, a benzene ring fused to a 5 membered heteroalkyl ring containing 1 N atom, a 5 membered heteroaromatic ring containing 1 or 2 N atoms, a 6 membered heteroaromatic ring containing 1 or 2 N atoms, a 6 membered heteroaromatic ring containing 1 N atom fused to a 5 membered heteroalkyl ring containing 1 N atom, or a 6 membered heteroaromatic ring containing 1 N atom fused to a 6 membered heteroalkyl ring containing 1 N atom, and the 6 membered heteroalkyl ring containing 1 N atom, the benzene ring, the benzene ring fused to a 5 membered heteroalkyl ring containing 1 N atom, the 5 membered heteroaromatic ring containing 1 or 2 N atoms, the 6 membered heteroaromatic ring containing 1 or 2 N atoms, the 6 membered heteroaromatic ring containing 1 N atom fused to a 5 membered heteroalkyl ring containing 1 N atom, or the 6 membered heteroaromatic ring containing 1 N atom fused to a 6 membered heteroalkyl ring containing 1 N atom is optionally independently substituted with 1, 2 or 3 $R^a$; and the other variables are as defined herein.

In further embodiments of the present application, ring A is selected from the group consisting of a 6 membered heteroalkyl ring containing 1 N atom, a benzene ring, a benzene ring fused to a 5 membered heteroalkyl ring containing 1 N atom, a 6 membered heteroaromatic ring containing 1 N atom fused to a 5 membered heteroalkyl ring containing 1 N atom, or a 6 membered heteroaromatic ring containing 1 N atom fused to a 6 membered heteroalkyl ring containing 1 N atom, and the 6 membered heteroalkyl ring containing 1 N atom, the benzene ring, the benzene ring fused to a 5 membered heteroalkyl ring containing 1 N atom, the 6 membered heteroaromatic ring containing 1 N atom fused to a 5 membered heteroalkyl ring containing 1 N atom, or the 6 membered heteroaromatic ring containing 1 N atom fused to a 6 membered heteroalkyl ring containing 1 N atom is optionally independently substituted with 1, 2 or 3 $R^a$; and the other variables are as defined herein.

In some embodiments of the present application, ring A is selected from the group consisting of a pyrrolidine ring, a pyrazolidine ring, an imidazolidine ring, a tetrahydrothiophene ring, a tetrahydrofuran ring, a tetrahydropyran ring, a thiazolidine ring, an isothiazolidine ring, an oxazolidine ring, an isoxazolidine ring, a piperidine ring, a piperazine ring, a morpholine ring, a thiazinane ring, a benzene ring, a benzene ring fused dioxolane ring, a benzene ring fused to a pyrrolidine ring, a benzene ring fused to a pyrazole ring, a benzimidazoline ring, a benzene ring fused to a tetrahydrothiophene ring, a benzene ring fused to a tetrahydrofuran ring, a benzene ring fused to a tetrahydropyran ring, a benzene ring fused to a thiazoline ring, a benzene ring fused to an isothiazole ring, a benzene ring fused to an oxazoline ring, a benzene ring fused to an isoxazoline ring, a benzene ring fused to a piperidine ring, a benzene ring fused to a piperazine ring, a benzene ring fused to a morpholine ring, a benzene ring fused to a thiazinane ring, a pyrrole ring, a pyrazole ring, an imidazole ring, an oxazole ring, an isoxazole ring, a thiazole ring, an isothiazole ring, a triazole ring, a furan ring, a thiophene ring, a pyridine ring, a pyrazine ring, a pyrimidine ring, a pyridazine ring, a pyridine ring fused to a pyrrolidine ring, a pyridine ring fused to a pyrazolidine ring, a pyridine ring fused to an imidazolidine ring, a pyridine ring fused to a tetrahydrothiophene ring, a pyridine ring fused to a tetrahydrofuran ring, a pyridine ring fused to a tetrahydropyran ring, a pyridine ring fused to a thiazoline ring, a pyridine ring fused to an isothiazole ring, a pyridine ring fused to an oxazoline ring, a pyridine ring fused to an isoxazoline ring, a pyridine ring fused to a piperidine ring, a pyridine ring fused to a piperazine ring, a pyridine ring fused to a morpholine ring, a pyridine ring fused to a thiazinane ring, a pyrazine ring fused to a pyrrolidine ring, a pyrazine ring fused to a pyrazolidine ring, a pyrazine ring fused to an imidazolidine ring, a pyrazine ring fused to a tetrahydrothiophene ring, a pyrazine ring fused to a tetrahydrofuran ring, a pyrazine ring fused to a tetrahydropyran ring, a pyrazine ring fused to a thiazoline ring, a pyrazine ring fused to an isothiazole ring, a pyrazine ring fused to an oxazoline ring, a pyrazine ring fused to an isoxazoline ring, a pyrazine ring fused to a piperidine ring, a pyrazine ring fused to a piperazine ring, a pyrazine ring fused to a morpholine ring, a pyrazine ring fused to a thiazinane ring, a pyrimidine ring fused to a pyrrolidine ring, a pyrimidine ring fused to a pyrazolidine ring, a pyrimidine ring fused to an imidazolidine ring, a pyrimidine ring fused to a tetrahydrothiophene ring, a pyrimidine ring fused to a tetrahydrofuran ring, a pyrimidine ring fused to a tetrahydropyran ring, a pyrimidine ring fused to a thiazoline ring, a pyrimidine ring fused to an isothiazole ring, a pyrimidine ring fused to an oxazoline ring, a pyrimidine ring fused to an isoxazoline ring, a pyrimidine ring fused to a piperidine ring, a pyrimidine ring fused to a piperazine ring, a pyrimidine ring fused to a morpholine ring, a pyrimidine ring fused to a thiazinane ring, a benzofuran ring, a benzothiophene ring, an indole ring, an isoindole ring, a benzimidazole ring, an indazole ring, a pyrrolo[2,3-b]pyridine ring, a pyrrolo[2,3-c]pyridine ring, a pyrrolo[3,2-c]pyridine ring, a pyrrolo[3,2-b]pyridine ring, an imidazo[4,5-b]pyridine ring, an imidazo[4,5-c]pyridine ring, an imidazo[1,2-a]pyridine ring, an imidazo[1,5-a]pyridine ring, a pyrazolo[4,3-d]pyridine ring, a pyrazolo[4,3-c]pyridine ring, a pyrazolo[3,4-c]pyridine ring, a pyrazolo[1,5-a]pyridine ring, a purine ring, an indolizine ring, a pyrrolo[1,2-a]pyridazine ring, an imidazo[1,2-c]pyrimidine ring, a pyrazolo[1,5-a]pyrazine ring, or a pyrazolo[1,2-a]pyrazine ring, and ring A is optionally independently substituted with 1, 2 or 3 $R^a$; and the other variables are as defined herein.

In some embodiments of the present application, ring A is selected from the group consisting of a piperidine ring, a benzene ring, a benzene ring fused to a dioxolane ring, a benzene ring fused to a pyrrolidine ring, a benzene ring fused to a tetrahydrothiophene ring, a benzene ring fused to an isothiazolidine ring, an imidazole ring, an oxazole ring, a thiazole ring, a pyridine ring, a pyridine ring fused to a tetrahydrofuran ring, a pyridine ring fused to an isothiazolidine ring, or a pyridine ring fused to a thiazinane ring, and ring A is optionally independently substituted with 1, 2 or 3 $R^a$; and the other variables are as defined herein.

In some embodiments of the present application, ring A is selected from the group consisting of a piperidine ring, a benzene ring, a benzene ring fused to an isothiazolidine ring, an imidazole ring, an oxazole ring, a thiazole ring, a pyridine ring, a pyrazine ring, a pyrimidine ring, a pyridazine ring, a pyridine ring fused to an isothiazolidine ring, a pyridine ring fused to a thiazinane ring, a pyrrolo[3,2-c]pyridine ring, a pyrazolo[4,3-c]pyridine ring, a pyrazolo[1,5-a]pyrazine ring, or a pyrrolo[1,2-a]pyrazine ring, and ring A is optionally independently substituted with 1, 2 or 3 $R^a$; and the other variables are as defined herein.

In further embodiments of the present application, ring A is selected from the group consisting of a piperidine ring, a benzene ring, a benzene ring fused to an isothiazolidine ring, an imidazole ring, an oxazole ring, a thiazole ring, a pyridine ring fused to an isothiazolidine ring, or a pyridine ring fused to a thiazinane ring, and ring A is optionally independently substituted with 1, 2 or 3 $R^a$; and the other variables are as defined herein.

In other embodiments of the present application, ring A is selected from the group consisting of

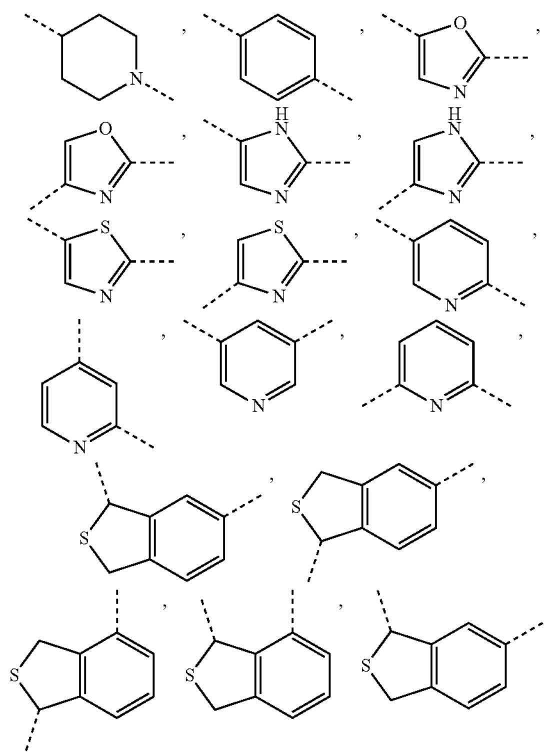

-continued
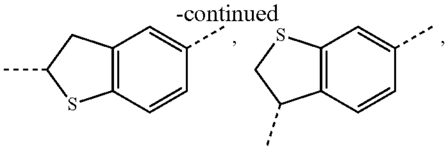
,
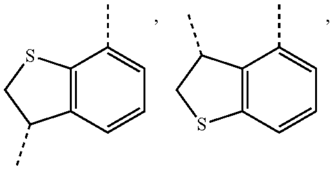
,
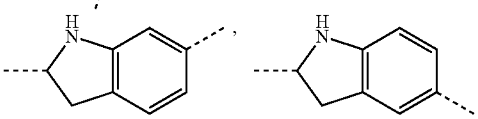
,
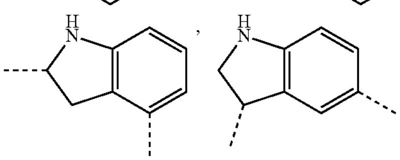
,
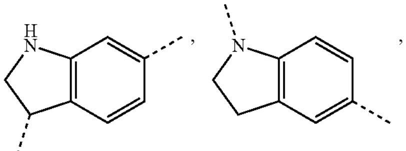
,
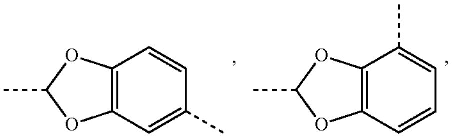
,
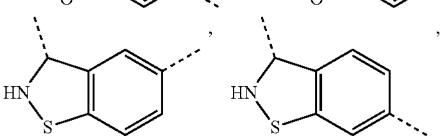
,
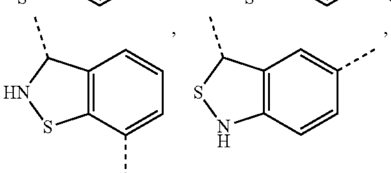
,
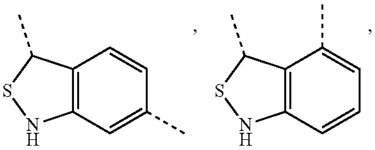
,
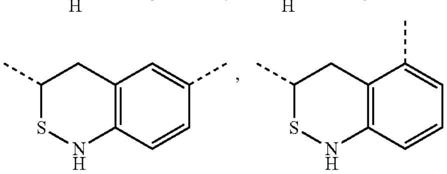
,
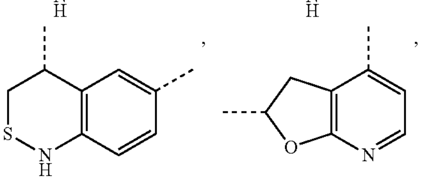
,
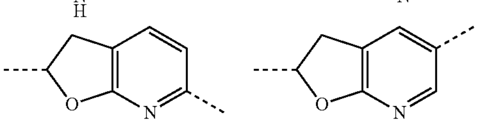
,
-continued
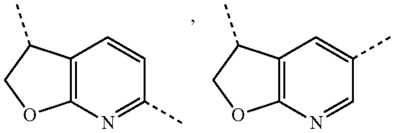
,
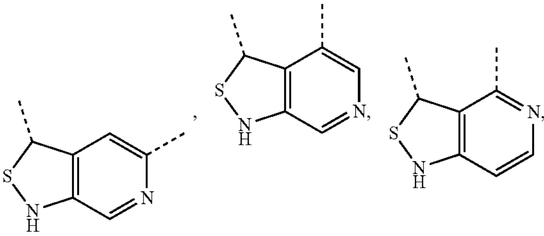
,
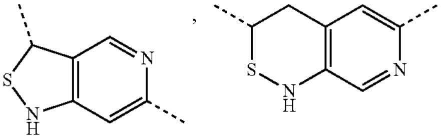
,
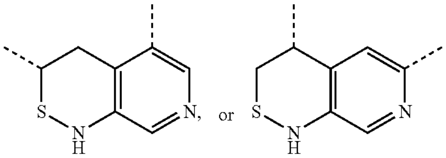
,
and ring A is optionally independently substituted with 1, 2 or 3 $R^a$; and the other variables are as defined herein.
In other embodiments of the present application, ring A is selected from the group consisting of
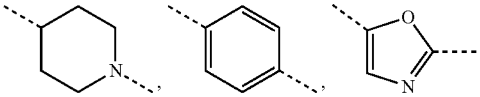
,
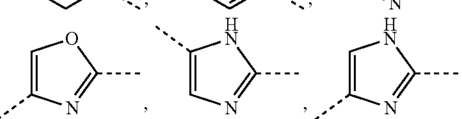
,
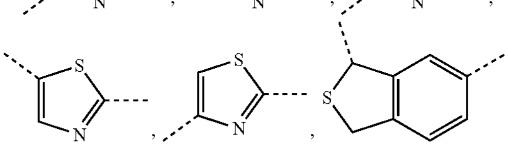
,
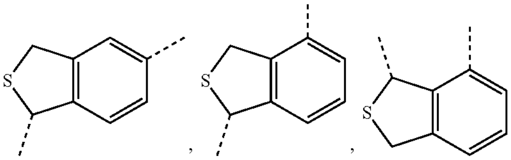
,
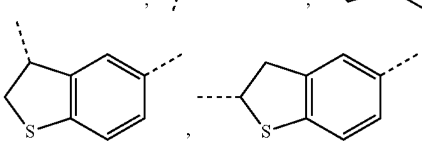
,
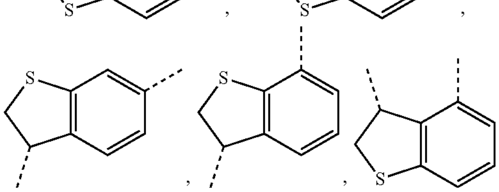
, -continued
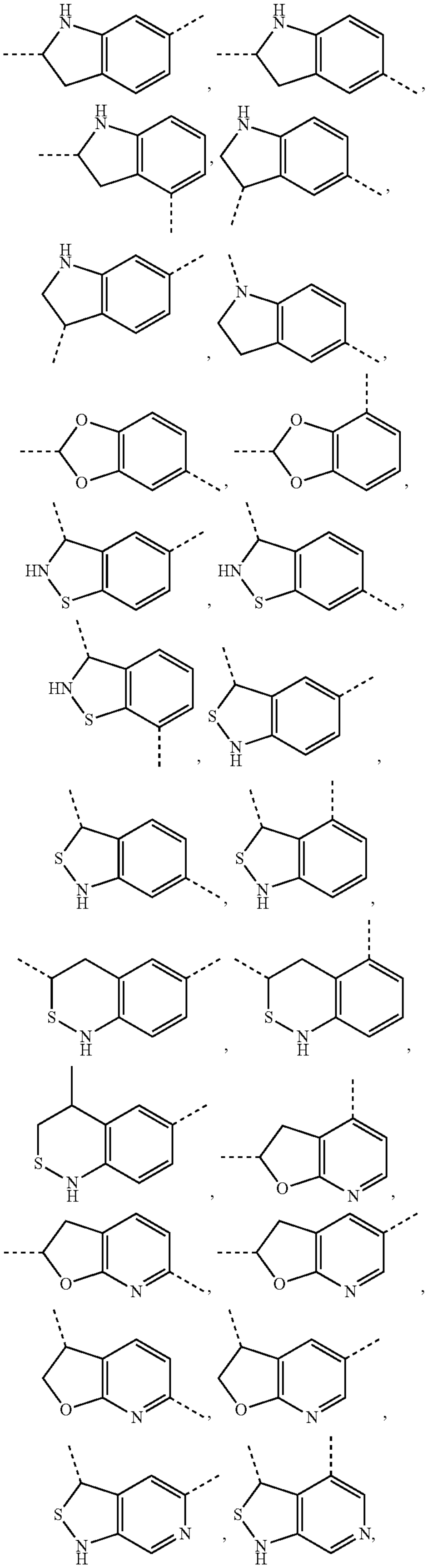
-continued
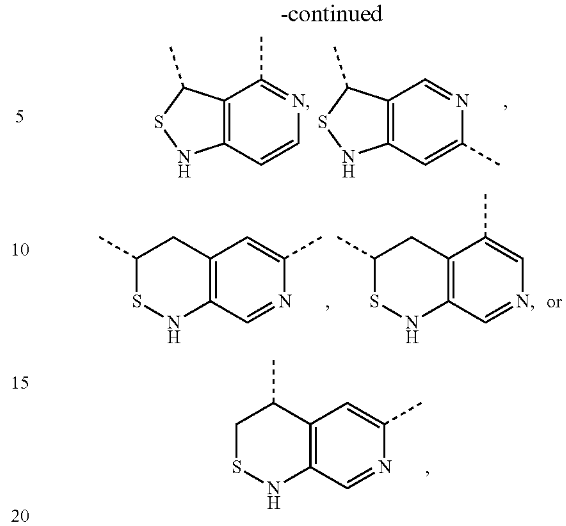
and ring A is optionally independently substituted with 1, 2 or 3 $R^a$; and the other variables are as defined herein.
In some embodiments of the present application, ring A is selected from the group consisting of
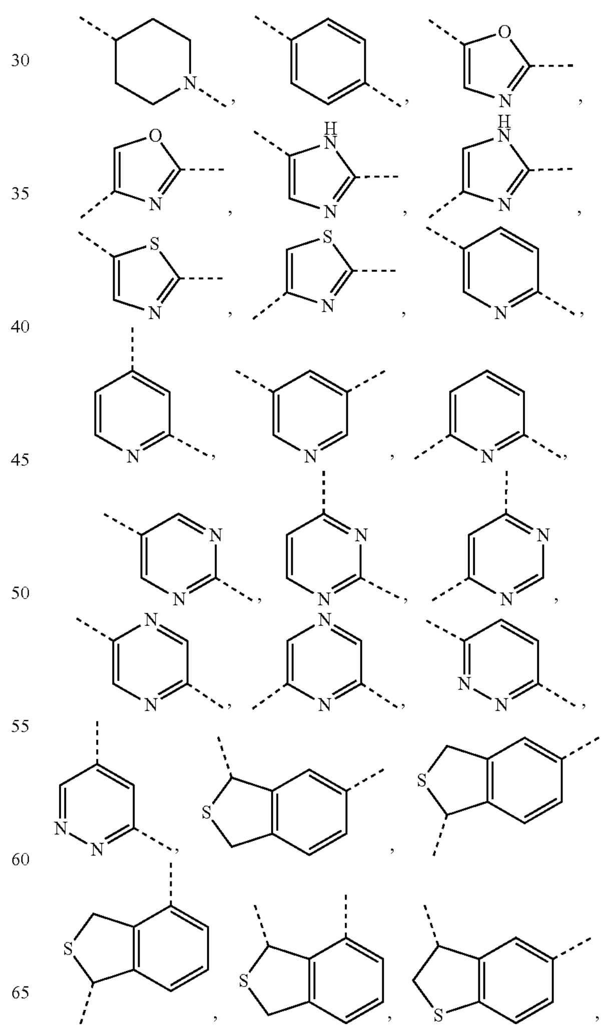

-continued
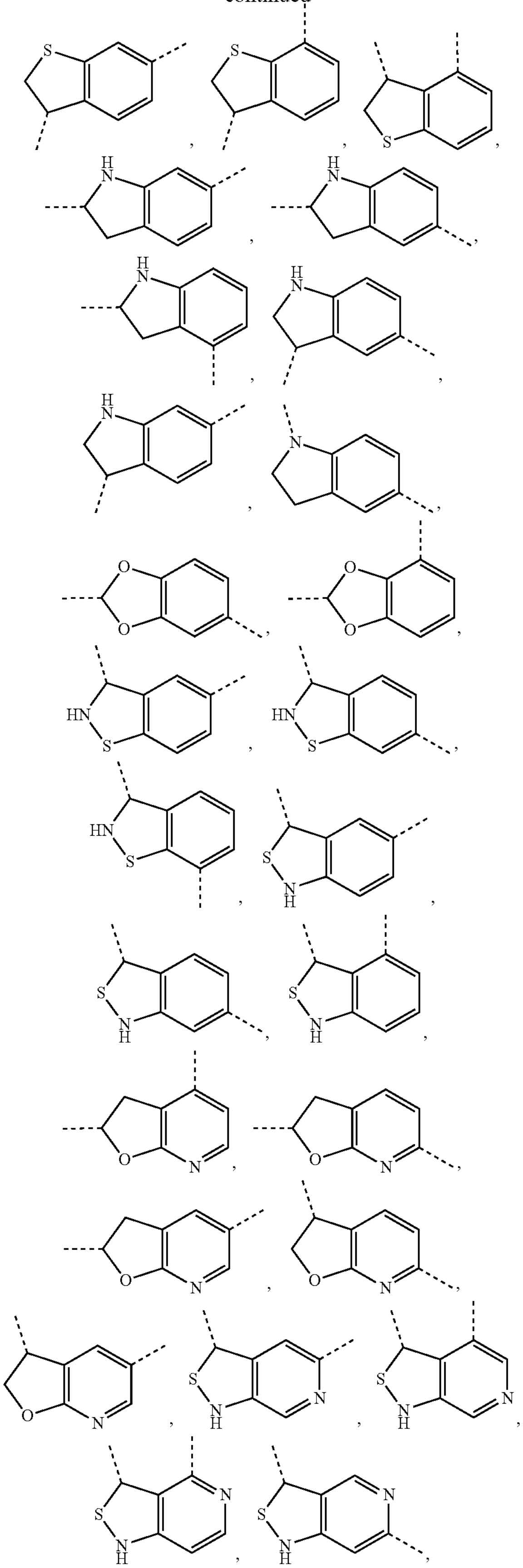
-continued
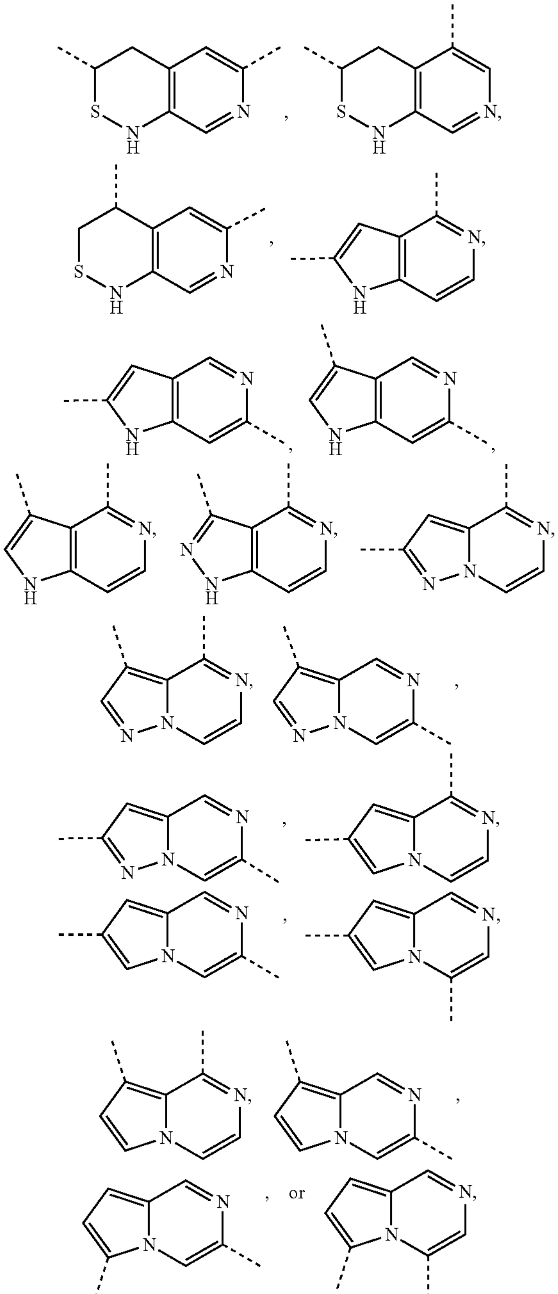
and ring A is optionally independently substituted with 1, 2 or 3 $R^a$; and the other variables are as defined herein.
In some embodiments of the present application, ring A is selected from the group consisting of
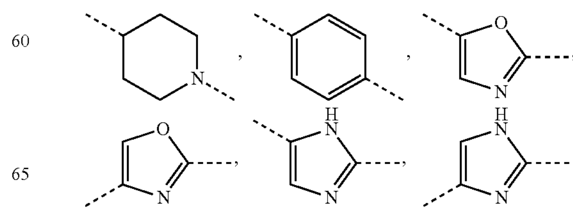

-continued
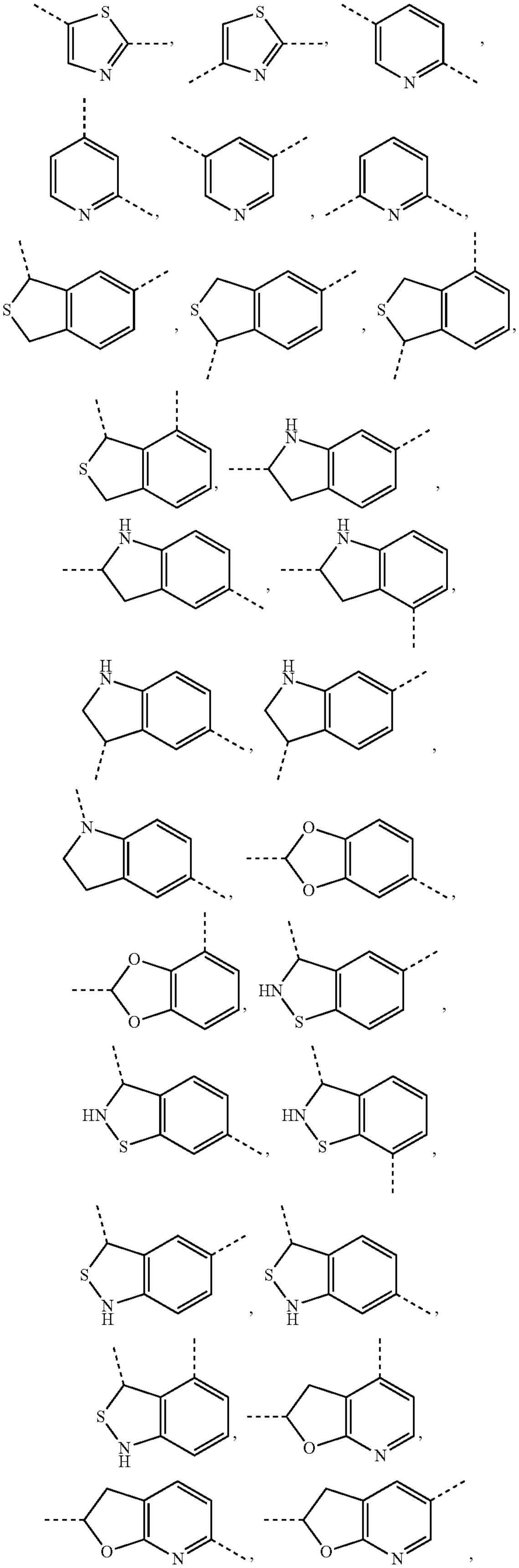
-continued
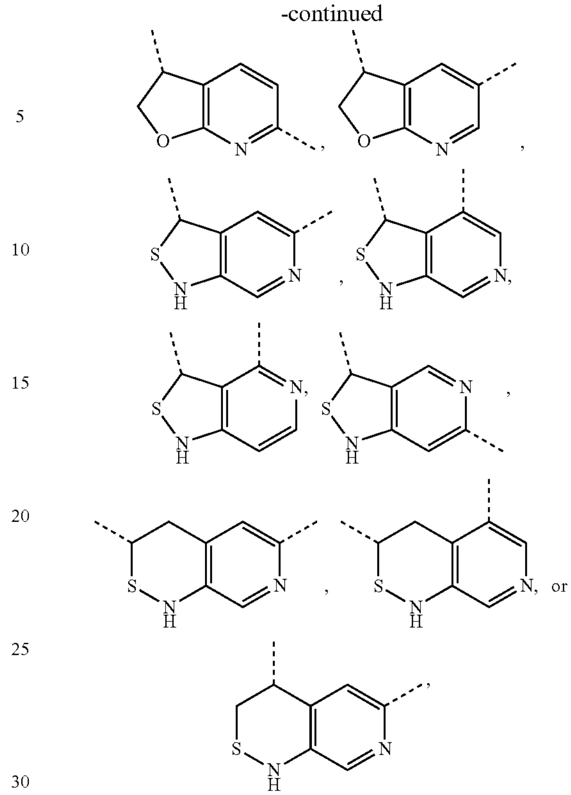
and ring A is optionally independently substituted with 1, 2 or 3 $R^a$; and the other variables are as defined herein.
In some embodiments of the present application, ring A is selected from the group consisting of
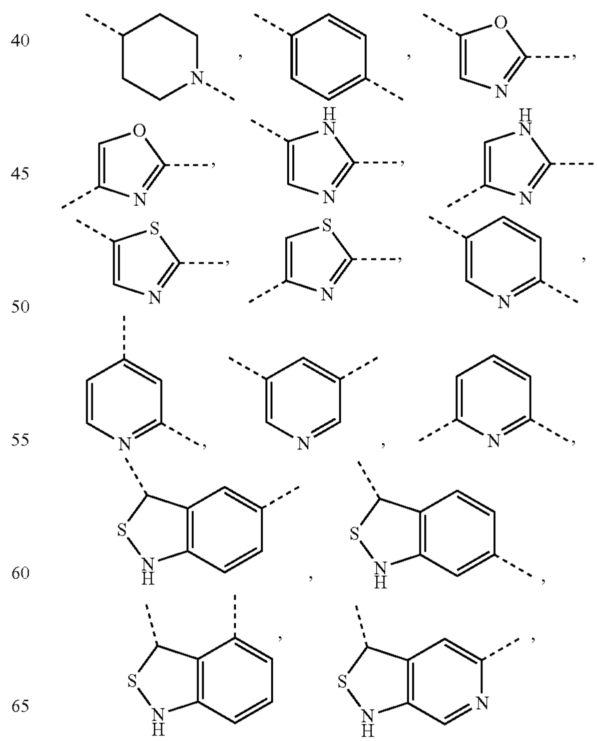

-continued

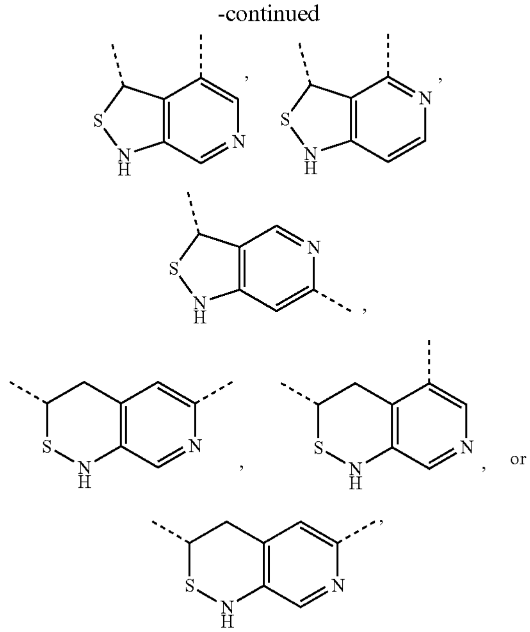

or and ring A is optionally independently substituted with 1, 2 or 3 $R^a$; and the other variables are as defined herein.

In other embodiments of the present application, ring A is selected from the group consisting of

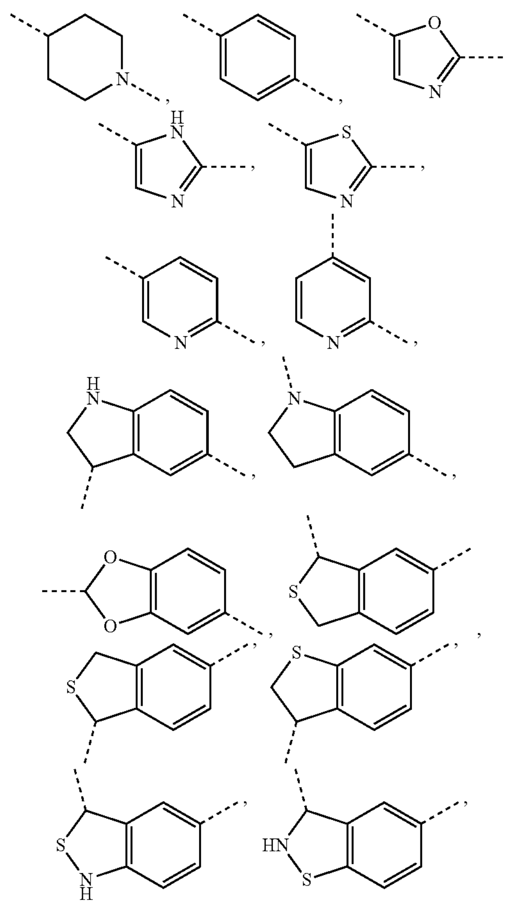

-continued

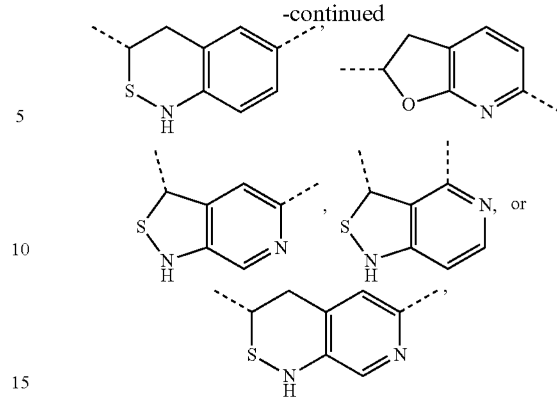

or and ring A is optionally independently substituted with 1, 2, 3 or 4 $R^a$; and the other variables are as defined herein.

In further embodiments of the present application, ring A is selected from the group consisting of

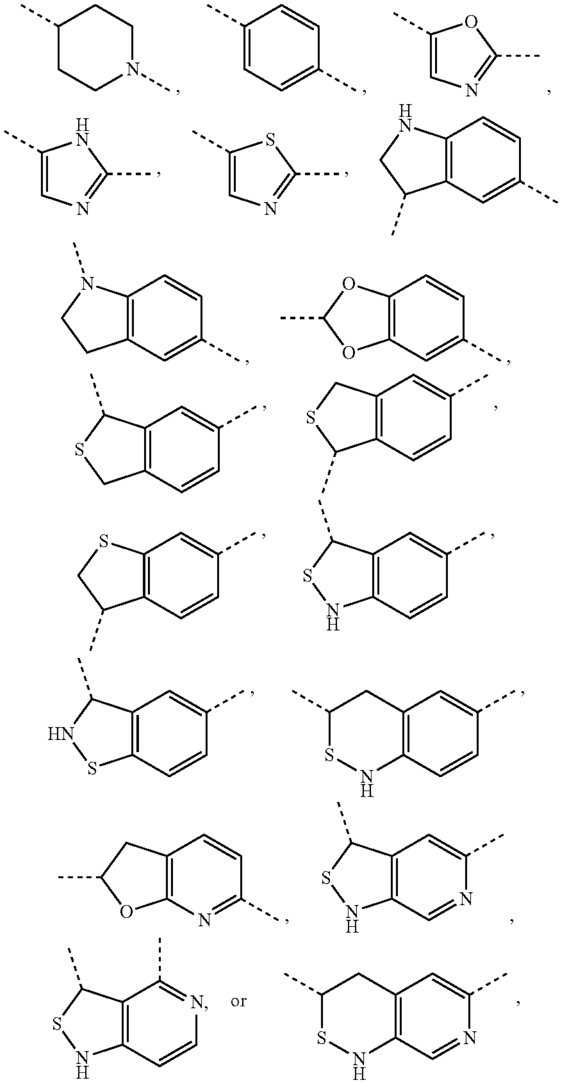

or and ring A is optionally independently substituted with 1, 2, 3 or 4 $R^a$; and the other variables are as defined herein.

In some embodiments of the present application, ring A is selected from the group consisting of
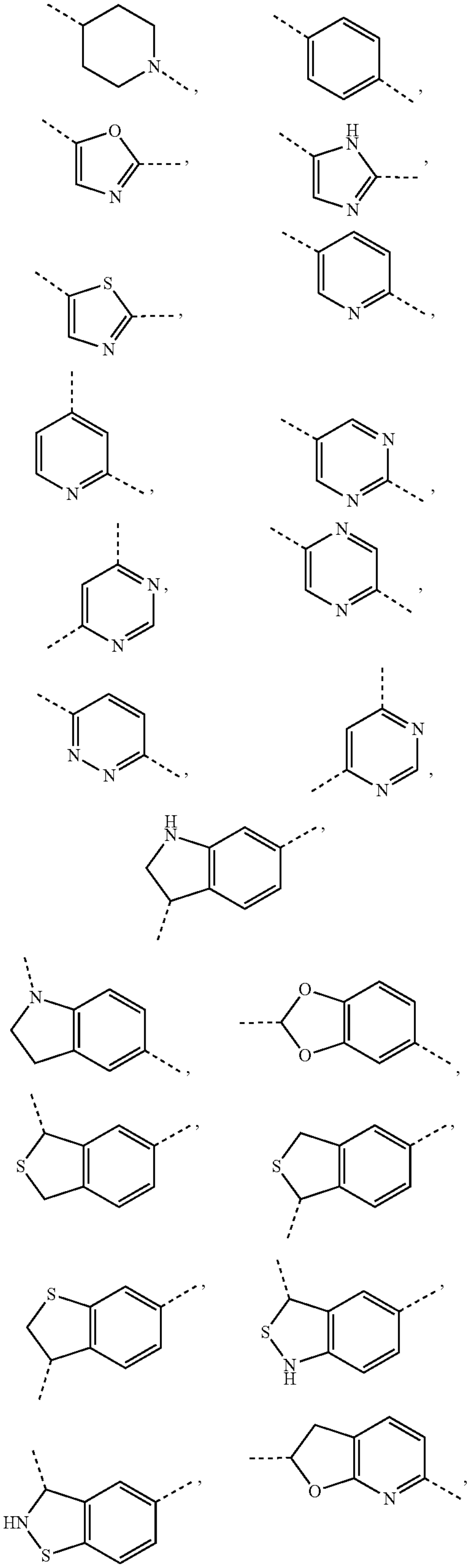
-continued
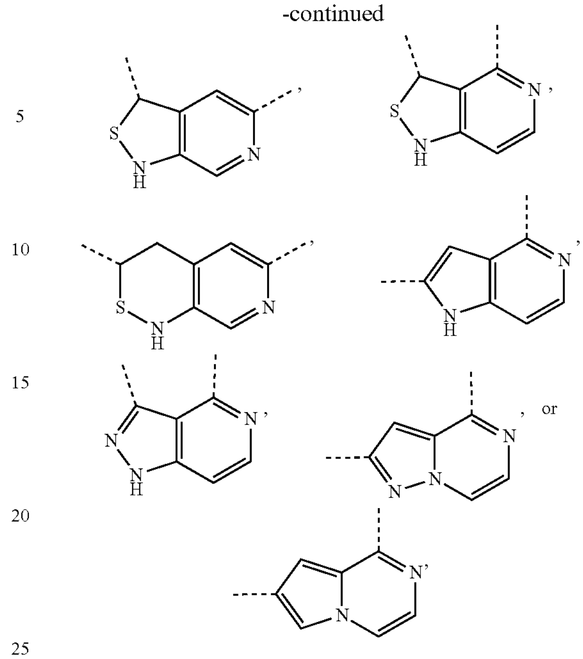
and ring A is optionally independently substituted with 1, 2, 3 or 4 $R^a$; and the other variables are as defined herein.
In some embodiments of the present application, ring A is selected from the group consisting of
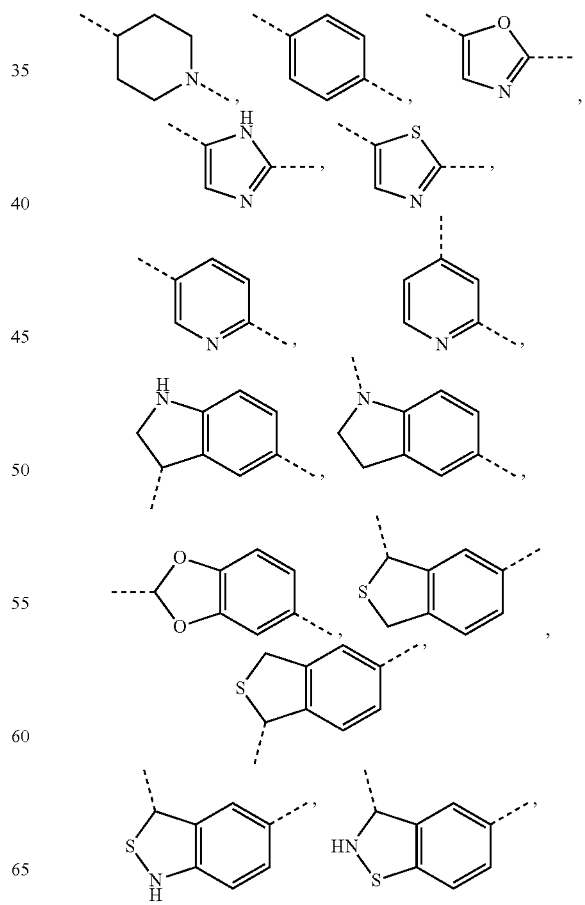

-continued

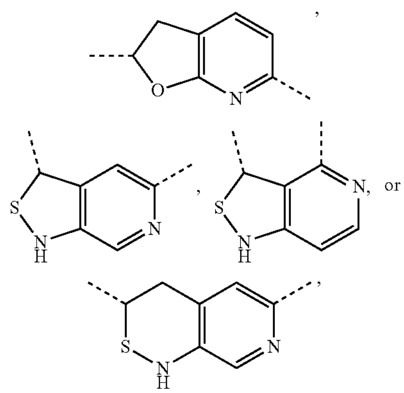

and ring A is optionally independently substituted with 1, 2 or 3 $R^a$; and the other variables are as defined herein.

In some embodiments of the present application, ring A is selected from the group consisting of

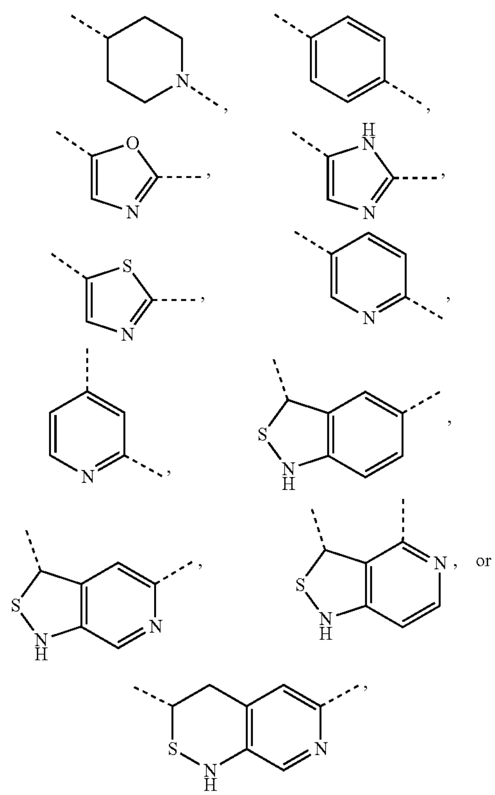

and ring A is optionally independently substituted with 1, 2 or 3 $R^a$; and the other variables are as defined herein.

In some embodiments of the present application, ring A is selected from the group consisting of

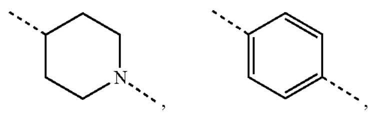

-continued

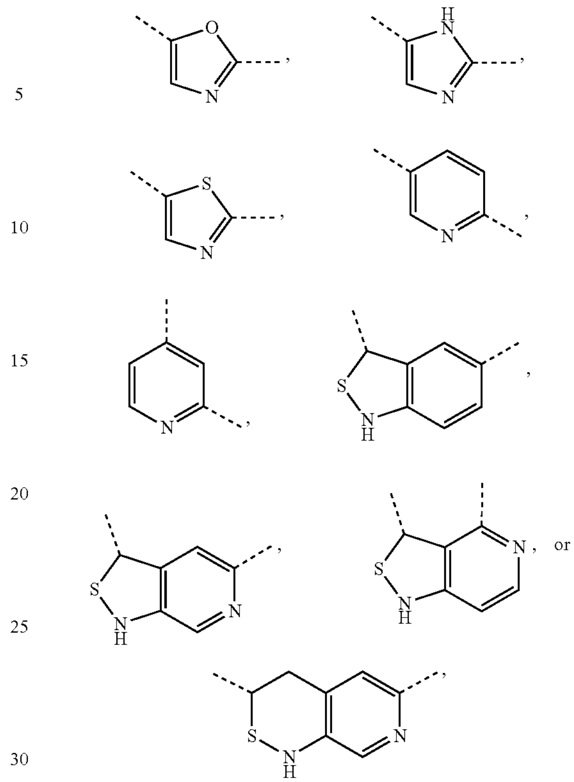

and ring A is optionally independently substituted with 1, 2 or 3 $R^a$; and the other variables are as defined herein.

In other embodiments of the present application, ring A is selected from the group consisting of

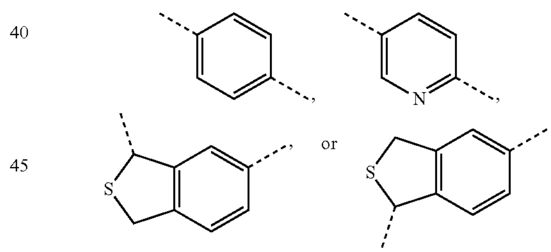

and ring A is optionally independently substituted with 1, 2 or 3 $R^a$; and the other variables are as defined herein.

In other embodiments of the present application, ring A is selected from the group consisting of

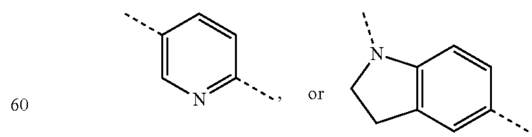

and ring A is optionally independently substituted with 1, 2 or 3 $R^a$; and the other variables are as defined herein.

In other embodiments of the present application, ring A is selected from the group consisting of

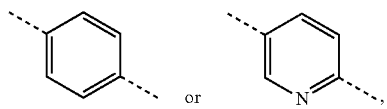

and ring A is optionally independently substituted with 1, 2 or 3 $R^a$; and the other variables are as defined herein.

In other embodiments of the present application, ring A is selected from

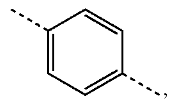

and ring A is optionally independently substituted with 1, 2 or 3 $R^a$; and the other variables are as defined herein. In some embodiments of the present application, the sulfur heteroatom in ring A is oxidized to S(O) or $S(O)_2$, and the other variables are as defined herein.

In some embodiments of the present application, the sulfur heteroatom in ring A is oxidized to $S(O)_2$, and the other variables are as defined herein.

In some embodiments of the present application, $R^a$ is each independently selected from the group consisting of deuterium, F, Cl, Br, I, CN, =O, $C_{1-3}$ alkyl, or $C_{1-3}$ alkoxy, and the $C_{1-3}$ alkyl or the $C_{1-3}$ alkoxy is optionally independently substituted with 1, 2 or 3 $R^x$; and the other variables are as defined herein.

In other embodiments of the present application, $R^a$ is each independently selected from the group consisting of F, Cl, CN, =O, $C_{1-3}$ alkyl, or $C_{1-3}$ alkoxy, and the $C_{1-3}$ alkyl or the $C_{1-3}$ alkoxy is optionally independently substituted with 1, 2 or 3 $R^x$; and the other variables are as defined herein.

In some embodiments of the present application, $R^a$ is each independently selected from the group consisting of F, Cl, Br, I, =O, $C_{1-3}$ alkyl, or $C_{1-3}$ alkoxy, and the $C_{1-3}$ alkyl or the $C_{1-3}$ alkoxy is optionally independently substituted with 1, 2 or 3 $R^x$; and the other variables are as defined herein.

In some embodiments of the present application, $R^a$ is each independently selected from the group consisting of F, Cl, Br, I, =O, or $C_{1-3}$ alkyl, and the $C_{1-3}$ alkyl is optionally independently substituted with 1, 2 or 3 $R^x$; and the other variables are as defined herein.

In some embodiments of the present application, $R^a$ is each independently selected from the group consisting of F, Cl, CN, =O, methyl, or methoxy, and the methyl or the methoxy is optionally independently substituted with 1, 2 or 3 halogens; and the other variables are as defined herein.

In some embodiments of the present application, $R^a$ is each independently selected from the group consisting of F, =O, or methyl, and the methyl is optionally independently substituted with 1, 2 or 3 halogens; and the other variables are as defined herein.

In some embodiments of the present application, $R^a$ is each independently selected from the group consisting of F, =O, methyl, or methoxy, and the methyl or the methoxy is optionally independently substituted with 1, 2 or 3 halogens; and the other variables are as defined herein.

In some embodiments of the present application, $R^a$ is each independently selected from the group consisting of F, Cl, CN, =O, methyl, monofluoromethyl, difluoromethyl, trifluoromethyl, methoxy, monofluoromethoxy, difluoromethoxy, or trifluoromethoxy, and the other variables are as defined herein.

In some embodiments of the present application, $R^a$ is each independently selected from the group consisting of F, =O, methyl, monofluoromethyl, difluoromethyl, or trifluoromethyl, and the other variables are as defined herein.

In other embodiments of the present application, $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In some embodiments of the present application, $R^a$ is each independently selected from the group consisting of F, Cl, =O, methyl, methoxy, trifluoromethyl, or trifluoromethoxy, and the other variables are as defined herein.

In some embodiments of the present application, $R^a$ is each independently selected from the group consisting of F, =O, methyl, or trifluoromethyl, and the other variables are as defined herein.

In some embodiments of the present application, $R^a$ is each independently selected from the group consisting of F, =O, methyl, methoxy, or trifluoromethyl, and the other variables are as defined herein.

In other embodiments of the present application, ring A is selected from the group consisting of a piperidine ring, a benzene ring, a benzene ring fused to a dioxolane ring, a benzene ring fused to a pyrrolidine ring, a benzene ring fused to a tetrahydrothiophene ring, a benzene ring fused to an isothiazolidine ring, a benzene ring fused to a thiazinane ring, an imidazole ring, an oxazole ring, a thiazole ring, a pyridine ring, a pyridine ring fused to a tetrahydrofuran ring, a pyridine ring fused to an isothiazolidine ring, or a pyridine ring fused to a thiazinane ring, and ring A is optionally independently substituted with 1, 2 or 3 $R^a$; and $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In further embodiments of the present application, ring A is selected from the group consisting of a piperidine ring, a benzene ring, a benzene ring fused to a dioxolane ring, a benzene ring fused to a pyrrolidine ring, a benzene ring fused to a tetrahydrothiophene ring, a benzene ring fused to an isothiazolidine ring, a benzene ring fused to a thiazinane ring, an imidazole ring, an oxazole ring, a thiazole ring, a pyridine ring fused to a tetrahydrofuran ring, a pyridine ring fused to an isothiazolidine ring, or a pyridine ring fused to a thiazinane ring, and ring A is optionally independently substituted with 1, 2 or 3 $R^a$; and $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In some embodiments of the present application, ring A is selected from the group consisting of a piperidine ring, a benzene ring, a benzene ring fused to a dioxolane ring, a benzene ring fused to a pyrrolidine ring, a benzene ring fused to a tetrahydrothiophene ring, a benzene ring fused to an isothiazolidine ring, an imidazole ring, an oxazole ring, a thiazole ring, a pyridine ring, a pyrazine ring, a pyrimidine ring, a pyridazine ring, a pyridine ring fused to a tetrahydrofuran ring, a pyridine ring fused to an isothiazolidine ring, a pyridine ring fused to a thiazinane ring, a pyrrolo[3,2-c]pyridine ring, a pyrazolo[4,3-c]pyridine ring, a pyrazolo[1,5-a]pyrazine ring, or a pyrrolo[1,2-a]pyrazine ring, and ring A is optionally independently substituted with 1, 2 or 3

$R^a$; and $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In some embodiments of the present application, ring A is selected from the group consisting of a piperidine ring, a benzene ring, a benzene ring fused to a dioxolane ring, a benzene ring fused to a pyrrolidine ring, a benzene ring fused to a tetrahydrothiophene ring, a benzene ring fused to an isothiazolidine ring, an imidazole ring, an oxazole ring, a thiazole ring, a pyridine ring, a pyridine ring fused to a tetrahydrofuran ring, a pyridine ring fused to an isothiazolidine ring, or a pyridine ring fused to a thiazinane ring, and ring A is optionally independently substituted with 1, 2 or 3 $R^a$; and $R^a$ is each independently selected from the group consisting of F, Cl, =O, methyl, methoxy, trifluoromethyl, or trifluoromethoxy, and the other variables are as defined herein.

In some embodiments of the present application, ring A is selected from a piperidine ring, a benzene ring, a benzene ring fused to an isothiazolidine ring, an imidazole ring, an oxazole ring, a thiazole ring, a pyridine ring, a pyridine ring fused to an isothiazolidine ring, or a pyridine ring fused to a thiazinane ring, and ring A is optionally independently substituted with 1, 2 or 3 $R^a$; and $R^a$ is each independently selected from the group consisting of F, =O, methyl, or trifluoromethyl, and the other variables are as defined herein.

In other embodiments of the present application, ring A is selected from the group consisting of

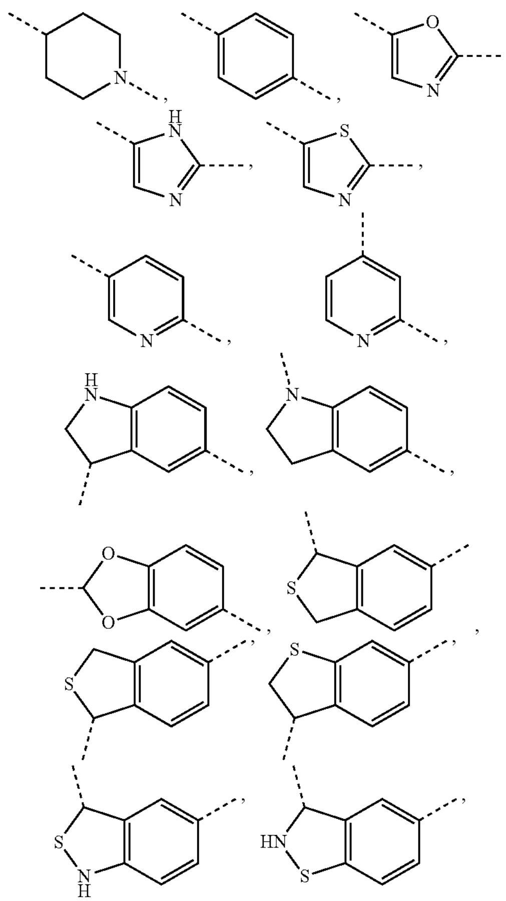

-continued

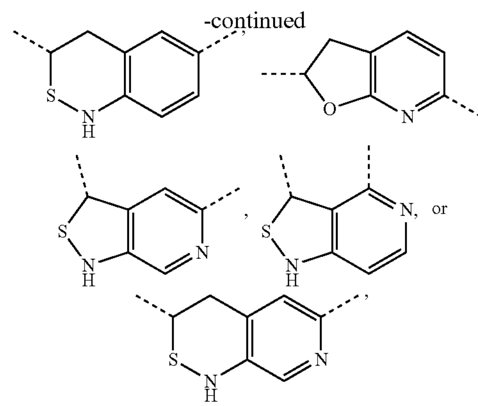

and ring A is optionally independently substituted with 1, 2 or 3 $R^a$; and $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In further embodiments of the present application, ring A is selected from the group consisting of

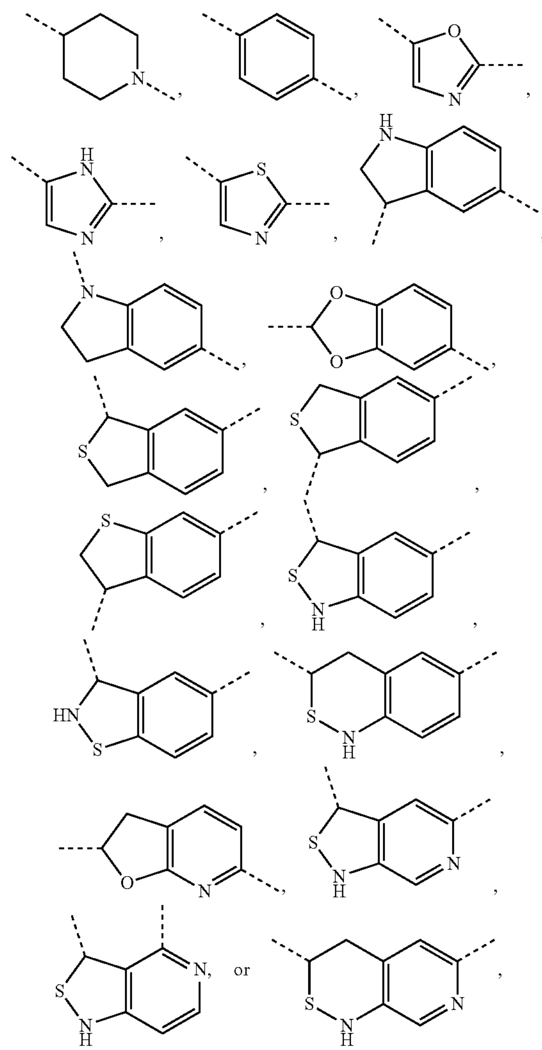

and ring A is optionally independently substituted with 1, 2 or 3 $R^a$; and $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In some embodiments of the present application, ring A is selected from the group consisting of

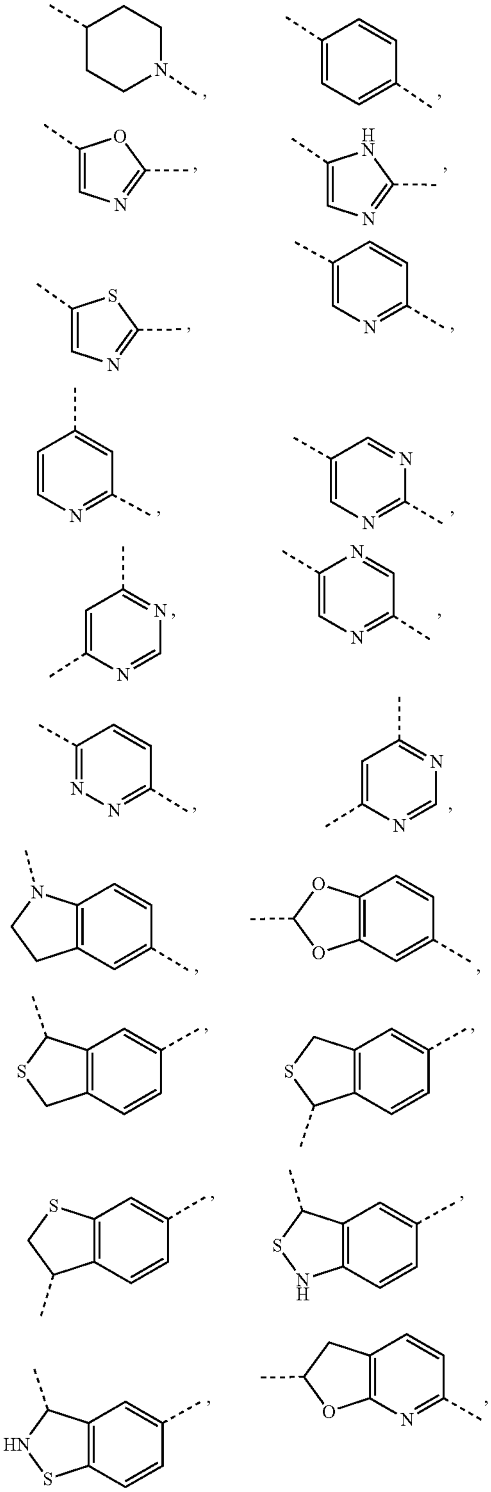

-continued

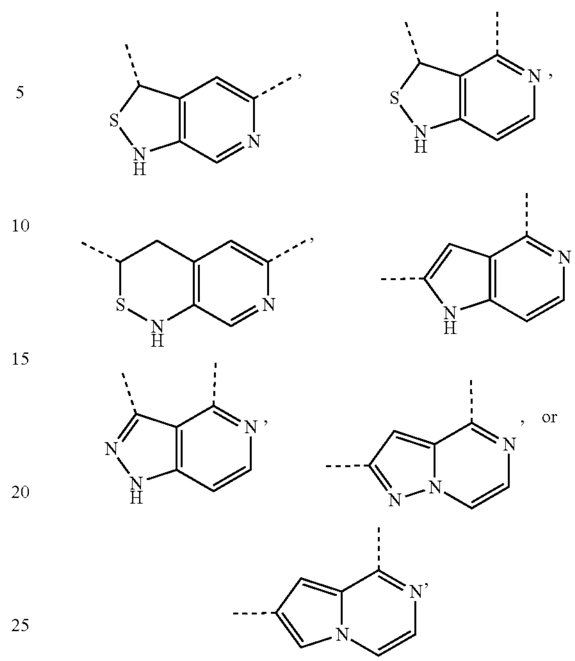

and ring A is optionally independently substituted with 1, 2 or 3 $R^a$; and $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In some embodiments of the present application, ring A is selected from the group consisting of

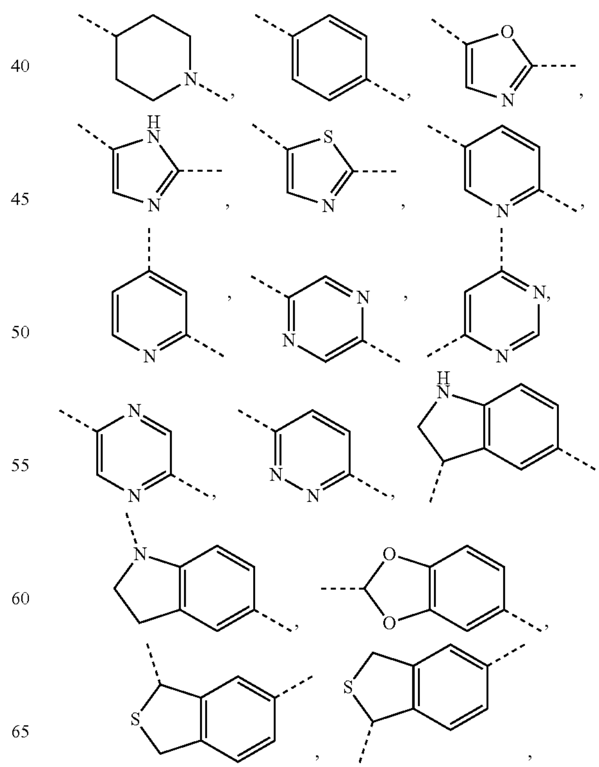

-continued

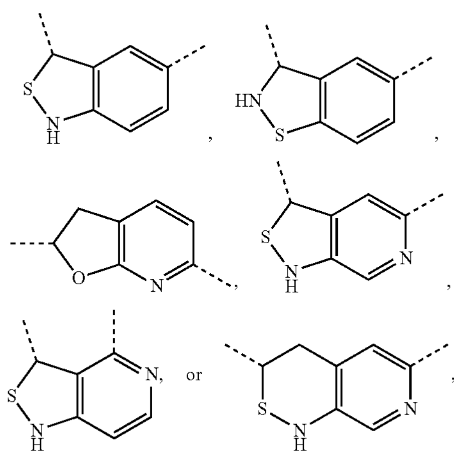

and ring A is optionally independently substituted with 1, 2 or 3 $R^a$; and $R^a$ is each independently selected from the group consisting of F, Cl, =O, methyl, methoxy, trifluoromethyl, or trifluoromethoxy, and the other variables are as defined herein.

In some embodiments of the present application, ring A is selected from the group consisting of

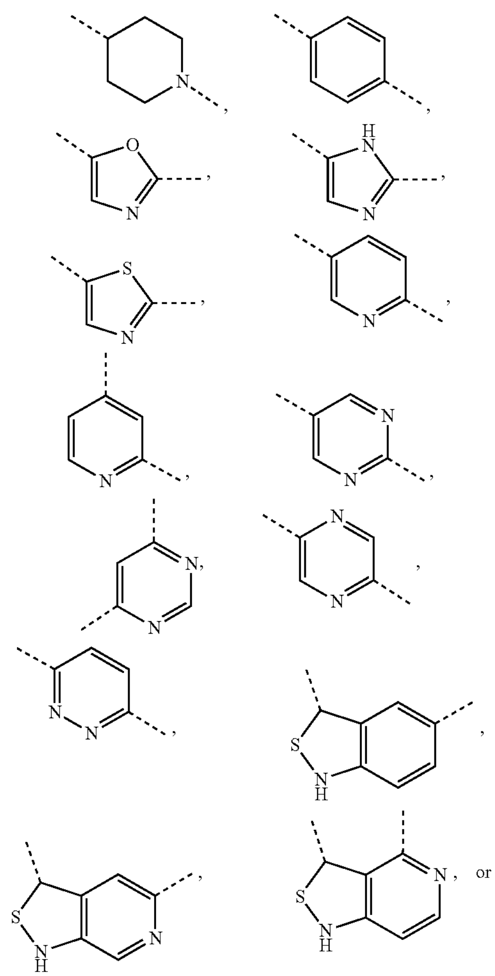

-continued

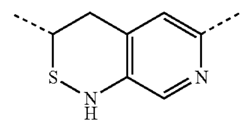

and ring A is optionally independently substituted with 1, 2 or 3 $R^a$; and $R^a$ is each independently selected from the group consisting of F, =O, methyl, or trifluoromethyl, and the other variables are as defined herein.

In some embodiments of the present application, ring A is selected from the group consisting of

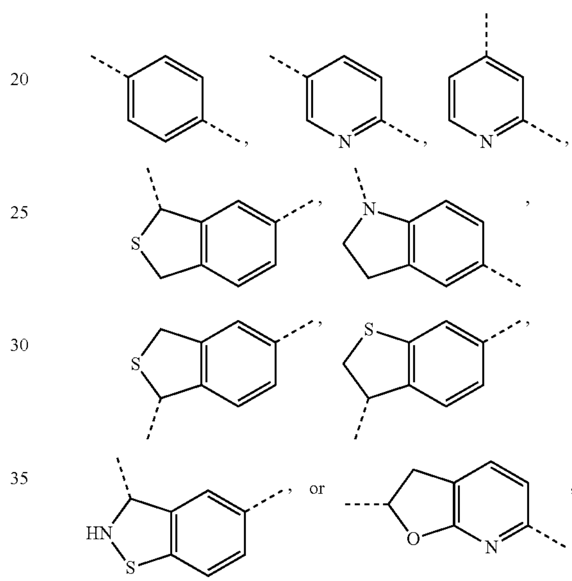

and ring A is optionally independently substituted with 1, 2 or 3 $R^a$; and $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In some embodiments of the present application, ring A is selected from the group consisting of

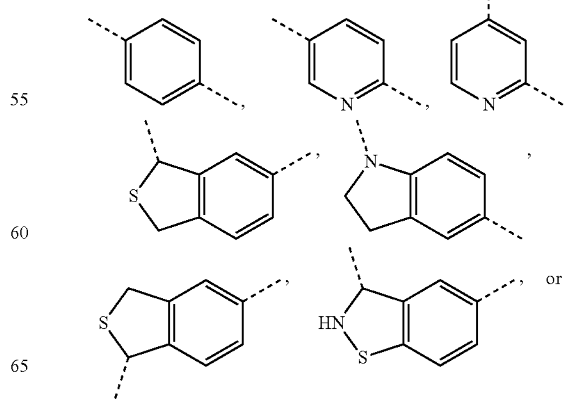

-continued

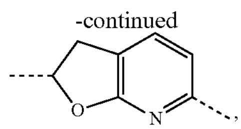

and ring A is optionally independently substituted with 1, 2 or 3 $R^a$; and $R^a$ is each independently selected from the group consisting of F, Cl, =O, methyl, methoxy, trifluoromethyl, or trifluoromethoxy, and the other variables are as defined herein.

In some embodiments of the present application, ring A is selected from the group consisting of

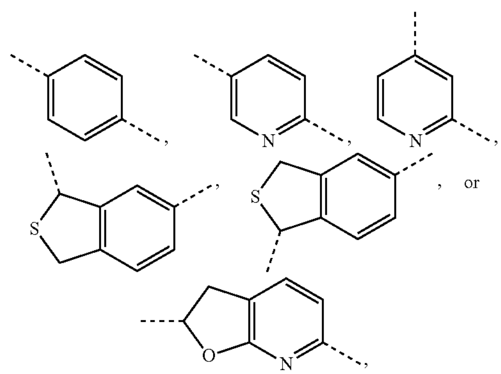

and ring A is optionally independently substituted with 1, 2 or 3 $R^a$; and $R^a$ is each independently selected from the group consisting of F, Cl, =O, methyl, methoxy, trifluoromethyl, or trifluoromethoxy, and the other variables are as defined herein.

In some embodiments of the present application, ring A is selected from the group consisting of

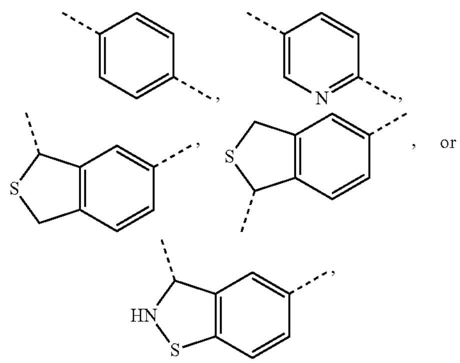

and ring A is optionally independently substituted with 1, 2 or 3 $R^a$; and $R^a$ is each independently selected from the group consisting of F, Cl, =O, methyl, methoxy, trifluoromethyl, or trifluoromethoxy, and the other variables are as defined herein.

In some embodiments of the present application, ring A is selected from the group consisting of

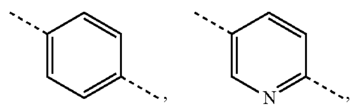

-continued

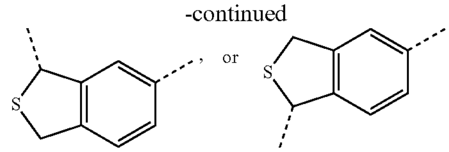

and ring A is optionally independently substituted with 1, 2 or 3 $R^a$; and $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In some embodiments of the present application, ring A is selected from the group consisting of

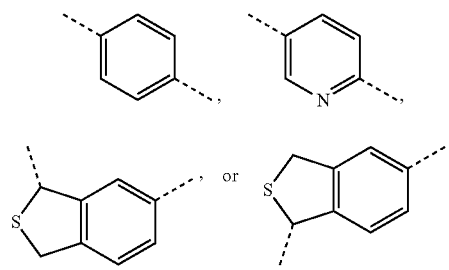

and ring A is optionally independently substituted with 1, 2 or 3 $R^a$; and $R^a$ is each independently selected from the group consisting of F, Cl, =O, methyl, methoxy, trifluoromethyl, or trifluoromethoxy, and the other variables are as defined herein.

In some embodiments of the present application, ring A is selected from the group consisting of

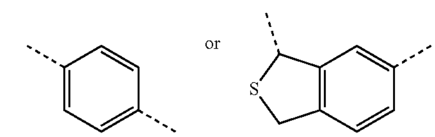

and ring A is optionally independently substituted with 1, 2 or 3 $R^a$; and $R^a$ is each independently selected from the group consisting of F, Cl, =O, methyl, methoxy, trifluoromethyl, or trifluoromethoxy, and the other variables are as defined herein.

In other embodiments of the present application, ring A is selected from the group consisting of

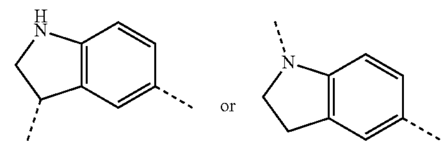

and ring A is optionally independently substituted with 1, 2 or 3 $R^a$; and the other variables are as defined herein.

In other embodiments of the present application, ring A is selected from the group consisting of

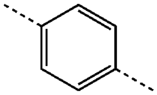 or 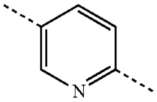, and ring A is optionally independently substituted with 1, 2 or 3 $R^a$; and $R^a$ is each independently selected from the group consisting of F, Cl, =O, methyl, methoxy, trifluoromethyl, or trifluoromethoxy, and the other variables are as defined herein.

In other embodiments of the present application, ring A is selected from the group consisting of

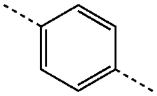, and ring A is optionally independently substituted with 1, 2 or 3 $R^a$; and $R^a$ is each independently selected from the group consisting of F, Cl, =O, methyl, methoxy, trifluoromethyl, or trifluoromethoxy, and the other variables are as defined herein.

In some embodiments of the present application, ring A is selected from the group consisting of

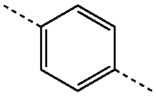 or 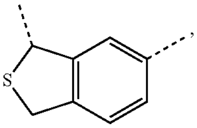, and ring A is optionally independently substituted with 1, 2 or 3 $R^a$; and $R^a$ is each independently selected from the group consisting of F or trifluoromethyl, and the other variables are as defined herein.

In other embodiments of the present application, ring A is selected from the group consisting of

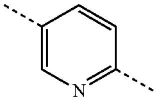, or 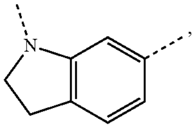, and ring A is optionally independently substituted with 1, 2 or 3 $R^a$; and $R^a$ is each independently selected from the group consisting of F or trifluoromethyl, and the other variables are as defined herein.

In some embodiments of the present application, ring A is selected from the group consisting of

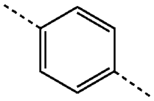, 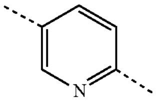, 

-continued

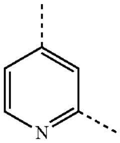, 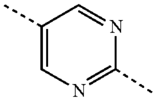, or 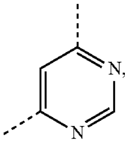

and ring A is optionally independently substituted with 1, 2 or 3 $R^a$; and $R^a$ is each independently selected from the group consisting of F, =O, methyl, or trifluoromethyl, and the other variables are as defined herein.

In some embodiments of the present application, ring A is selected from the group consisting of

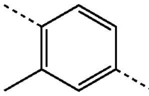 or 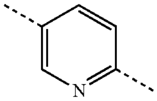, and ring A is optionally independently substituted with 1, 2 or 3 $R^a$; and $R^a$ is each independently selected from the group consisting of F, =O, methyl, or trifluoromethyl, and the other variables are as defined herein.

In other embodiments of the present application, ring A is selected from the group consisting of

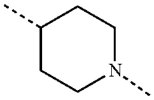, 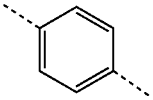,

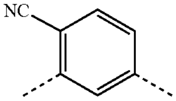, 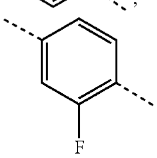,

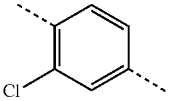, 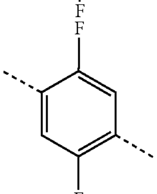,

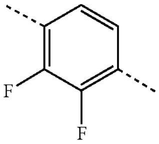, 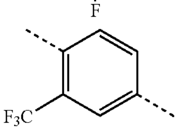,

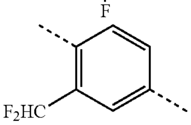, 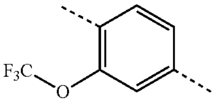,

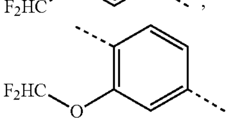, 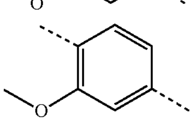,

-continued
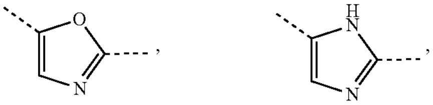
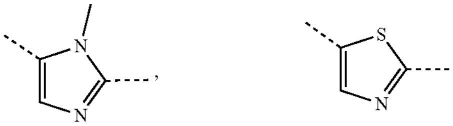
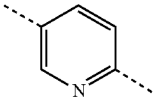
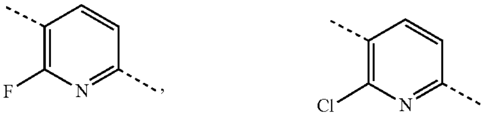
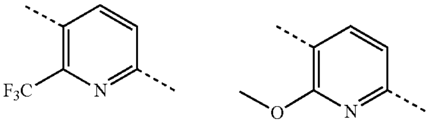
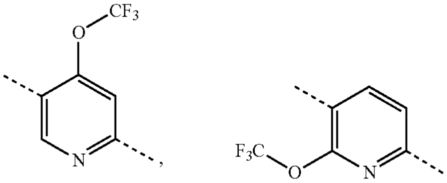
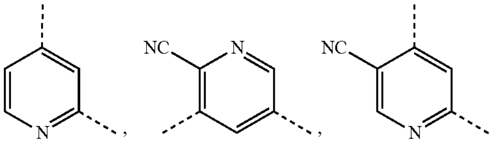
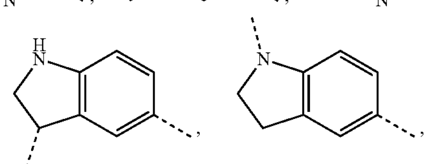
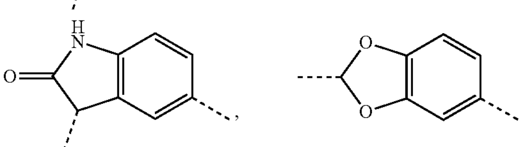
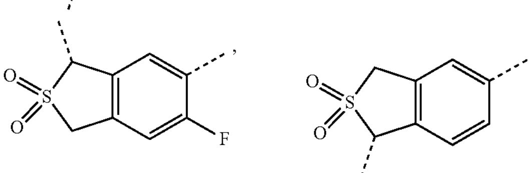
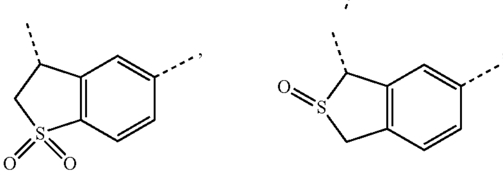
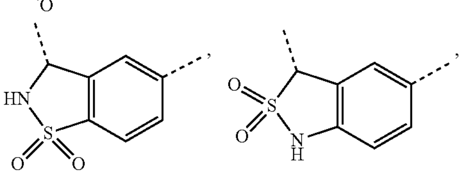
-continued
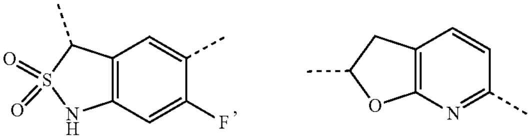
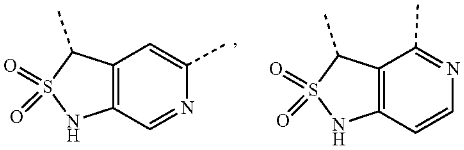
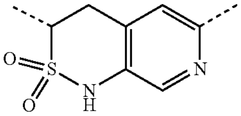
or
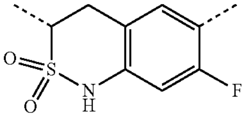
and the other variables are as defined herein.
In further embodiments of the present application, ring A is selected from the group consisting of
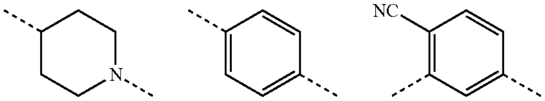
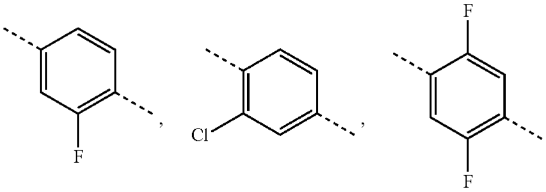
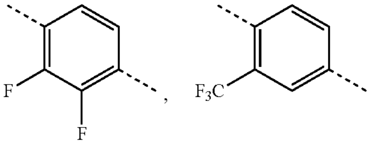
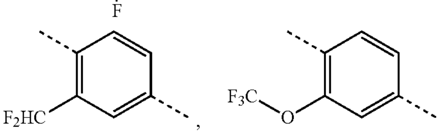
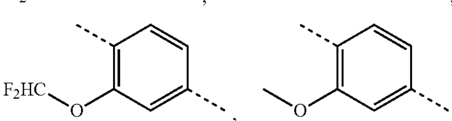
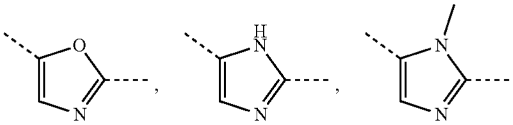
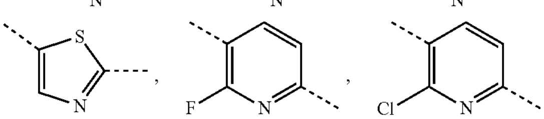
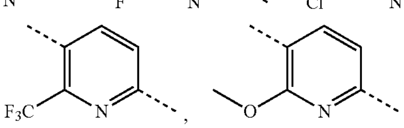

-continued
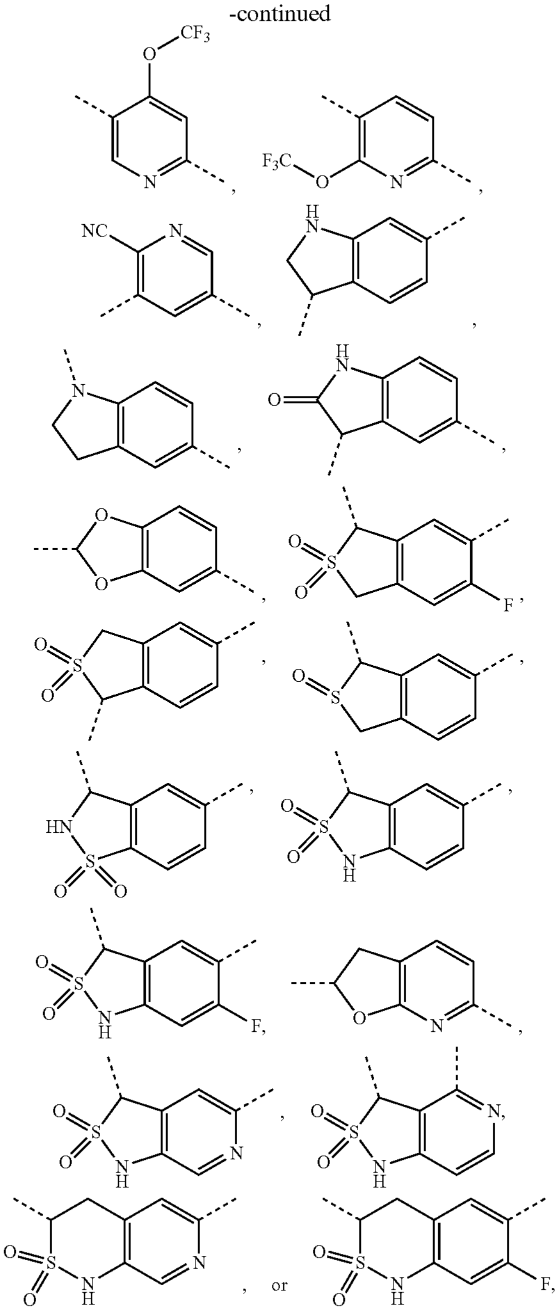
and the other variables are as defined herein.
In some embodiments of the present application, ring A is selected from the group consisting of
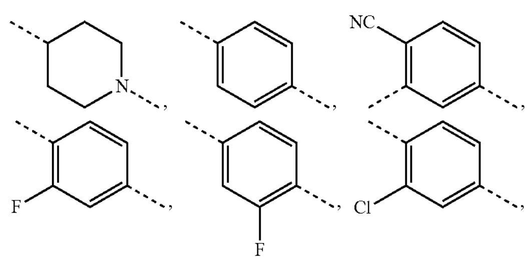
-continued
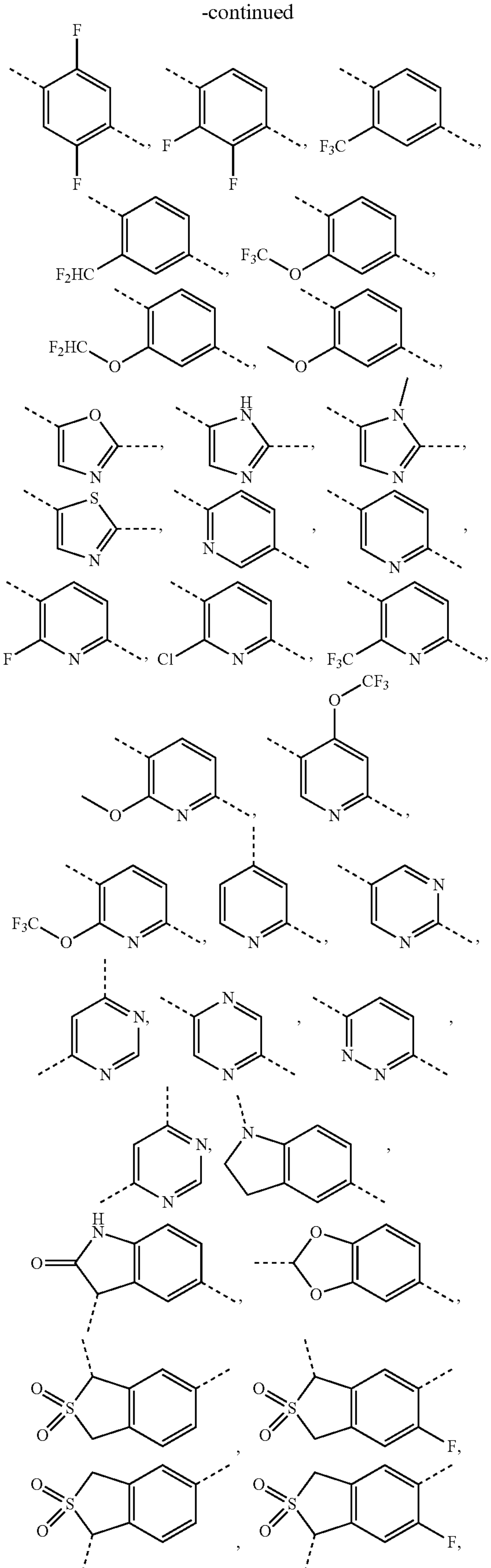

-continued
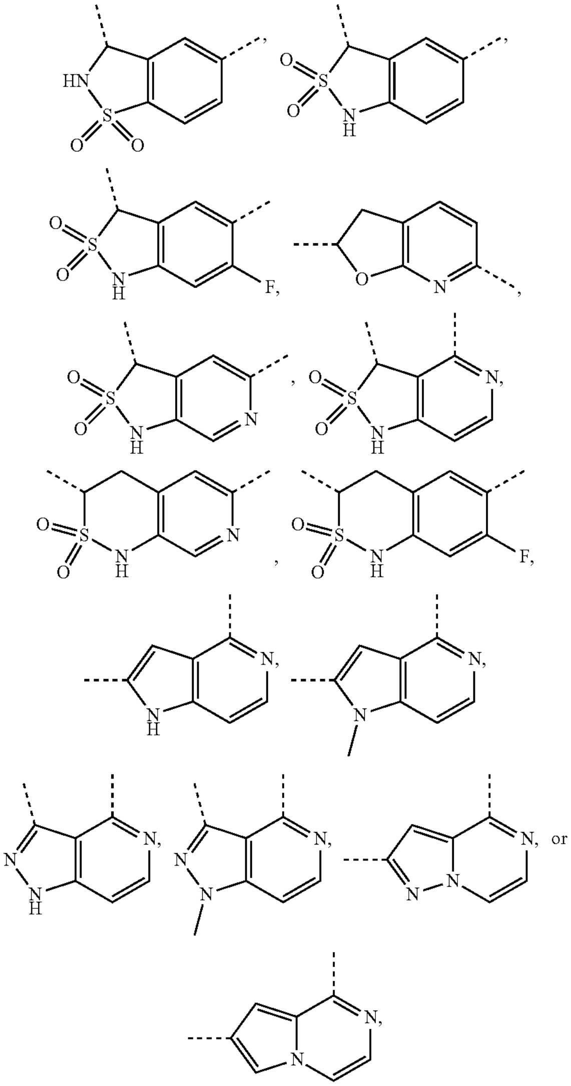
and the other variables are as defined herein.
In some embodiments of the present application, ring A is selected from the group consisting of
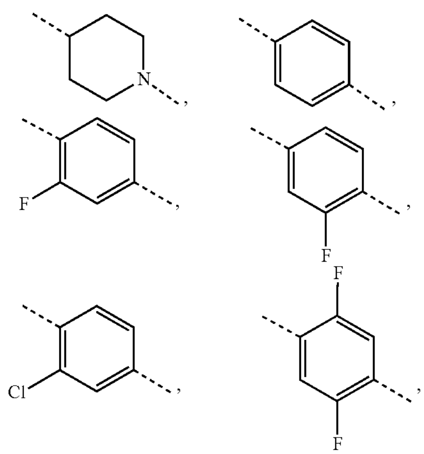
-continued
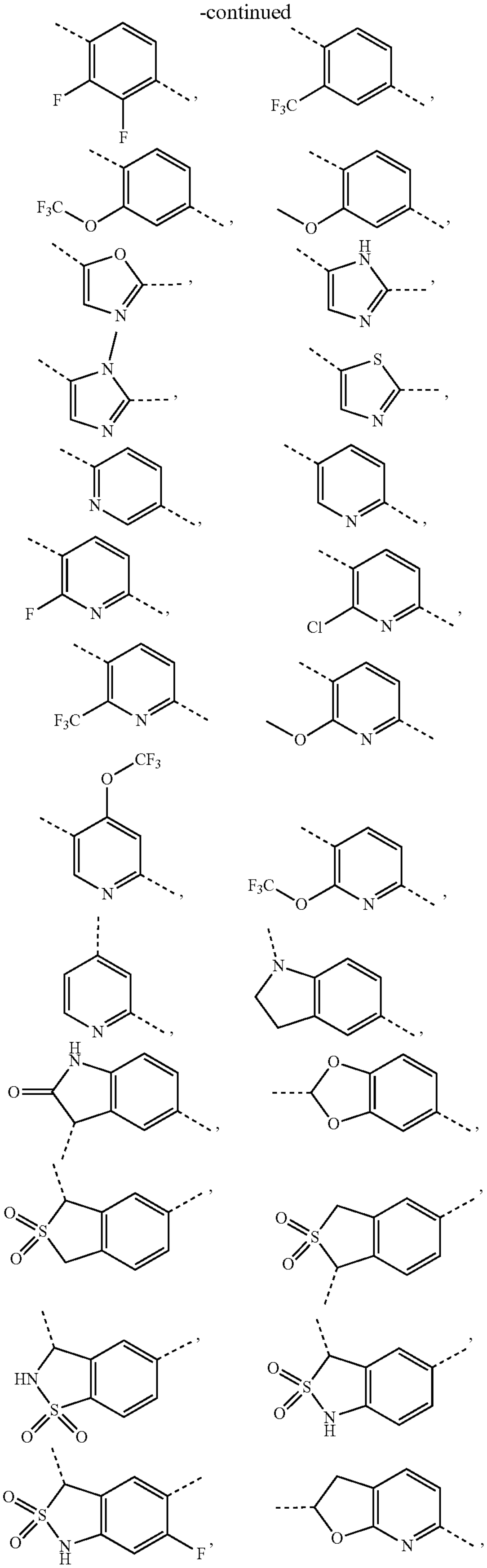

-continued
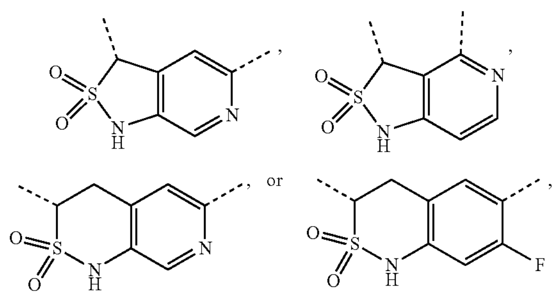
or
and the other variables are as defined herein.
In some embodiments of the present application, ring A is selected from the group consisting of
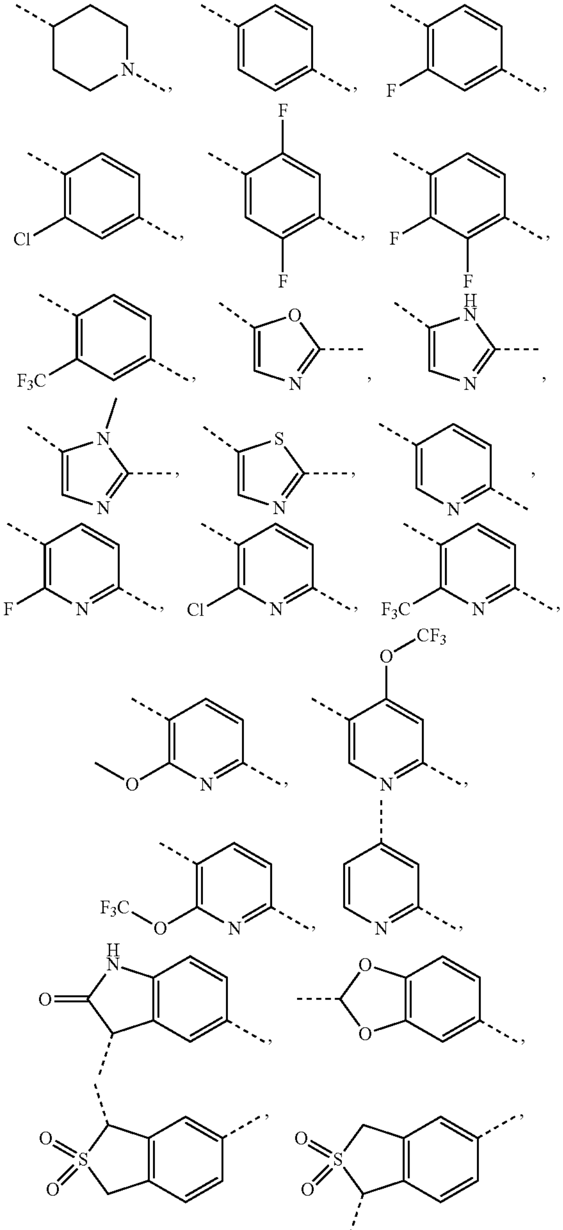
-continued
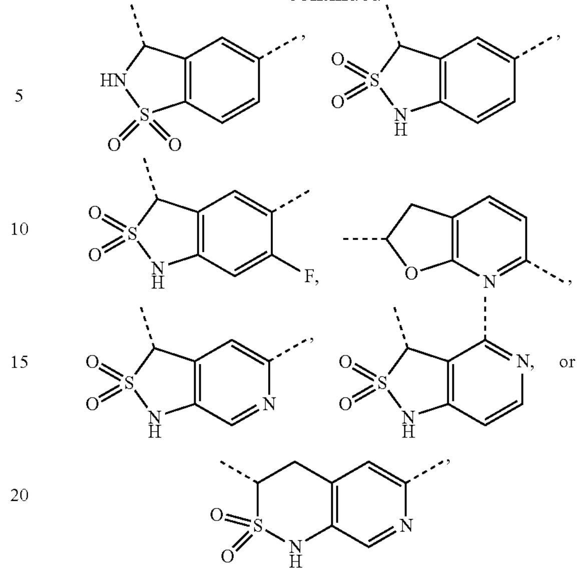
or
and the other variables are as defined herein.
In some embodiments of the present application, ring A is selected from the group consisting of
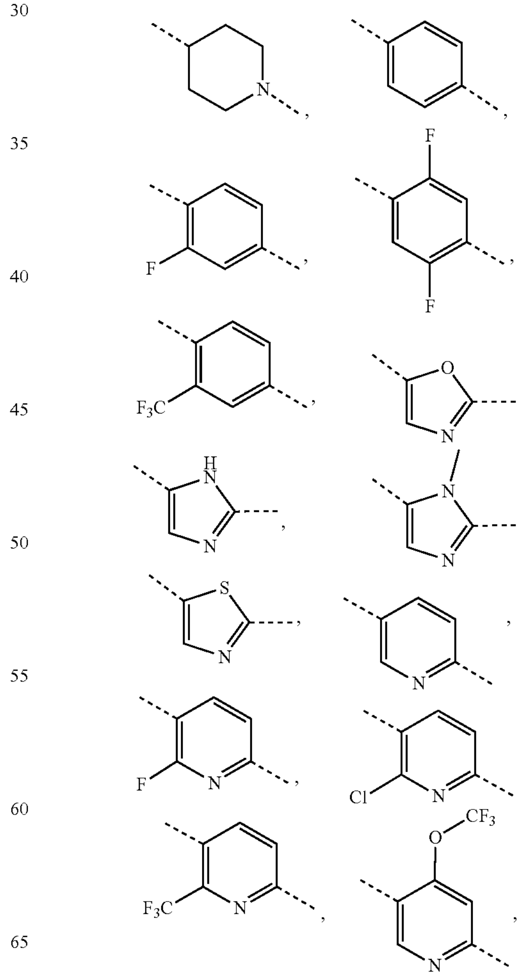

-continued
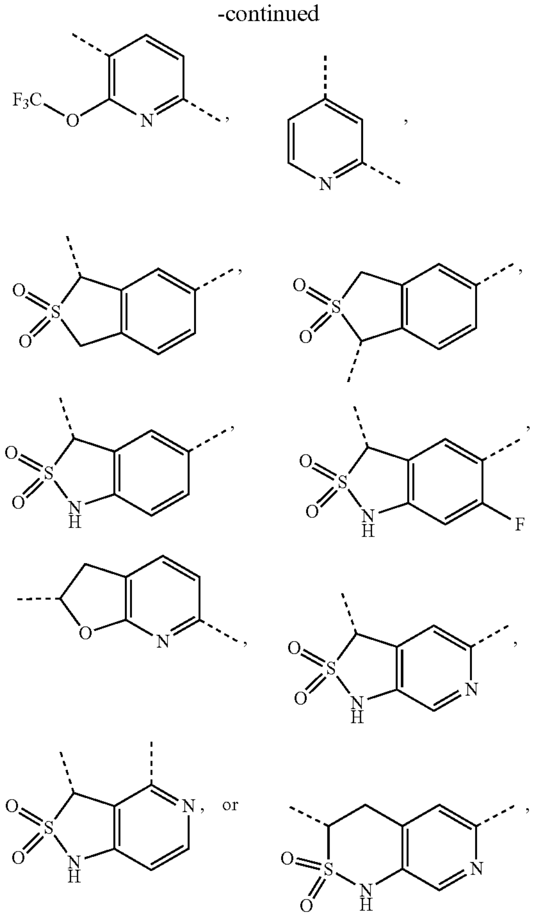
and the other variables are as defined herein.
In some embodiments of the present application, ring A is selected from the group consisting of
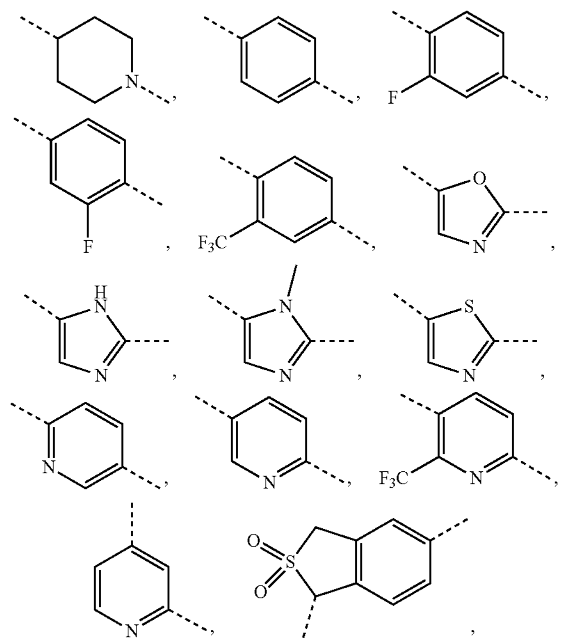
-continued
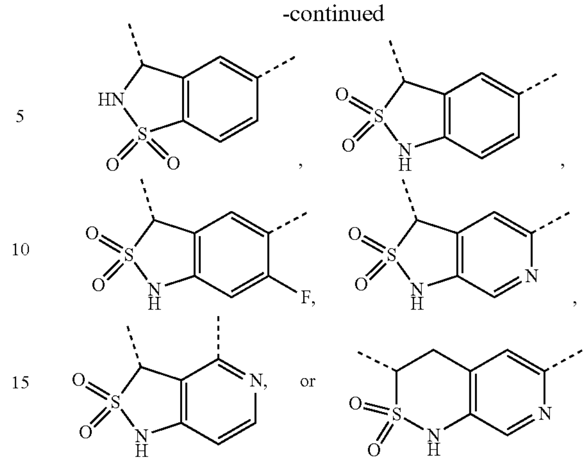
and the other variables are as defined herein.
In some embodiments of the present application, ring A is selected from the group consisting of
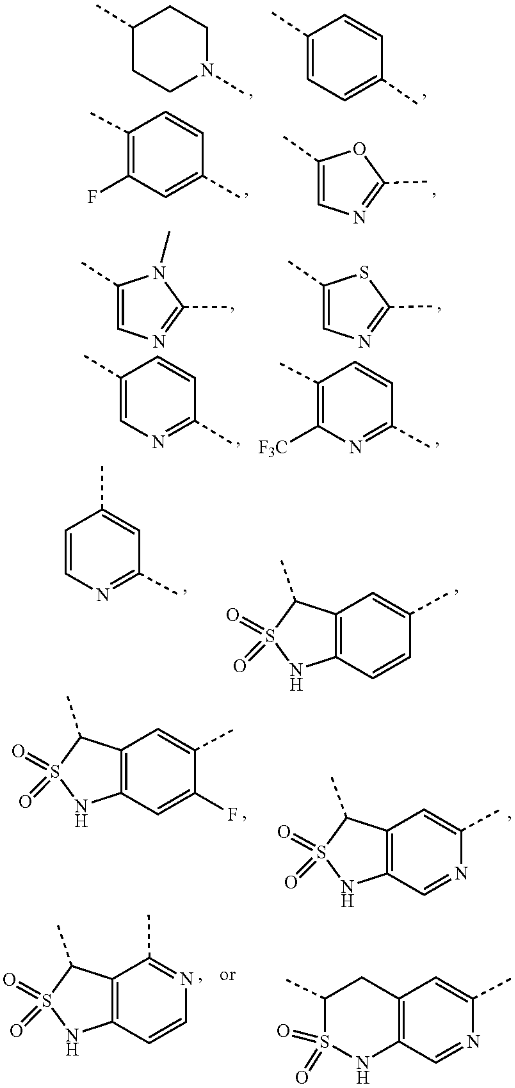
and the other variables are as defined herein.

In some embodiments of the present application, ring A is selected from the group consisting of

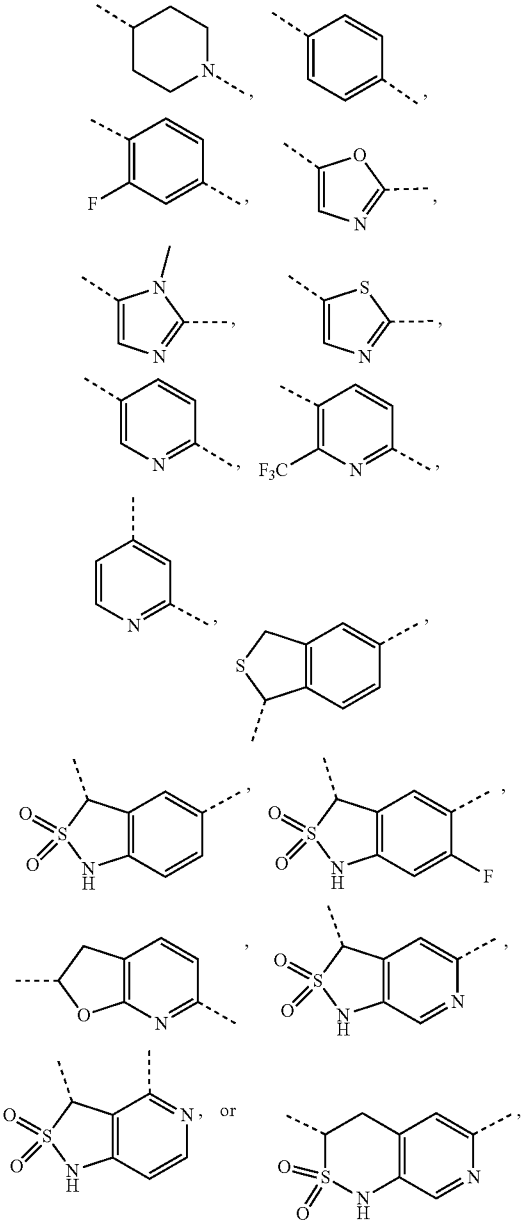

and the other variables are as defined herein.

In some embodiments of the present application, ring A is selected from the group consisting of

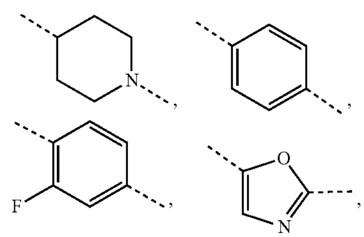

-continued

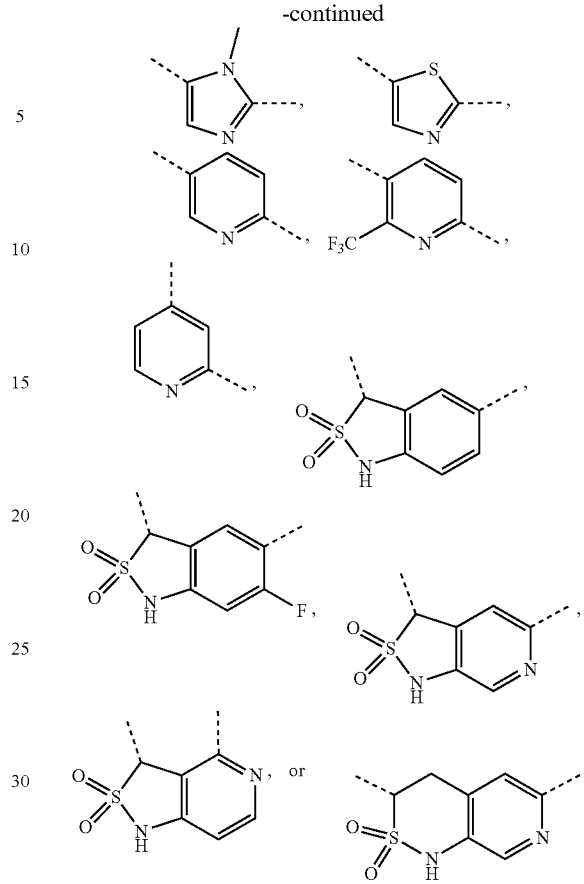

and the other variables are as defined herein.

In some embodiments of the present application, ring A is selected from the group consisting of

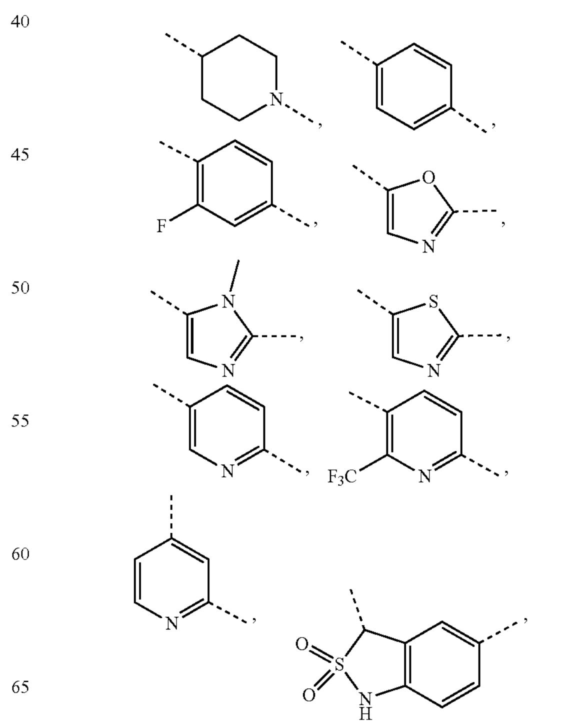

-continued

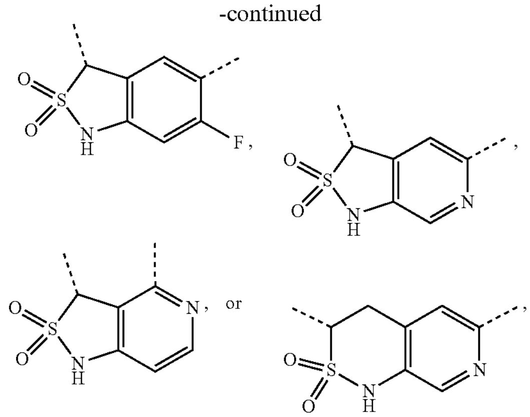

and the other variables are as defined herein.

In some embodiments of the present application, ring A is selected from the group consisting of

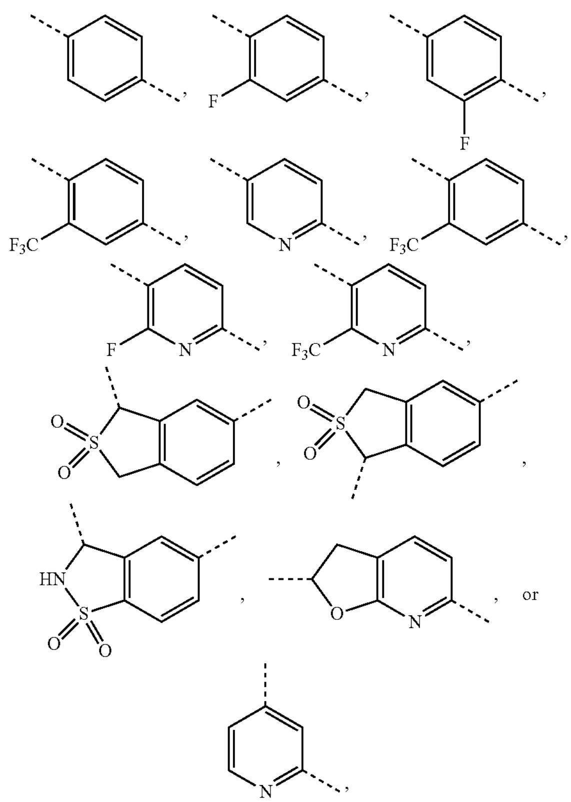

and the other variables are as defined herein.

In some embodiments of the present application, ring A is selected from the group consisting of

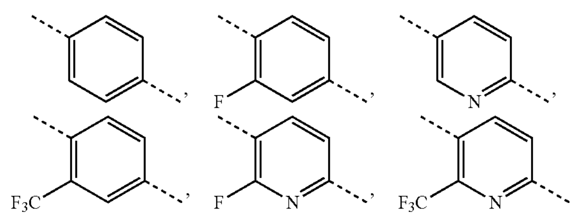

-continued

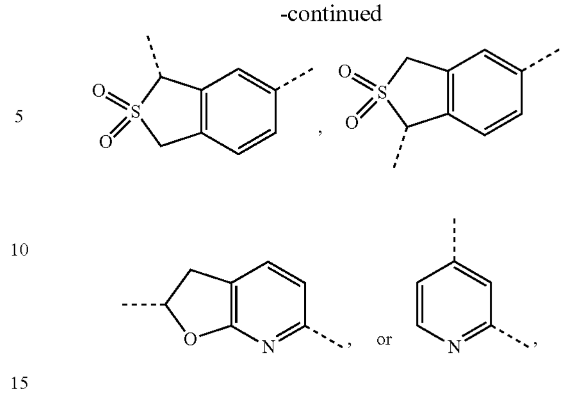

and the other variables are as defined herein.

In some embodiments of the present application, ring A is selected from the group consisting of

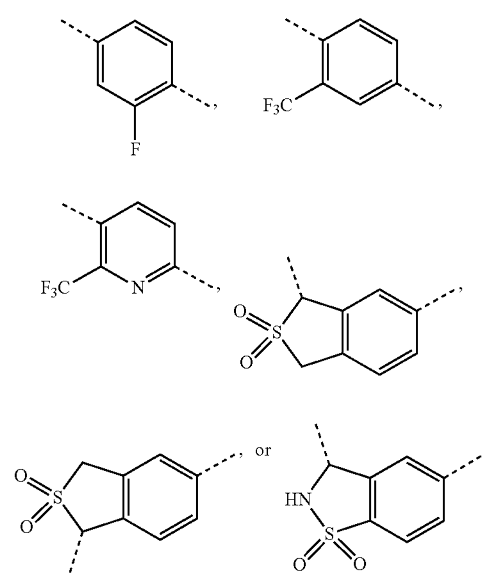

and the other variables are as defined herein.

In some embodiments of the present application, ring A is selected from the group consisting of

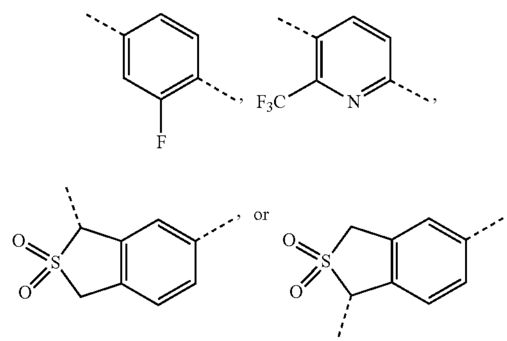

and the other variables are as defined herein.

In other embodiments of the present application, ring A is selected from the group consisting of

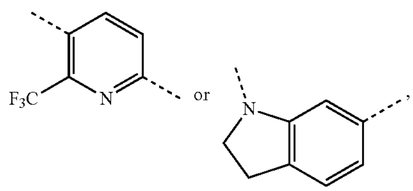

and the other variables are as defined herein.

In other embodiments of the present application, ring A is selected from the group consisting of

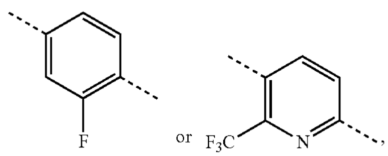

and the other variables are as defined herein.

In other embodiments of the present application, ring A is selected from

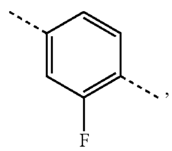

and the other variables are as defined herein.

In some embodiments of the present application, ring A is selected from the group consisting of

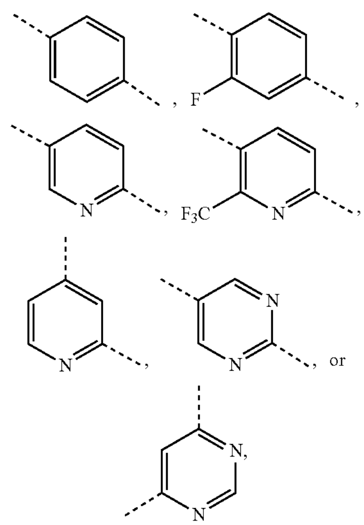

and the other variables are as defined herein.

In some embodiments of the present application, ring A is selected from the group consisting of

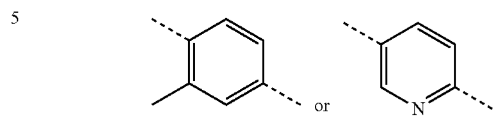

and the other variables are as defined herein.

In other embodiments of the present application, the structural unit

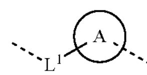

is selected from the group consisting of

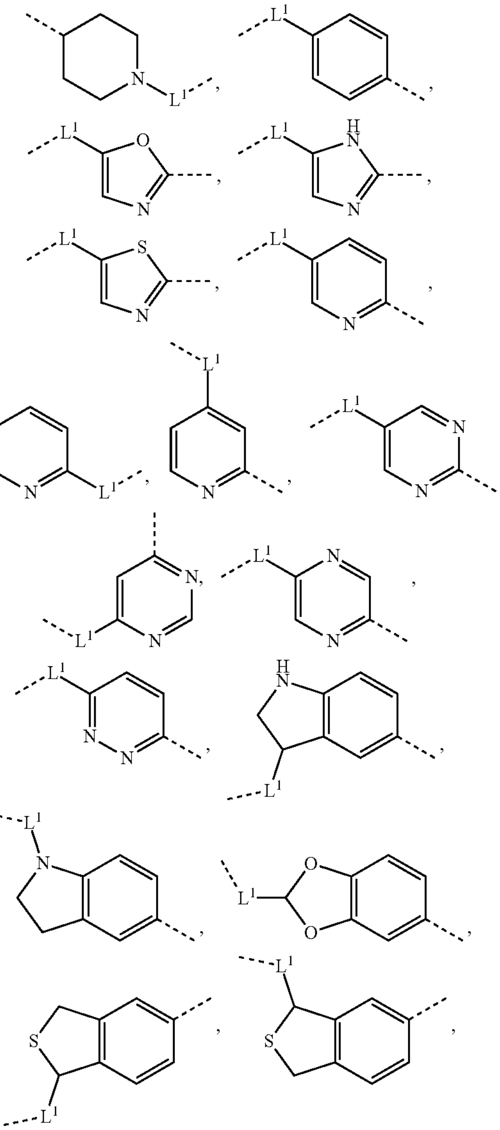

-continued

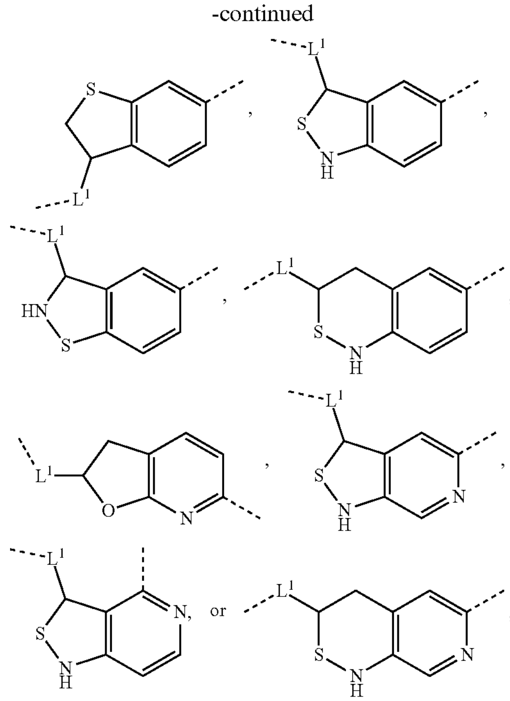

and ring A is optionally independently substituted with 1, 2 or 3 $R^a$; and the other variables are as defined herein. In some embodiments of the present application, $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In further embodiments of the present application, the structural unit

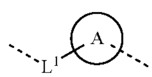

is selected from the group consisting of

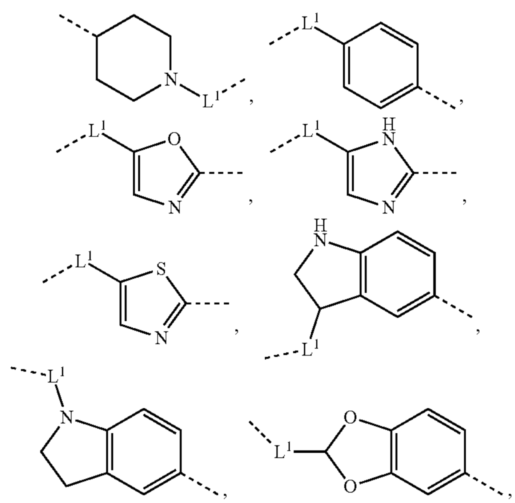

-continued

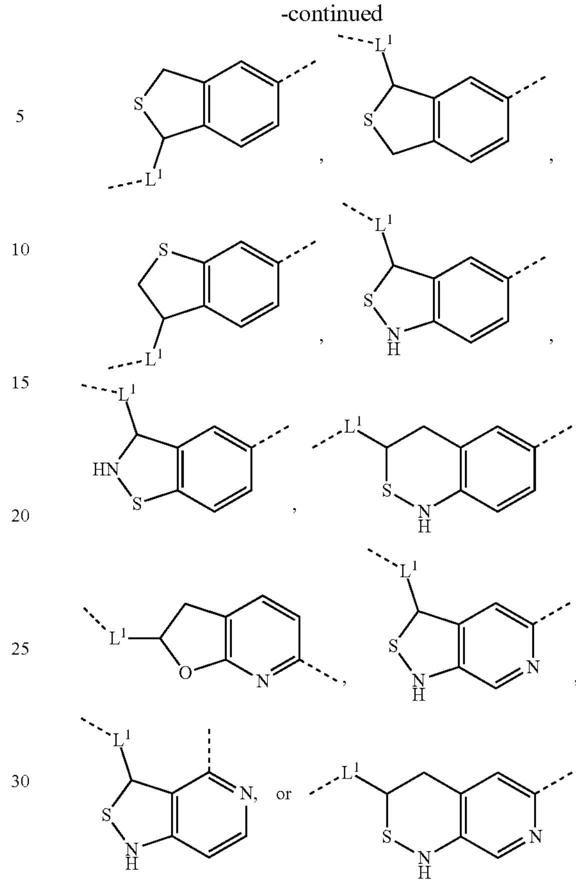

ring A is optionally independently substituted with 1, 2 or 3 $R^a$; and the other variables are as defined herein. In some embodiments of the present application, $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In some embodiments of the present application, the structural unit

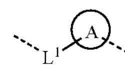

is selected from the group consisting of

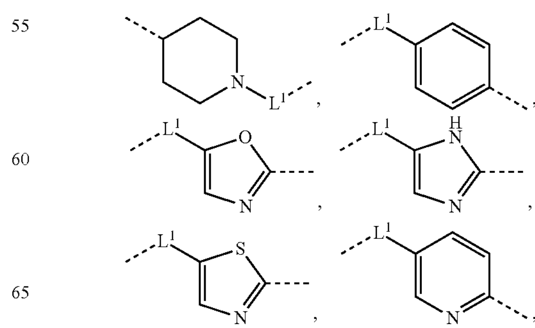

-continued

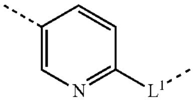, 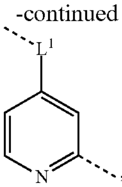, 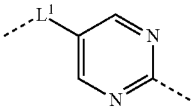,

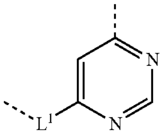, 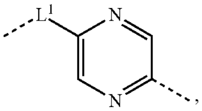,

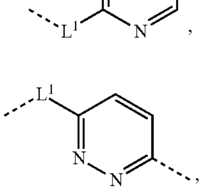, 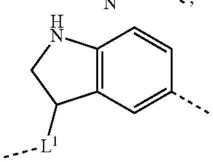,

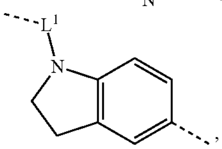, 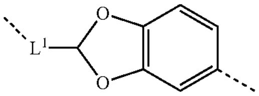,

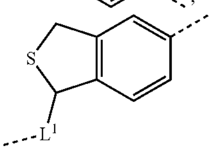, 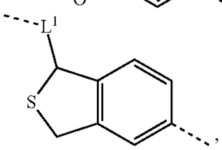,

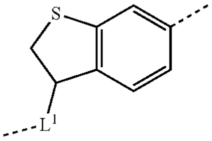, 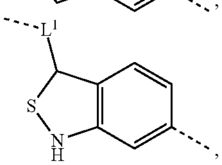,

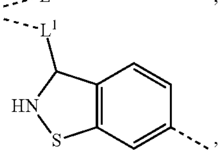, 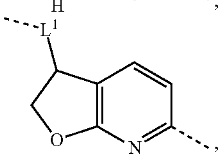,

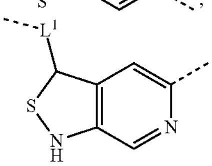, 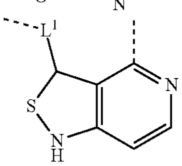,

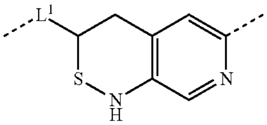, 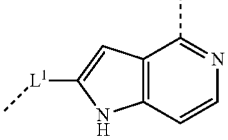,

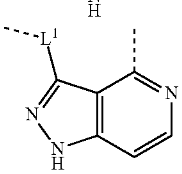, or 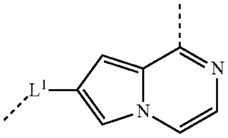, and ring A is optionally independently substituted with 1, 2 or 3 $R^a$; and the other variables are as defined herein. In some embodiments of the present application, $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In some embodiments of the present application, the structural unit

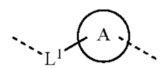

is selected from the group consisting of

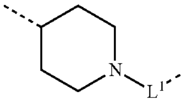, 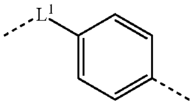,

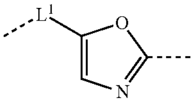, 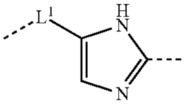,

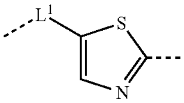, 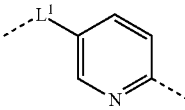,

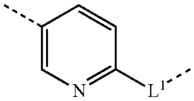, 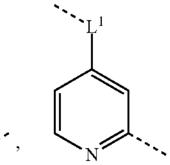,

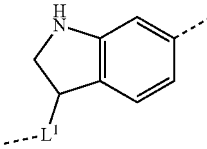, 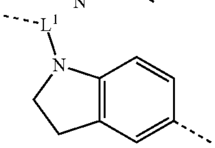,

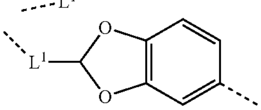, 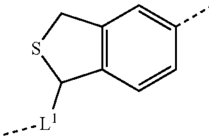,

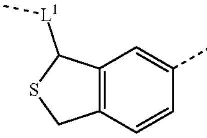, 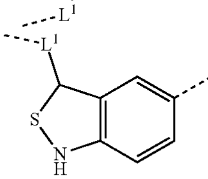,

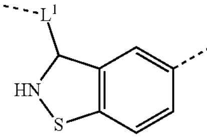, 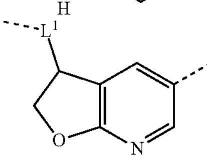,

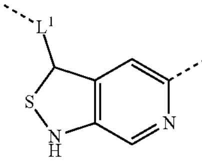, 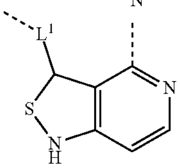 or

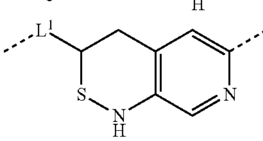, and ring A is optionally independently substituted with 1, 2 or 3 $R^a$; and the other variables are as defined herein. In some embodiments of the present application, $R^a$ is each independently selected from the group consisting of F, Cl, =O, methyl, methoxy, trifluoromethyl, or trifluoromethoxy, and the other variables are as defined herein.

In some embodiments of the present application, the structural unit

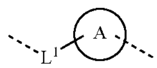

is selected from the group consisting of

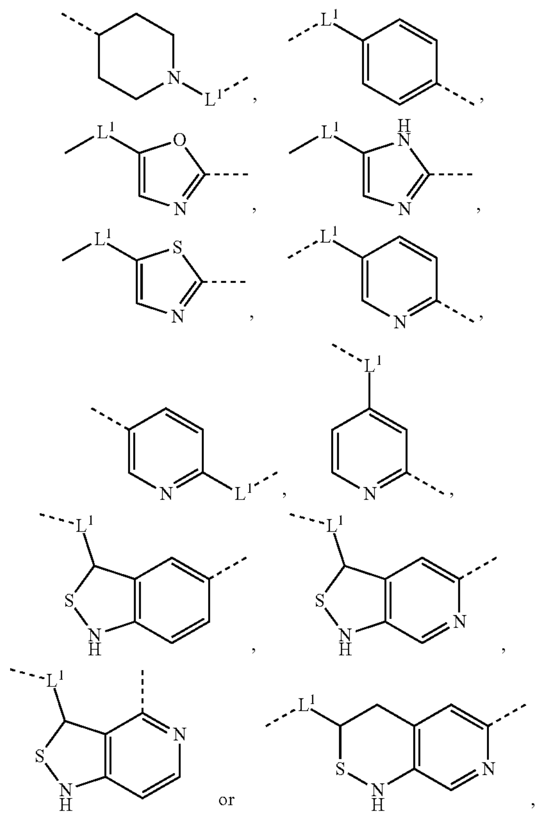

and ring A is optionally independently substituted with 1, 2 or 3 $R^a$; and the other variables are as defined herein. In some embodiments of the present application, $R^a$ is each independently selected from the group consisting of F, =O, methyl, or trifluoromethyl, and the other variables are as defined herein.

In some embodiments of the present application, the structural unit

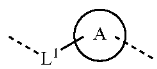

is selected from the group consisting of

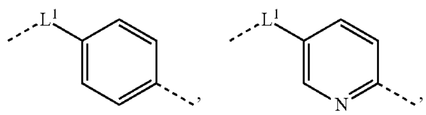

-continued

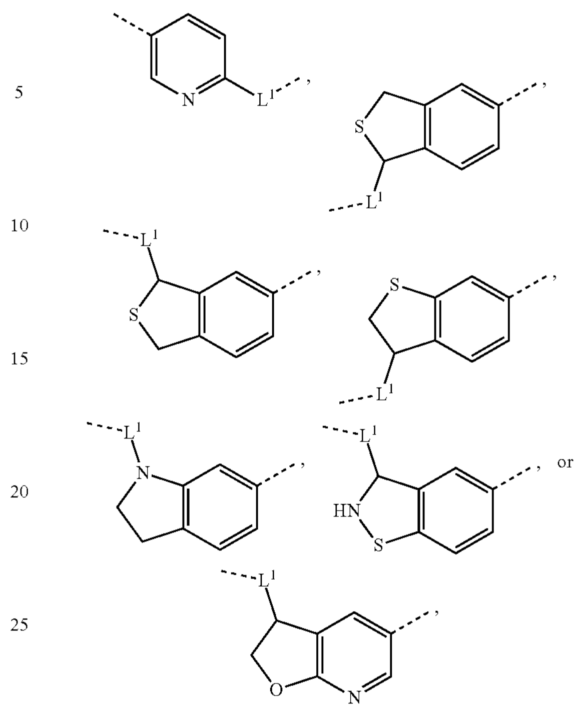

and ring A is optionally independently substituted with 1, 2 or 3 $R^a$; and the other variables are as defined herein. In some embodiments of the present application, $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In some embodiments of the present application, the structural unit

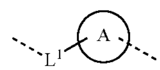

is selected from the group consisting of

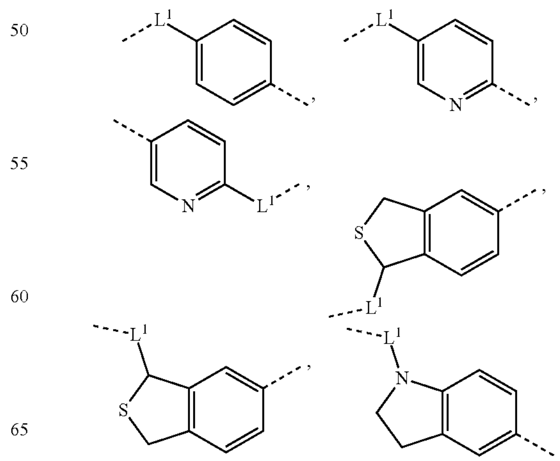

-continued

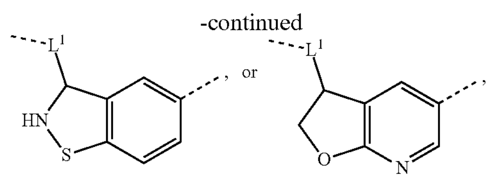

and ring A is optionally independently substituted with 1, 2 or 3 $R^a$; and the other variables are as defined herein. In some embodiments of the present application, $R^a$ is each independently selected from the group consisting of F, Cl, =O, methyl, trifluoromethyl, or trifluoromethoxy, and the other variables are as defined herein.

In some embodiments of the present application, the structural unit

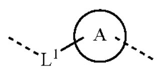

is selected from the group consisting of

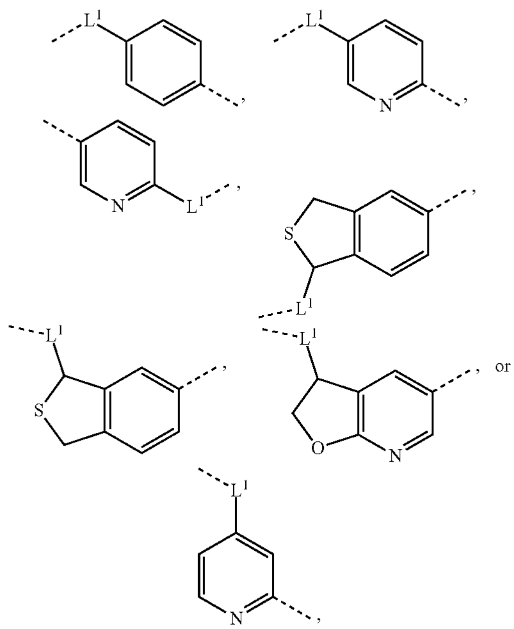

and ring A is optionally independently substituted with 1, 2 or 3 $R^a$; and the other variables are as defined herein. In some embodiments of the present application, $R^a$ is each independently selected from the group consisting of F, Cl, =O, methyl, trifluoromethyl, or trifluoromethoxy, and the other variables are as defined herein.

In some embodiments of the present application, the structural unit

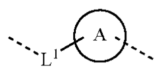

is selected from the group consisting of

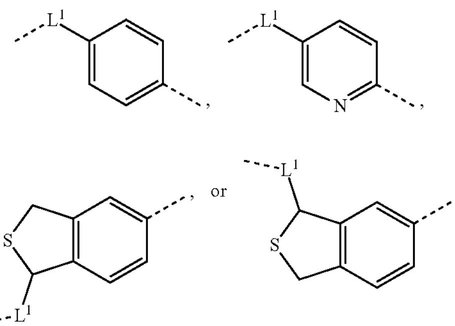

and ring A is optionally independently substituted with 1, 2 or 3 $R^a$; and the other variables are as defined herein. In some embodiments of the present application, $R^a$ is each independently selected from the group consisting of F, Cl, CN, =O, methyl, methoxy, difluoromethyl, trifluoromethyl, difluoromethoxy, or trifluoromethoxy, and the other variables are as defined herein. In some embodiments of the present application, $R^a$ is each independently selected from the group consisting of F, Cl, =O, methyl, trifluoromethyl, or trifluoromethoxy, and the other variables are as defined herein.

In other embodiments of the present application, the structural unit

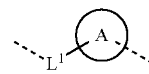

is selected from the group consisting of

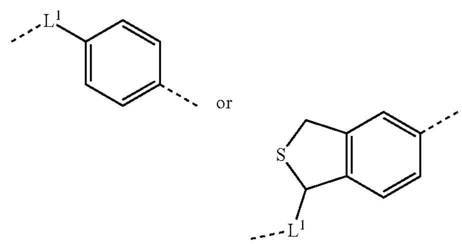

and ring A is optionally independently substituted with 1, 2 or 3 $R^a$; and the other variables are as defined herein. In some embodiments of the present application, $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In other embodiments of the present application, the structural unit

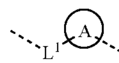

is selected from the group consisting of

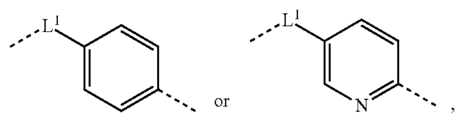

and ring A is optionally independently substituted with 1, 2 or 3 $R^a$; and the other variables are as defined herein. In some embodiments of the present application, $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In other embodiments of the present application, the structural unit

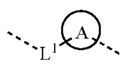

is selected from the group consisting of

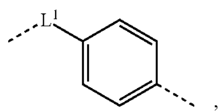

and ring A is optionally independently substituted with 1, 2 or 3 $R^a$; and the other variables are as defined herein. In some embodiments of the present application, $R^a$ is each independently selected from the group consisting of F, Cl, CN, =O, methyl, methoxy, difluoromethyl, trifluoromethyl, difluoromethoxy, or trifluoromethoxy, and the other variables are as defined herein.

In some embodiments of the present application, the structural unit

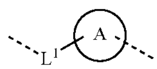

is selected from the group consisting of

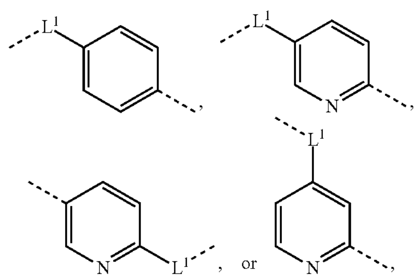

and ring A is optionally independently substituted with 1, 2 or 3 $R^a$; and the other variables are as defined herein. In some embodiments of the present application, $R^a$ is each independently selected from the group consisting of F, =O, methyl, or trifluoromethyl, and the other variables are as defined herein.

In some embodiments of the present application, the structural unit

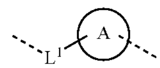

is selected from the group consisting of

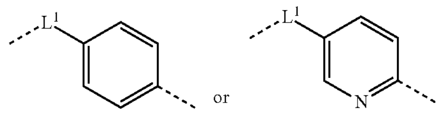

and ring A is optionally independently substituted with 1, 2 or 3 $R^a$; and the other variables are as defined herein. In some embodiments of the present application, $R^a$ is each independently selected from the group consisting of F, =O, methyl, or trifluoromethyl, and the other variables are as defined herein.

In other embodiments of the present application, the structural unit

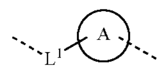

is selected from the group consisting of

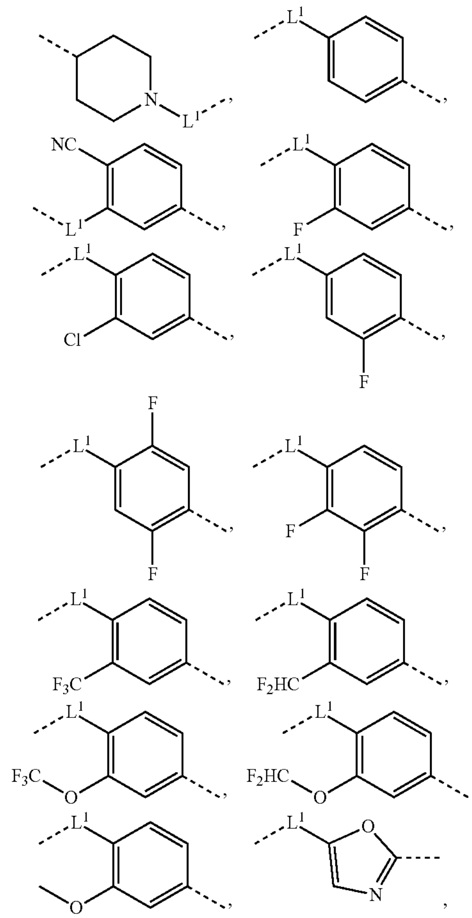

-continued
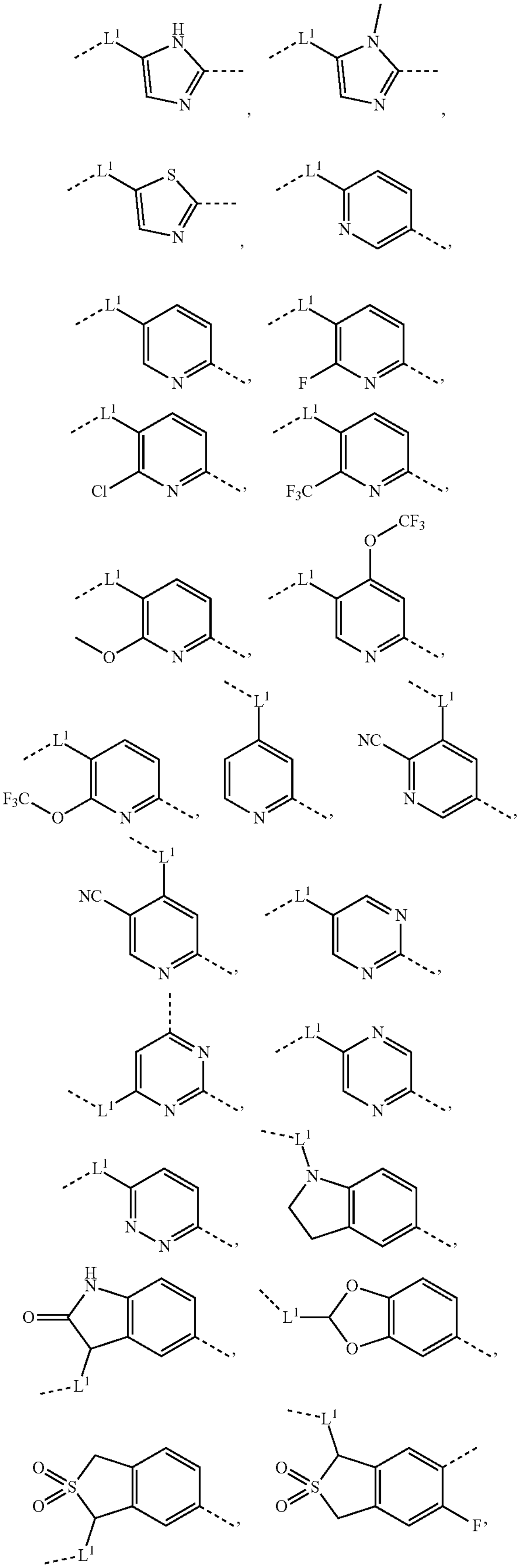
-continued
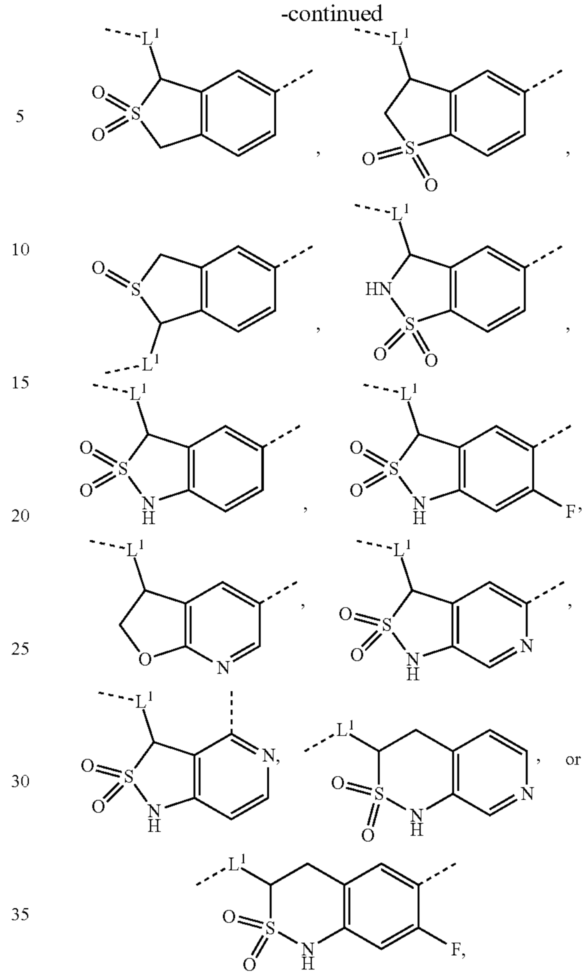
and the other variables are as defined herein.
In further embodiments of the present application the structural unit
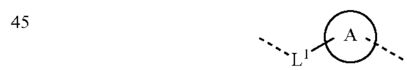
is selected from the group consisting of
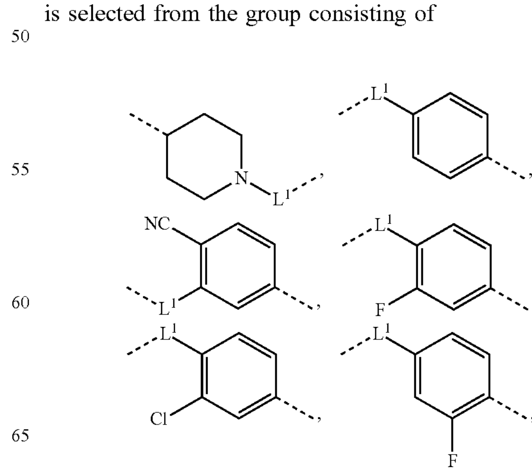

-continued
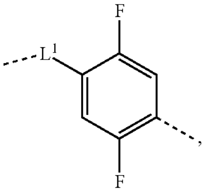
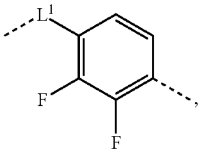
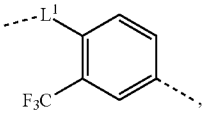
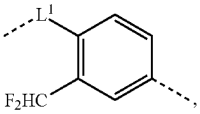
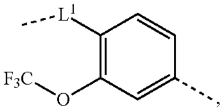
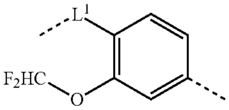
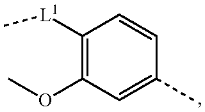
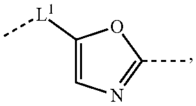
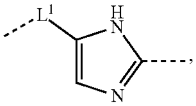
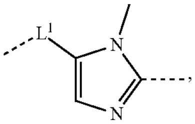
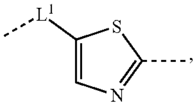
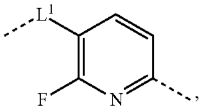
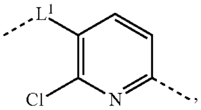
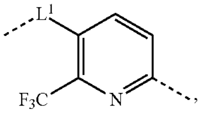
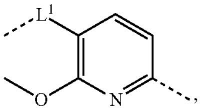
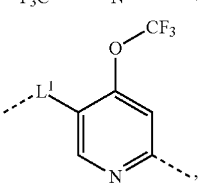
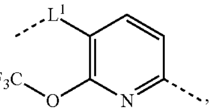
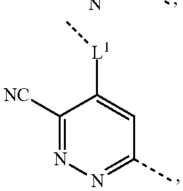
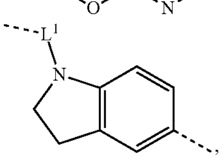
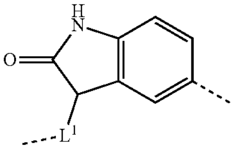
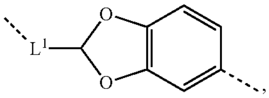
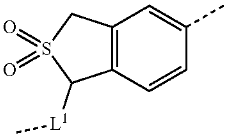
-continued
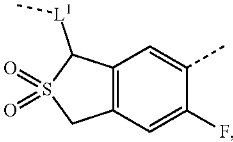
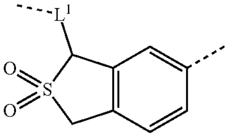
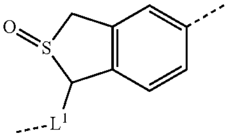
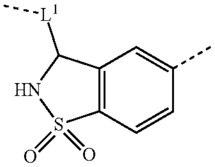
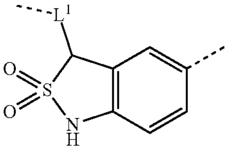
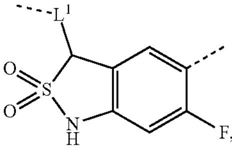
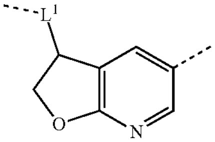
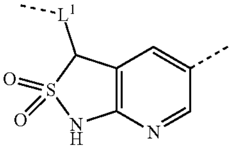
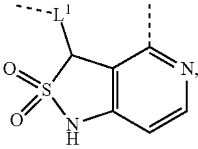
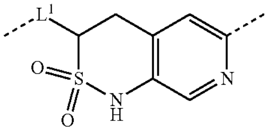
or
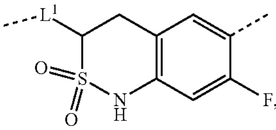
and the other variables are as defined herein.
In some embodiments of the present application, the structural unit
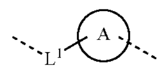
is selected from the group consisting of
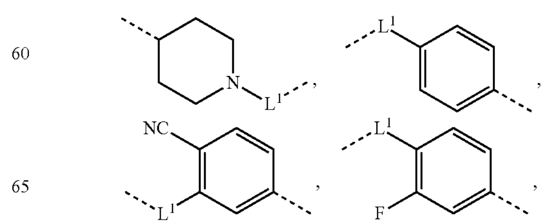

-continued
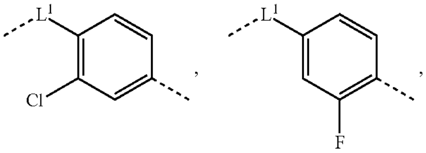
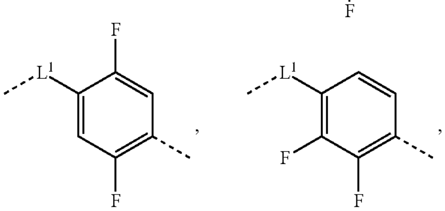
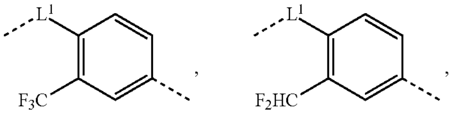
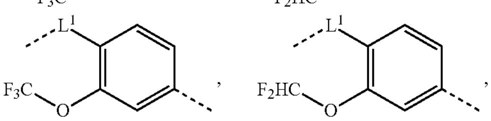
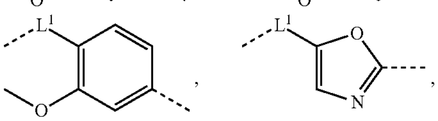
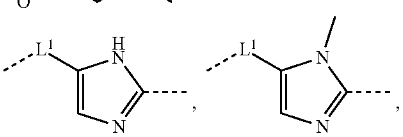
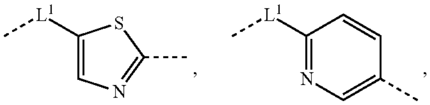
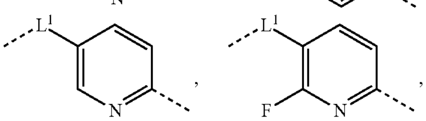
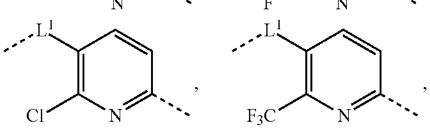
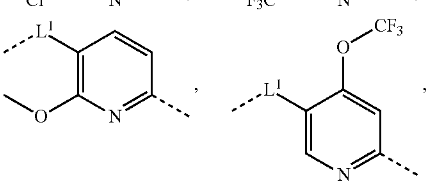
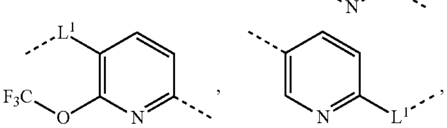
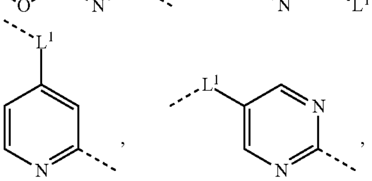
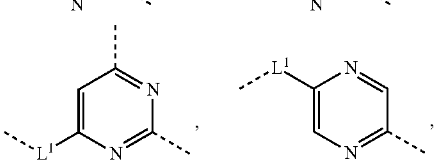
-continued
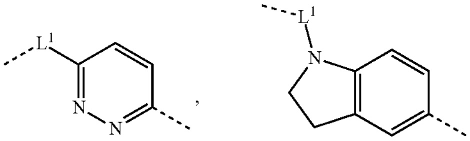
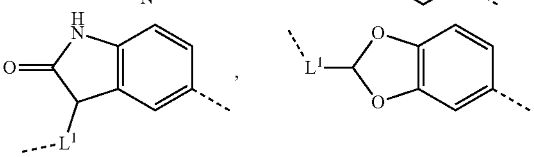
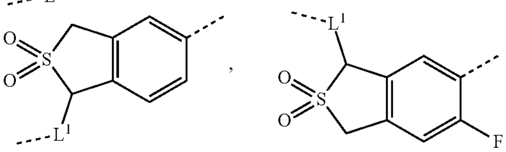
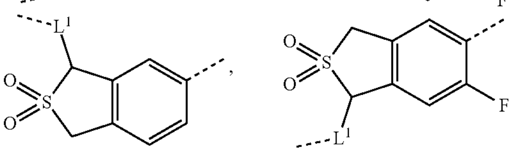
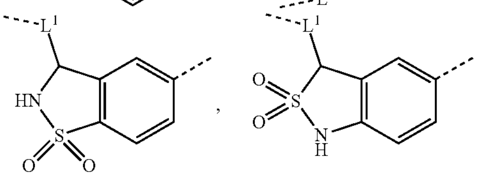
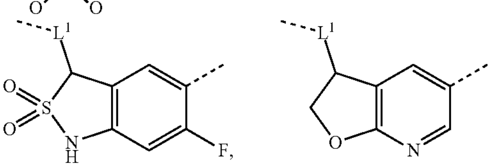
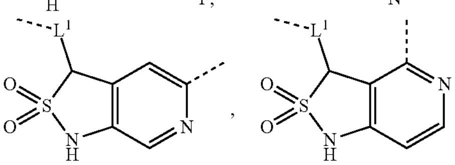
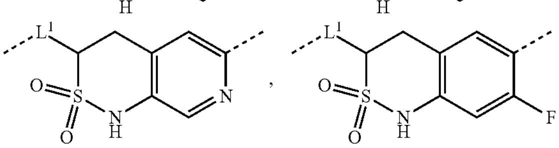
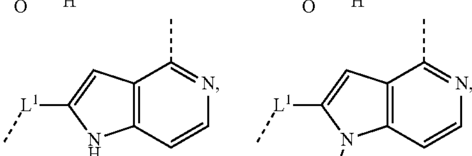
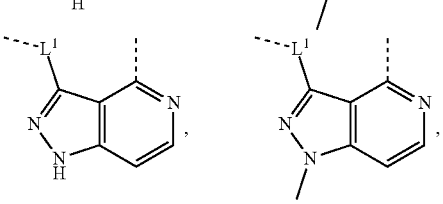
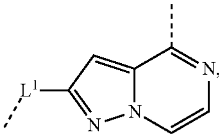
or
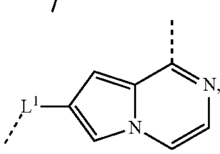
and the other variables are as defined herein.
In some embodiments of the present application, the structural unit

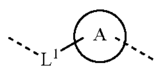
is selected from the group consisting of
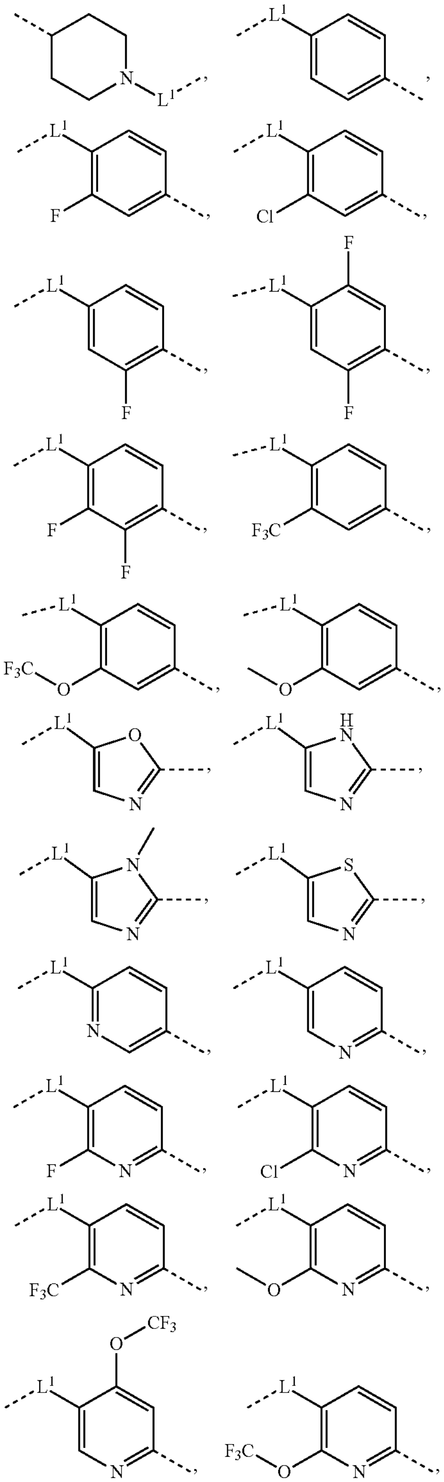
-continued
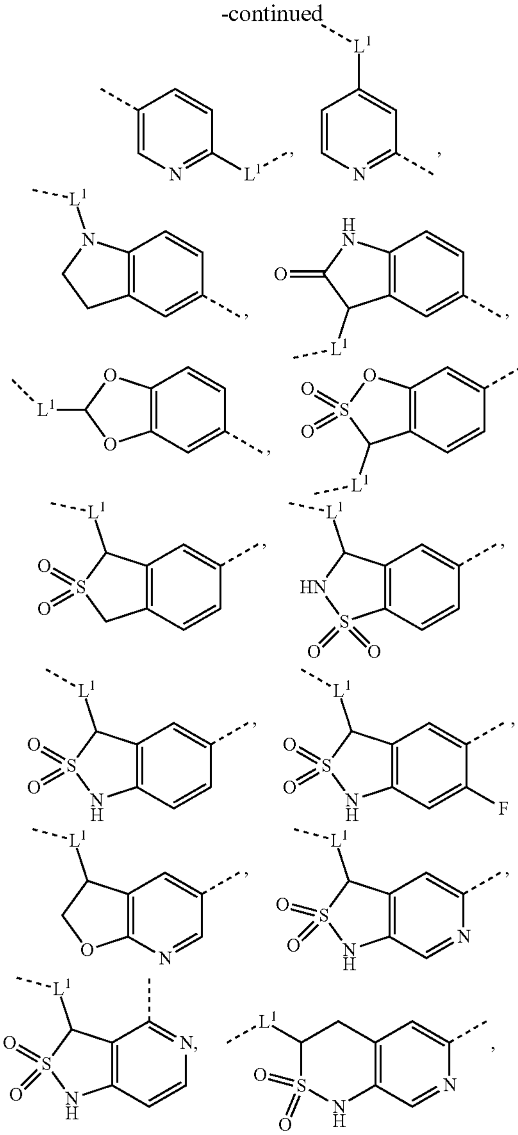
or
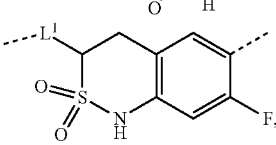
and the other variables are as defined herein.
In some embodiments of the present application, the structural unit
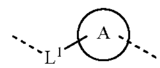
is selected from the group consisting of
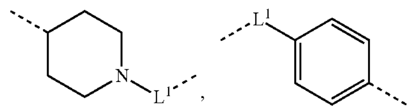

-continued
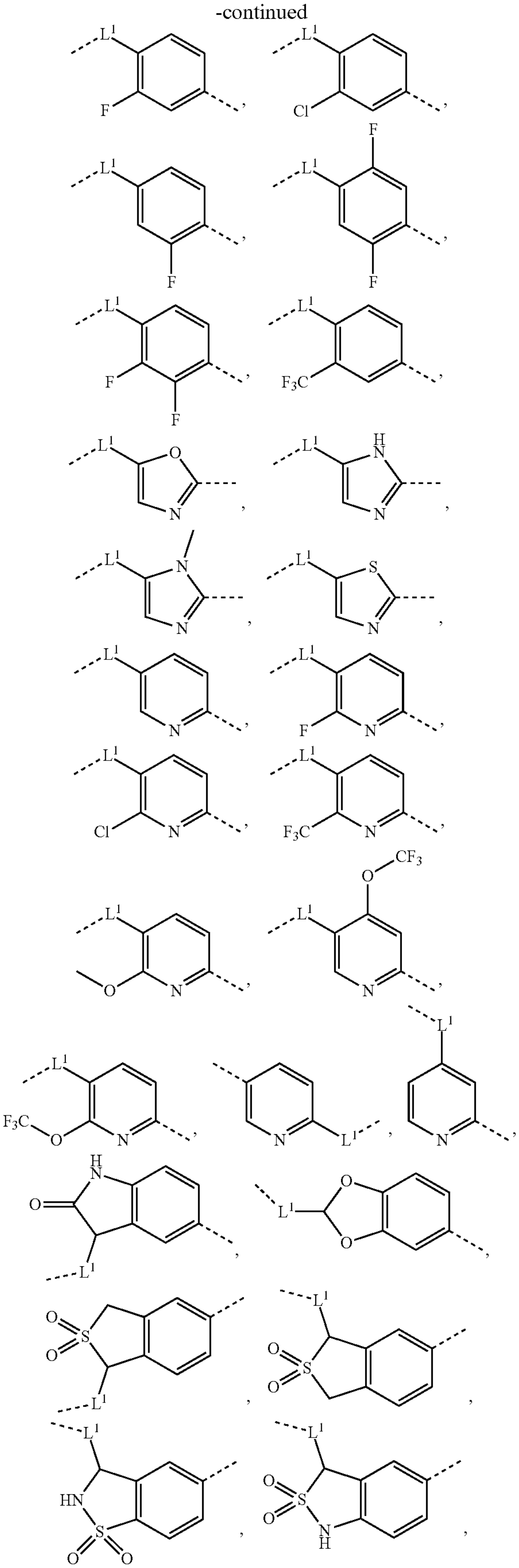
-continued
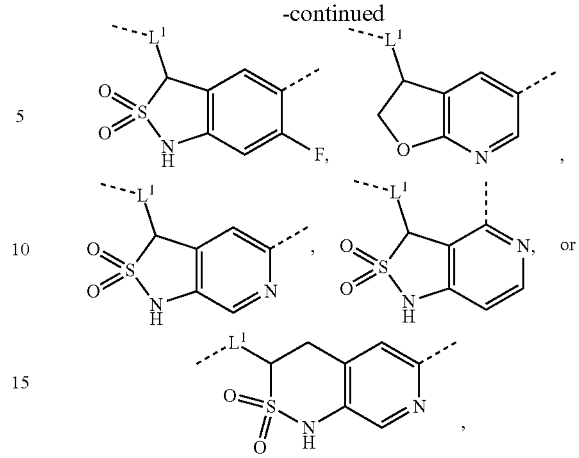
and the other variables are as defined herein.
In some embodiments of the present application, the structural unit
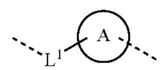
is selected from the group consisting of
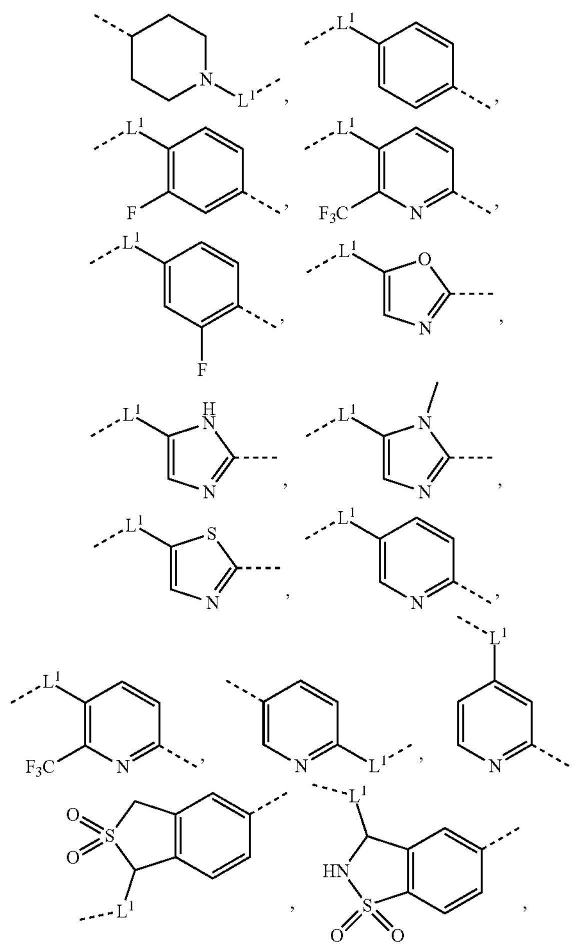

-continued

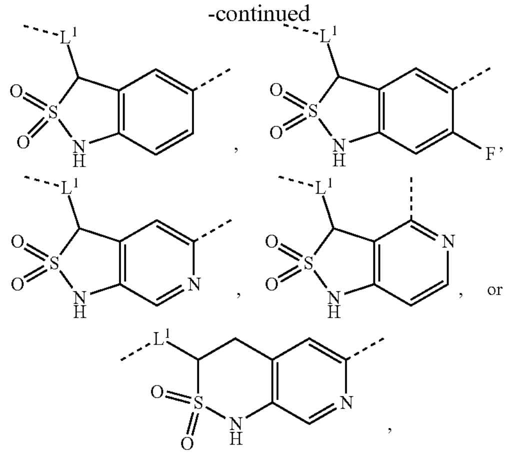

and the other variables are as defined herein.

In some embodiments of the present application the structural unit

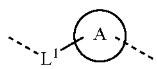

is selected from the group consisting of

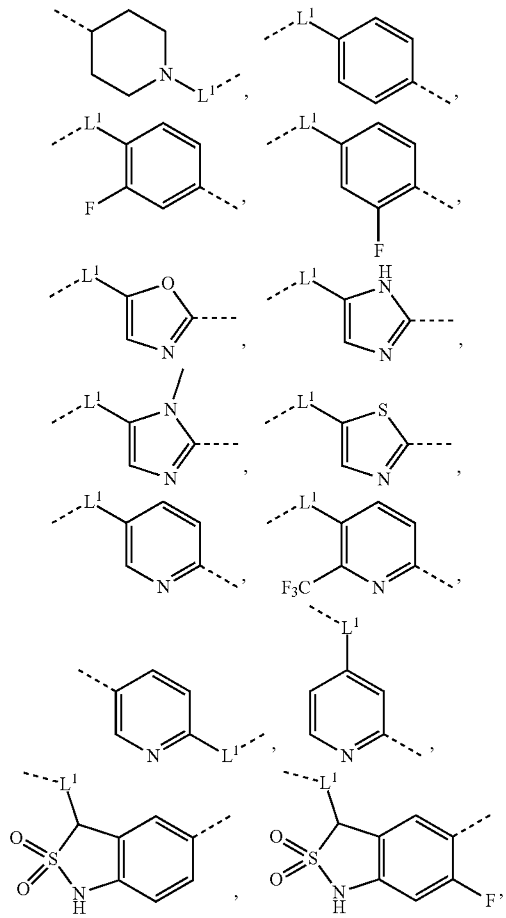

-continued

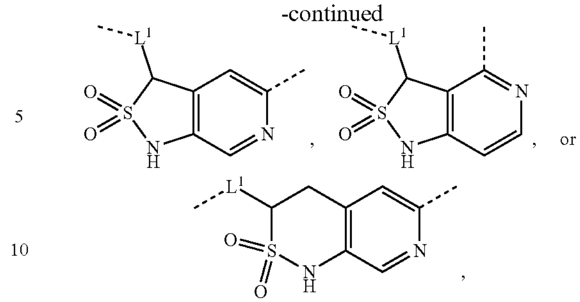

and the other variables are as defined herein.

In some embodiments of the present application, the structural unit

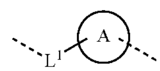

is selected from the group consisting of

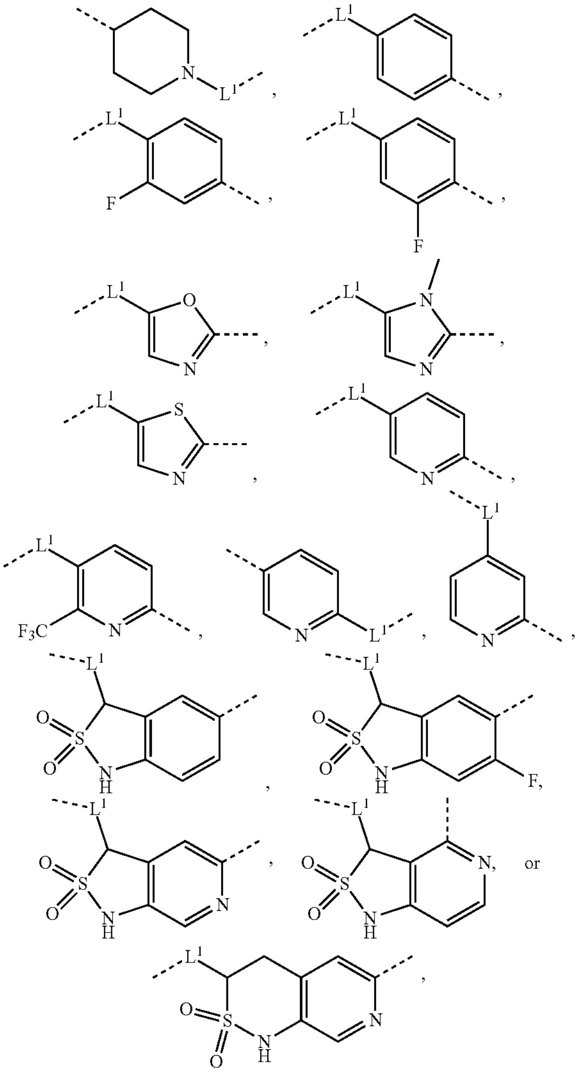

and the other variables are as defined herein.

In some embodiments of the present application, the structural unit

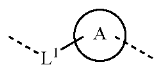

is selected from the group consisting of

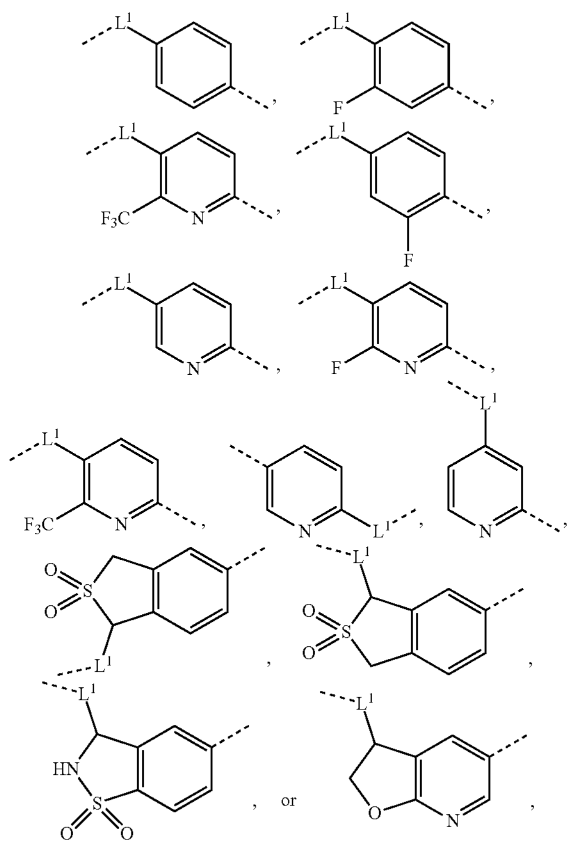

and the other variables are as defined herein.

In some embodiments of the present application, the structural unit

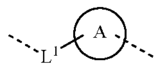

is selected from the group consisting of

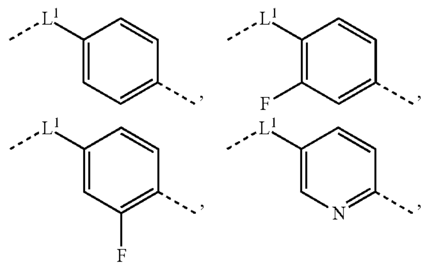

-continued

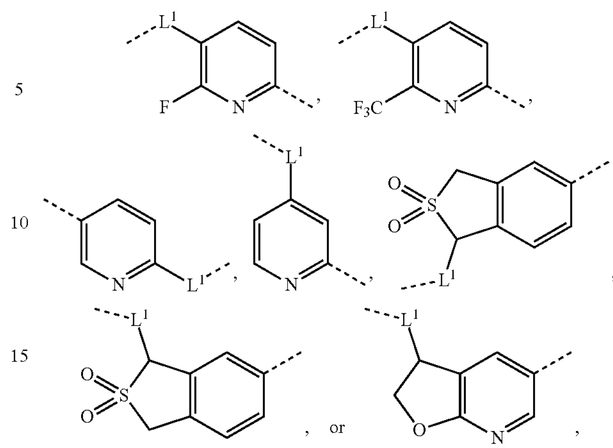

and the other variables are as defined herein.

In some embodiments of the present application, the structural unit

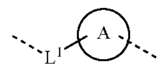

is selected from the group consisting of

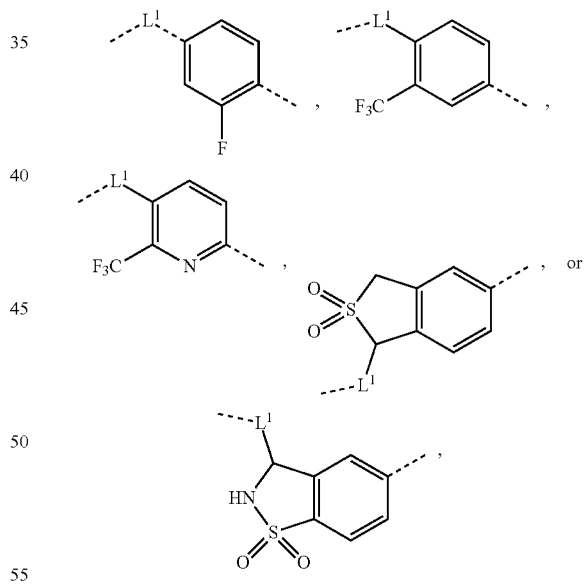

and the other variables are as defined herein.

In some embodiments of the present application, the structural unit

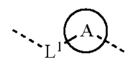

is selected from the group consisting of

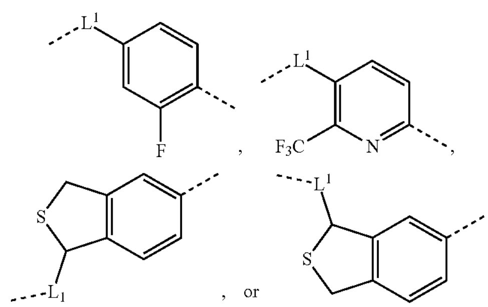

and the other variables are as defined herein.

In other embodiments of the present application, the structural unit

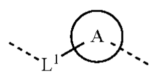

is selected from the group consisting of

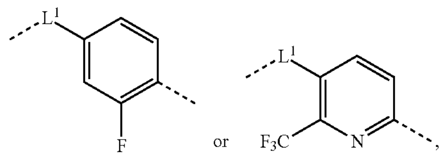

and the other variables are as defined herein.

In other embodiments of the present application, the structural unit

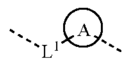

is selected from

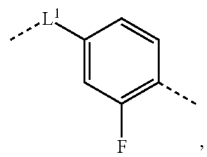

and the other variables are as defined herein.

In some embodiments of the present application, the structural unit

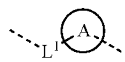

is selected from the group consisting of

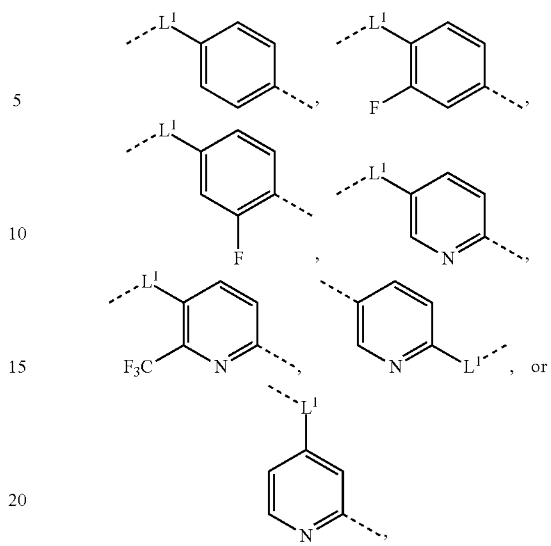

and the other variables are as defined herein.

In some embodiments of the present application, the structural unit

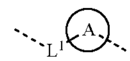

is selected from the group consisting of

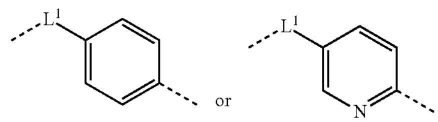

and the other variables are as defined herein.

In some embodiments of the present application, $L^1$ is selected from the group consisting of a single bond, $—N(R_b)—$, $—N═$, $—O—$, $—S(═O)_2—$, $—S—$, $—(CH_2)_m—$, or $—C(═O)—$, and the other variables are as defined herein.

In some embodiments of the present application, $L^1$ is selected from the group consisting of a single bond, $—N(R_b)—$, $—O—$, $—S(═O)_2—$, $—S—$, $—(CH_2)_m—$, or $—C(═O)—$, and the other variables are as defined herein.

In some embodiments of the present application, $L^1$ is selected from the group consisting of a single bond, $—NH—$, $—N═$, $—N(C(═O)H)—$, $—N(C_{1-3}$ alkyl)-, $—S(═O)_2—$, $—CH_2—$, $—CH_2—CH_2—$, $—CH_2—CH_2—CH_2—$, $—N(S(═O)_2C_{1-3}$ alkyl)-, or $—C(═O)—$, and the other variables are as defined herein.

In some embodiments of the present application, $L^1$ is selected from the group consisting of a single bond, $—NH—$, $—N(C(═O)H)—$, $—N(C_{1-3}$ alkyl)-, $—S(═O)_2—$, $—CH_2—$, $—CH_2—CH_2—$, $—CH_2—CH_2—CH_2—$, or $—C(═O)—$, and the other variables are as defined herein.

In some embodiments of the present application, $L^1$ is selected from the group consisting of a single bond, $—NH—$, $—N═$, $—N(C(═O)H)—$, $—N(CH_3)—$, $—S(═O)_2—$, $—CH_2—$, $—CH_2—CH_2—$, $—CH_2—CH_2—CH_2—$, $—C(═O)—$, or $—N(S(═O)_2CH_3)—$, and the other variables are as defined herein.

In other embodiments of the present application, $L^1$ is selected from the group consisting of a single bond, —NH—, —N═, —N(C(═O)H)—, —N($CH_3$)—, —S(═O)$_2$—, —$CH_2$—, —C(═O)—, or —N(S(═O)$_2$ $CH_3$)—, and the other variables are as defined herein.

In some embodiments of the present application, $L^1$ is selected from the group consisting of a single bond, —NH—, —N(C(═O)H)—, —N($CH_3$)—, —S(═O)$_2$—, —$CH_2$—, —$CH_2$—$CH_2$—, —$CH_2$—$CH_2$—$CH_2$—, or —C(═O)—, and the other variables are as defined herein.

In some embodiments of the present application, $L^1$ is selected from the group consisting of a single bond, —NH—, —N($CH_3$)—, —S(═O)$_2$—, —$CH_2$—, or —C(═O)—, and the other variables are as defined herein.

In some embodiments of the present application, $L^1$ is selected from the group consisting of a single bond, —NH—, or —S(═O)$_2$—, and the other variables are as defined herein.

In some embodiments of the present application, $L^1$ is selected from the group consisting of a single bond, —N($R_b$)—, —O—, —S—, —($CH_2$)$_m$—, or —C(═O)—, and the other variables are as defined herein.

In some embodiments of the present application, $L^1$ is selected from the group consisting of a single bond, —NH—, —N(C(═O)H)—, —N($C_{1-3}$ alkyl)-, —$CH_2$—, —$CH_2$—$CH_2$—, —$CH_2$—$CH_2$—$CH_2$—, or —C(═O)—, and the other variables are as defined herein.

In some embodiments of the present application, $L^1$ is selected from the group consisting of a single bond, —NH—, —N($C_{1-3}$ alkyl)-, —$CH_2$—, —$CH_2$—$CH_2$—, —$CH_2$—$CH_2$—$CH_2$—, or —C(═O)—, and the other variables are as defined herein.

In some embodiments of the present application, $L^1$ is selected from the group consisting of a single bond, —NH—, —N(C(═O)H)—, —N($CH_3$)—, —$CH_2$—, —$CH_2$—$CH_2$—, —$CH_2$—$CH_2$—$CH_2$—, or —C(═O)—, and the other variables are as defined herein.

In some embodiments of the present application, $L^1$ is selected from the group consisting of a single bond, —NH—, —N($CH_3$)—, —$CH_2$—, —$CH_2$—$CH_2$—, —$CH_2$—$CH_2$—$CH_2$—, or —C(═O)—, and the other variables are as defined herein.

In some embodiments of the present application, $L^1$ is selected from the group consisting of a single bond, —NH—, —N($CH_3$)—, —$CH_2$—, or —C(═O)—, and the other variables are as defined herein.

In some embodiments of the present application, $L^1$ is selected from the group consisting of a single bond or —NH—, and the other variables are as defined herein.

In some embodiments of the present application, $L^1$ is selected from —NH—, and the other variables are as defined herein.

In some embodiments of the present application, $L^2$ is selected from the group consisting of a single bond, —NH—, —N($C_{1-3}$ alkyl)-, —$CH_2$—, —$CH_2$—$CH_2$—, —$CH_2$—$CH_2$—$CH_2$—, —C(═O)—, —S(═O)—, —S(═O)$_2$—, —S(═O)(═NH)—, —S(═O)($C_{1-3}$ alkyl)-, —P(═O)($C_{1-3}$ alkyl)-, —P(═O)($NH_2$)—, or —P(═O)(NH($C_{1-3}$ alkyl))-, and the other variables are as defined herein.

In some embodiments of the present application, $L^2$ is selected from the group consisting of a single bond, —NH—, —N($CH_3$)—, —$CH_2$—, —$CH_2$—$CH_2$—, —$CH_2$—$CH_2$—$CH_2$—, —C(═O)—, —S(═O)—, —S(═O)$_2$—, —S(═O)(═NH)—, —S(═O)($CH_3$)—, —P(═O)($CH_3$)—, —P(═O)($NH_2$)—, or —P(═O)($NHCH_3$)—, and the other variables are as defined herein.

In some embodiments of the present application, $L^2$ is selected from the group consisting of a single bond, —NH—, —N($CH_3$)—, —$CH_2$—, —$CH_2$—$CH_2$—, —$CH_2$—$CH_2$—$CH_2$—, —C(═O)—, —S(═O)—, —S(═O)$_2$—, —S(═O)(═NH)—, —P(═O)($CH_3$)—, —P(═O)($NH_2$)—, or —P(═O)($NHCH_3$)—, and the other variables are as defined herein.

In other embodiments of the present application, $L^2$ is selected from the group consisting of a single bond, —NH—, —N($CH_3$)—, —$CH_2$—$CH_2$—, —C(═O)—, —S(═O)$_2$—, —S(═O)(═NH)—, —S(═O)($CH_3$)—, —P(═O)($CH_3$)—, or —P(═O)($NHCH_3$)—, and the other variables are as defined herein.

In some embodiments of the present application, $L^2$ is selected from the group consisting of a single bond, —NH—, —N($CH_3$)—, —$CH_2$—$CH_2$—, —C(═O)—, —S(═O)$_2$—, —S(═O)(═NH)—, —P(═O)($CH_3$)—, or —P(═O)($NHCH_3$)—, and the other variables are as defined herein.

In some embodiments of the present application, $L^2$ is selected from the group consisting of a single bond, —NH—, or —S(═O)$_2$—, and the other variables are as defined herein.

In some embodiments of the present application, $L^2$ is selected from the group consisting of a single bond or —S(═O)$_2$—, and the other variables are as defined herein.

In some embodiments of the present application, $L^2$ is selected from —S(═O)$_2$—, and the other variables are as defined herein.

In some embodiments of the present application, -$L^2$-$L^1$- is selected from the group consisting of a single bond, —NH—, —N($CH_3$)—, —C(═O)—, —$CH_2$—, —$CH_2$—$CH_2$—, —S(═O)$_2$—, —$CH_2$—NH—, —NH—$CH_2$—, —$CH_2$—N($CH_3$)—, —$CH_2$—N(C(═O)H)—, —N($CH_3$)—$CH_2$—, —N(C(═O)H)—$CH_2$—, —C(═O)—$CH_2$—, —$CH_2$—C(═O)—, —C(═O)—NH—, —NH—C(═O)—, —NH—S(═O)$_2$—, —S(═O)$_2$—NH—, —N($CH_3$)—S(═O)$_2$—, —N(S(═O)$_2$$CH_3$)—S(═O)$_2$—, —S(═O)$_2$—N(S(═O)$_2$$CH_3$)—, —S(═O)($CH_3$)═N—, —S(═O)$_2$—N($CH_3$)—, —N($CH_3$)—C(═O)—, —C(═O)—N($CH_3$)—, —NH—S(═O)(═NH)—, —S(═O)(═NH)—NH—, —S(═O)(═NH)—, —P(═O)($CH_3$)—, —$CH_2$—S(═O)(═NH)—, —S(═O)(═NH)—$CH_2$—, —$CH_2$—P(═O)($CH_3$)—, —P(═O)($CH_3$)—$CH_2$—, —NH—P(═O)($CH_3$)—, —P(═O)($CH_3$)—NH—, —NH—P(═O)($NHCH_3$)—, —P(═O)($NHCH_3$)—NH—, —NH—P(═O)($NH_2$)—, —P(═O)($NH_2$)—NH—, —$CH_2$—P(═O)($NHCH_3$)—, —P(═O)($NHCH_3$)—$CH_2$—, —N($CH_3$)—$CH_2$—$CH_2$—, —N(C(═O)H)—$CH_2$—$CH_2$—, —$CH_2$—$CH_2$—N($CH_3$)—, —$CH_2$—$CH_2$—N(C(═O)H)—, —NH—$CH_2$—$CH_2$—, or —$CH_2$—$CH_2$—NH—, and the other variables are as defined herein.

In some embodiments of the present application, -$L^2$-$L^1$- is selected from the group consisting of a single bond, —NH—, —N($CH_3$)—, —C(═O)—, —$CH_2$—, —$CH_2$—$CH_2$—, —S(═O)$_2$—, —$CH_2$—NH—, —NH—$CH_2$—, —$CH_2$—N($CH_3$)—, —$CH_2$—N(C(═O)H)—, —N($CH_3$)—$CH_2$—, —N(C(═O)H)—$CH_2$—, —C(═O)—$CH_2$—, —$CH_2$—C(═O)—, —C(═O)—NH—, —NH—C(═O)—, —NH—S(═O)$_2$—, —S(═O)$_2$—NH—, —N($CH_3$)—S(═O)$_2$—, —S(═O)$_2$—N($CH_3$)—, —N($CH_3$)—C(═O)—, —C(═O)—N($CH_3$)—, —NH—S(═O)(═NH)—, —S(═O)(═NH)—NH—, —S(═O)(═NH)—, —P(═O)($CH_3$)—, —$CH_2$—S(═O)(═NH)—, —S(═O)(═NH)—$CH_2$—, —$CH_2$—P(═O)($CH_3$)—, —P(═O)($CH_3$)—$CH_2$—, —NH—P(═O)($CH_3$)—, —P(═O)($CH_3$)—NH—, —NH—P(═O)($NHCH_3$)—, —P(═O)($NHCH_3$)—NH—, —NH—P(=O)(NH$_2$)—, —P(=O)(NH$_2$)—NH—, —CH$_2$—P(=O)(NHCH$_3$)—, —P(=O)(NHCH$_3$)—CH$_2$—, —N(CH$_3$)—CH$_2$—CH$_2$—, —N(C(=O)H)—CH$_2$—CH$_2$—, —CH$_2$—CH$_2$—N(CH$_3$)—, —CH$_2$—CH$_2$—N(C(=O)H)—, —NH—CH$_2$—CH$_2$—, or —CH$_2$—CH$_2$—NH—, and the other variables are as defined herein.

In some embodiments of the present application, -L$^2$-L$^1$- is selected from the group consisting of a single bond, —NH—, —N(CH$_3$)—, —C(=O)—, —CH$_2$—, —CH$_2$—CH$_2$—, —S(=O)$_2$—, —CH$_2$—NH—, —NH—CH$_2$—, —CH$_2$—N(CH$_3$)—, —N(CH$_3$)—CH$_2$—, —C(=O)—CH$_2$—, —CH$_2$—C(=O)—, —C(=O)—NH—, —NH—C(=O)—, —NH—S(=O)$_2$—, —S(=O)$_2$—NH—, —N(CH$_3$)—S(=O)$_2$—, —S(=O)$_2$—N(CH$_3$)—, —N(CH$_3$)—C(=O)—, —C(=O)—N(CH$_3$)—, —NH—S(=O)(=NH)—, —S(=O)(=NH)—NH—, —S(=O)(=NH)—, —P(=O)(CH$_3$)—, —CH$_2$—P(=O)(CH$_3$)—, —P(=O)(CH$_3$)—CH$_2$—, —NH—P(=O)(CH$_3$)—, —P(=O)(CH$_3$)—NH—, —NH—P(=O)(NHCH$_3$)—, —P(=O)(NHCH$_3$)—NH—, —NH—P(=O)(NH$_2$)—, —P(=O)(NH$_2$)—NH—, —CH$_2$—P(=O)(NHCH$_3$)—, —P(=O)(NHCH$_3$)—CH$_2$—, —N(CH$_3$)—CH$_2$—CH$_2$—, —CH$_2$—CH$_2$—N(CH$_3$)—, —NH—CH$_2$—CH$_2$—, or —CH$_2$—CH$_2$—NH—, and the other variables are as defined herein.

In other embodiments of the present application, -L$^2$-L$^1$- is selected from the group consisting of a single bond, —NH—, —CH$_2$—, —S(=O)$_2$—, —N(CH$_3$)—CH$_2$—, —NH—C(=O)—, —N(CH$_3$)—C(=O)—, —S(=O)$_2$—NH—, —NH—S(=O)$_2$—, —S(=O)(CH$_3$)=N—, —S(=O)$_2$—N(CH$_3$)—, —C(=O)—NH—, —C(=O)—N(CH$_3$)—, —S(=O)(=NH)—NH—, —S(=O)(=NH)—, —P(=O)(CH$_3$)—, —S(=O)(=NH)—CH$_2$—, —P(=O)(CH$_3$)—CH$_2$—, —P(=O)(CH$_3$)—NH—, —P(=O)(NHCH$_3$)—NH—, —CH$_2$—CH$_2$—N(CH$_3$)—, —CH$_2$—CH$_2$—N(C(=O)H)—, —CH$_2$—CH$_2$—NH—, or —S(=O)$_2$ —N(S(=O)$_2$CH$_3$)—, and the other variables are as defined herein.

In some embodiments of the present application, -L$^2$-L$^1$- is selected from the group consisting of a single bond, —NH—, —CH$_2$—, —S(=O)$_2$—, —N(CH$_3$)—CH$_2$—, —NH—C(=O)—, —S(=O)$_2$—NH—, —NH—S(=O)$_2$—, —S(=O)(CH$_3$)=N—, —S(=O)$_2$—N(CH$_3$)—, —C(=O)—NH—, —C(=O)—N(CH$_3$)—, —S(=O)(=NH)—NH—, —S(=O)(=NH)—, —P(=O)(CH$_3$)—, —CH$_2$—S(=O)(=NH)—, —P(=O)(CH$_3$)—CH$_2$—, —P(=O)(CH$_3$)—NH—, —P(=O)(NHCH$_3$)—NH—, —CH$_2$—CH$_2$—N(CH$_3$)—, —CH$_2$—CH$_2$—N(C(=O)H)—, —CH$_2$—CH$_2$—NH—, or —S(=O)$_2$—N(S(=O)$_2$CH$_3$)—, and the other variables are as defined herein.

In some embodiments of the present application, -L$^2$-L$^1$- is selected from the group consisting of a single bond, —NH—, —CH$_2$—, —S(=O)$_2$—, —N(CH$_3$)—CH$_2$—, —NH—C(=O)—, —C(=O)—NH—, —S(=O)$_2$—NH—, —S(=O)$_2$—N(CH$_3$)—, —C(=O)—NH—, —C(=O)—N(CH$_3$)—, —S(=O)(=NH)—NH—, —S(=O)(=NH)—, —P(=O)(CH$_3$)—, —CH$_2$—S(=O)(=NH)—, —P(=O)(CH$_3$)—CH$_2$—, —P(=O)(CH$_3$)—NH—, —P(=O)(NHCH$_3$)—NH—, —CH$_2$—CH$_2$—N(CH$_3$)—, —CH$_2$—CH$_2$—N(C(=O)H)—, or —CH$_2$—CH$_2$—NH—, and the other variables are as defined herein.

In some embodiments of the present application, -L$^2$-L$^1$- is selected from the group consisting of a single bond, —NH—, —CH$_2$—, —S(=O)$_2$—, —N(CH$_3$)—CH$_2$—, —NH—C(=O)—, —C(=O)—NH—, —S(=O)$_2$—NH—, —S(=O)$_2$—N(CH$_3$)—, —C(=O)—NH—, —C(=O)—N(CH$_3$)—, —S(=O)(=NH)—NH—, —S(=O)(=NH)—, —P(=O)(CH$_3$)—, —P(=O)(CH$_3$)—CH$_2$—, —P(=O)(CH$_3$)—NH—, —P(=O)(NHCH$_3$)—NH—, —CH$_2$—CH$_2$—N(CH$_3$)—, or —CH$_2$—CH$_2$—NH—, and the other variables are as defined herein.

In some embodiments of the present application, -L$^2$-L$^1$- is selected from the group consisting of a single bond, —NH—, —CH$_2$—, —NH—S(=O)$_2$—, or —S(=O)$_2$—NH—, and the other variables are as defined herein.

In some embodiments of the present application, -L$^2$-L$^1$- is selected from the group consisting of a single bond, —NH—, —CH$_2$—, or —S(=O)$_2$—NH—, and the other variables are as defined herein.

In some embodiments of the present application, -L$^2$-L$^1$- is selected from the group consisting of a single bond or —S(=O)$_2$—NH—, and the other variables are as defined herein.

In some embodiments of the present application, -L$^2$-L$^1$- is selected from —S(=O)$_2$—NH—, and the other variables are as defined herein.

In some embodiments of the present application, -L$^2$-L$^1$- is selected from —NH—S(=O)$_2$—, and the other variables are as defined herein.

In some embodiments of the present application, -L$^2$-L$^1$- is selected from a single bond, and the other variables are as defined herein.

In some embodiments of the present application, R$^1$ is selected from the group consisting of H, C$_{1-3}$ alkyl, C$_{1-3}$ alkoxy, —NH$_2$, —NH(C$_{1-3}$ alkyl), cyclopropyl, cyclobutyl, cyclopentyl, 4-6 membered heterocycloalkyl containing 1 or 2 atoms selected from the group consisting of N, O, and S atoms, or 5-6 membered heteroaryl containing 1 or 2 N atoms; the C$_{1-3}$ alkyl or the C$_{1-3}$ alkoxy is optionally independently substituted with 1, 2 or 3 R$^d$, and the 4-6 membered heterocycloalkyl or the 5-6 membered heteroaryl is optionally independently substituted with 1, 2 or 3 R$^e$; and the other variables are as defined herein.

In some embodiments of the present application, R$^1$ is selected from the group consisting of H, methyl, ethyl, methoxy, —NH$_2$, —NH(CH$_3$), —NH(CH$_2$CH$_3$), cyclopropyl, cyclobutyl, cyclopentyl, 4-6 membered heterocycloalkyl containing 1 or 2 atoms selected from the group consisting of N, O, and S atoms, or 5-6 membered heteroaryl containing 1 or 2 N atoms; the methyl, the ethyl, or the methoxy is optionally independently substituted with 1, 2 or 3 R$^d$, and the 4-6 membered heterocycloalkyl or the 5-6 membered heteroaryl is optionally independently substituted with 1, 2 or 3 R$^e$; and the other variables are as defined herein.

In some embodiments of the present application, R$^1$ is selected from the group consisting of H, methyl, ethyl, methoxy, —NH$_2$, —NH(CH$_3$), —NH(CH$_2$CH$_3$), cyclopropyl, cyclobutyl, cyclopentyl, oxetanyl, thietanyl, azetidinyl, pyrrolidinyl, pyrazolidinyl, imidazolidinyl, tetrahydrothienyl, tetrahydrofuranyl, tetrahydropyranyl, thiazolidinyl, isothiazolidinyl, oxazolidinyl, isoxazolidinyl, piperidinyl, piperazinyl, morpholinyl, pyrrolyl, pyrazolyl, imidazolyl, oxazolyl, isoxazolyl, a thiazole ring, isothiazolyl, triazolyl, furanyl, thienyl, pyridinyl, pyrazinyl, pyrimidinyl, or pyridazinyl; the methyl, the ethyl, or the methoxy is optionally independently substituted with 1, 2 or 3 R$^d$, and the cyclopropyl, the cyclobutyl, the cyclopentyl, the oxetanyl, the thietanyl, the azetidinyl, the pyrrolidinyl, the pyrazolidinyl, the imidazolidinyl, the tetrahydrothienyl, the tetrahydrofuranyl, the tetrahydropyranyl, the thiazolidinyl, the isothiazolidinyl, the oxazolidinyl, the isoxazolidinyl, the piperidinyl, the piperazinyl, the morpholinyl, the pyrrolyl, the pyrazolyl, the imidazolyl, the oxazolyl, the isoxazolyl, the thiazole ring, the isothiazolyl, the triazolyl, the furanyl, the thienyl, the pyridinyl, the pyrazinyl, the pyrimidinyl, or the pyridazinyl is optionally independently substituted with 1, 2 or 3 $R^e$; and the other variables are as defined herein.

In some embodiments of the present application, $R^1$ is selected from the group consisting of H, methyl, ethyl, methoxy, —$NH_2$, —$NH(CH_3)$, —$NH(CH_2CH_3)$, cyclopropyl, oxetanyl, pyrrolidinyl, pyrazolidinyl, isothiazolidinyl, isoxazolidinyl, imidazolyl, pyrazolyl, oxazolyl, or pyrimidinyl; the methyl, the ethyl, or the methoxy is optionally independently substituted with 1, 2 or 3 $R^d$, and the cyclopropyl, the oxetanyl, the pyrazolidinyl, the isothiazolidinyl, the isoxazolidinyl, the imidazolyl, the oxazolyl, or the pyrimidinyl is optionally independently substituted with 1, 2 or 3 $R^e$; and the other variables are as defined herein.

In some embodiments of the present application, $R^1$ is selected from the group consisting of H, methyl, methoxy, —$NH_2$, —$NH(CH_3)$, —$NH(CH_2CH_3)$, cyclopropyl, oxetanyl, pyrazolidinyl, isothiazolidinyl, isoxazolidinyl, imidazolyl, oxazolyl, or pyrimidinyl; the methyl, the ethyl, or the methoxy is optionally independently substituted with 1, 2 or 3 $R^d$, and the cyclopropyl, the oxetanyl, the pyrazolidinyl, the isothiazolidinyl, the isoxazolidinyl, the imidazolyl, the oxazolyl, or the pyrimidinyl is optionally independently substituted with 1, 2 or 3 $R^e$; and the other variables are as defined herein.

In some embodiments of the present application, $L^1$ is selected from the group consisting of H or methyl, and the other variables are as defined herein.

In some embodiments of the present application, $R^d$ is each independently selected from the group consisting of F, Cl, Br, I, or OH, and the other variables are as defined herein.

In some embodiments of the present application, $R^d$ is each independently selected from the group consisting of F or OH, and the other variables are as defined herein.

In some embodiments of the present application, $R^e$ is each independently selected from the group consisting of F, Cl, Br, I, =O, or $C_{1-3}$ alkyl, and the $C_{1-3}$ alkyl is optionally independently substituted with 1, 2 or 3 $R^x$; and the other variables are as defined herein.

In some embodiments of the present application, $R^x$ is each independently selected from halogen, and the other variables are as defined herein.

In some embodiments of the present application, $R^e$ is each independently selected from the group consisting of F, Cl, Br, I, =O, or $C_{1-3}$ alkyl, and the other variables are as defined herein.

In other embodiments of the present application, $R^e$ is each independently selected from the group consisting of =O or methyl, and the other variables are as defined herein.

In other embodiments of the present application, $R^y$ is each independently selected from halogen, and the other variables are as defined herein.

In some embodiments of the present application, $R^1$ is selected from the group consisting of H, methyl, ethyl, methoxy, —$NH_2$, —$NH(CH_3)$, —$NH(CH_2CH_3)$, cyclopropyl, oxetanyl, pyrrolidinyl, pyrazolidinyl, isothiazolidinyl, isoxazolidinyl, pyrazolyl, imidazolyl, oxazolyl, or pyrimidinyl; the methyl, the ethyl, or the methoxy is optionally independently substituted with 1, 2 or 3 $R^d$, and the cyclopropyl, the oxetanyl, the pyrazolidinyl, the isothiazolidinyl, the isoxazolidinyl, the imidazolyl, the oxazolyl, or the pyrimidinyl is optionally independently substituted with 1, 2 or 3 $R^e$; and the other variables are as defined herein. In some embodiments of the present application, $R^d$ is each independently selected from the group consisting of F, Cl, Br, I, and OH, and $R^e$ is selected from the group consisting of F, Cl, Br, I, =O, or $C_{1-3}$ alkyl; and the other variables are as defined herein.

In some embodiments of the present application, $R^1$ is selected from the group consisting of H, methyl, methoxy, —$NH_2$, —$NH(CH_3)$, —$NH(CH_2CH_3)$, cyclopropyl, oxetanyl, pyrazolidinyl, isothiazolidinyl, isoxazolidinyl, pyrazolyl, oxazolyl, or pyrimidinyl; the methyl, the ethyl, or the methoxy is optionally independently substituted with 1, 2 or 3 $R^d$, and the cyclopropyl, the oxetanyl, the pyrazolidinyl, the isothiazolidinyl, the isoxazolidinyl, the imidazolyl, the oxazolyl, or the pyrimidinyl is optionally independently substituted with 1, 2 or 3 $R^e$; and the other variables are as defined herein. In some embodiments of the present application, $R^d$ is each independently selected from the group consisting of F, Cl, Br, I, and OH, and $R^e$ is selected from the group consisting of F, Cl, Br, I, =O, or $C_{1-3}$ alkyl; and the other variables are as defined herein.

In some embodiments of the present application, $R^1$ is selected from the group consisting of H, methyl, methoxy, —$NH_2$, —$NH(CH_3)$, —$NH(CH_2CH_3)$, cyclopropyl, oxetanyl, pyrazolidinyl, isothiazolidinyl, isoxazolidinyl, imidazolyl, oxazolyl, or pyrimidinyl; the methyl, the ethyl, or the methoxy is optionally independently substituted with 1, 2 or 3 $R^d$, and the cyclopropyl, the oxetanyl, the pyrazolidinyl, the isothiazolidinyl, the isoxazolidinyl, the imidazolyl, the oxazolyl, or the pyrimidinyl is optionally independently substituted with 1, 2 or 3 $R^e$; and the other variables are as defined herein. In some embodiments of the present application, $R^d$ is each independently selected from the group consisting of F or OH, and $R^e$ is selected from the group consisting of =O or methyl; and the other variables are as defined herein.

In some embodiments of the present application, $R^1$ is selected from the group consisting of H, methyl, ethyl, methoxy, —$NH_2$, —$NH(CH_3)$, —$NH(CH_2CH_3)$,

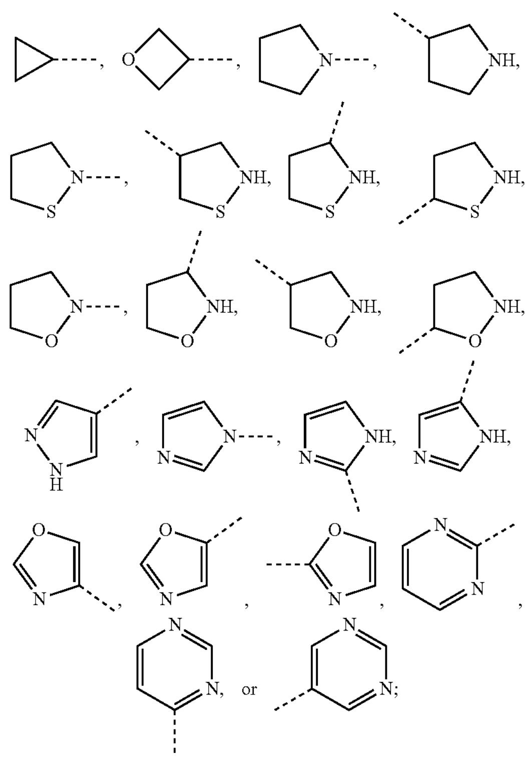

the methyl, the ethyl, or the methoxy is optionally independently substituted with 1, 2 or 3 $R^d$, and

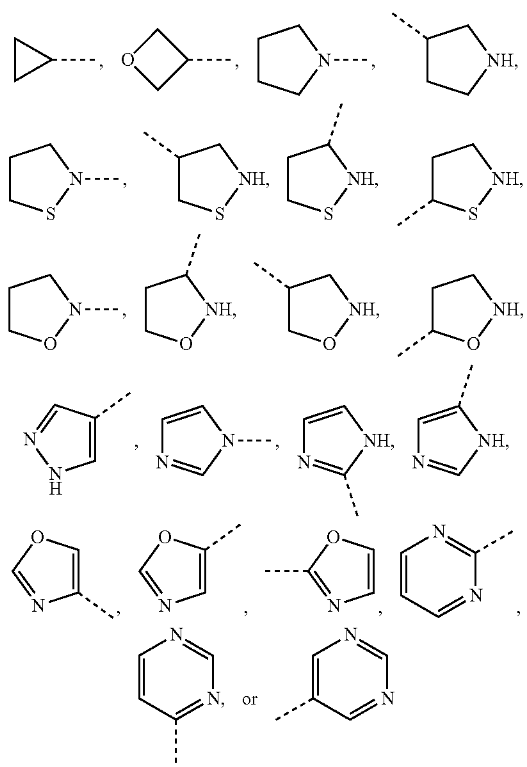

is optionally independently substituted with 1, 2 or 3 $R^e$; and the other variables are as defined herein. In some embodiments of the present application, $R^d$ is each independently selected from the group consisting of F or OH, and $R^e$ is each selected from the group consisting of =O or methyl; and the other variables are as defined herein.

In other embodiments of the present application, $R^1$ is selected from the group consisting of H, methyl, ethyl, methoxy, —$NH_2$, —$NH(CH_3)$, —$NH(CH_2CH_3)$,

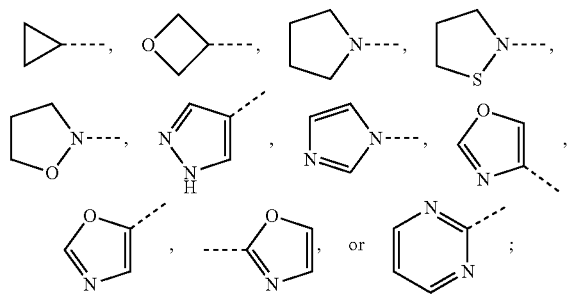

the methyl, the ethyl, or the methoxy is optionally independently substituted with 1, 2 or 3 $R^d$, and

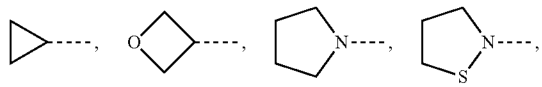

-continued

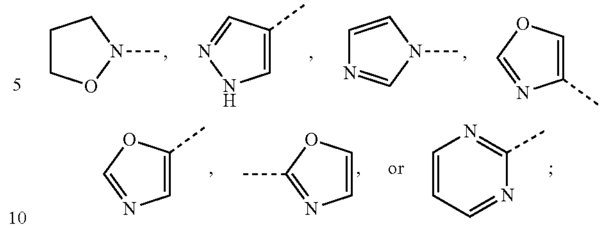

is optionally independently substituted with 1, 2 or 3 $R^e$; and the other variables are as defined herein. In some embodiments of the present application, $R^d$ is each independently selected from the group consisting of F or OH, and $R^e$ is each selected from the group consisting of =O or methyl; and the other variables are as defined herein.

In some embodiments of the present application, $R^1$ is selected from the group consisting of H, methyl, methoxy, —$NH_2$, —$NH(CH_3)$, —$NH(CH_2CH_3)$,

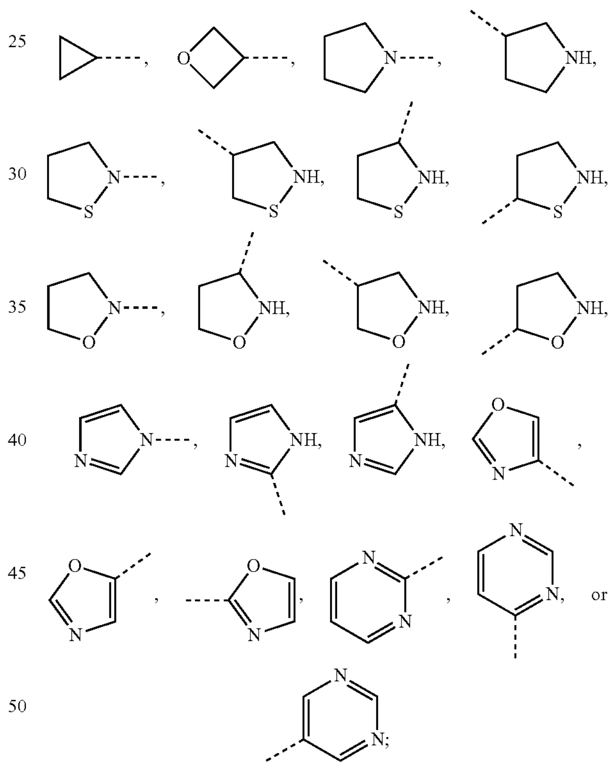

the methyl or the methoxy is optionally independently substituted with 1, 2 or 3 $R^d$, and

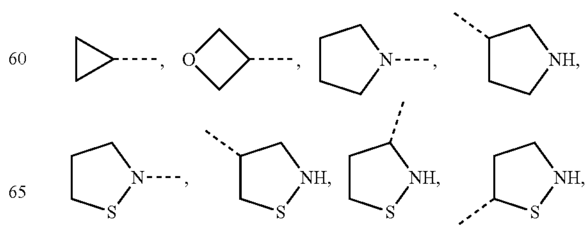

-continued

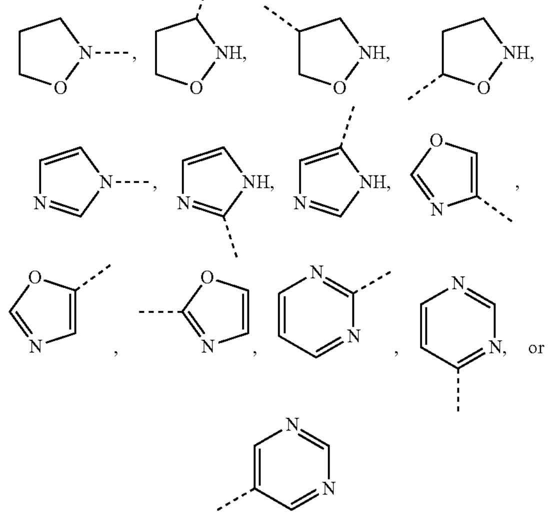

is optionally independently substituted with 1, 2 or 3 $R^e$; and the other variables are as defined herein. In some embodiments of the present application, $R^d$ is each independently selected from the group consisting of F or OH, and $R^e$ is each selected from the group consisting of =O or methyl; and the other variables are as defined herein.

In other embodiments of the present application, $R^1$ is selected from the group consisting of H, methyl, methoxy, —$NH_2$, —$NH(CH_3)$, —$NH(CH_2CH_3)$,

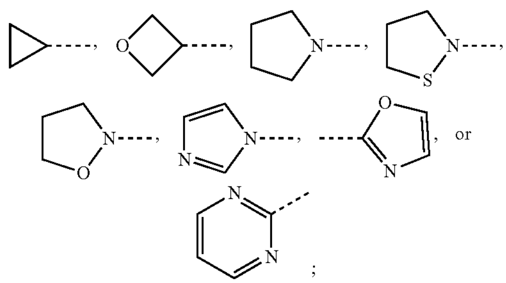

the methyl, the ethyl, or the methoxy is optionally independently substituted with 1, 2 or 3 $R^d$, and

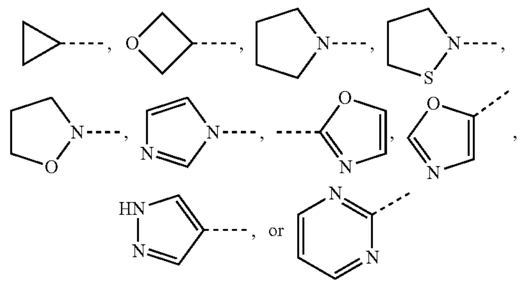

is optionally independently substituted with 1, 2 or 3 $R^e$; and the other variables are as defined herein. In some embodiments of the present application, $R^d$ is each independently selected from the group consisting of F or OH, and $R^e$ is each selected from the group consisting of =O or methyl; and the other variables are as defined herein.

In some embodiments of the present application, $R^1$ is selected from the group consisting of H, methyl, methoxy, —$NH_2$, —$NH(CH_3)$, —$NH(CH_2CH_3)$,

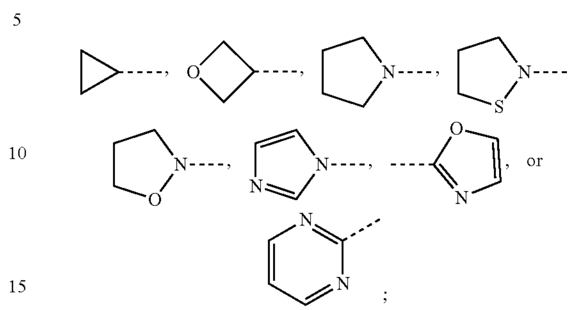

the methyl, the ethyl, or the methoxy is optionally independently substituted with 1, 2 or 3 $R^d$, and

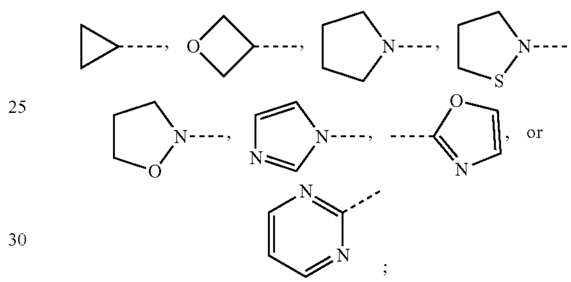

is optionally independently substituted with 1, 2 or 3 $R^e$; and the other variables are as defined herein. In some embodiments of the present application, $R^d$ is each independently selected from the group consisting of F or OH, and $R^e$ is each selected from the group consisting of =O or methyl; and the other variables are as defined herein.

In other embodiments of the present application, $R^1$ is selected from the group consisting of H, methyl, —$CH_2CH_2OH$, methoxy, —$OCF_3$, —$CH_2OH$, —$NH_2$, —$NH(CH_3)$, —$NH(CH_2CH_2OH)$,

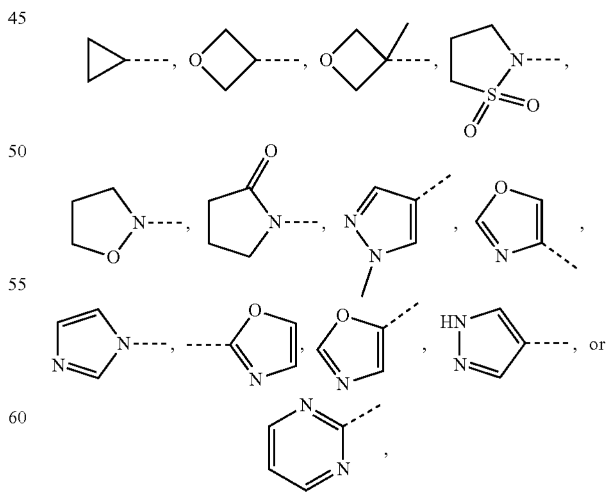

and the other variables are as defined herein.

In some embodiments of the present application, $R^1$ is selected from the group consisting of H, methyl, —$CH_2CH_2OH$, methoxy, —$OCF_3$, —$CH_2OH$, —$NH_2$, —$NH(CH_3)$, —$NH(CH_2CH_2OH)$,

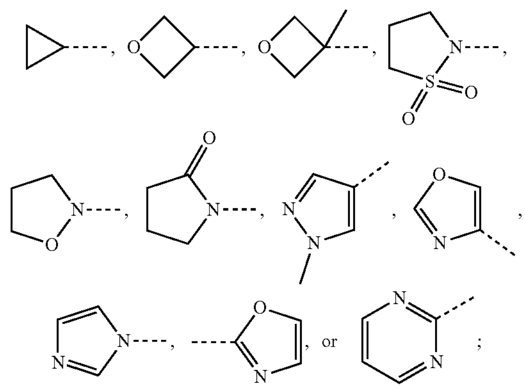

and the other variables are as defined herein.

In some embodiments of the present application, $R^1$ is selected from the group consisting of H, methyl, methoxy, —$OCF_3$, —$CH_2OH$, —$NH_2$, —$NH(CH_3)$, —$NH(CH_2CH_2H)$,

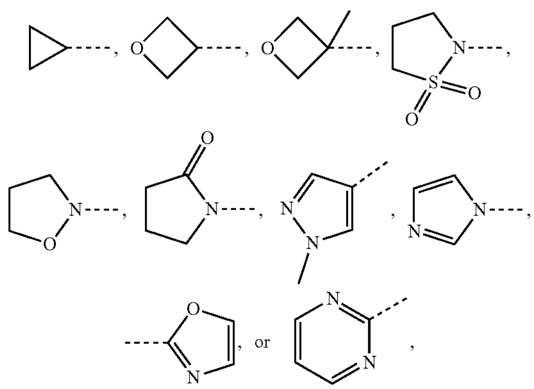

and the other variables are as defined herein.

In some embodiments of the present application, $R^1$ is selected from the group consisting of H, methyl, or methoxy, and the other variables are as defined herein.

In some embodiments of the present application, $R^1$ is selected from methyl, and the other variables are as defined herein.

In some embodiments of the present application, $R^1$ is selected from H, and the other variables are as defined herein.

In some embodiments of the present application, $R^b$ is each independently selected from the group consisting of H, $C_{1-3}$ alkyl, $C_{1-3}$ alkoxy, $C_{3-6}$ cycloalkyl, or 3-6 membered heterocycloalkyl; the $C_{1-3}$ alkyl or the $C_{1-3}$ alkoxy is optionally independently substituted with 1, 2 or 3 $R^x$, and the $C_{3-6}$ cycloalkyl or the 3-6 membered heterocycloalkyl is optionally independently substituted with 1, 2 or 3 $R^y$; and the other variables are as defined herein.

In other embodiments of the present application, $R^b$ is each independently selected from the group consisting of H, —C(═O)H, —$S(═O)_2CH_3$, or methyl, and the methyl is optionally independently substituted with 1, 2 or 3 $R^x$; and the other variables are as defined herein.

In some embodiments of the present application, $R^b$ is each independently selected from the group consisting of H or $C_{1-3}$ alkyl, and the $C_{1-3}$ alkyl is optionally independently substituted with 1, 2 or 3 $R^x$; and the other variables are as defined herein.

In some embodiments of the present application, $R^b$ is each independently selected from the group consisting of H or methyl, and the methyl is optionally independently substituted with 1, 2 or 3 $R^x$; and the other variables are as defined herein.

In other embodiments of the present application, $R^b$ is each independently selected from the group consisting of H, —C(═O)H, —$S(═O)_2CH_3$, or methyl, and the other variables are as defined herein.

In some embodiments of the present application, $R^b$ is each independently selected from the group consisting of H or methyl, and the other variables are as defined herein.

In some embodiments of the present application, $R^c$ is selected from $C_{1-3}$ alkyl, and the $C_{1-3}$ alkyl is optionally independently substituted with 1, 2 or 3 $R^x$; and the other variables are as defined herein.

In some embodiments of the present application, $R^c$ is selected from methyl, and the methyl is optionally independently substituted with 1, 2 or 3 $R^x$; and the other variables are as defined herein.

In some embodiments of the present application, $R^c$ is selected from methyl, and the other variables are as defined herein.

In some embodiments of the present application, m is selected from the group consisting of 1 or 2, and the other variables are as defined herein.

In some embodiments of the present application, $R^2$, $R^3$, and $R^4$ are each independently selected from the group consisting of H, deuterium, or $C_{1-3}$ alkyl, and the $C_{1-3}$ alkyl is optionally independently substituted with 1, 2 or 3 $R^z$; and the other variables are as defined herein.

In some embodiments of the present application, $R^2$, $R^3$, and $R^4$ are each independently selected from the group consisting of H or $C_{1-3}$ alkyl, and the $C_{1-3}$ alkyl is optionally independently substituted with 1, 2 or 3 $R^z$; and the other variables are as defined herein.

In some embodiments of the present application, $R^2$, $R^3$, and $R^4$ are each independently selected from the group consisting of H, deuterium, methyl, —$CD_3$, difluoromethyl, trifluoromethyl, or ethyl, and the other variables are as defined herein.

In other embodiments of the present application, $R^2$, $R^3$, and $R^4$ are each independently selected from the group consisting of H, deuterium, methyl, —$CD_3$, or trifluoromethyl, and the other variables are as defined herein.

In some embodiments of the present application, $R^2$, $R^3$, and $R^4$ are each independently selected from the group consisting of H, methyl, or ethyl, and the other variables are as defined herein. In some embodiments of the present application, $R^2$, $R^3$, and $R^4$ are each independently selected from the group consisting of H or methyl, and the other variables are as defined herein.

In some embodiments of the present application, at least one of $R^2$, $R^3$, and $R^4$ is selected from H, and the other variables are as defined herein.

In other embodiments of the present application, $R^2$ is selected from the group consisting of H or deuterium; $R^3$ and $R^4$ are each independently selected from the group consisting of H, methyl, —$CD_3$, or trifluoromethyl; and the other variables are as defined herein.

In some embodiments of the present application, $R^2$ is selected from the group consisting of H or deuterium; $R^3$ and $R^4$ are each independently selected from the group consisting of methyl, —$CD_3$, or trifluoromethyl; and the other variables are as defined herein.

In some embodiments of the present application, $R^2$ is selected from deuterium; $R^3$ and $R^4$ are each independently selected from —$CD_3$; and the other variables are as defined herein.

In some embodiments of the present application, $R^2$ is selected from H; $R^3$ and $R^4$ are each independently selected from methyl; and the other variables are as defined herein.

In other embodiments of the present application, $R^2$ is selected from H; $R^3$ and $R^4$ are each independently selected from methyl and $CF_3$; and the other variables are as defined herein.

In some embodiments of the present application, $R^2$ is selected from methyl; $R^3$ and $R^4$ are each independently selected from H; and the other variables are as defined herein.

In some embodiments of the present application, $R^2$, $R^3$, and $R^4$ are all H, and the other variables are as defined herein.

In some embodiments of the present application, $R^2$ and $R^3$, together with the carbon atom linked thereto, form $C_{3-4}$ cycloalkyl or 3-4 membered heterocycloalkyl, and $R^4$ is selected from the group consisting of H or $C_{1-3}$ alkyl; the $C_{1-3}$ alkyl, the $C_{3-4}$ cycloalkyl, or the 3-4 membered heterocycloalkyl is optionally independently substituted with 1, 2 or 3 $R^z$; and the other variables are as defined herein.

In some embodiments of the present application, $R^2$ and $R^3$, together with the carbon atom linked thereto, form cyclopropyl, oxiranyl, or aziridinyl, and $R^4$ is selected from the group consisting of H, methyl, or ethyl; the methyl, the ethyl, the cyclopropyl, the oxiranyl, or the aziridinyl is optionally independently substituted with 1, 2 or 3 $R^z$; and the other variables are as defined herein.

In some embodiments of the present application, $R^2$ and $R^3$, together with the carbon atom linked thereto, form cyclopropyl, and $R^4$ is selected from the group consisting of H or methyl; the methyl or the cyclopropyl is optionally independently substituted with 1, 2 or 3 $R^z$; and the other variables are as defined herein.

In some embodiments of the present application, $R^2$ and $R^3$, together with the carbon atom linked thereto, form cyclopropyl, and $R^4$ is selected from methyl; and the other variables are as defined herein.

In some embodiments of the present application, $R^2$ and $R^3$, together with the carbon atom linked thereto, form cyclopropyl, and $R^4$ is selected from H; and the other variables are as defined herein.

In some embodiments of the present application, $R^z$ is each independently selected from the group consisting of deuterium, halogen, or OH, and the other variables are as defined herein.

In some embodiments of the present application, $R^z$ is each independently selected from the group consisting of halogen or OH, and the other variables are as defined herein.

In some embodiments of the present application, $R^z$ is each independently selected from F, and the other variables are as defined herein.

In some embodiments of the present application, provided is the compound of formula (I), the isomer thereof, or the pharmaceutically acceptable salt thereof, wherein, ring A is selected from the group consisting of a $C_{3-10}$ alkyl ring, a 5-10 membered heteroalkyl ring, a benzene ring, a naphthyl ring, a benzene ring fused to a $C_{5-6}$ alkyl ring, a benzene ring fused to a 5-6 membered heteroalkyl ring, a 5-6 membered heteroaromatic ring, a 5-6 membered heteroaromatic ring fused to a $C_{5-6}$ alkyl ring, or a 5-6 membered heteroaromatic ring fused to a 5-6 membered heteroalkyl ring, and the $C_{3-10}$ alkyl ring, the 5-10 membered heteroalkyl ring, the benzene ring, the naphthyl ring, the benzene ring fused to a $C_{5-6}$ alkyl ring, the benzene ring fused to a 5-6 membered heteroalkyl ring, the 5-6 membered heteroaromatic ring, the 5-6 membered heteroaromatic ring fused to a $C_{5-6}$ alkyl ring, or the 5-6 membered heteroaromatic ring fused to a 5-6 membered heteroalkyl ring is optionally independently substituted with 1, 2 or 3 $R^a$;

$L^1$ and $L^2$ are each independently selected from the group consisting of a single bond, —$N(R^b)$—, —N═, —O—, —S—, —$(CH_2)_m$—, —C(═O)—, —S(═O)—, —$S(=O)_2$—, —S(═O)(═$N(R^b)$)—, —S(═O)($R^c$)—, —P(═O)($R^c$)—, or —P(═O)($NR^bR^b$)—;

$R^1$ is selected from the group consisting of H, $C_{1-3}$ alkyl, $C_{1-3}$ alkoxy, —$NH_2$, —NH($C_{1-3}$ alkyl), —$N(C_{1-3}\ alkyl)_2$, $C_{3-6}$ cycloalkyl, 3-6 membered heterocycloalkyl, phenyl, or 5-6 membered heteroaryl; the $C_{1-3}$ alkyl or the $C_{1-3}$ alkoxy is optionally independently substituted with 1, 2 or 3 $R^d$, and the $C_{3-6}$ cycloalkyl, the 3-6 membered heterocycloalkyl, the phenyl, or the 5-6 membered heteroaryl is optionally independently substituted with 1, 2 or 3 $R^e$;

$R^2$, $R^3$, and $R^4$ are each independently selected from the group consisting of H, halogen, OH, CN, $NH_2$, $C_{1-3}$ alkyl, or $C_{1-3}$ alkoxy, and the $C_{1-3}$ alkyl or the $C_{1-3}$ alkoxy is optionally independently substituted with 1, 2 or 3 $R^z$;

or $R^2$ and $R^3$, together with the carbon atom linked thereto, form $C_{3-6}$ cycloalkyl or 3-6 membered heterocycloalkyl, and $R^4$ is selected from the group consisting of H, halogen, OH, CN, $NH_2$, $C_{1-3}$ alkyl, or $C_{1-3}$ alkoxy; the $C_{1-3}$ alkyl, the $C_{1-3}$ alkoxy, the $C_{3-6}$ cycloalkyl, or the 3-6 membered heterocycloalkyl is optionally independently substituted with 1, 2 or 3 $R^z$;

$R^a$ is each independently selected from the group consisting of halogen, OH, CN, $NH_2$, ═O, $C_{1-3}$ alkyl, or $C_{1-3}$ alkoxy, and the $C_{1-3}$ alkyl or the $C_{1-3}$ alkoxy is optionally independently substituted with 1, 2 or 3 $R^x$;

$R^b$ is each independently selected from the group consisting of H, $C_{1-3}$ alkyl, $C_{1-3}$ alkoxy, —C(═O)H, —$S(=O)_2C_{1-3}$ alkyl, $C_{3-6}$ cycloalkyl, or 3-6 membered heterocycloalkyl; the $C_{1-3}$ alkyl or the $C_{1-3}$ alkoxy is optionally independently substituted with 1, 2 or 3 $R^x$, and the $C_{3-6}$ cycloalkyl or the 3-6 membered heterocycloalkyl is optionally independently substituted with 1, 2 or 3 $R^y$;

$R^c$ is selected from the group consisting of halogen, OH, CN, or $C_{1-3}$ alkyl, and the $C_{1-3}$ alkyl is optionally independently substituted with 1, 2 or 3 $R^x$;

$R^d$ is each independently selected from the group consisting of halogen, OH, CN, or $NH_2$;

$R^e$ is each independently selected from the group consisting of halogen, OH, CN, $NH_2$, ═O, $C_{1-3}$ alkyl, or $C_{1-3}$ alkoxy, and the $C_{1-3}$ alkyl or the $C_{1-3}$ alkoxy is optionally independently substituted with 1, 2 or 3 $R^x$;

$R^x$ is each independently selected from the group consisting of halogen, OH, CN, or $NH_2$;

$R^y$ is each independently selected from the group consisting of halogen, OH, CN, $NH_2$, ═O, $C_{1-3}$ alkyl, or $C_{1-3}$ alkoxy, and the $C_{1-3}$ alkyl or the $C_{1-3}$ alkoxy is optionally independently substituted with 1, 2 or 3 substituents selected from the group consisting of halogen, OH, CN, or $NH_2$;

$R^z$ is each independently selected from the group consisting of halogen, OH, CN, or $NH_2$;

m is selected from the group consisting of 1, 2, or 3;

the carbon atom with "*" is a chiral carbon atom present in a form of a single (R) or (S) enantiomer or in a form enriched with one enantiomer.

The present application provides a compound of formula (II), an isomer thereof, or a pharmaceutically acceptable salt thereof, (II)

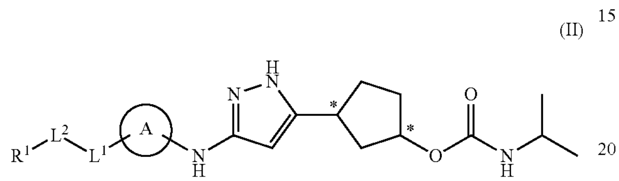

wherein, ring A is selected from the group consisting of a $C_{3-10}$ alkyl ring, a 5-10 membered heteroalkyl ring, a benzene ring, a naphthyl ring, a benzene ring fused to a $C_{5-6}$ alkyl ring, a benzene ring fused to a 5-6 membered heteroalkyl ring, a 5-6 membered heteroaromatic ring, a 5-6 membered heteroaromatic ring fused to a $C_{5-6}$ alkyl ring, or a 5-6 membered heteroaromatic ring fused to a 5-6 membered heteroalkyl ring, and the $C_{3-10}$ alkyl ring, the 5-10 membered heteroalkyl ring, the benzene ring, the naphthyl ring, the benzene ring fused to a $C_{5-6}$ alkyl ring, the benzene ring fused to a 5-6 membered heteroalkyl ring, the 5-6 membered heteroaromatic ring, the 5-6 membered heteroaromatic ring fused to a $C_{5-6}$ alkyl ring, or the 5-6 membered heteroaromatic ring fused to a 5-6 membered heteroalkyl ring is optionally independently substituted with 1, 2 or 3 $R^a$;

$L^1$ and $L^2$ are each independently selected from the group consisting of a single bond, —N($R^b$)—, —O—, —S—, —$(CH_2)_m$—, —C(=O)—, —S(=O)—, —S(=O)$_2$—, —S(=O)(=N($R^b$))—, —P(=O)($R^c$)—, or —P(=O)(N$R^b$$R^b$)—;

$R^1$ is selected from the group consisting of H, $C_{1-3}$ alkyl, $C_{1-3}$ alkoxy, —$NH_2$, —NH($C_{1-3}$ alkyl), —N($C_{1-3}$ alkyl)$_2$, $C_{3-6}$ cycloalkyl, 3-6 membered heterocycloalkyl, phenyl, or 5-6 membered heteroaryl; the $C_{1-3}$ alkyl or the $C_{1-3}$ alkoxy is optionally independently substituted with 1, 2 or 3 $R^d$, and the $C_{3-6}$ cycloalkyl, the 3-6 membered heterocycloalkyl, the phenyl, or the 5-6 membered heteroaryl is optionally independently substituted with 1, 2 or 3 $R^e$;

$R^a$ is each independently selected from the group consisting of halogen, OH, CN, $NH_2$, =O, $C_{1-3}$ alkyl, or $C_{1-3}$ alkoxy, and the $C_{1-3}$ alkyl or the $C_{1-3}$ alkoxy is optionally independently substituted with 1, 2 or 3 $R^x$;

$R^b$ is each independently selected from the group consisting of H, $C_{1-3}$ alkyl, $C_{1-3}$ alkoxy, —C(=O)H, $C_{3-6}$ cycloalkyl, or 3-6 membered heterocycloalkyl; the $C_{1-3}$ alkyl or the $C_{1-3}$ alkoxy is optionally independently substituted with 1, 2 or 3 $R^x$, and the $C_{3-6}$ cycloalkyl or the 3-6 membered heterocycloalkyl is optionally independently substituted with 1, 2 or 3 $R^y$;

$R^c$ is selected from the group consisting of halogen, OH, CN, or $C_{1-3}$ alkyl, and the $C_{1-3}$ alkyl is optionally independently substituted with 1, 2 or 3 $R^x$;

$R^d$ is each independently selected from the group consisting of halogen, OH, CN, or $NH_2$;

$R^e$ is each independently selected from the group consisting of halogen, OH, CN, $NH_2$, =O, $C_{1-3}$ alkyl, or $C_{1-3}$ alkoxy, and the $C_{1-3}$ alkyl or the $C_{1-3}$ alkoxy is optionally independently substituted with 1, 2 or 3 $R^x$;

$R^x$ is each independently selected from the group consisting of halogen, OH, CN, or $NH_2$;

$R^y$ is each independently selected from the group consisting of halogen, OH, CN, $NH_2$, =O, $C_{1-3}$ alkyl, or $C_{1-3}$ alkoxy, and the $C_{1-3}$ alkyl or the $C_{1-3}$ alkoxy is optionally independently substituted with 1, 2 or 3 substituents selected from the group consisting of halogen, OH, CN, or $NH_2$;

m is selected from the group consisting of 1, 2, or 3;

the carbon atom with "*" is a chiral carbon atom present in a form of a single (R) or (S) enantiomer or in a form enriched with one enantiomer.

In some embodiments of the present application, provided is the compound of formula (II), the isomer thereof, or the pharmaceutically acceptable salt thereof, wherein ring A, $R^1$, $L^1$, and $L^2$ may be further defined as in the compound of formula (I) above.

In some embodiments of the present application, the compound of formula (II), the isomer thereof, or the pharmaceutically acceptable salt thereof is selected from a compound of formula (II-1), (II-1)

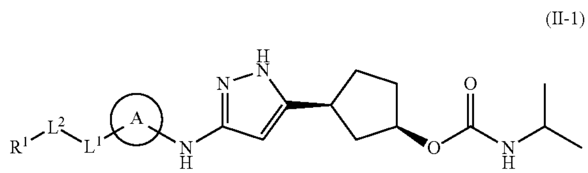

wherein, ring A, $R^1$, $L^1$ and $L^2$ are defined as in the compound of formula (II).

In some embodiments of the present application, the compound of formula (II), the isomer thereof, or the pharmaceutically acceptable salt thereof is selected from a compound of formula (II-2)

(II-2)

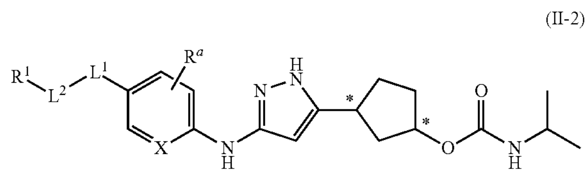

wherein, wherein X is selected from the group consisting of CH or N;

$R^1$, $R^a$, $L^1$ and $L^2$ are defined as in the compound of formula (II);

the carbon atom with "*" is a chiral carbon atom present in a form of a single (R) or (S) enantiomer or in a form enriched with one enantiomer.

In some embodiments of the present application, X is selected from N, and the other variables are as defined herein.

In some embodiments of the present application, the compound of formula (II), the isomer thereof, or the pharmaceutically acceptable salt thereof is selected from a compound of formula (II-2a)

(II-2a)

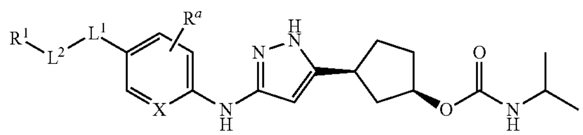

wherein, wherein X is selected from the group consisting of CH or N;

$R^1$, $R^a$, $L^1$ and $L^2$ are defined as in the compound of formula (II).

In some embodiments of the present application, X is selected from N, and the other variables are as defined herein.

In some embodiments of the present application, the compound of formula (II), the isomer thereof, or the pharmaceutically acceptable salt thereof is selected from a compound of formula (II-3)

(II-3)

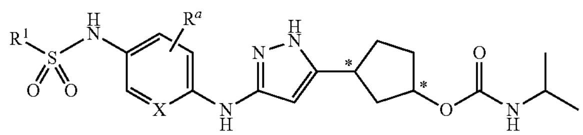

wherein, wherein X is selected from the group consisting of CH or N;

$R^1$ and $R^a$ are as defined in the compound of formula (II);

the carbon atom with "*" is a chiral carbon atom present in a form of a single (R) or (S) enantiomer or in a form enriched with one enantiomer.

In some embodiments of the present application, X is selected from N, and the other variables are as defined herein.

In some embodiments of the present application, the compound of formula (II), the isomer thereof, or the pharmaceutically acceptable salt thereof is selected from a compound of formula (II-3a)

(II-3a)

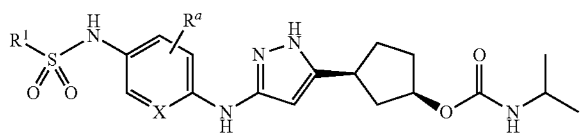

wherein, wherein X is selected from the group consisting of CH or N;

$R^1$ and $R^a$ are as defined in the compound of formula (II).

In some embodiments of the present application, X is selected from N, and the other variables are as defined herein.

In some embodiments of the present application, the compound of formula (I), the isomer thereof, or the pharmaceutically acceptable salt thereof is selected from a compound of formula (I-4), (I-1)

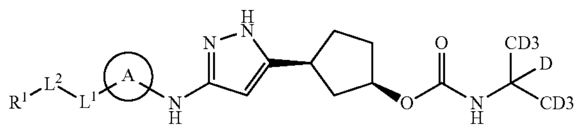

wherein, ring A, $R^1$, $L^1$ and $L^2$ are defined as in the compound of formula (I).

In some embodiments of the present application, the compound of formula (I), formula (II), formula (II-1), formula (II-2), or formula (II-2a) does not include the following structures:

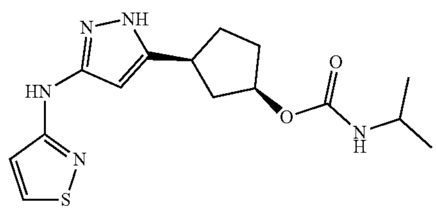

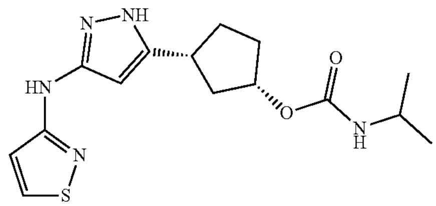

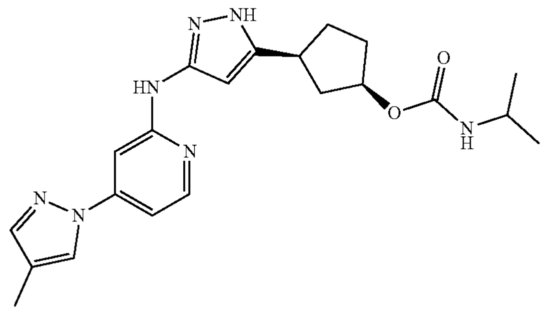

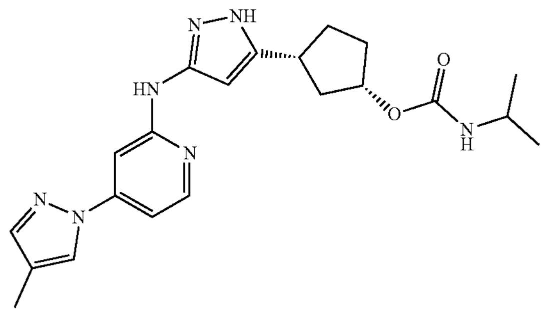

-continued
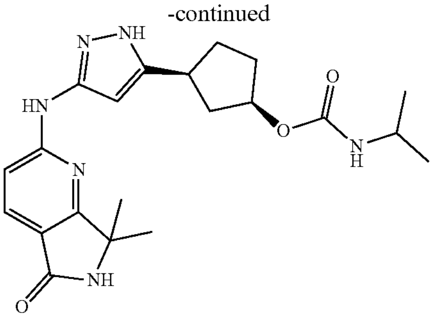
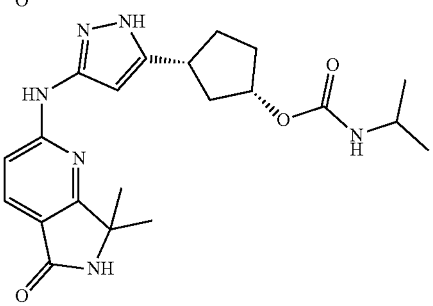
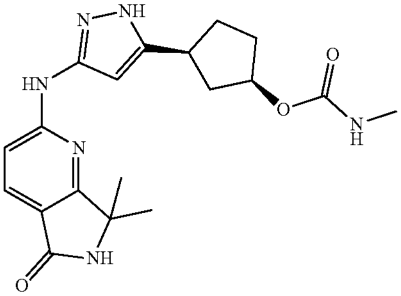
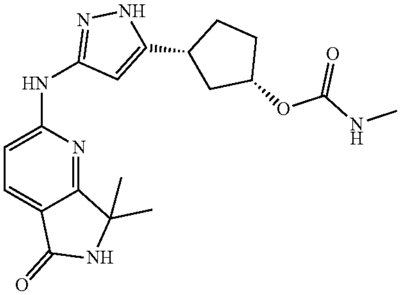
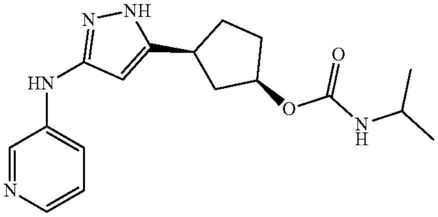
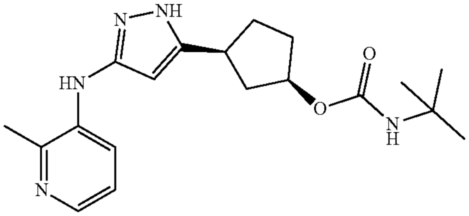
-continued
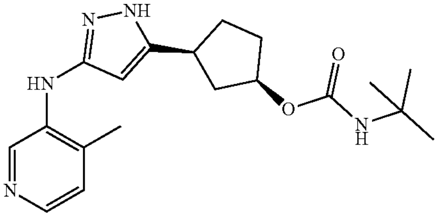
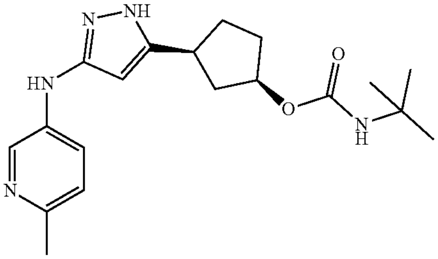
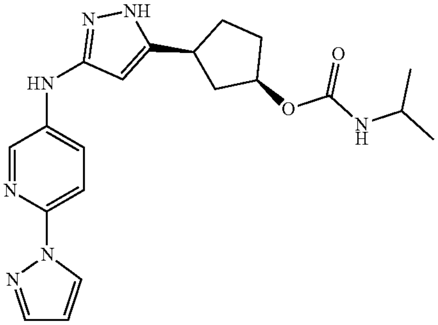
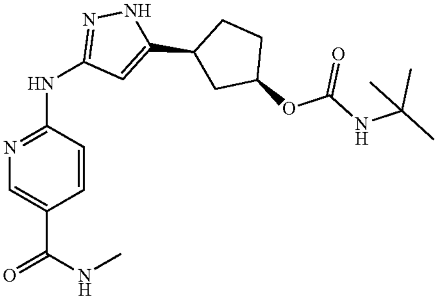
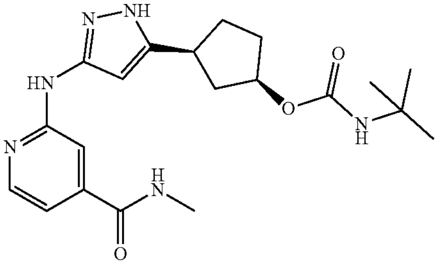
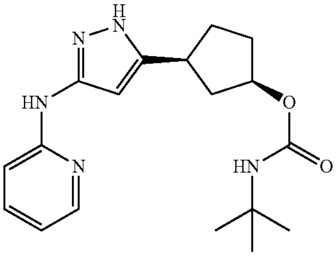

-continued
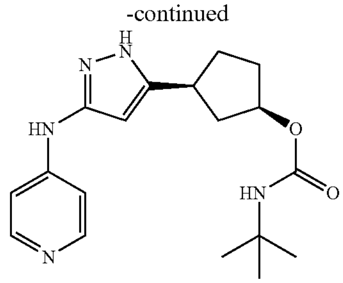
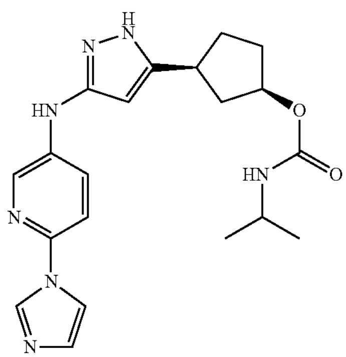
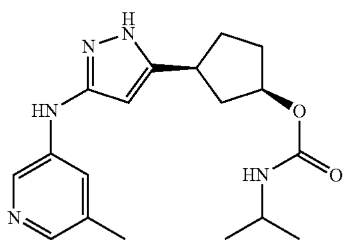
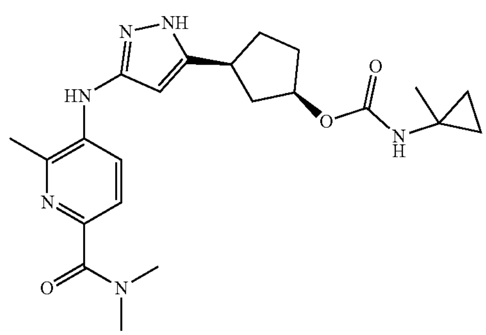
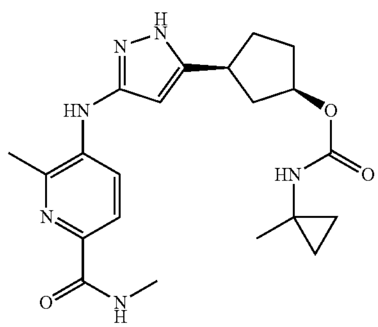
-continued
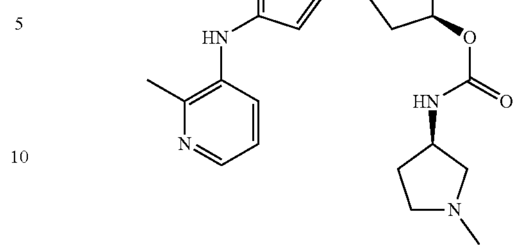
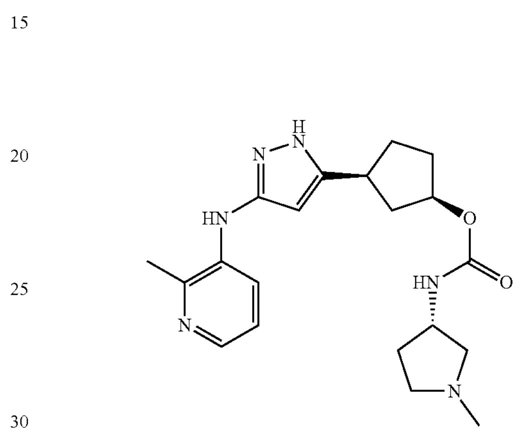
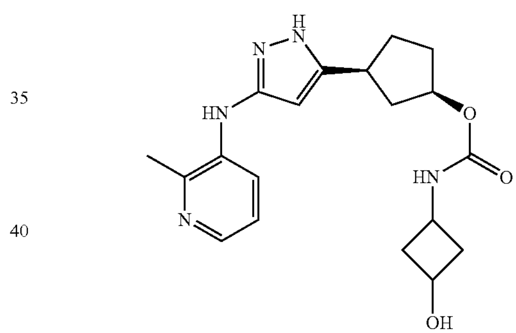
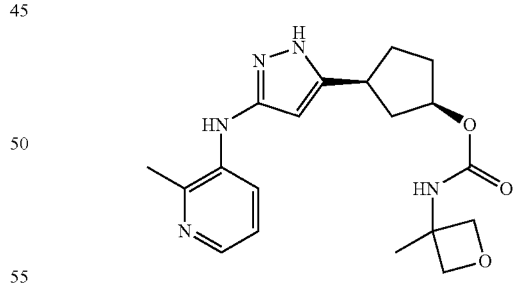
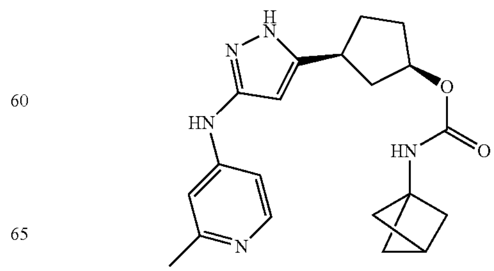

-continued
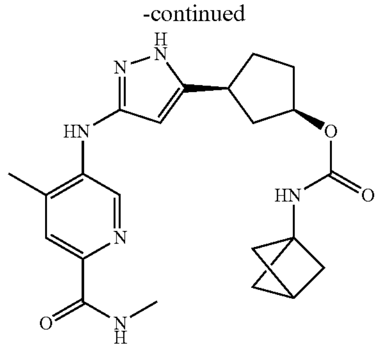
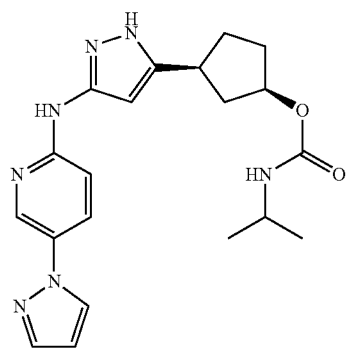
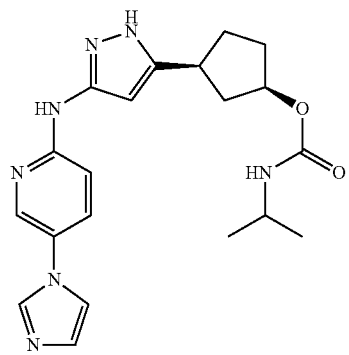
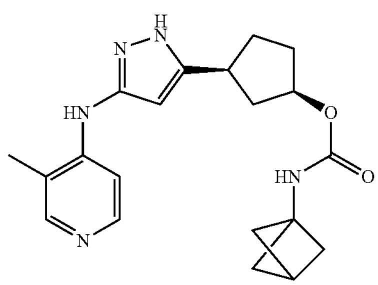
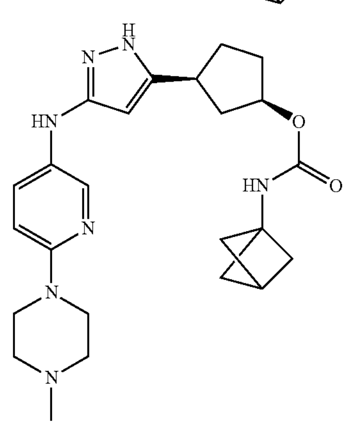
-continued
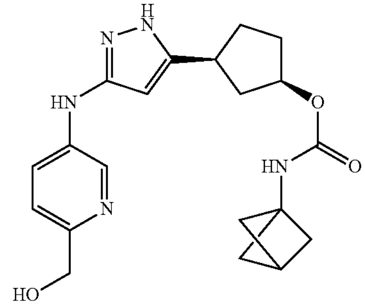
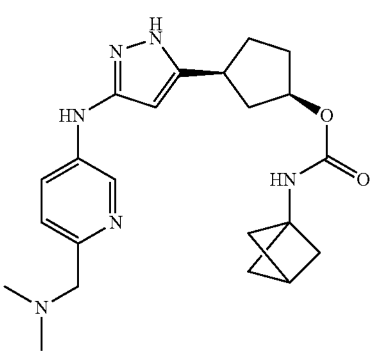
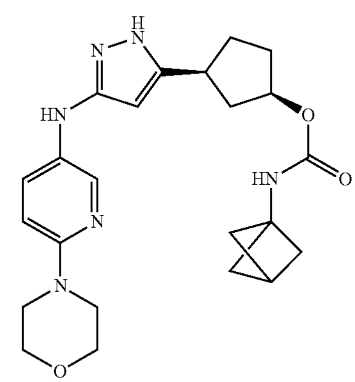
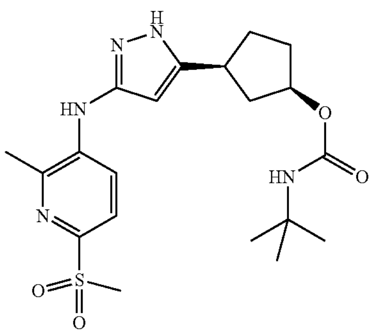
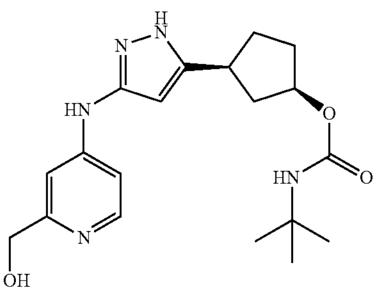

-continued
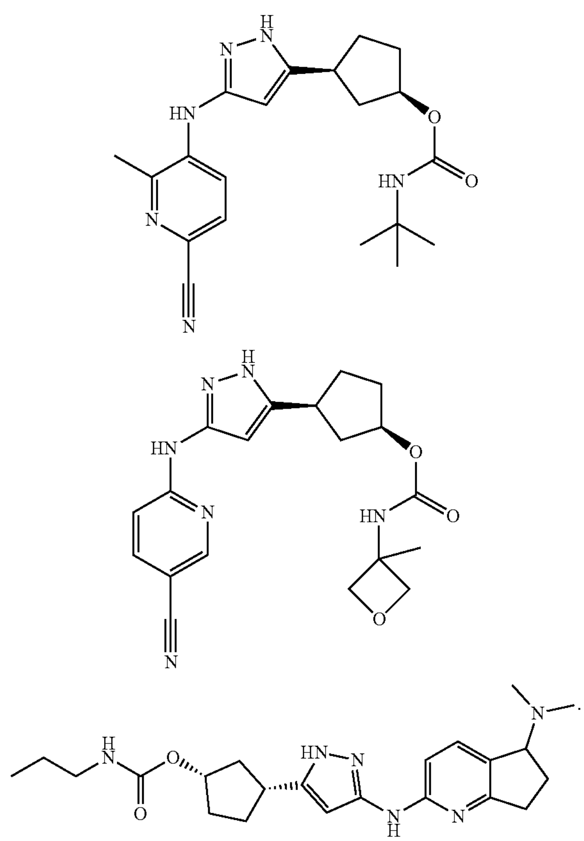
Some other embodiments of the present application are derived from any combination of the variables.
In another aspect, the present application further provides a compound of the formulas below, an isomer thereof, or a pharmaceutically acceptable salt thereof,
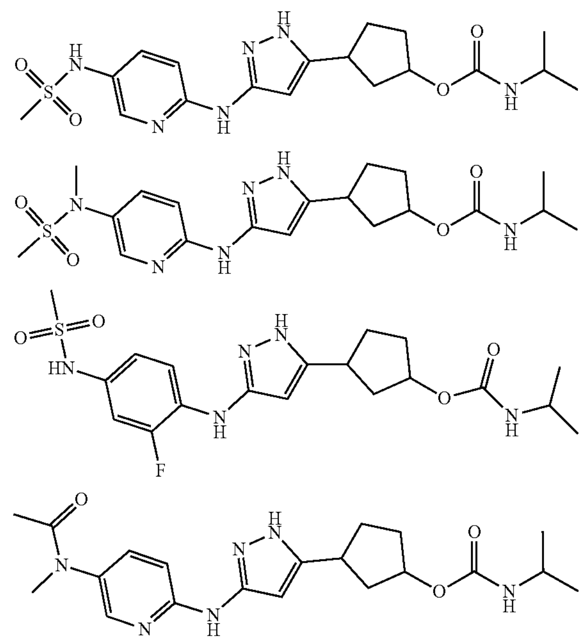
-continued
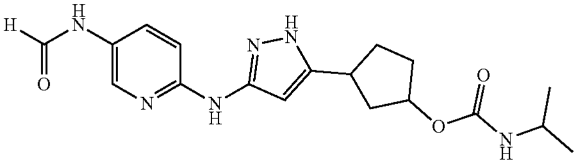
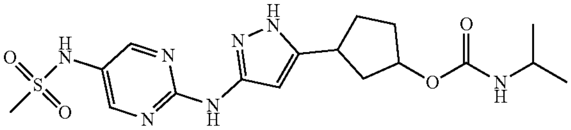
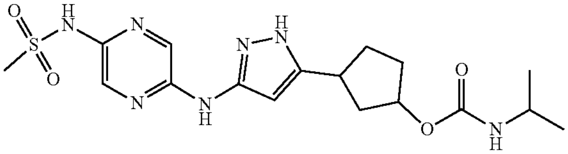
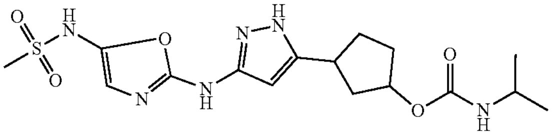
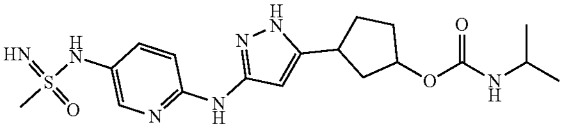
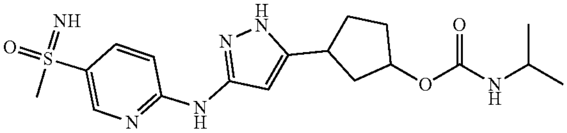
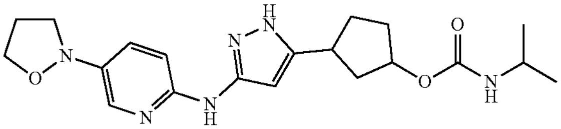
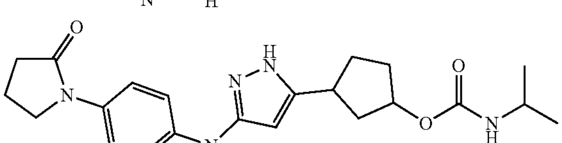
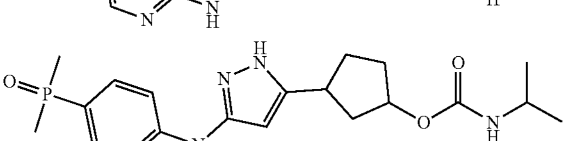
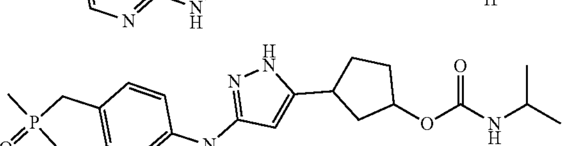
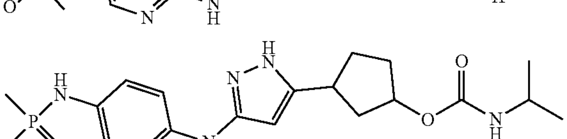
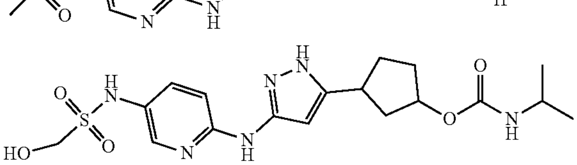

-continued
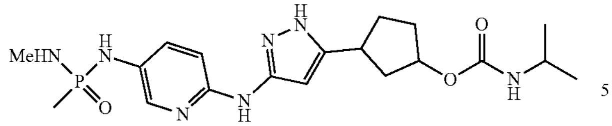
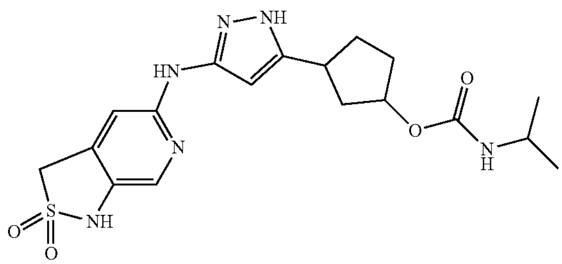
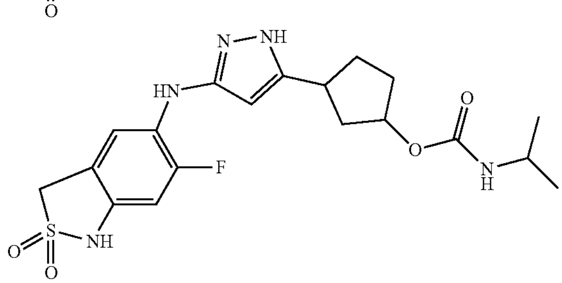
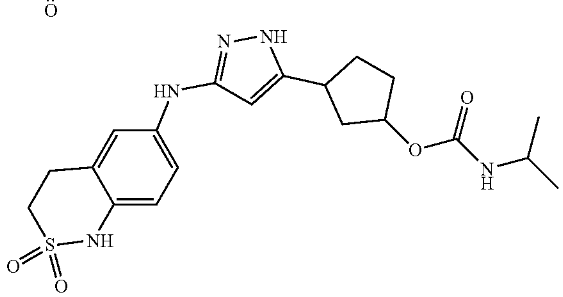
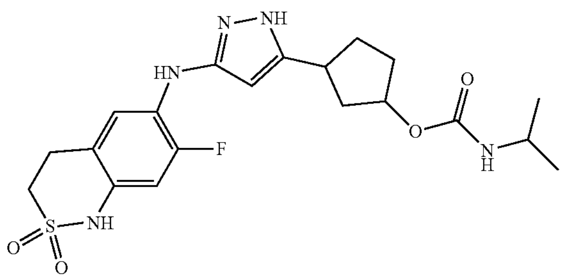
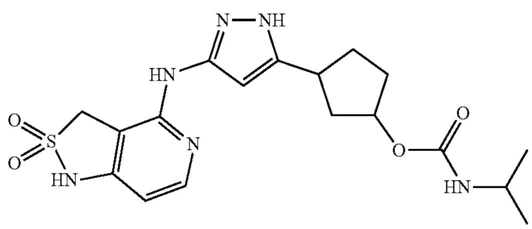
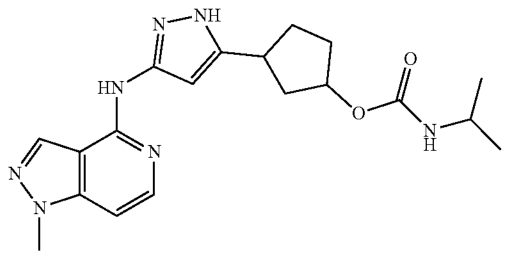
-continued
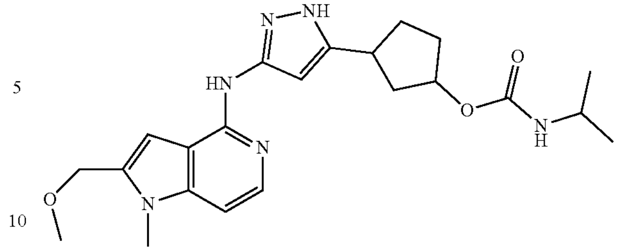
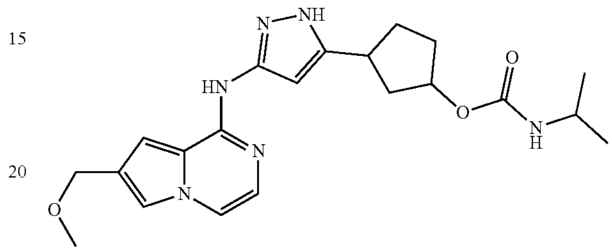
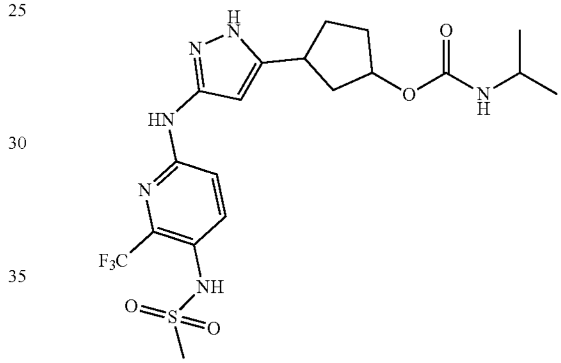
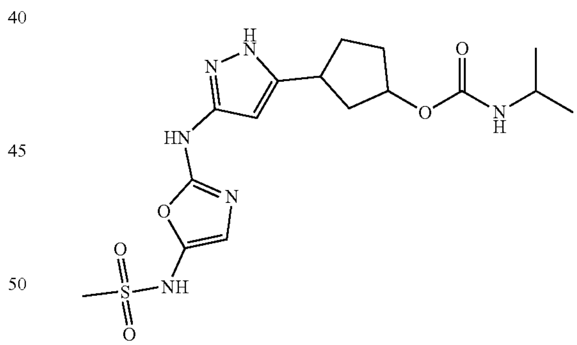
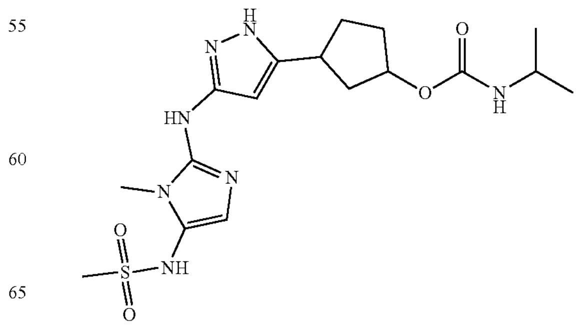

-continued
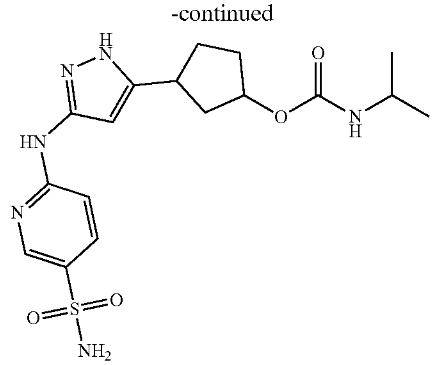
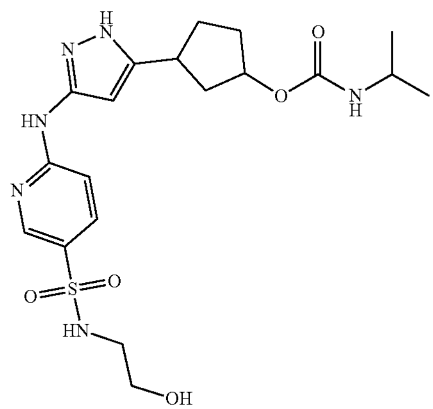
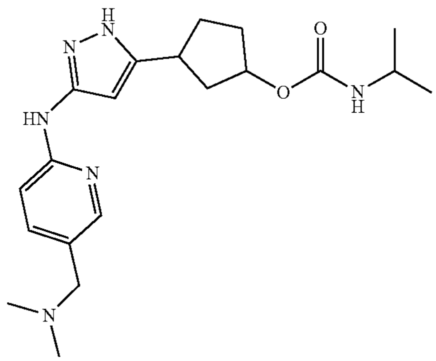
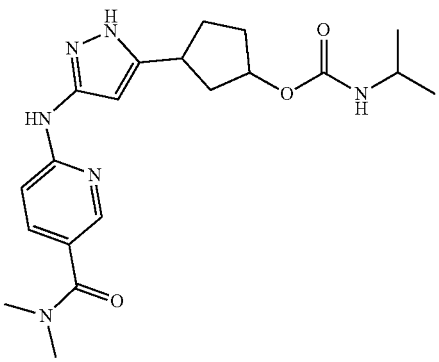
-continued
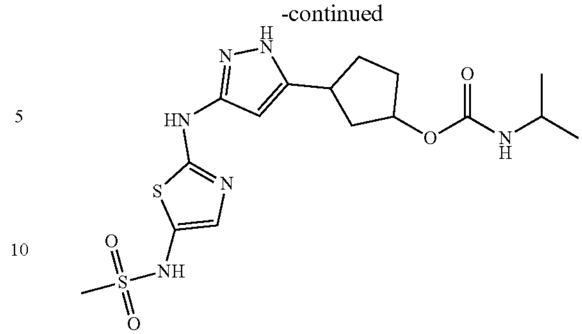
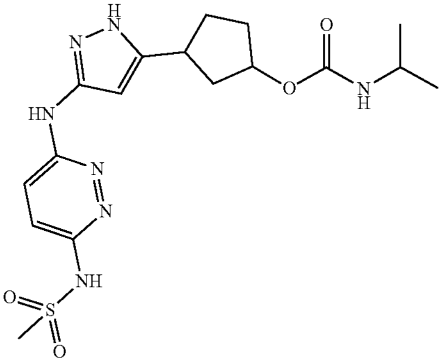
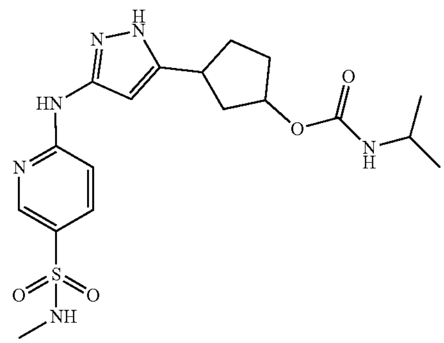
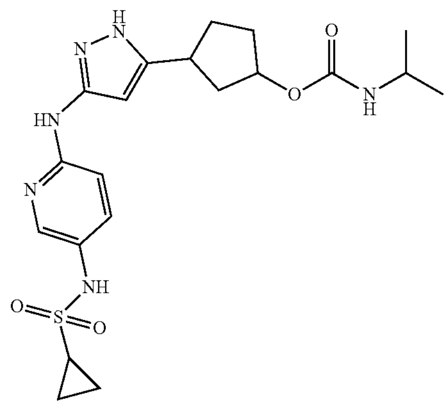

-continued
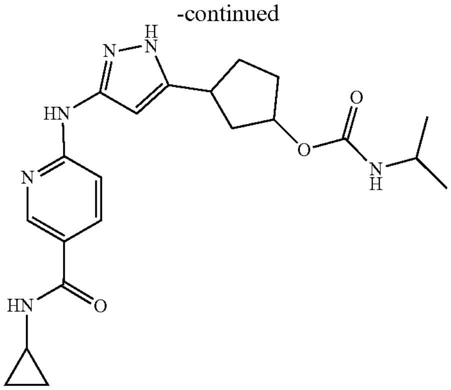
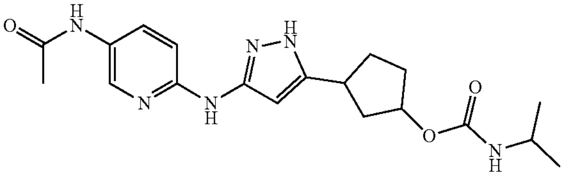
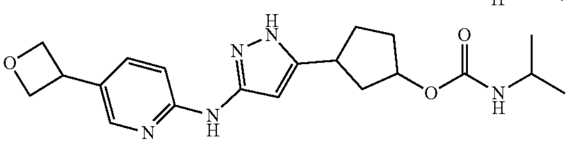
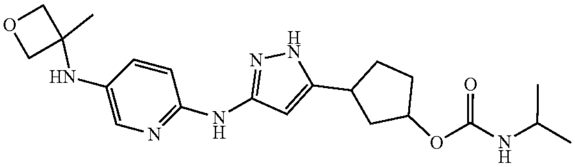
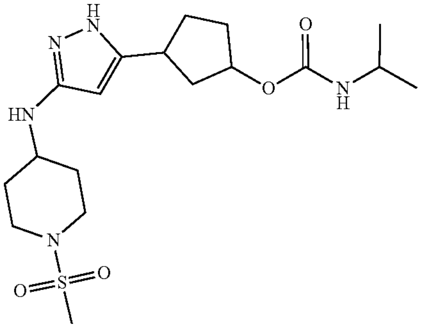
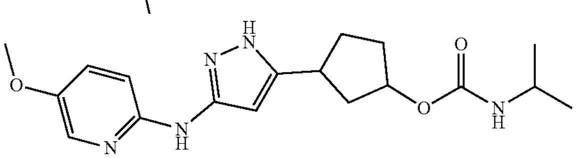
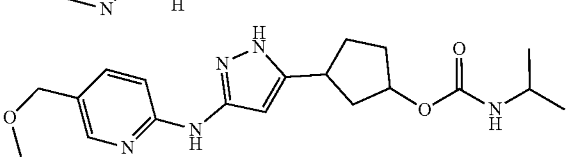
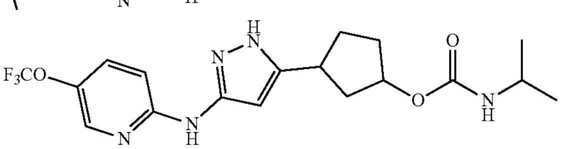
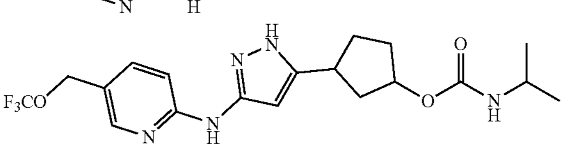
-continued
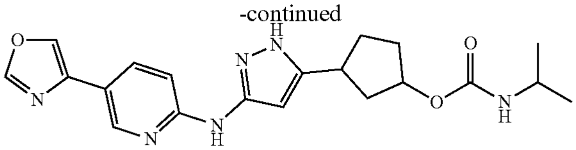
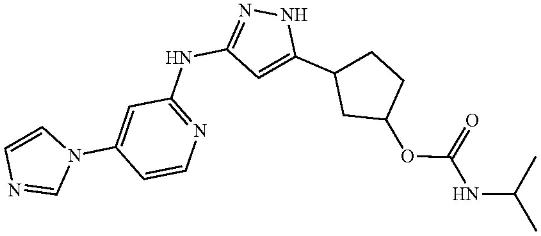
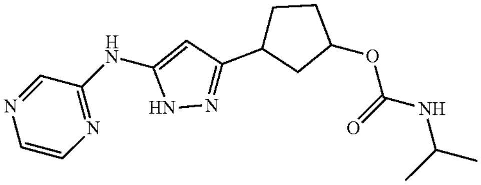
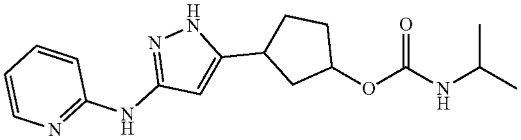
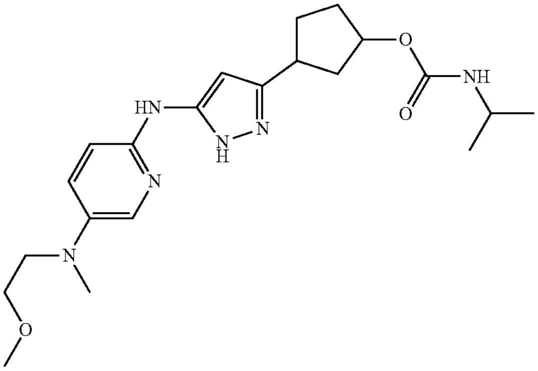
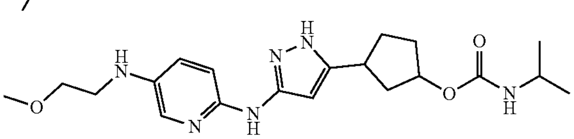
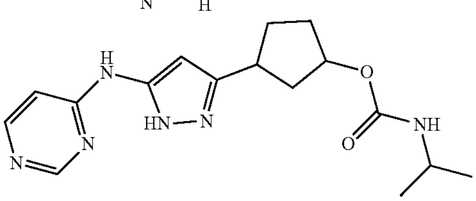
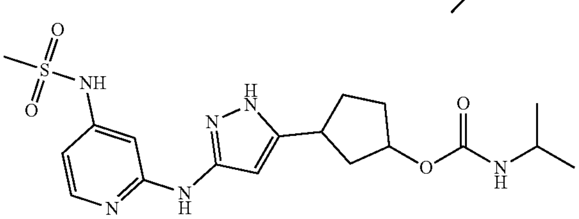
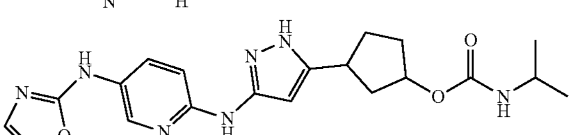

-continued
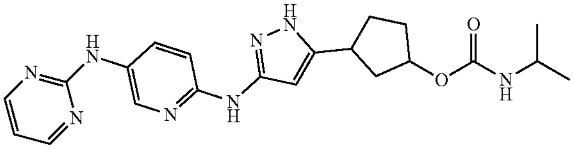
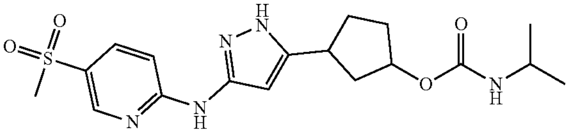
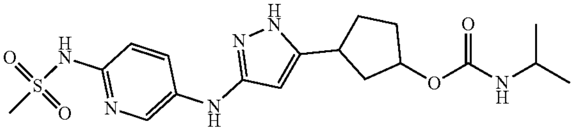
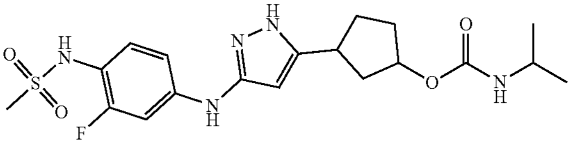
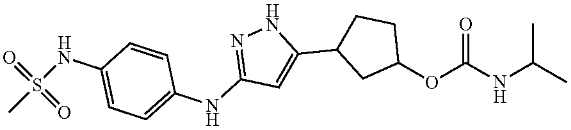
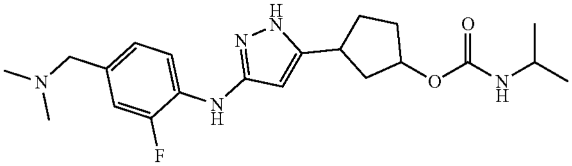
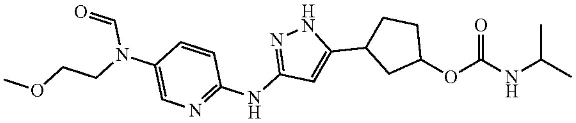
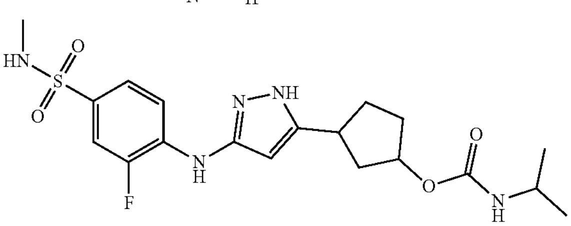
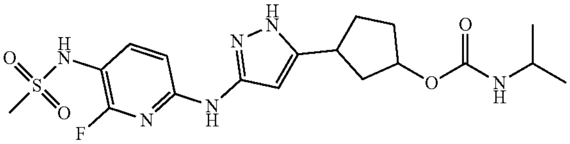
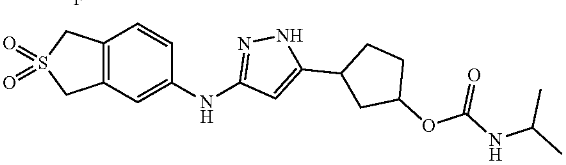
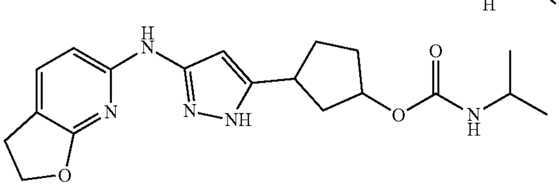
-continued
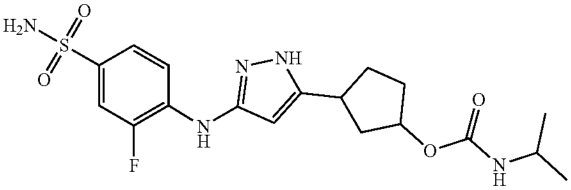
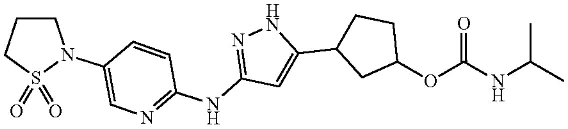
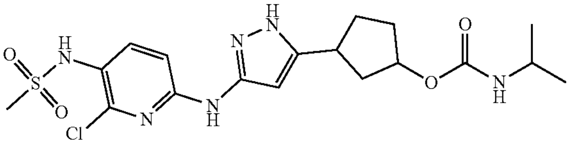
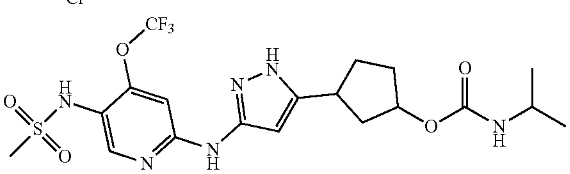
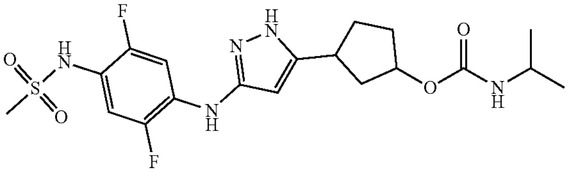
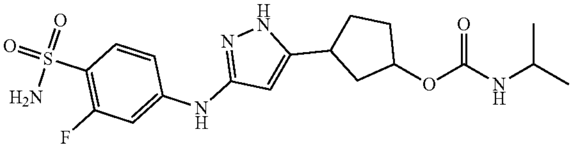
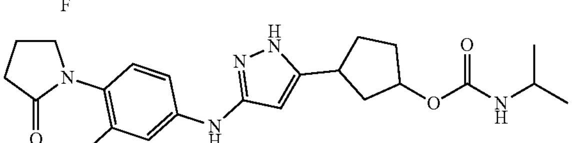
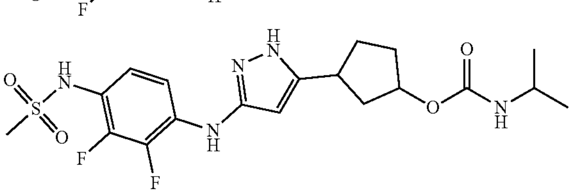
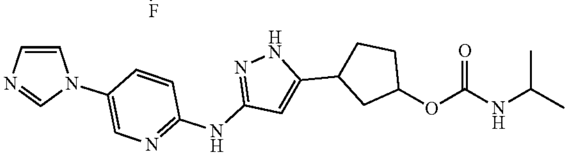
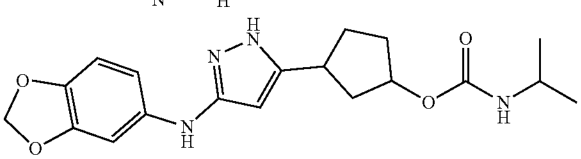
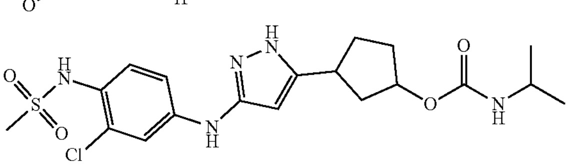

-continued
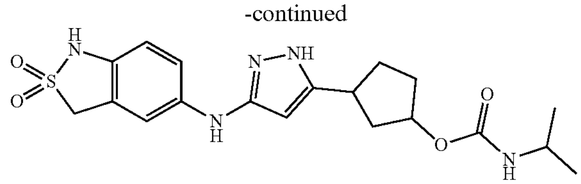
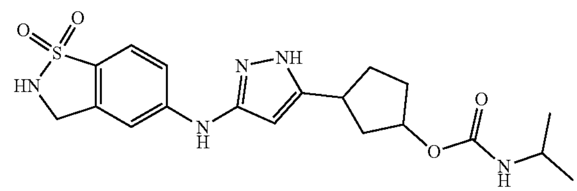
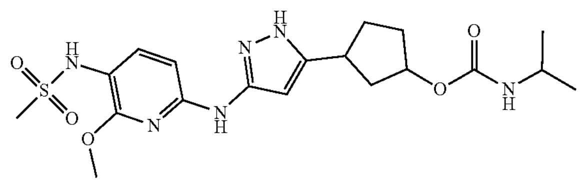
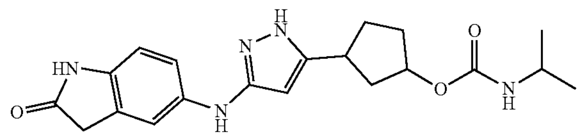
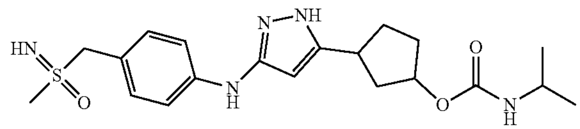
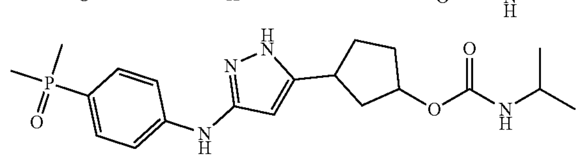
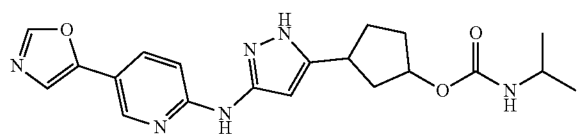
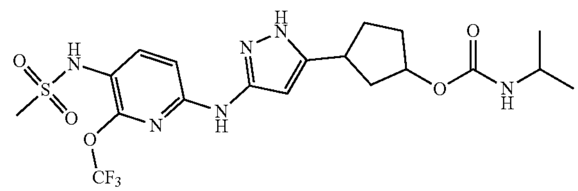
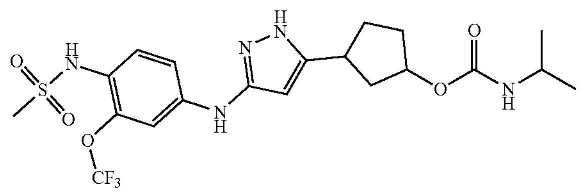
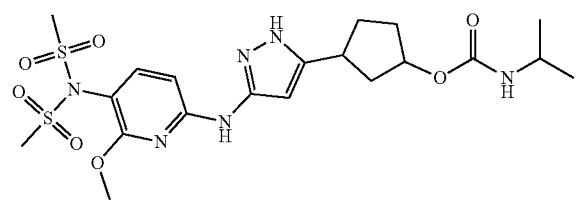
-continued
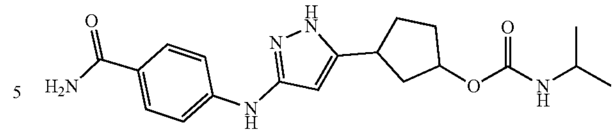
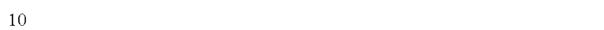
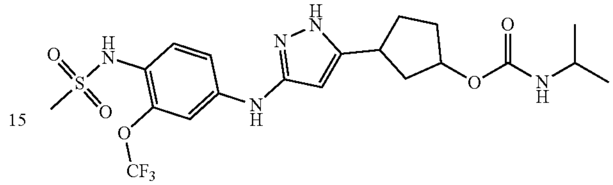
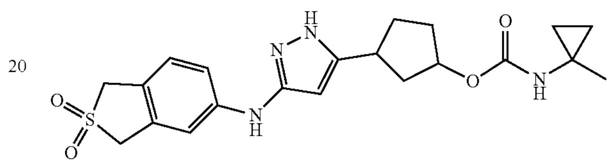
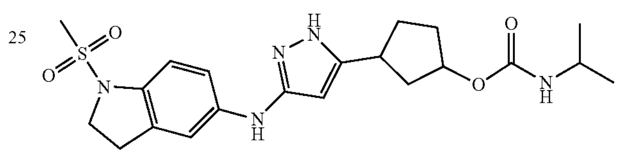
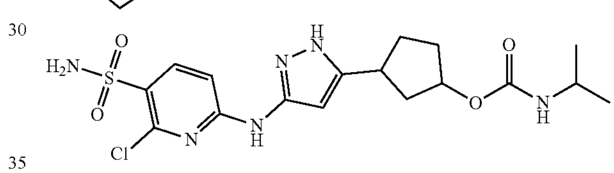
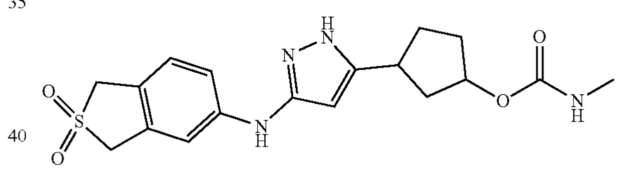
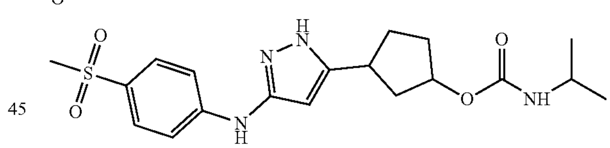
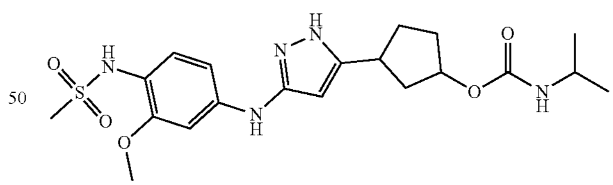
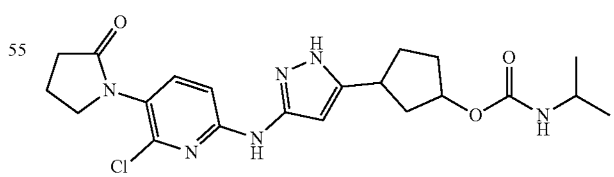
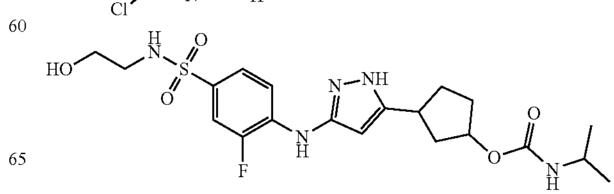

-continued
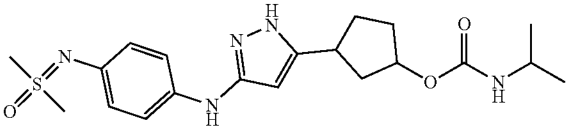
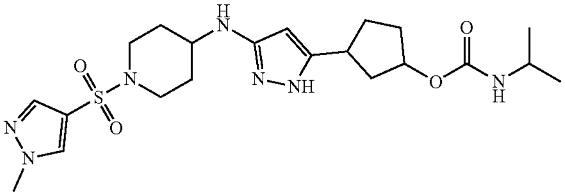
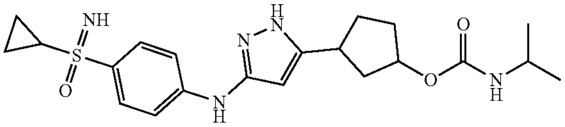
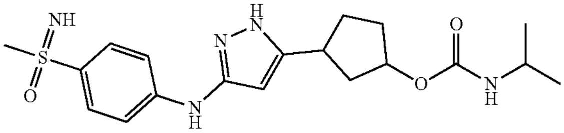
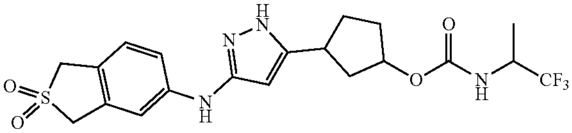
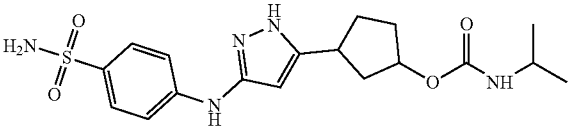
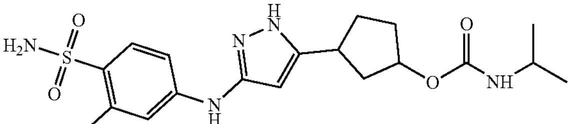
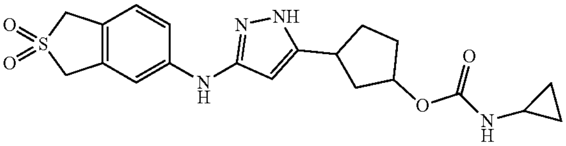
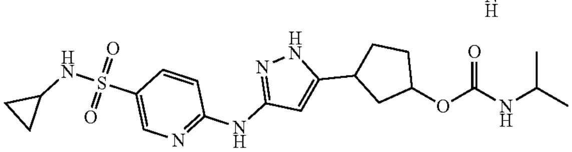
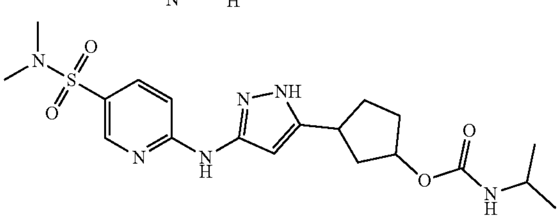
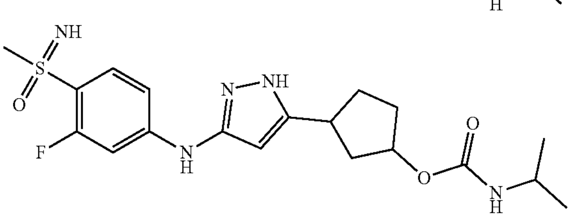
-continued
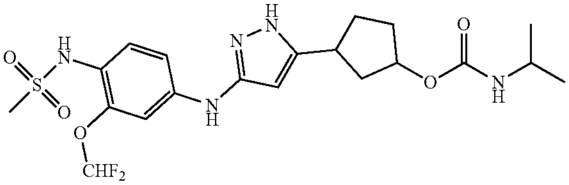
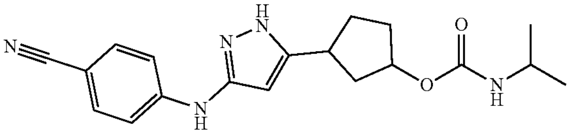
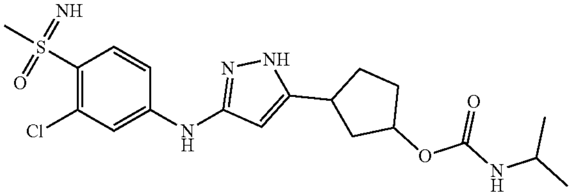
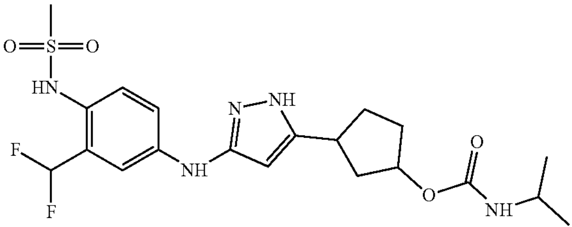
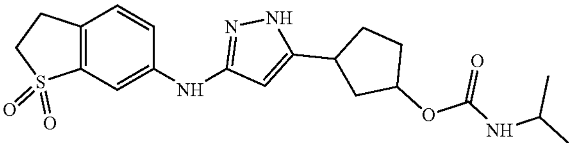
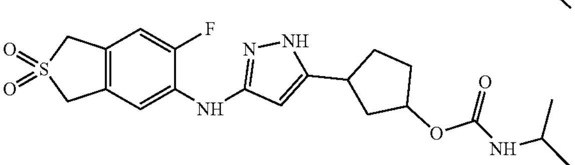
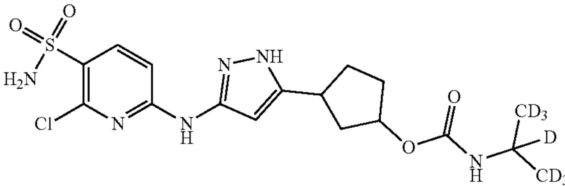
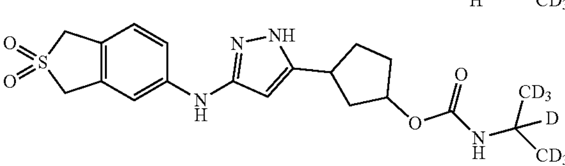
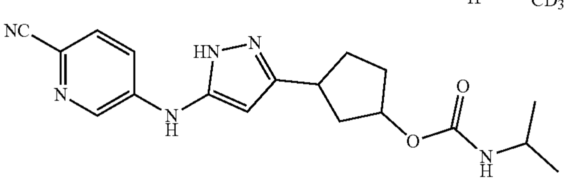
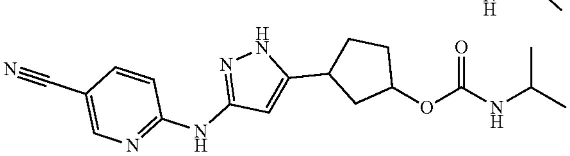

-continued
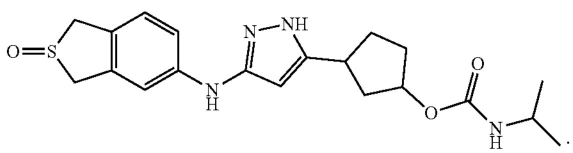
In another aspect, the present application further provides a compound of the formulas below, an isomer thereof, or a pharmaceutically acceptable salt thereof,
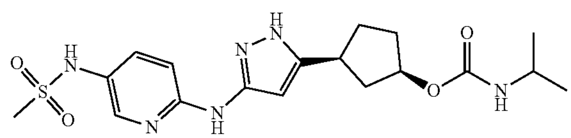
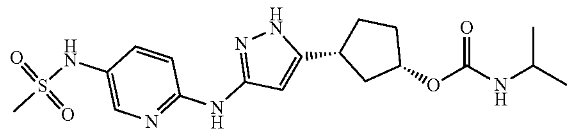
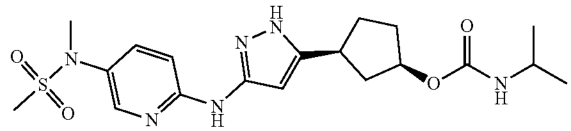
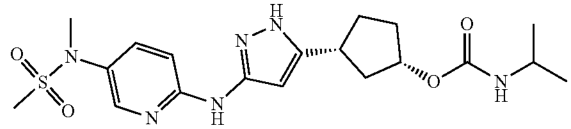
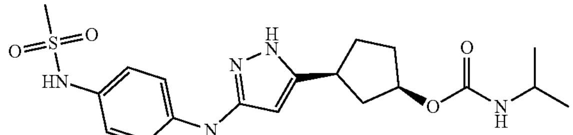
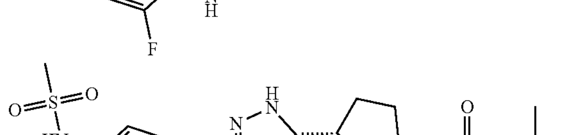
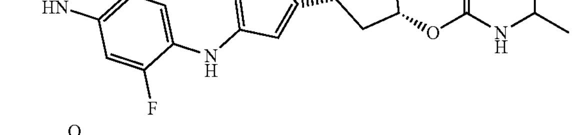
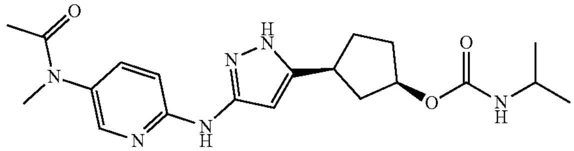
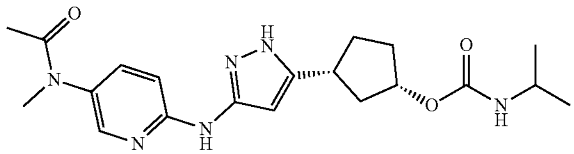
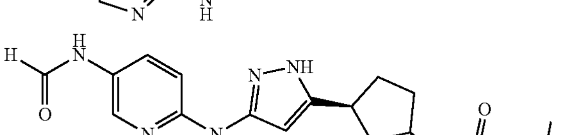
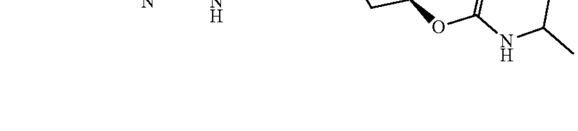
-continued
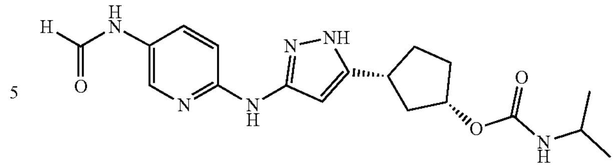
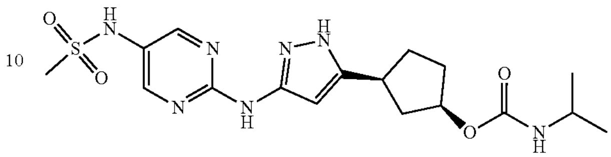
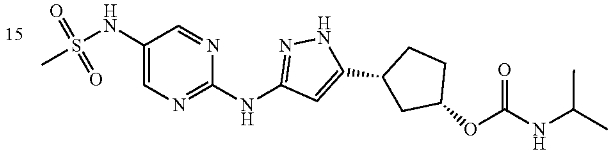
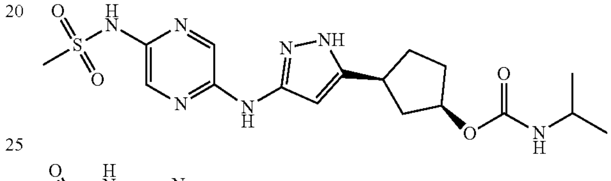
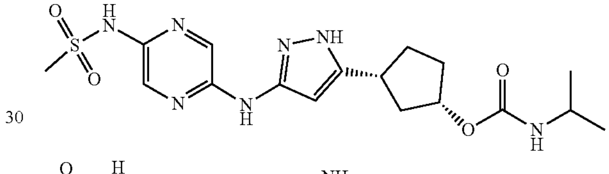
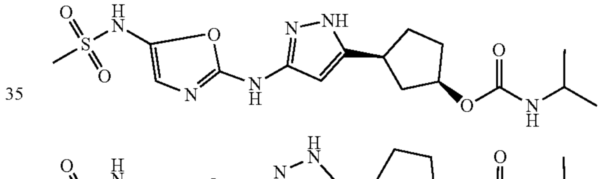
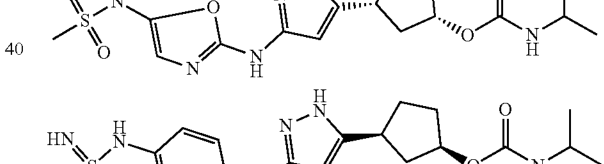
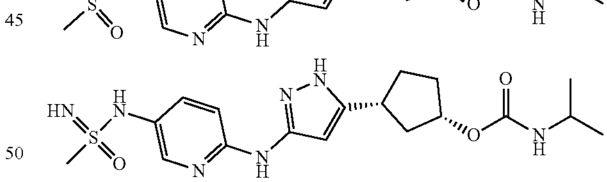
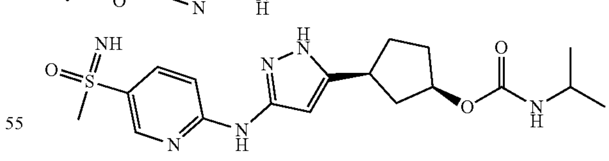
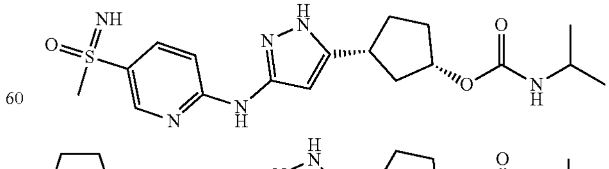
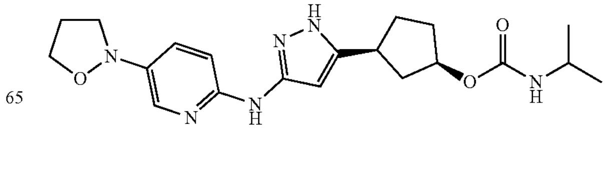

-continued
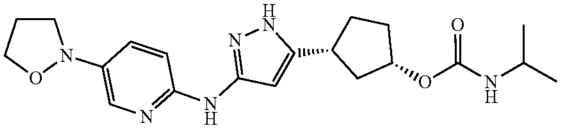
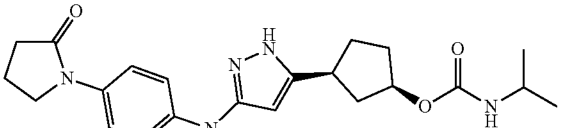
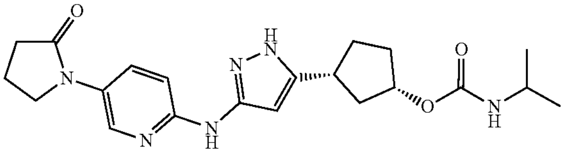
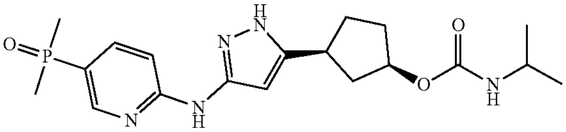
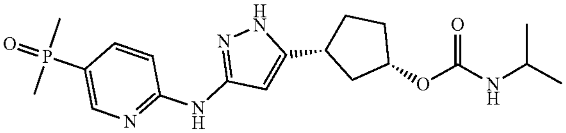
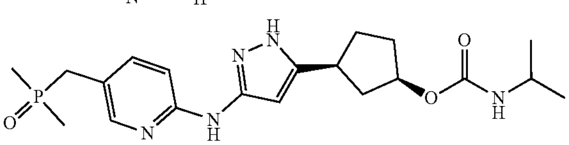
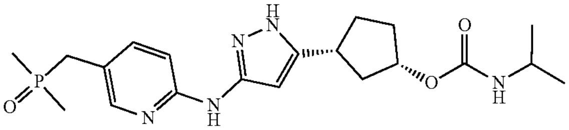
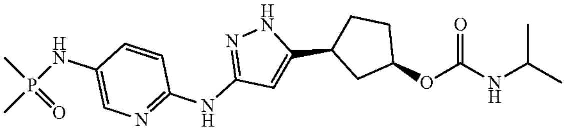
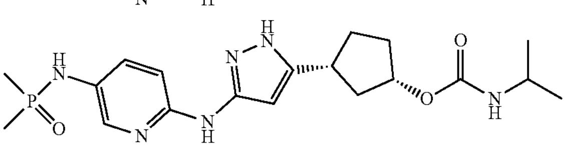
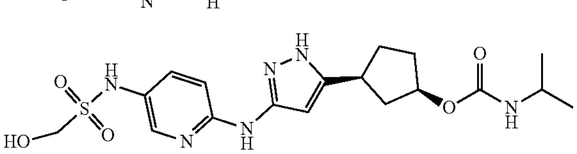
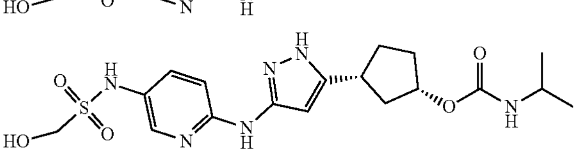
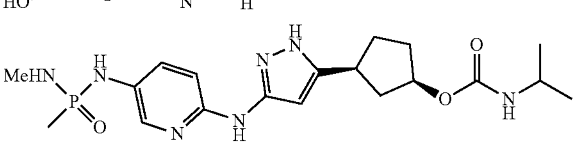
-continued
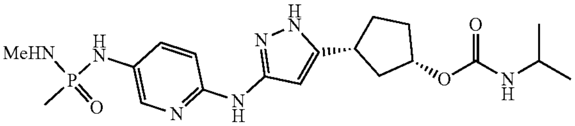
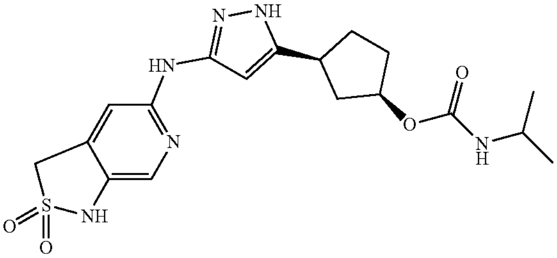
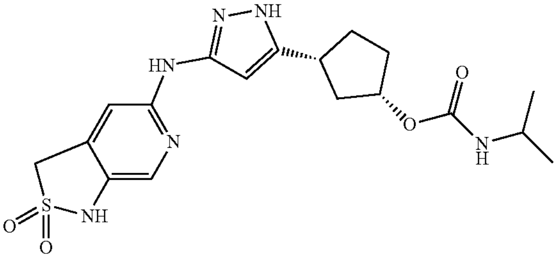
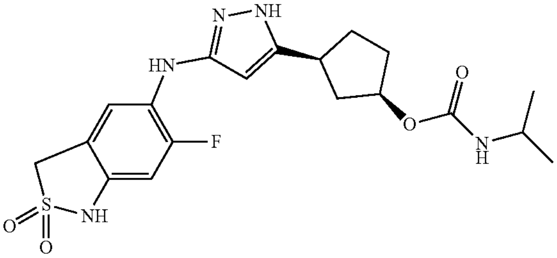
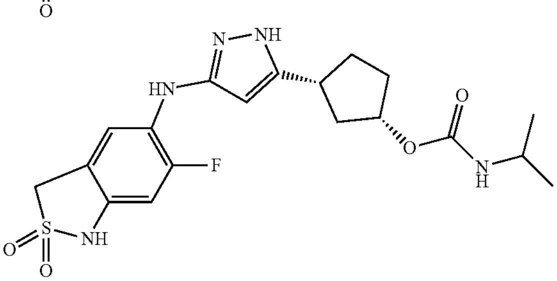
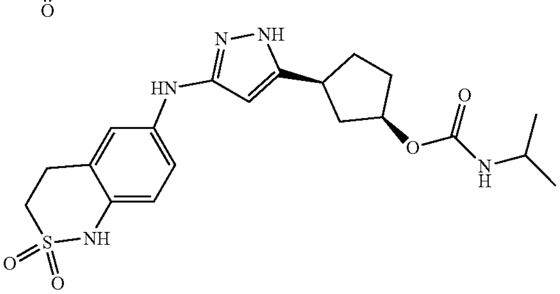
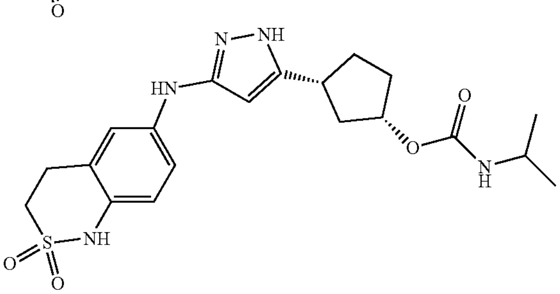

-continued
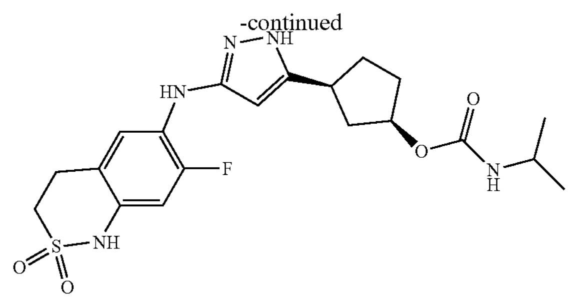
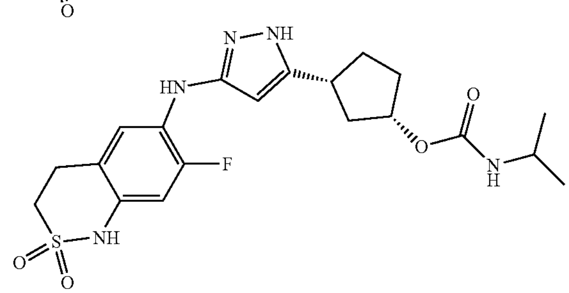
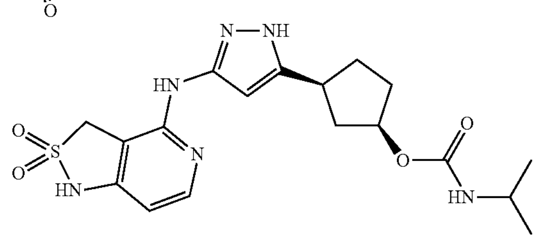
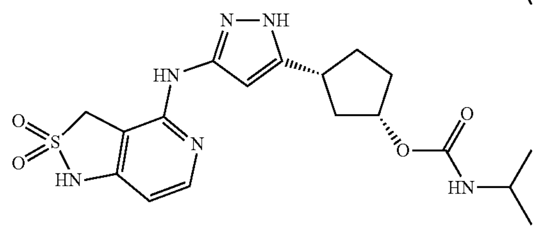
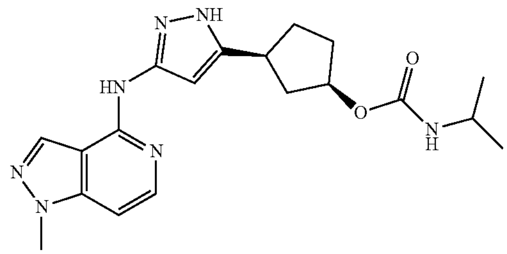
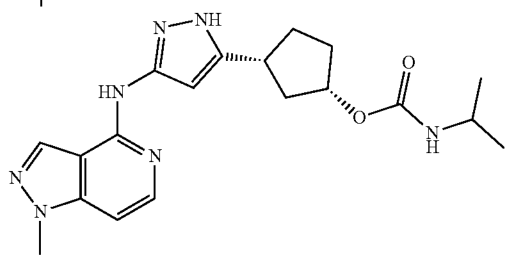
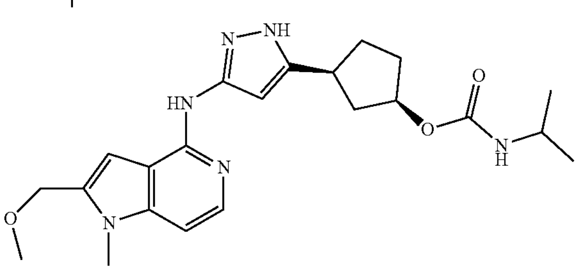
-continued
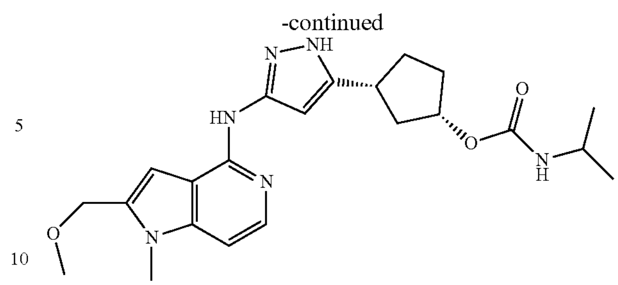
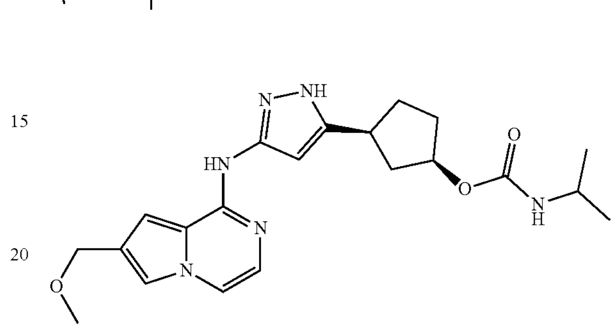
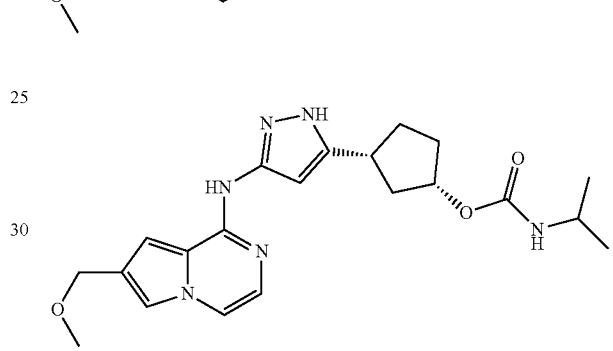
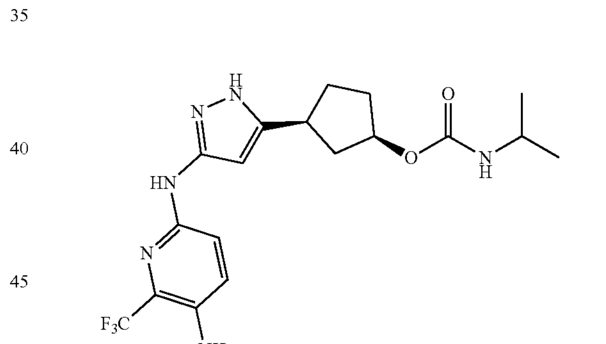
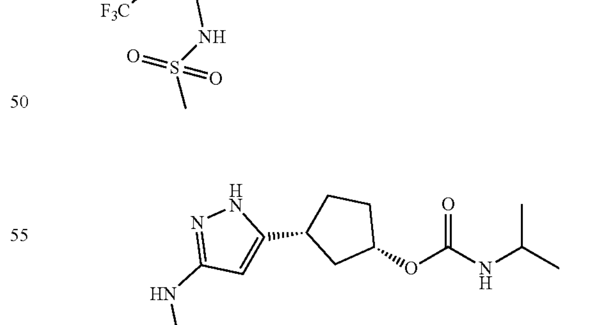
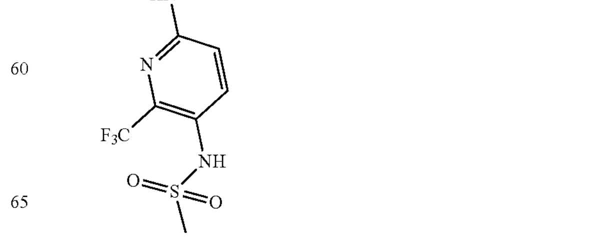

-continued
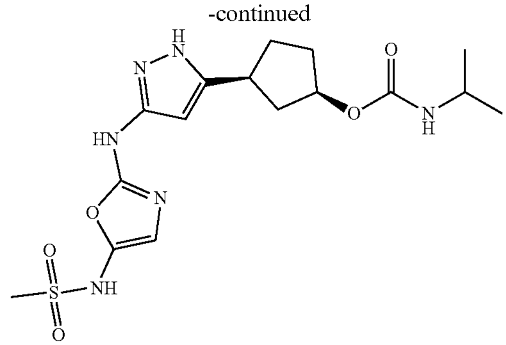
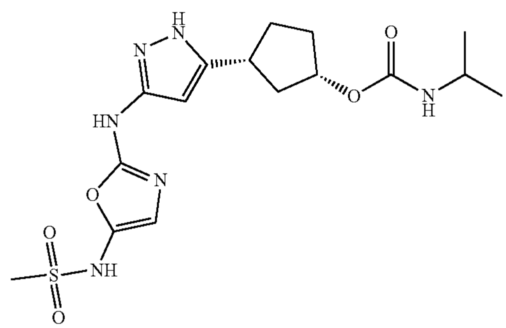
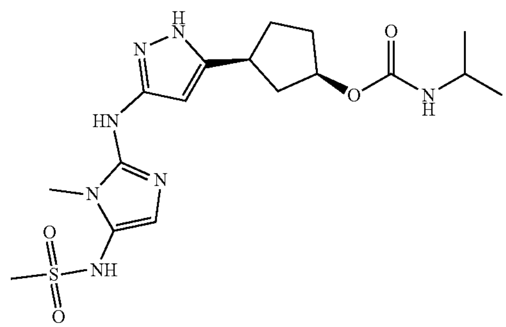
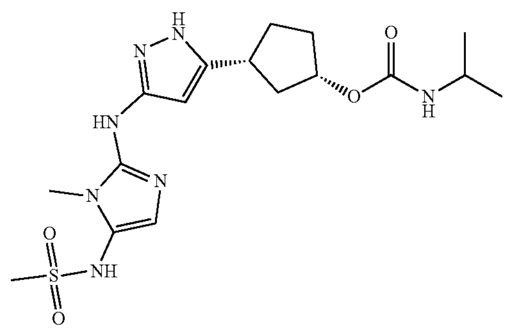
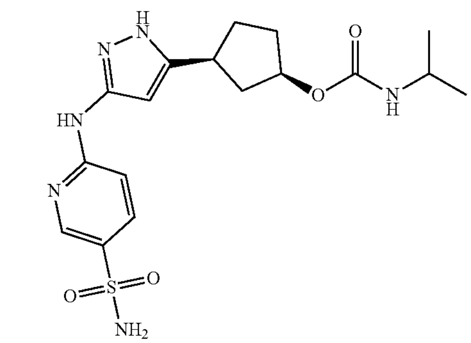
-continued
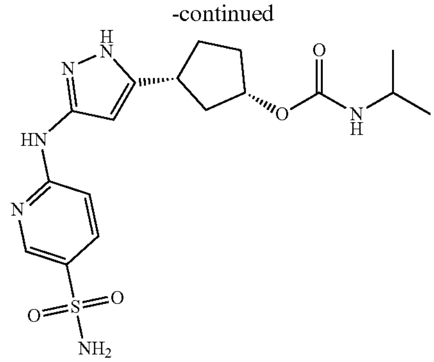
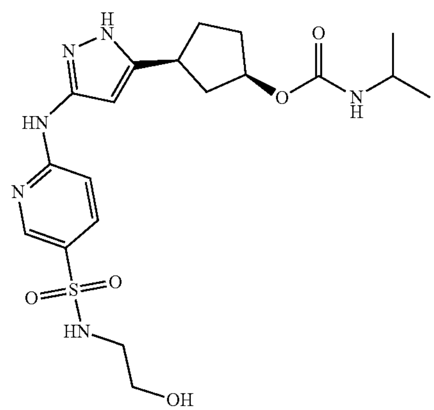
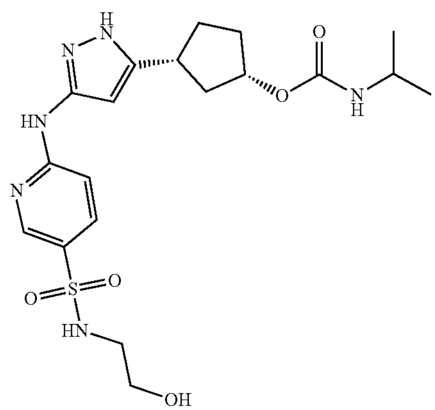
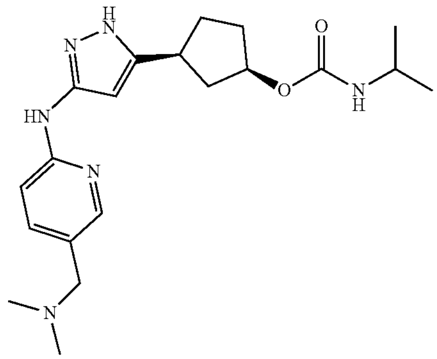

-continued
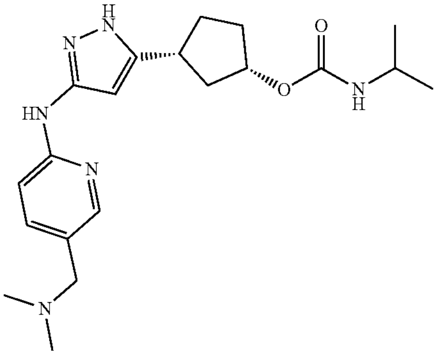
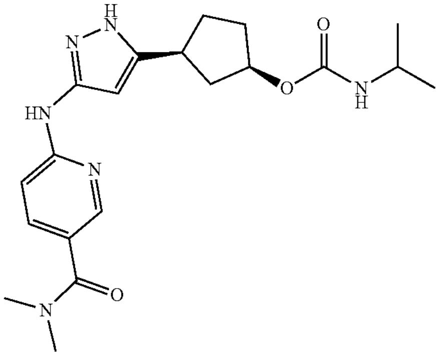
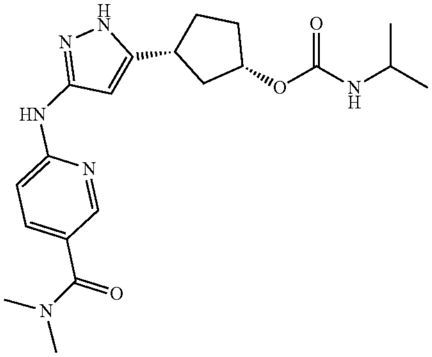
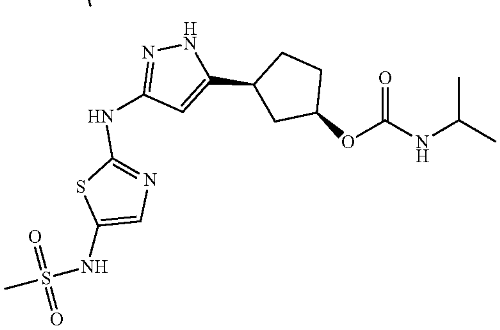
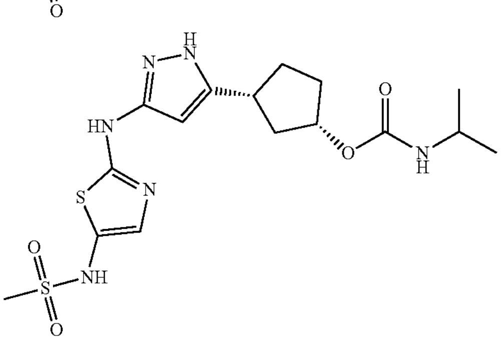
-continued
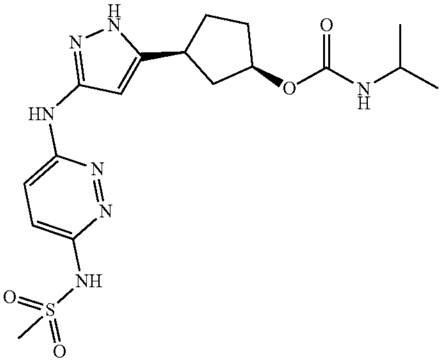
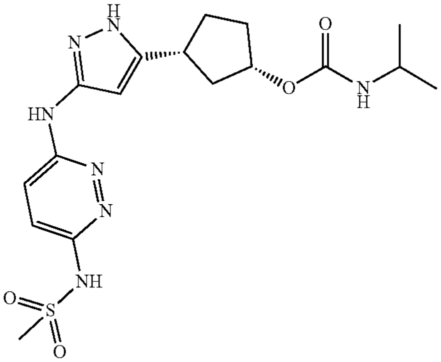
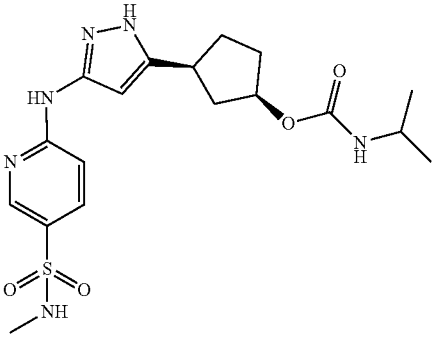
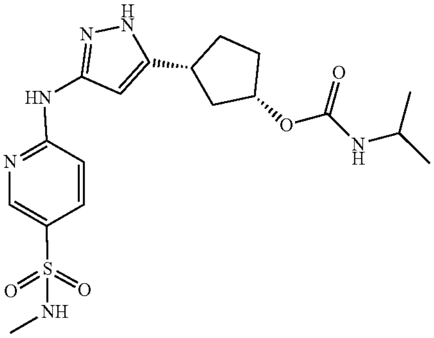

-continued
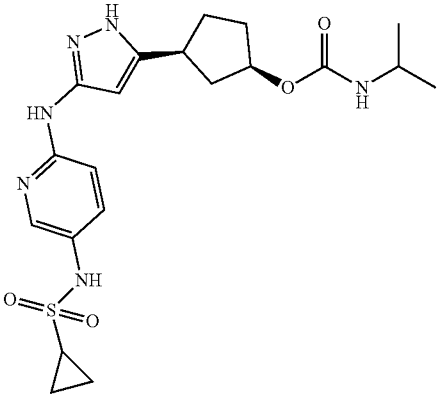
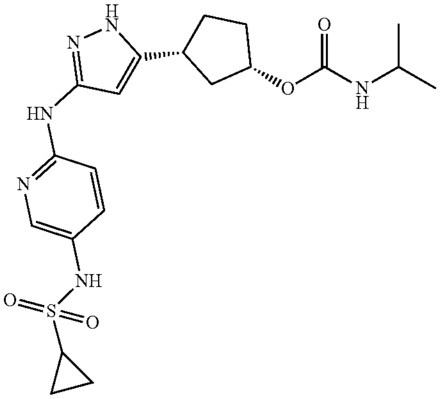
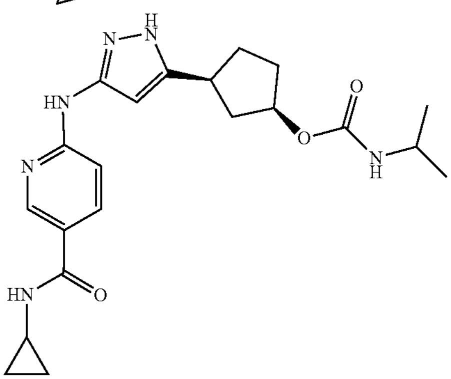
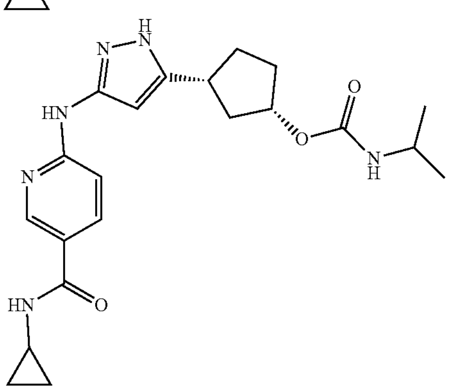
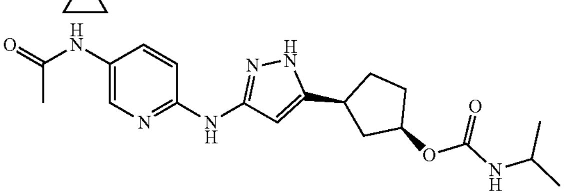
-continued
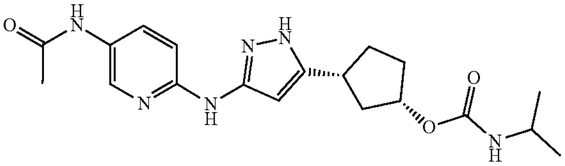
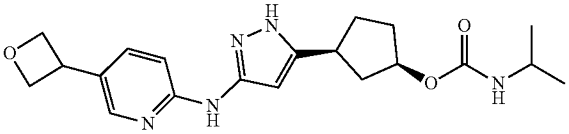
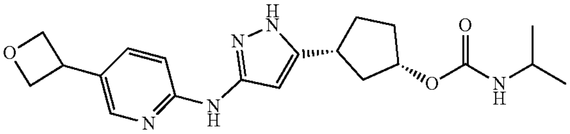
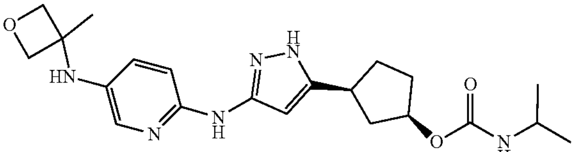
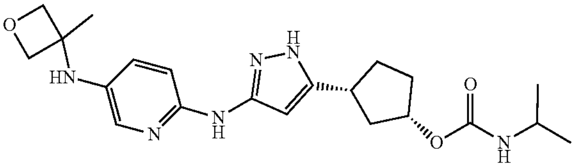
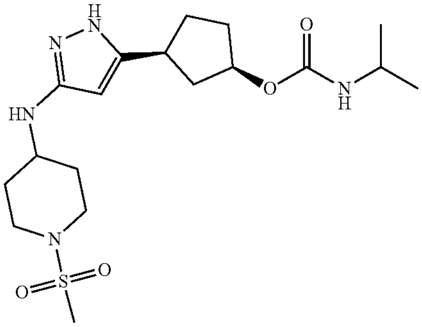
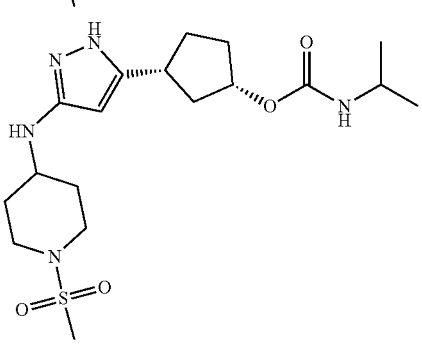
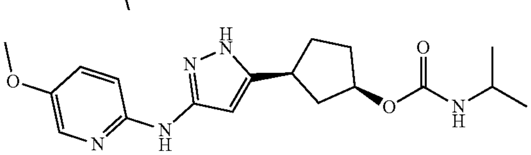

-continued
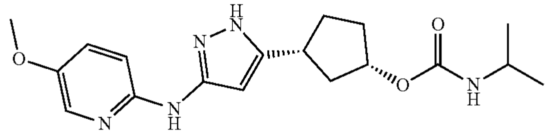
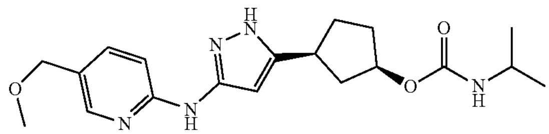
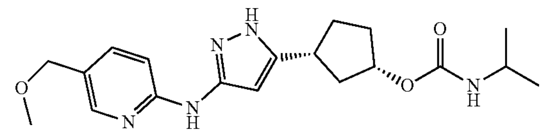
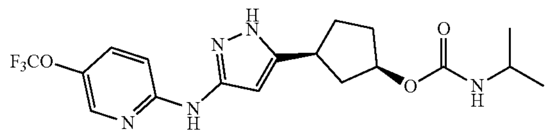
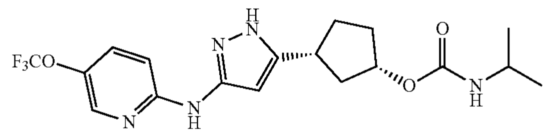
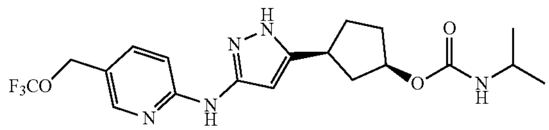
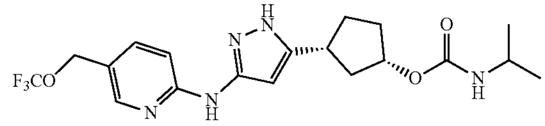
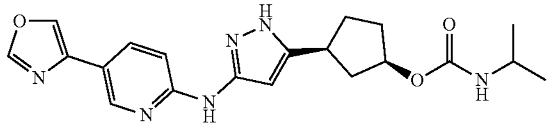
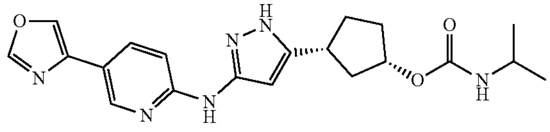
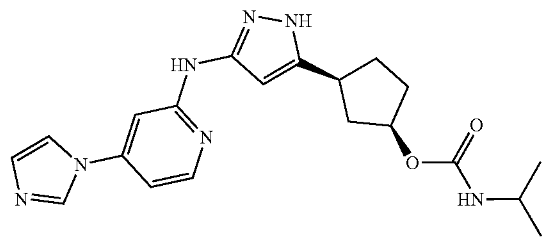
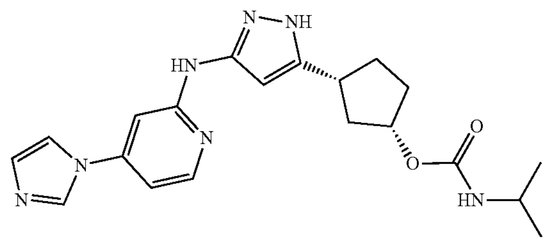
-continued
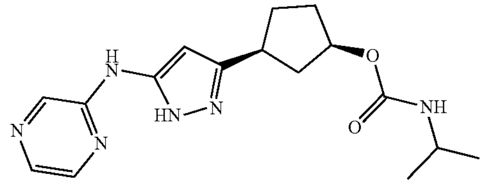
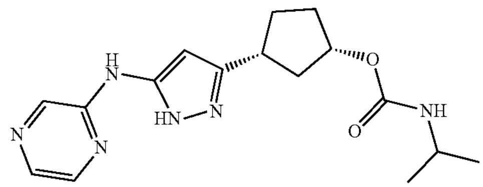
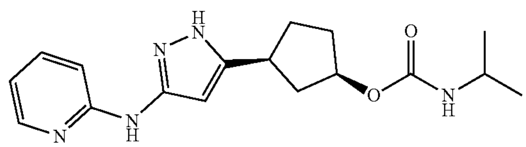
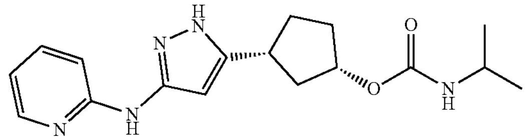
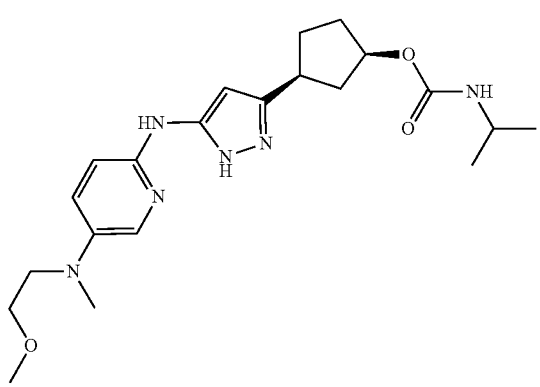
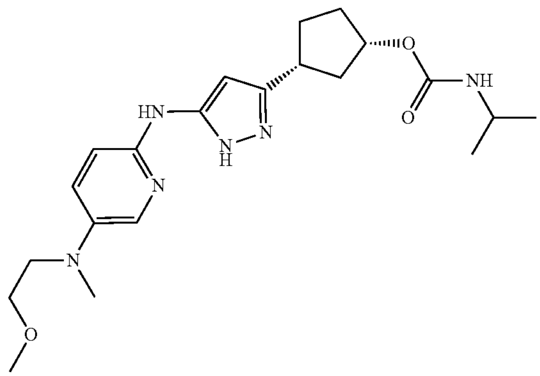
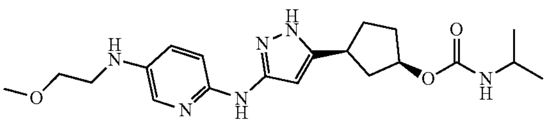
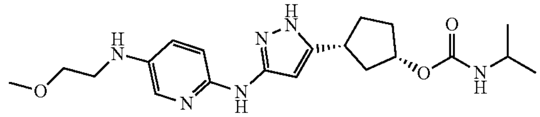

-continued
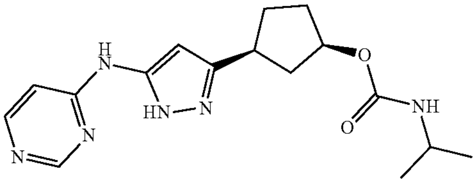
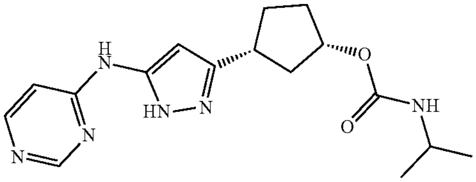
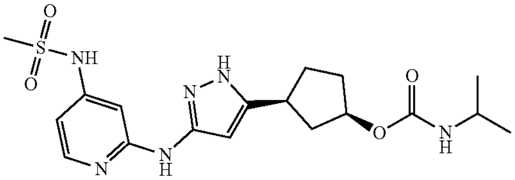
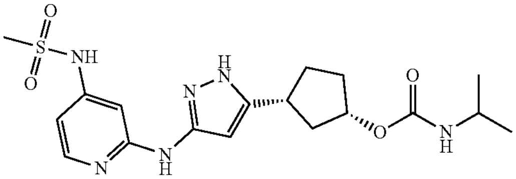
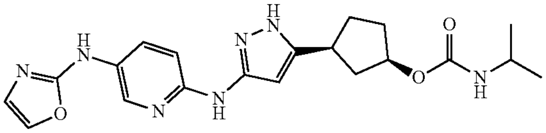
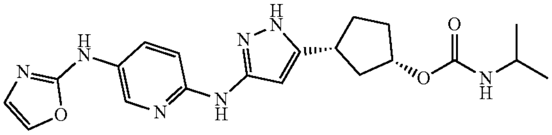
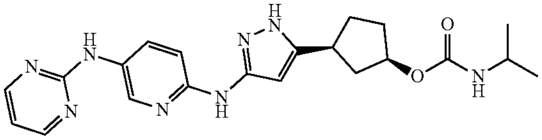
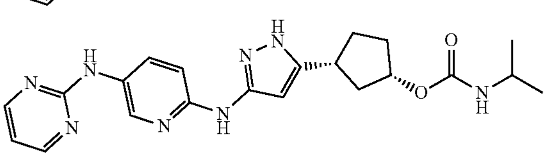
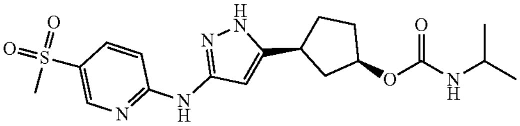
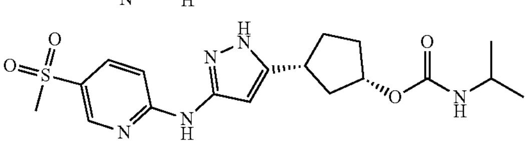
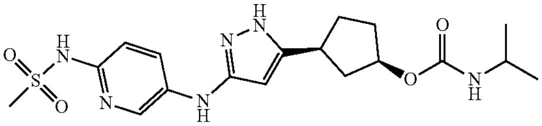
-continued
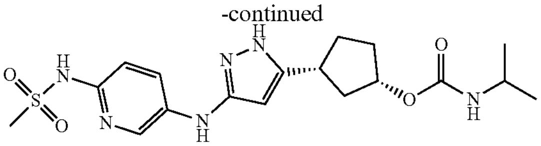
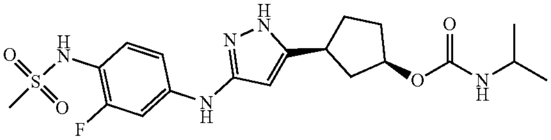
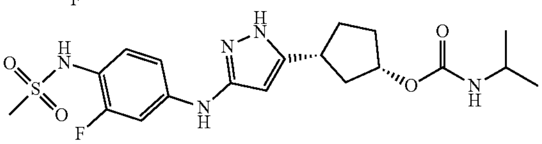
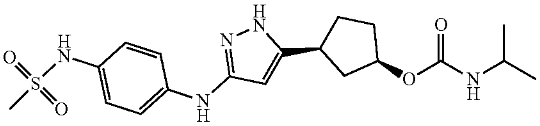
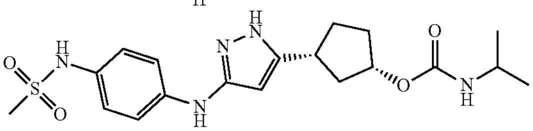
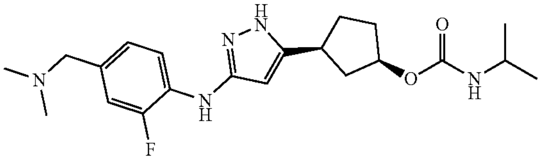
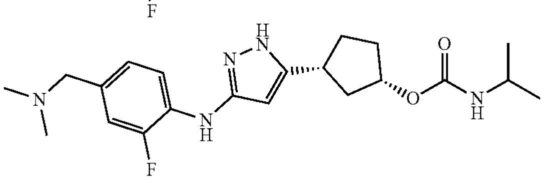
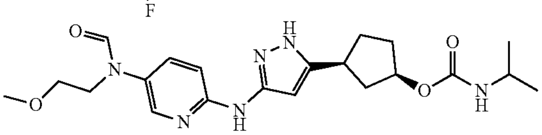
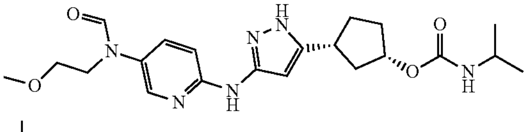
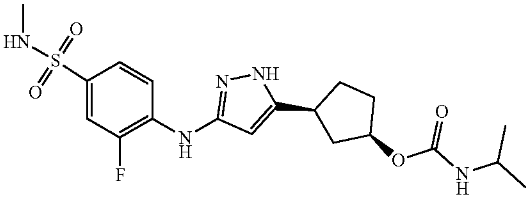
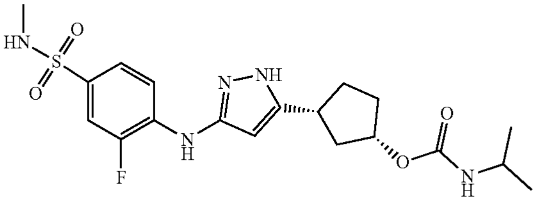
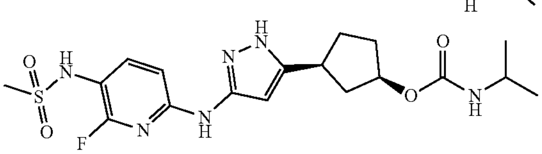

-continued
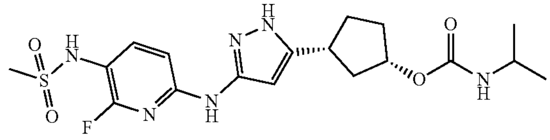
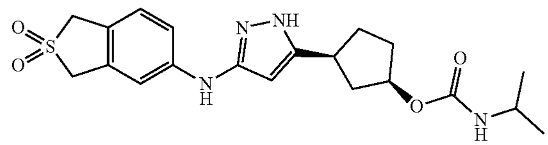
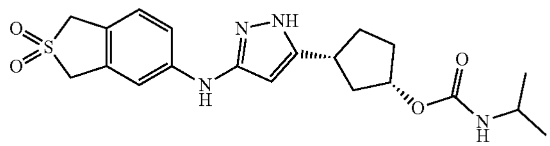
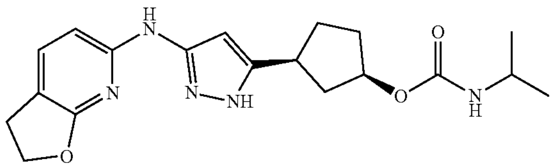
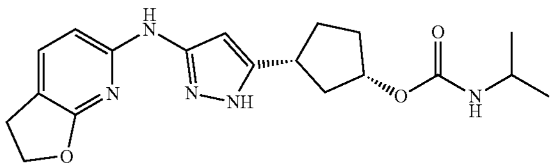
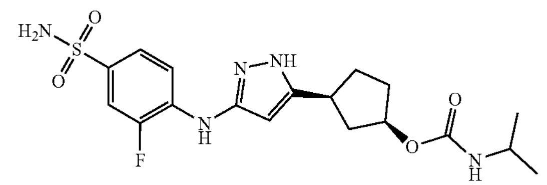
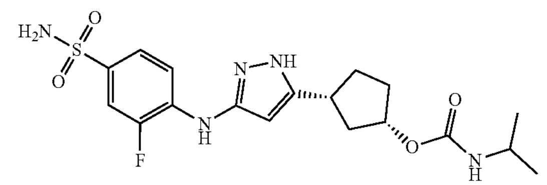
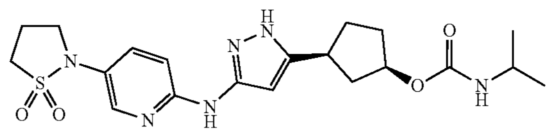
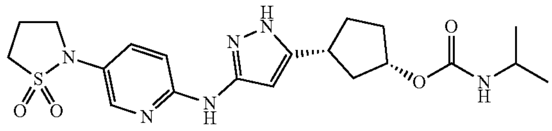
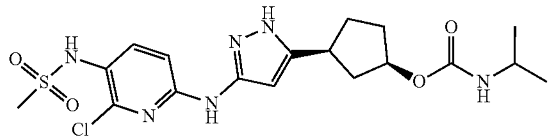
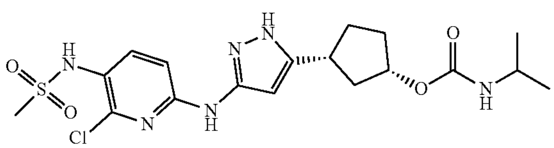
-continued
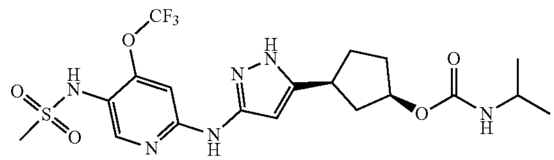
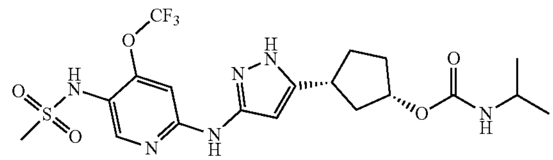
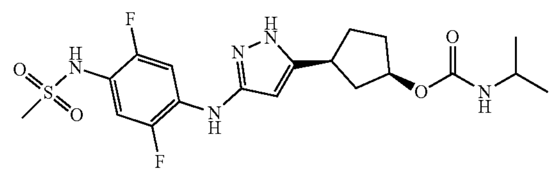
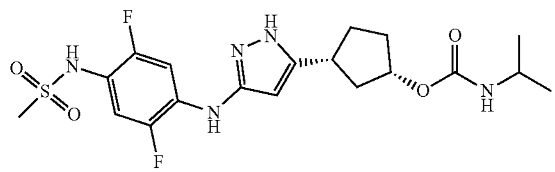
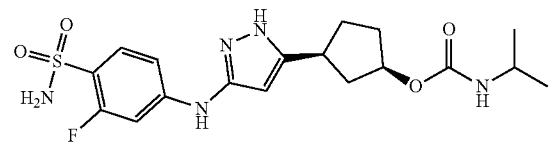
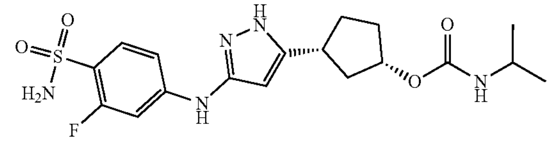
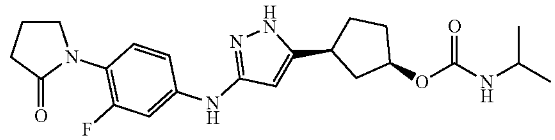
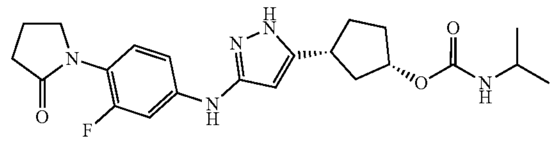
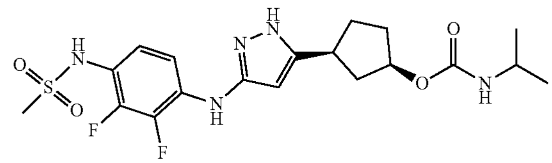
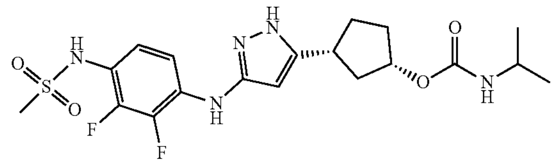
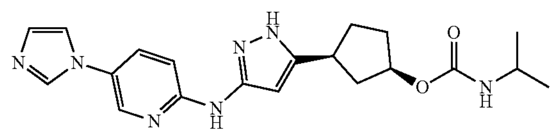

-continued
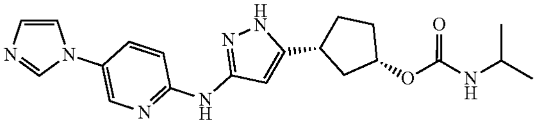
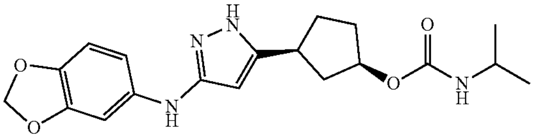
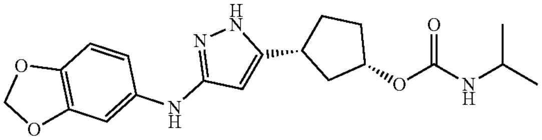
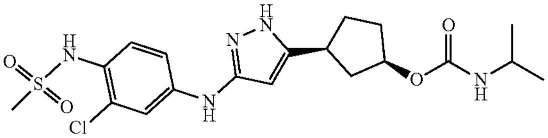
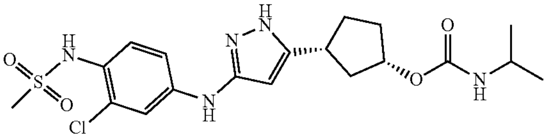
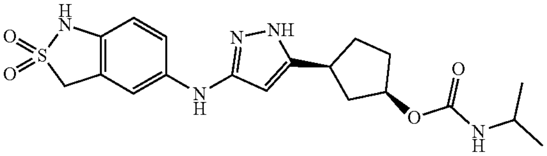
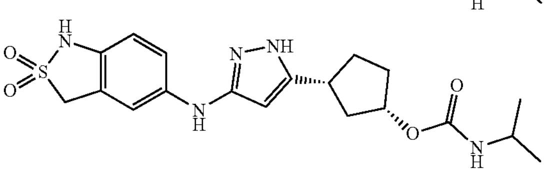
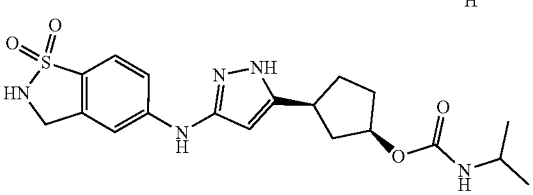
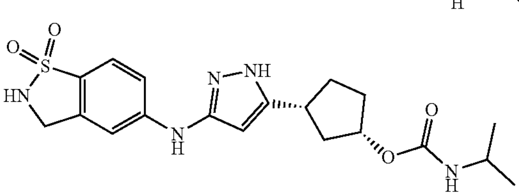
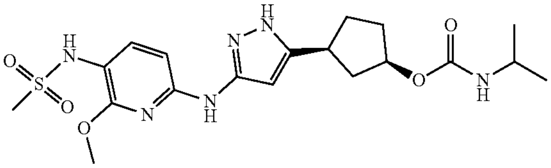
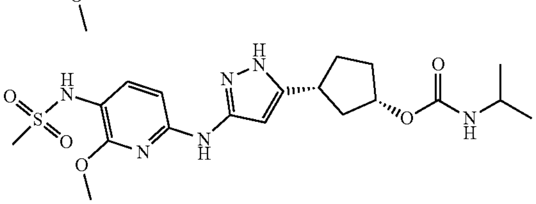
-continued
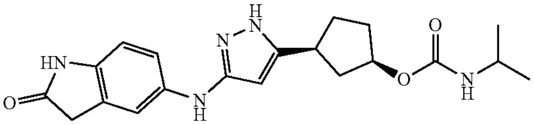
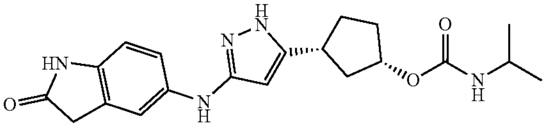
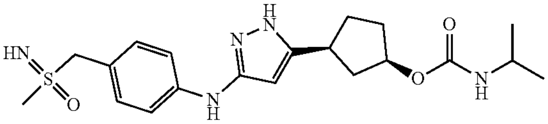
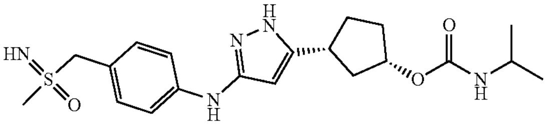
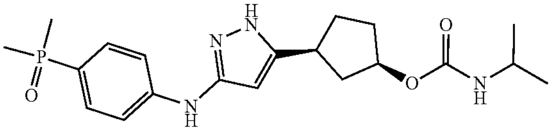
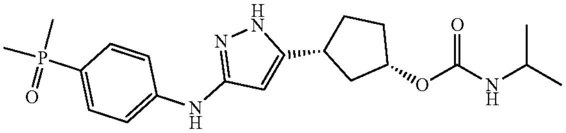
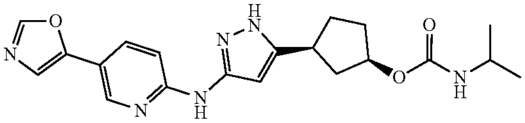
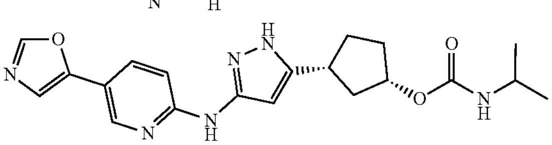
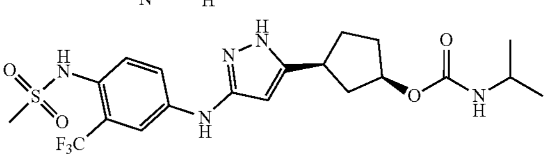
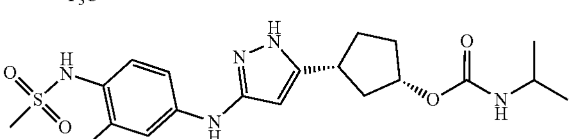
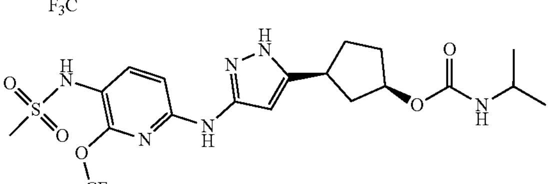
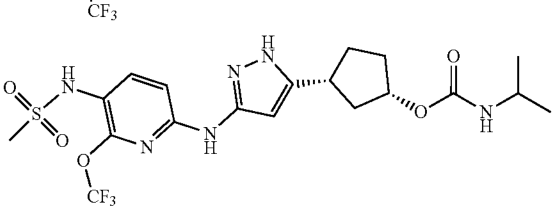

-continued
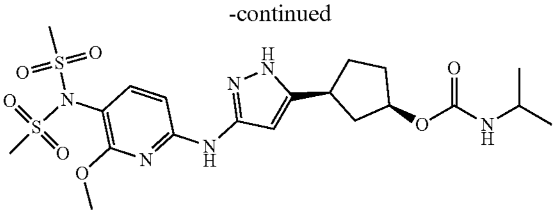
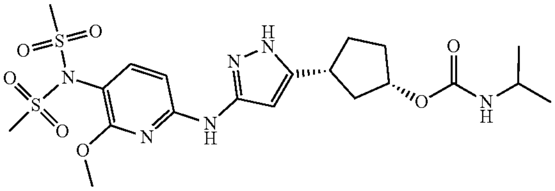
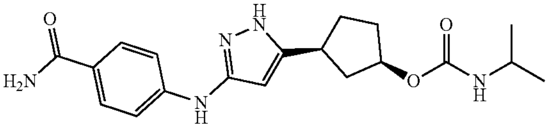
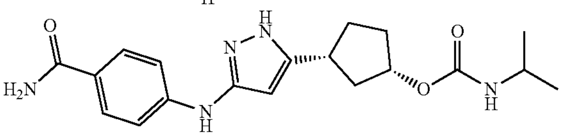
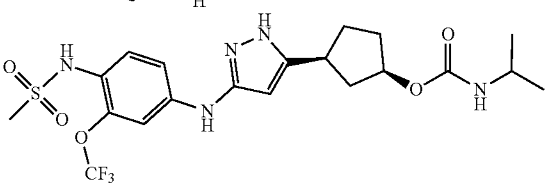
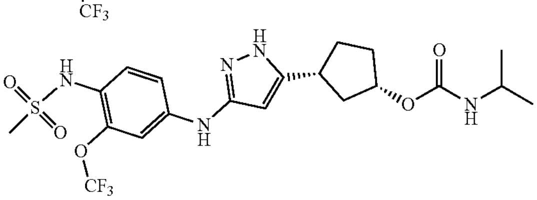
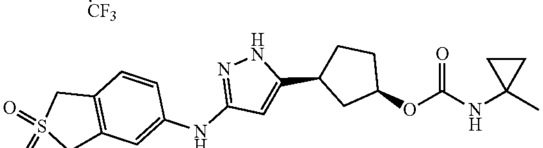
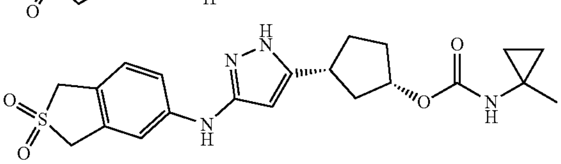
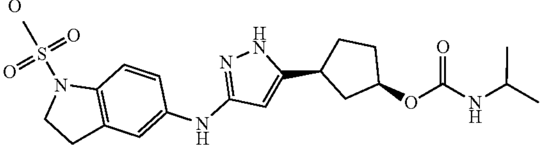
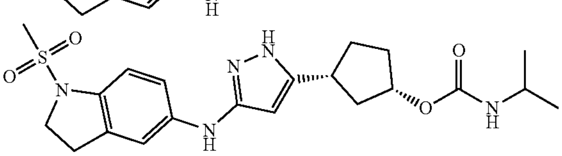
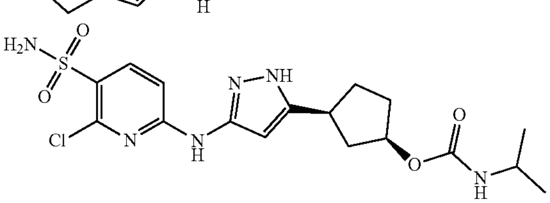
-continued
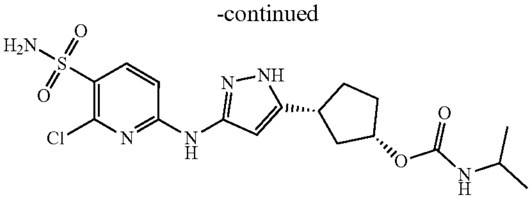
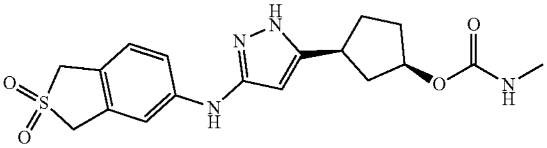
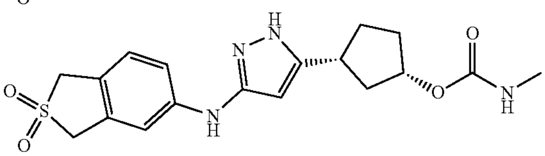
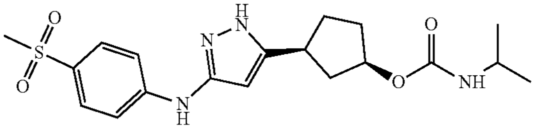
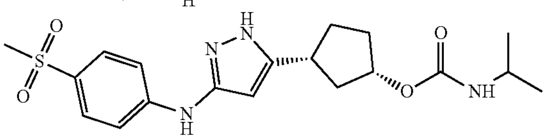
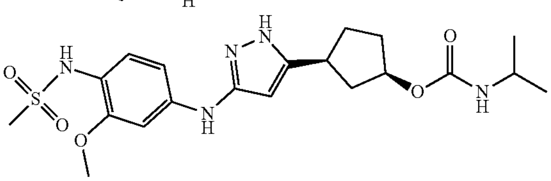
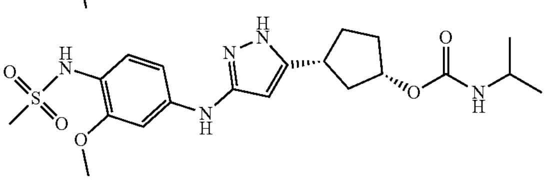
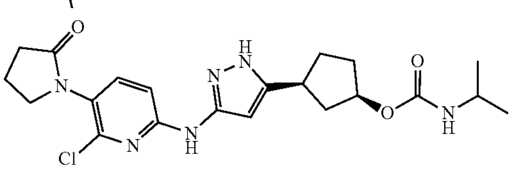
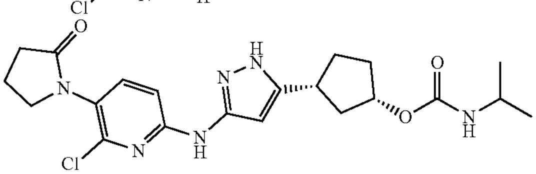
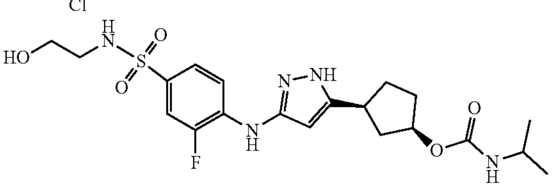
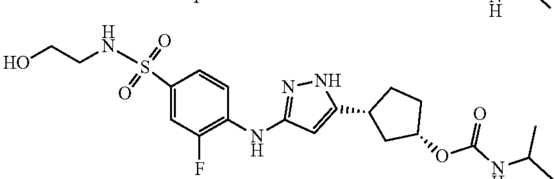

-continued
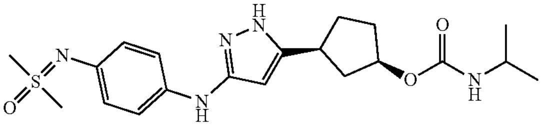
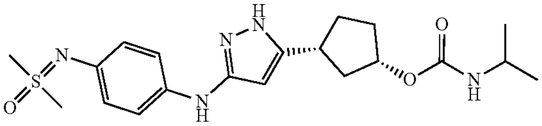
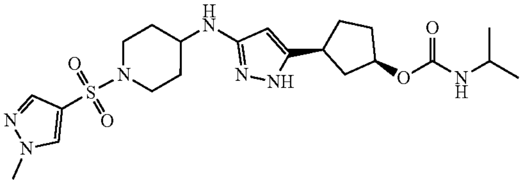
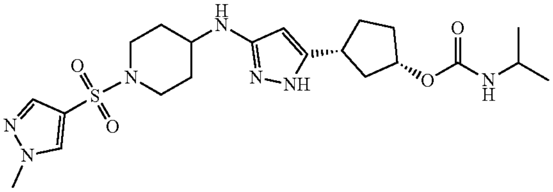
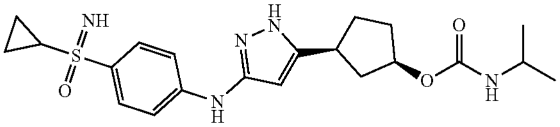
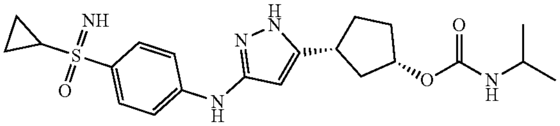
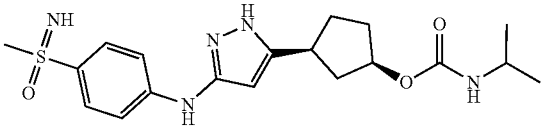
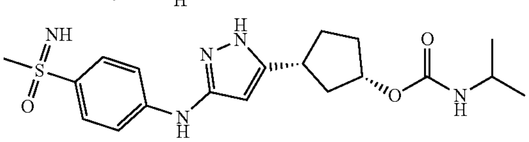
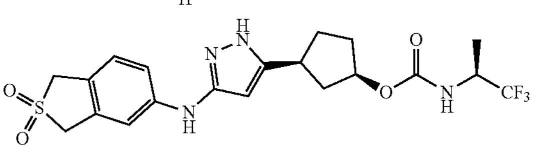
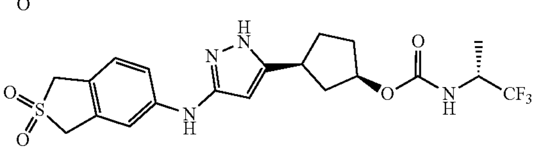
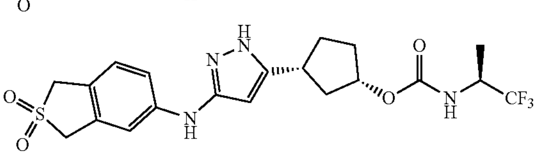
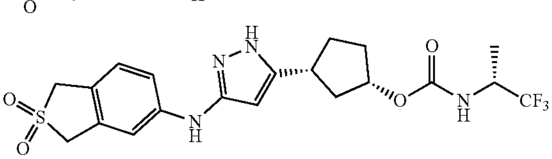
-continued
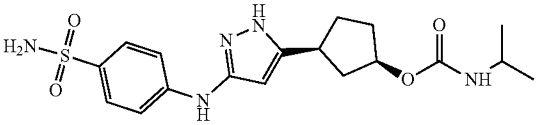
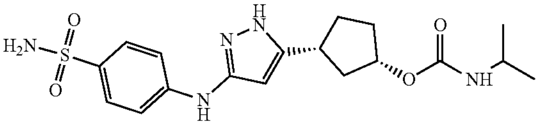
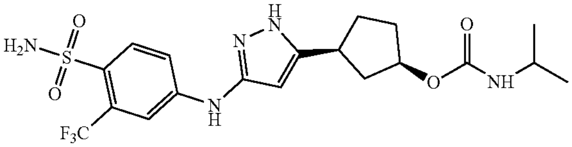
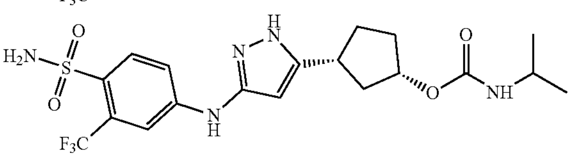
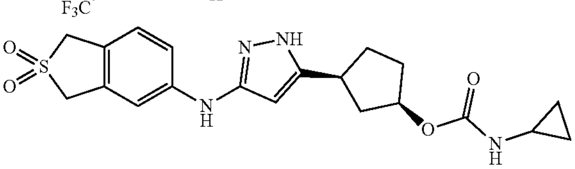
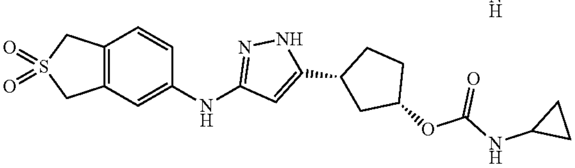
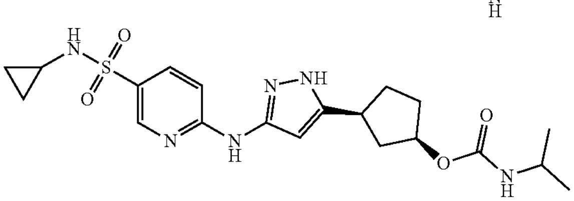
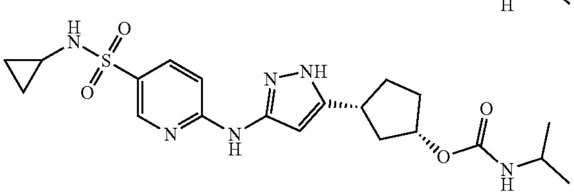
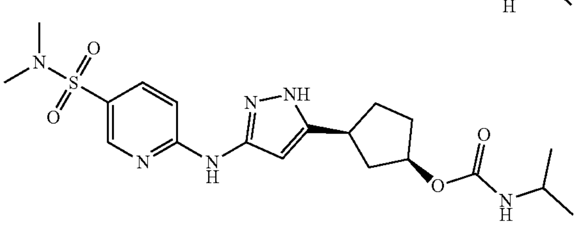
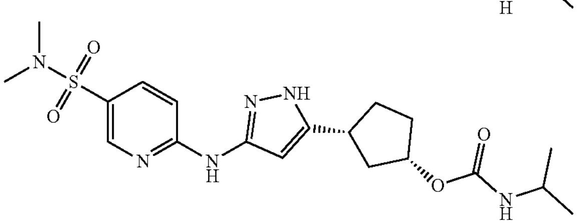

-continued
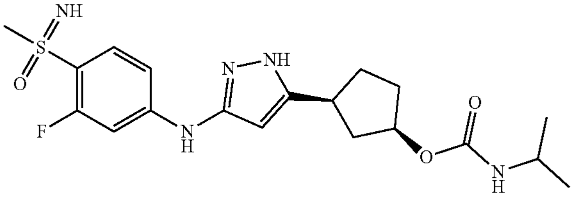
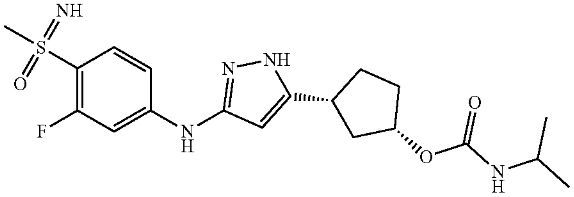
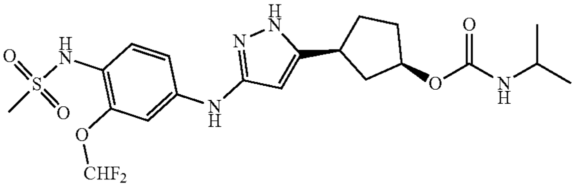
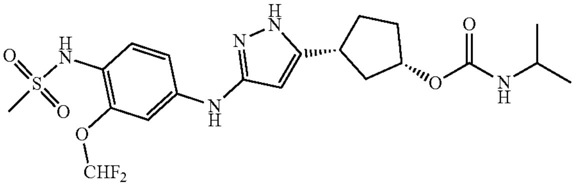
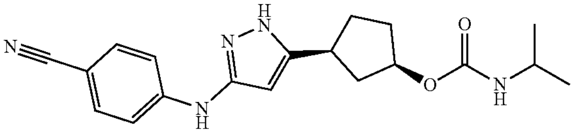
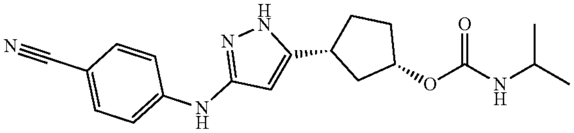
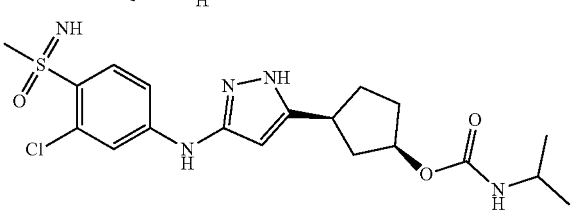
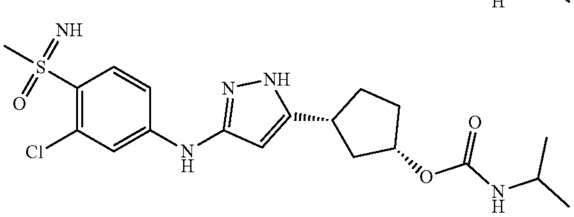
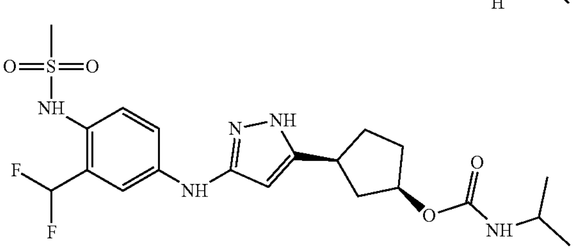
-continued
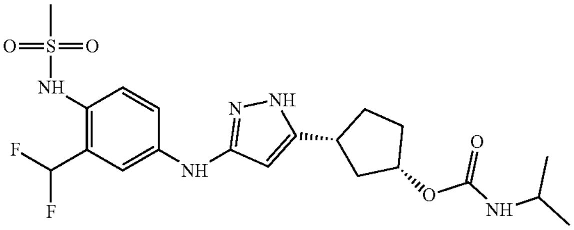
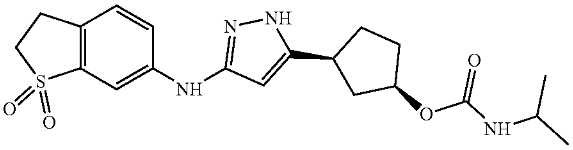
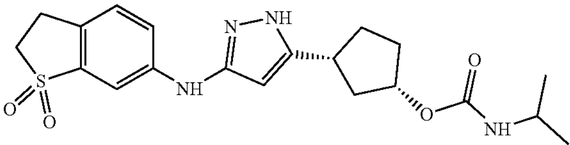
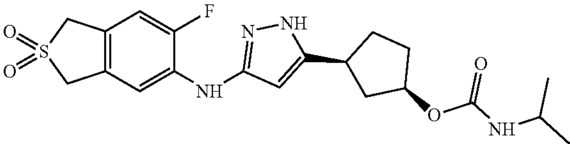
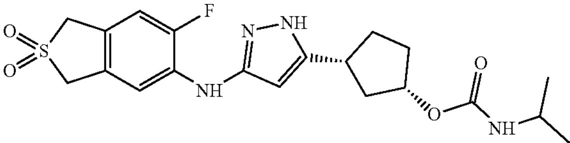
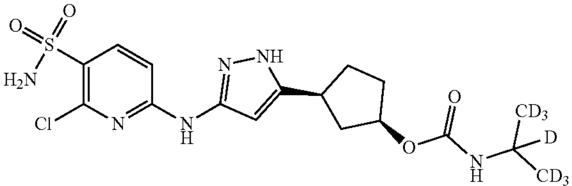
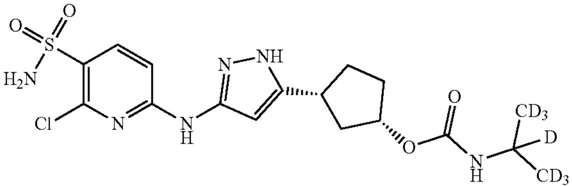
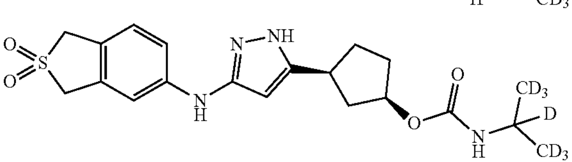
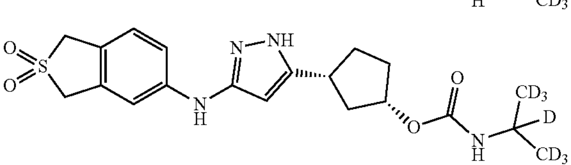
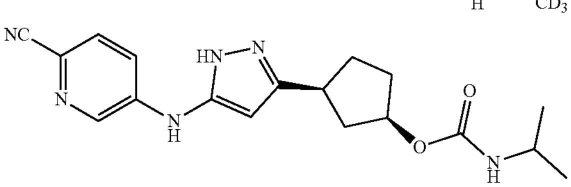

-continued

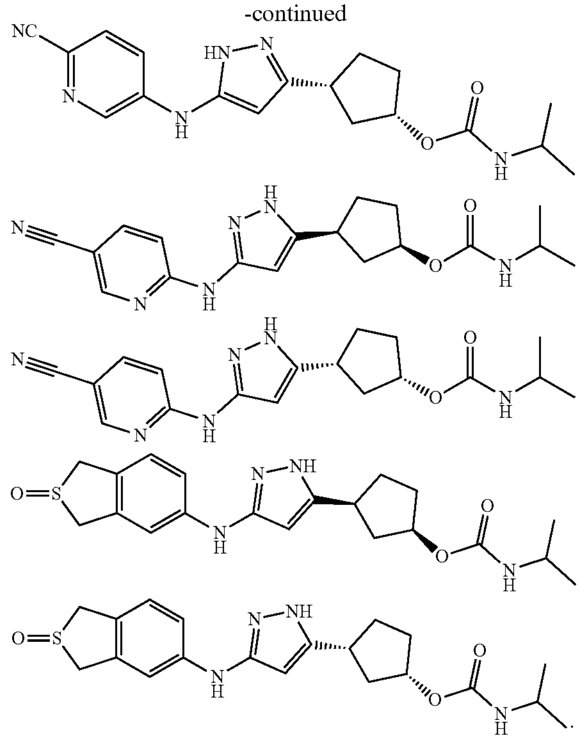

In another aspect, the present application further provides a pharmaceutical composition comprising a therapeutically or prophylactically effective amount of the compound, the isomer thereof, or the pharmaceutically acceptable salt thereof described herein. In some embodiments, the pharmaceutical composition of the present application further comprises a pharmaceutically acceptable excipient.

In another aspect, the present application further provides use of the compound, the isomer thereof, or the pharmaceutically acceptable salt thereof, or the pharmaceutical composition thereof described herein in preparing a medicament for treating or preventing a CDK2-mediated disease.

In another aspect, the present application further provides a method for treating or preventing a CDK2-mediated disease, which comprises administering to a mammal (preferably a human) in need of the treatment or the prevention a therapeutically or prophylactically effective amount of the compound, the isomer thereof, or the pharmaceutically acceptable salt thereof, or the pharmaceutical composition thereof described herein.

In another aspect, the present application further provides use of the compound, the isomer thereof, or the pharmaceutically acceptable salt thereof, or the pharmaceutical composition thereof described herein in treating or preventing a CDK2-mediated disease.

In another aspect, the present application further provides the compound, the isomer thereof, or the pharmaceutically acceptable salt thereof, or the pharmaceutical composition thereof described herein for use in treating or preventing a CDK2-mediated disease.

In another aspect, in some embodiments of the present application, the CDK2-mediated disease is selected from the group consisting of a tumor or a cancer.

In the present application, the "isomer" includes, but is not limited to, stereoisomers or tautomers.

Technical Effects

The compound in the present application, as a CDK2 inhibitor with a brand-new structure, has a good inhibition effect on CDK2-induced signal transduction and a good inhibition activity on CDK2 CycA2 and CDK2 CycE1 kinases, and possesses favorable properties in at least one or more aspects such as in vivo and in vitro inhibitory activity, safety (e.g., low toxicity), and CDK2 selectivity. The compound of the present application has a good pharmacokinetic property, and can be developed into a novel CDK2 inhibitor drug.

Definitions

Unless otherwise stated, the following terms and phrases used herein are intended to have the following meanings. A particular term or phrase, unless otherwise specifically defined, should not be considered indefinite or unclear, but construed according to its common meaning. When referring to a trade name, it is intended to refer to its corresponding commercial product or its active ingredient.

The term "pharmaceutically acceptable" is used herein for those compounds, materials, compositions, and/or dosage forms that are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound disclosed herein, which is prepared from the compound having particular substituents discovered by the present application and a relatively nontoxic acid or base. When the compound disclosed herein contains a relatively acidic functional group, a base addition salt can be obtained by allowing such a compound to be in contact with a sufficient amount of a base in a pure solution or a suitable inert solvent. When the compound disclosed herein contains a relatively basic functional group, an acid addition salt can be obtained by allowing such a compound to be in contact with a sufficient amount of an acid in a pure solution or a suitable inert solvent. Certain specific compounds disclosed herein contain both basic and acidic functional groups that allow the compounds to be converted into either base or acid addition salt.

The pharmaceutically acceptable salts disclosed herein can be synthesized from a parent compound having an acidic or basic group using conventional chemical methods. In general, such salts are prepared by subjecting the compounds in a free acid or base form to a reaction with a stoichiometric amount of appropriate base or acid in water or an organic solvent or a mixture thereof.

The compounds disclosed herein can be in the form of a stereoisomer. All such compounds are contemplated herein, including cis- and trans-isomers, (−)- and (+)-enantiomers, (R)- and (S)-enantiomers, diastereoisomers, (D)-isomers, (L)-isomers, and racemic mixtures and other mixtures thereof, such as an enantiomer or diastereoisomer enriched mixture, all of which are encompassed within the scope of the present application. The substituents such as alkyl may have an additional asymmetric carbon atom. All these isomers and mixtures thereof are encompassed within the scope of the present application.

Unless otherwise specified, the absolute configuration of a stereogenic center is represented by a wedged solid bond ( ) and a wedged dashed bond ( ), and the relative configuration of a stereogenic center is represented by a straight solid bond ( ) and a straight dashed bond ( ).

The compounds and intermediates disclosed herein may also exist in different tautomeric forms, and all such forms are included within the scope of the present application. The term "tautomer" or "tautomeric form" refers to structural isomers of different energies that can interconvert via a low energy barrier. For example, a proton tautomer (also referred to as prototropic tautomer) includes interconversion via proton transfer, such as keto-enol isomerism and imine-enamine isomerization. A specific example of a proton tautomer is an imidazole moiety where a proton can transfer between two ring nitrogen atoms. A valence tautomer includes the interconversion via recombination of some bonding electrons.

The compound disclosed herein may contain an unnatural proportion of atomic isotope at one or more of the atoms that constitute the compound. For example, the compound may be labeled with a radioisotope, such as tritium ($^3H$), iodine-125 ($^{125}I$), or C-14 ($^{14}C$). For another example, hydrogen can be substituted with deuterium to form a deuterated drug, and the bond formed by deuterium and carbon is firmer than that formed by common hydrogen and carbon. Compared with an un-deuterated drug, the deuterated drug has the advantages of reduced toxic side effects, increased stability, enhanced efficacy, prolonged biological half-life, and the like. All isotopic variations of the compound disclosed herein, whether radioactive or not, are encompassed within the scope of the present application.

The term "optional" or "optionally" means that the subsequently described event or circumstance may, but not necessarily, occur, and the description includes instances where the event or circumstance occurs and instances where it does not.

The term "substituted" means that one or more hydrogen atoms on a specific atom are substituted with substituents, wherein the substituents may include deuterium and hydrogen variants, as long as the valence of the specific atom is normal and the substituted compound is stable. When the substituent is oxygen (i.e., =O), it means that two hydrogen atoms are substituted. Substitution with oxygen does not occur on aromatic groups. The term "optionally substituted" means that an atom can be or cannot be substituted with a substituent. Unless otherwise specified, the type and number of the substituent may be arbitrary as long as being chemically achievable.

The term "1 or more substitutions" means that any one or more hydrogen atoms on a specific atom are substituted with substituents, wherein the substituents may include deuterium and hydrogen variants, and the number of the substituents includes 1, 2, 3, 4, 5, 6, 7, 8, 9, or 10 as long as being chemically achievable.

The "substituent" described herein includes, but is not limited to, the terms "alkyl", "alkoxy", "cycloalkyl", "heterocycloalkyl", "heteroaryl", "alkyl ring", "heteroalkyl ring", "heteroaromatic ring", and the like, and the corresponding non-limiting or exemplary groups mentioned in the context, wherein some non-limiting examples of the "substituent" include protium, deuterium, tritium, —OH, —SH, halogen, —$NH_2$, nitro, nitroso, —CN, an azide group, a sulfoxide group, a sulfone group, a sulfonamide group, carboxyl, a carboxaldehyde group, an imine group, alkyl, halogenated alkyl, cycloalkyl, halogenated cycloalkyl, alkenyl, halogenated alkenyl, cycloalkenyl, halogenated cycloalkenyl, alkynyl, halogenated alkynyl, cycloalkynyl, halogenated cycloalkynyl, heteroalkyl, halogenated heteroalkyl, alkoxy, alkylthio, aryl, aryloxy, arylthio, arylalkyl, arylalkoxy, arylalkylthio, heteroaryl, heteroaryloxy, heteroarylthio, heteroarylalkyl, heteroarylalkoxy, heteroarylalkylthio, heterocyclyl, heterocyclyloxy, heterocyclylthio, heterocyclylalkyl, heterocyclylalkoxy, heterocyclylalkylthio, acyl, acyloxy, a carbamate group, an amido group, ureido, an epoxy group, an ester group, and the like, wherein the groups are optionally substituted with one or more substituents selected from the group consisting of the following substituents: oxo, hydroxy, amino, nitro, halogen, cyano, alkyl, alkenyl, alkynyl, alkoxy, halogenated alkoxy, alkylamino, dialkylamino, halogenated alkylamino, halogenated dialkylamino, carboxy, —C(O)O-alkyl, —OC(O)-alkyl, —C(O)$NH_2$, —C(O)NH-alkyl, —C(O)N$(alkyl)_2$, —NHC(O)-alkyl, —C(O)-alkyl, —S(O)-alkyl, —$S(O)_2$—alkyl, —$S(O)_2NH_2$, —$S(O)_2$NH-alkyl, —$S(O)_2$N$(alkyl)_2$, cycloalkyl, cycloalkylalkyl, cycloalkyloxy, heterocyclyl, heterocyclylalkyl, heterocyclyloxy, heterocycloalkyl, heterocycloalkylalkyl, heterocycloalkyloxy, heteroaryl, heteroarylalkyl, heteroaryloxy, aryl, arylalkyl, and aryloxy.

In some embodiments herein, the "substituent" is selected from the group consisting of deuterium, tritium, hydroxyl, sulfydryl, halogen, amino, nitro, nitroso, cyano, azido, a sulfoxide group, a sulfone group, a sulfonamide group, carboxyl, an aldehyde group, an imine group, $C_{1-12}$ alkyl, halogenated $C_{1-12}$ alkyl, 3-12 membered cycloalkyl, halogenated 3-12 membered cycloalkyl, $C_{2-12}$ alkenyl, halogenated $C_{2-12}$ alkenyl, 3-12 membered cycloalkenyl, halogenated 3-12 membered cycloalkenyl, $C_{2-12}$ alkynyl, halogenated $C_{2-12}$ alkynyl, 8-12 membered cycloalkynyl, halogenated 8-12 membered cycloalkynyl, $C_{1-12}$ heteroalkyl, halogenated $C_{1-12}$ heteroalkyl, $C_{1-12}$ alkoxy, $C_{1-12}$ alkylthio, 6-10 membered aryl, 6-10 membered aryloxy, 6-10 membered arylthio, 6-10 membered aryl $C_{1-12}$ alkylene, 6-10 membered aryl $C_{1-12}$ alkoxy, 6-10 membered aryl $C_{1-12}$ alkylthio, 5-10 membered heteroaryl, 5-10 membered heteroaryloxy, 5-10 membered heteroarylthio, 5-10 membered heteroarylalkylene, 5-10 membered heteroarylalkoxy, 5-10 membered heteroarylalkylthio, 3-12 membered heterocyclyl, 3-12 membered heterocyclyloxy, 3-12 membered heterocyclylthio, 3-12 membered heterocyclyl $C_{1-12}$ alkylene, 3- to 12-membered heterocyclyl $C_{1-12}$ alkoxy, 3-12 membered heterocyclyl $C_{1-12}$ alkylthio, $C_{1-12}$ acyl, $C_{1-12}$ acyloxy, a carbamate group, $C_{1-12}$ amido, ureido, an epoxy group, a $C_{2-12}$ ester group, and oxo, wherein these substituents are optionally substituted with one or more substituents selected from the group consisting of the following substituents: oxo, hydroxyl, amino, nitro, halogen, cyano, $C_{1-12}$ alkyl, $C_{2-12}$ alkenyl, $C_{2-12}$ alkynyl, $C_{1-12}$ alkoxy, halogenated $C_{1-12}$ alkoxy, $C_{1-12}$ alkylamino, di-$C_{1-12}$ alkylamino, halogenated $C_{1-12}$ alkylamino, halogenated di-$C_{1-12}$ alkylamino, carboxyl, —C(O)O—$C_{1-12}$ alkyl, —OC(O)—$C_{1-12}$ alkyl, —C(O)$NH_2$, —C(O)NH—$C_{1-12}$ alkyl, —C(O)N($C_{1-12}$ alkyl$)_2$, —NHC(O)—$C_{1-12}$ alkyl, —C(O)—$C_{1-12}$ alkyl, —S(O)—$C_{1-12}$ alkyl, —$S(O)_2$—$C_{1-12}$ alkyl, —$S(O)_2NH_2$, —$S(O)_2$NH—$C_{1-12}$ alkyl, —$S(O)_2$N($C_{1-12}$ alkyl$)_2$, 3-12 membered cycloalkyl, 3-12 membered cycloalkyl $C_{1-12}$ alkylene, 3-12 membered cycloalkyloxy, 3-12 membered heterocyclyl, 3-12 membered heterocyclyl $C_{1-12}$ alkylene, 3-12 membered heterocyclyloxy, 3-12 membered heterocycloalkyl, 3-12 membered heterocycloalkyl $C_{1-12}$ alkylene, 3-12 membered heterocycloalkyloxy, 5-10 membered heteroaryl, 5-10 membered heteroaryl $C_{1-12}$ alkylene, 5-10 membered heteroaryloxy, 6-10 membered aryl, 6-10 membered aryl $C_{1-12}$ alkylene, and 6-10 membered aryloxy.

$C_{m-n}$ used herein means that the moiety has an integer number of carbon atoms in the given range. For example, "$C_{1-6}$" means that the group may have 1 carbon atom, 2 carbon atoms, 3 carbon atoms, 4 carbon atoms, 5 carbon atoms, or 6 carbon atoms. For example, $C_{1-3}$ means that the group may have 1 carbon atom, 2 carbon atoms, or 3 carbon atoms.

When any variable (e.g., R) occurs once or more times in the constitution or structure of a compound, the definition of the variable in each case is independent. Thus, for example, if a group is substituted with 0-2 R, the group can be optionally substituted with up to two R, and the definition of R in each case is independent. Furthermore, a combination of the substituent and/or the variant thereof is permissible only if the combination can result in a stable compound.

When one of the variables is selected from a single bond, it means that the two groups linked by the single bond are connected directly. For example, in A-L-Z, when L represents a single bond, it means that the structure is actually A-Z.

When the direction for connection of the listed connecting group is not specified, the direction for connection is arbitrary. For example, when the connecting group L contained in

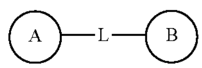

is -M-W-, -M-W- can either connect ring A and ring B in a direction same as left-to-right reading order to form

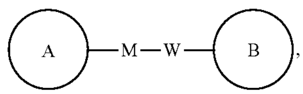, or connect ring A and ring B in a direction opposite to the left-to-right reading order to form

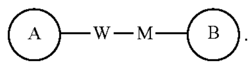.

A combination of the connecting group, the substituent, and/or the variant thereof is permissible only if the combination can result in a stable compound.

Unless otherwise specified, when a group has one or more connectable sites, any one or more of the sites of the group may be connected to other groups by chemical bonds. If there is no designated connecting mode for chemical bonds and H atoms are present at a connectable site, when the connectable site is connected to chemical bonds, the number of the H atoms at the connectable site is correspondingly reduced based on the number of the connected chemical bonds, so that the resulting groups have corresponding valences. The chemical bond that connects the site and another group may be represented by a straight solid bond (), a straight dashed bond (), or a wavy line ( 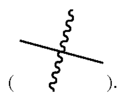 ).

For example, the straight solid bond in —$OCH_3$ refers to being connected to another group via the oxygen atom in the group; the straight dashed bond in

refers to being connected to another group via two ends of the nitrogen atom in the group; the wavy line in

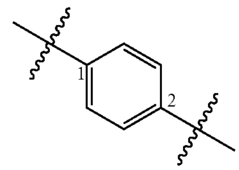 [SMILES: *c1ccc(*)cc1]

refers to being connected to another group via the carbon atoms at positions 1 and 2 in the phenyl group;

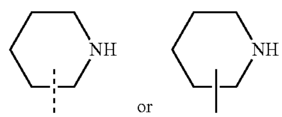

means that any connectable site on the piperidinyl can be connected to another group via 1 chemical bond in at least 4 connecting modes:

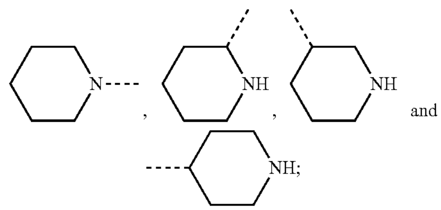

even if —N— is connected with an H atom,

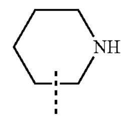

includes the connection mode of

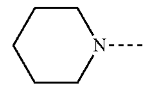, but when 1 chemical bond is connected to a site, the number of H at that site is correspondingly reduced by 1 and a monovalent piperidinyl is thus formed.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$, $C_{2-3}$ alkyl, and the like, and may be monovalent (e.g., methyl), divalent (e.g., methylene), or polyvalent (e.g., methenyl). Examples of $C_{1-3}$ alkyl include, but are not limited to, methyl (Me), ethyl (Et), propyl (including n-propyl and isopropyl), and the like.

Unless otherwise specified, the term "$C_{1-3}$ alkoxy" refers to those alkyl groups that each contain 1 to 3 carbon atoms and are linked to the rest part of the molecule via an oxygen atom. The $C_{1-3}$ alkoxy includes $C_{1-2}$, $C_{2-3}$, $C_3$ and $C_2$ alkoxy, and the like. Examples of $C_{1-3}$ alkoxy include, but are not limited to, methoxy, ethoxy, propoxy (including n-propoxy and isopropoxy), and the like.

Unless otherwise specified, the term "halogen", by itself or as part of another substituent, refers to a fluorine, chlorine, bromine, or iodine atom.

Unless otherwise specified, $C_{n-n+m}$ or $C_n$-$C_{n+m}$ includes any one of the specific cases of n to n+m carbon atoms. For example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$. Also, any range within n to n+m may be included. For example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$, etc. Similarly, n– to n+m-membered represents that the number of atoms on the ring is n to n+m. For example, 3-12 membered ring includes 3-membered ring, 4-membered ring, 5-membered ring, 6-membered ring, 7-membered ring, 8-membered ring, 9-membered ring, 10-membered ring, 11-membered ring, and 12-membered ring. n– to n+m-membered also represents any range within n to n+m. For example, 3-12 membered ring includes 3-6 membered ring, 3-9 membered ring, 5-6 membered ring, 5-7 membered ring, 6-7 membered ring, 6-8 membered ring, 6-10 membered ring, and the like.

Unless otherwise specified, the term "$C_{3-6}$ cycloalkyl" refers to a saturated cyclic hydrocarbon group consisting of 3 to 6 carbon atoms, including monocyclic and bicyclic ring systems. The $C_{3-6}$ cycloalkyl includes $C_{3-5}$ cycloalkyl, $C_{4-5}$ cycloalkyl, $C_{5-6}$ cycloalkyl, and the like, and may be monovalent, divalent, or polyvalent. Examples of $C_{3-6}$ cycloalkyl include, but are not limited to, cyclopropyl, cyclobutyl, cyclopentyl, cyclohexyl, and the like.

Unless otherwise specified, the term "3-6 membered heterocycloalkyl", by itself or in combination with other terms, refers to a saturated cyclic group consisting of 3 to 6 ring atoms, of which 1, 2, 3, or 4 ring atoms are heteroatoms independently selected from the group consisting of O, S, and N, with the remaining being carbon atoms. The nitrogen atom is optionally quaternized, and the nitrogen and sulfur heteroatoms can be optionally oxidized (i.e., NO and $S(O)_p$, wherein p is 1 or 2). It is a monocyclic ring system. Furthermore, with respect to the "3-6 membered heterocycloalkyl", a heteroatom may occupy the position where the heterocycloalkyl is linked to the rest part of the molecule. The 3-6 membered heterocycloalkyl includes 3-membered heterocycloalkyl, 4-membered heterocycloalkyl, 5-membered heterocycloalkyl, 6-membered heterocycloalkyl, and the like. Examples of 3-6 membered heterocycloalkyl include, but are not limited to, oxiranyl, thiiranyl, aziridinyl, azetidinyl, oxetanyl, thietanyl, pyrrolidinyl, pyrazolidinyl, imidazolidinyl, tetrahydrothienyl (including tetrahydrothien-2-yl, tetrahydrothien-3-yl, and the like), tetrahydrothien-1,1-dioxide-3-yl, tetrahydrothien-1,1-dioxide-2-yl, tetrahydrofuranyl (including tetrahydrofuran-2-yl, and the like), tetrahydropyranyl, piperidinyl (including 1-piperidinyl, 2-piperidinyl, 3-piperidinyl, and the like), piperazinyl (including 1-piperazinyl, 2-piperazinyl, and the like), morpholinyl (including 3-morpholinyl, 4-morpholinyl, and the like), dioxanyl, dithianyl, isoxazolidinyl, isothiazolidinyl, 1,2-oxazinyl, 1,2-thiazinyl, hexahydropyridazinyl, hyperpiperazinyl, hyperpiperidinyl, and the like.

Unless otherwise specified, the term "5-6 membered heteroaryl" refers to a cyclic group consisting of 5 to 6 ring atoms and having a conjugated π-electron system, of which 1, 2, or 3 ring atoms are heteroatoms independently selected from the group consisting of O, S, and N, with the remaining being carbon atoms. The nitrogen atom is optionally quaternized, and the carbon, nitrogen and sulfur heteroatoms may optionally be oxidized (i.e., C═O, NO and $S(O)_p$, wherein p is 1 or 2). The 5-6 membered heteroaryl can be connected to the rest of the molecule through a heteroatom or a carbon atom. The 5-6 membered heteroaryl includes 5-membered heteroaryl and 6-membered heteroaryl. Examples of the 5-6 membered heteroaryl include, but are not limited to, pyrrolyl (including N-pyrrolyl, 2-pyrrolyl, 3-pyrrolyl, and the like), pyrazolyl (including 2-pyrazolyl, 3-pyrazolyl, and the like), imidazolyl (including N-imidazolyl, 2-imidazolyl, 4-imidazolyl, 5-imidazolyl, and the like), oxazolyl (including 2-oxazolyl, 4-oxazolyl, 5-oxazolyl, and the like), triazolyl (including 1H-1,2,3-triazolyl, 2H-1,2,3-triazolyl, 1H-1,2,4-triazolyl, 4H-1,2,4-triazolyl, and the like), tetrazolyl, isoxazolyl (including 3-isoxazolyl, 4-isoxazolyl, 5-isoxazolyl, and the like), thiazolyl (including 2-thiazolyl, 4-thiazolyl, 5-thiazolyl, and the like), furanyl (including 2-furanyl, 3-furanyl, and the like), thienyl (including 2-thienyl, 3-thienyl, and the like), pyridinyl (including 2-pyridinyl, 3-pyridinyl, 4-pyridinyl, and the like), pyrazinyl, or pyrimidinyl (including 2-pyrimidinyl, 4-pyrimidinyl, and the like).

Unless otherwise specified, the term "$C_{3-10}$ alkyl ring" refers to a saturated hydrocarbon ring consisting of 3 to 10 carbon atoms. This includes monocyclic and bicyclic systems, wherein the bicyclic system includes spirocyclic, fused and bridged rings. The $C_{3-10}$ alkyl ring includes a $C_{3-6}$, $C_{3-5}$, $C_{4-8}$, $C_{4-6}$, $C_{4-5}$, $C_{5-8}$, or $C_{5-6}$ alkyl ring; it may be monovalent, divalent or polyvalent. Examples of the $C_{3-10}$ alkyl ring include, but are not limited to, a cyclopropane ring, a cyclobutane ring, a cyclopentane ring, a cyclohexane ring, a cycloheptane ring, a norbornane ring, [2.2.2]bicyclooctane ring, and the like.

Unless otherwise specified, the term "5-10 membered heteroalkyl ring" refers to a saturated cyclic group consisting of 5 to 10 ring atoms, of which 1, 2, 3, or 4 ring atoms are heteroatoms independently selected from the group consisting of O, S, and N, with the remaining being carbon atoms. The nitrogen atom is optionally quaternized, and the carbon, nitrogen and sulfur heteroatoms may optionally be oxidized (i.e., C═O, NO and $S(O)_p$, wherein p is 1 or 2). This includes monocyclic and bicyclic systems, wherein the bicyclic system includes spiro ring, fused ring, and bridged ring. Furthermore, with respect to the "5-10 membered heteroalkyl ring", a heteroatom may occupy the position where the heteroalkyl ring is linked to the rest part of the molecule. The 5-10 membered heteroalkyl ring includes a 5-6 membered heteroalkyl ring and the like. Examples of 5-10 membered heteroalkyl ring include, but are not limited to, an azetidine ring, an oxetane ring, a thietane ring, a pyrrolidine ring, a pyrazolidine ring, an imidazolidine ring, a tetrahydrothiophene ring (including a tetrahydrothiophene-2-ring, a tetrahydrothiophene-3-ring, and the like), a tetrahydrofuran ring (including a tetrahydrofuran-2-ring and the like), a tetrahydropyran ring, a piperidine ring (including a 1-piperidine ring, a 2-piperidine ring, a 3-piperidine ring, and the like), a piperazine ring (including a 1-piperazine ring, a 2-piperazine ring, and the like), a morpholine ring (including a 3-morpholine ring, a 4-morpholine ring, and the like), a dioxane ring, a dithiane ring, an isoxazolidine ring, a isothiazolidine ring, a 1,2-oxazine ring, a 1,2-thiazine ring, a hexahydropyridazine ring, a homopiperazine ring, a homopiperidine ring, a dioxepane ring, or the like. It should be understood that the term "5-10 membered heteroalkyl ring" includes situations where a ring heteroatom is oxidized. For example, when one substituent is represented as selected from the group consisting of

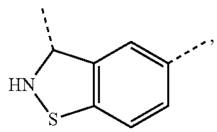

it includes at least the specific structure of

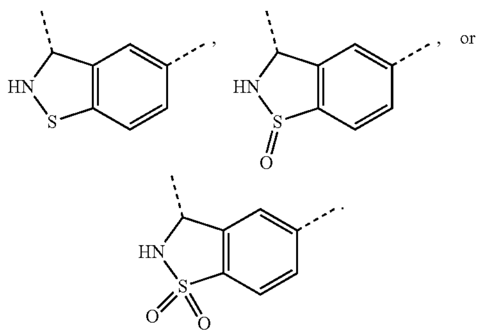

or

Unless otherwise specified, the term "benzene ring fused to $C_{5-6}$ alkyl ring" or "benzene ring fused to 5-6 membered heteroalkyl ring" refers to the fused bicyclic rings formed by a benzene ring and a $C_{5-6}$ alkyl ring or a 5-6 membered heteroalkyl ring, respectively, such as

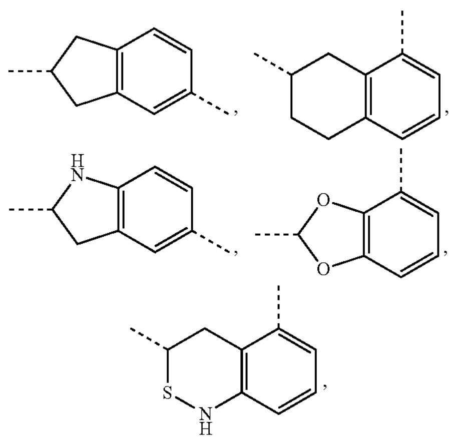

and the like.

Unless otherwise specified, the term "5-6 membered heteroaromatic ring fused to $C_{5-6}$ alkyl ring" or "5-6 membered heteroaromatic ring fused to 5-6 membered heteroalkyl ring" refers to the fused bicyclic rings formed by a 5-6 membered heteroaromatic ring and a $C_{5-6}$ alkyl ring or a 5-6 membered heteroalkyl ring, respectively, such as

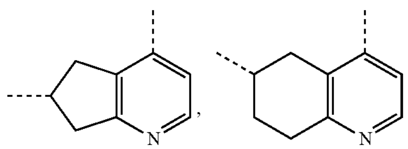

-continued

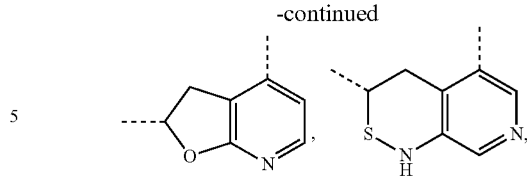

and the like.

Unless otherwise specified, the term "5-10 membered heteroaromatic ring" refers to a cyclic group consisting of 5 to 10 ring atoms and having a conjugated 7-electron system, of which 1, 2, 3, or 4 ring atoms are heteroatoms independently selected from the group consisting of O, S, and N, with the remaining being carbon atoms. The nitrogen atom is optionally quaternized, and the carbon, nitrogen and sulfur heteroatoms may optionally be oxidized (i.e., C═O, NO and $S(O)_p$, wherein p is 1 or 2). It can be a monocyclic, fused bicyclic or fused tricyclic system, wherein the rings are aromatic. The 5-10 membered heteroaromatic ring can be linked to the rest of the molecule via a heteroatom or a carbon atom. The 5-10 membered heteroaromatic ring includes 5-8 membered, 5-7 membered, 5-6 membered, 5 membered and 6 membered heteroaromatic rings, etc. Examples of the 5-10 membered heteroaromatic ring include, but are not limited to, a pyrrole ring (including an N-pyrrole ring, a 2-pyrrole ring, a 3-pyrrole ring, and the like), a pyrazole ring (including a 2-pyrazole ring, a 3-pyrazole ring, and the like), an imidazole ring (including an N-imidazole ring, a 2-imidazole ring, a 4-imidazole ring, a 5-imidazole ring, and the like), an oxazole ring (including a 2-oxazole ring, a 4-oxazole ring, a 5-oxazole ring, and the like), a triazole ring (a 1H-1,2,3-triazole ring, a 2H-1,2,3-triazole ring, a 1H-1,2,4-triazole ring, a 4H-1,2,4-triazole ring, and the like), tetrazole rings, isoxazole rings (3-isoxazole ring, 4-isoxazole ring, 5-isoxazole ring and the like), a thiazole ring (including a 2-thiazole ring, a 4-thiazole ring, a 5-thiazole ring, and the like), a furan ring (including a 2-furan ring, a 3-furan ring, and the like), a thiophene ring (including a 2-thiophene ring, a 3-thiophene ring, and the like), a pyridine ring (including a 2-pyridine ring, a 3-pyridine ring, a 4-pyridine ring, and the like), a pyrazine ring, a pyrimidine ring (including a 2-pyrimidine ring, a 4-pyrimidine ring, and the like), a benzothiazole ring (including 5-benzothiazole ring and the like), a purine ring, a benzimidazole ring (including a 2-benzimidazole ring and the like), a benzoxazole ring, an indole ring (including a 5-indole ring and the like), an isoquinoline ring (including a 1-isoquinoline ring, a 5-isoquinoline ring, and the like), a quinoxaline ring (including a 2-quinoxaline ring, a 5-quinoxaline ring, and the like), a quinoline ring (including a 3-quinoline ring, a 6-quinoline ring, and the like), and the like.

Unless otherwise specified, the term "fused" refers to a saturated or partially unsaturated non-aromatic cyclic system formed by two or more cyclic structures that share two adjacent atoms with each other, including a fused carbocyclic ring and a fused heterocyclic ring. The ring atoms of the fused heterocyclic ring contain one or more heteroatoms independently selected from the group consisting of oxygen, nitrogen, and sulfur.

The term "treat", "treating", or "treatment" refers to administering the compound or formulation described herein to ameliorate or eliminate a disease or one or more symptoms related to the disease, including:

(i) inhibiting a disease or disease state, i.e., arresting its development; and (ii) alleviating a disease or disease state, i.e., causing its regression.

The term "prevent" or "prevention" means administering a compound or formulation described herein to prevent a disease or one or more symptoms associated with the disease, including preventing the occurrence of the disease or disease state in a mammal, particularly when such a mammal is predisposed to the disease state but has not yet been diagnosed with it.

The term "therapeutically or prophylactically effective amount" refers to an amount of the compound disclosed herein for (i) treating a specific disease, condition or disorder, or (ii) alleviating, relieving or eliminating one or more symptoms of a specific disease, condition or disorder, or (iii) preventing or delaying the specific disease, condition or disorder described herein. The amount of the compound of the present application composing the "therapeutically or prophylactically effective amount" varies depending on the compound, the disease state and its severity, the mode of administration, and the age of the mammal to be treated, but may be determined routinely by those skilled in the art in accordance with their knowledge and the present disclosure.

Therapeutic or prophylactic dose of the compound of the present application may be determined by, for example, the specific use of a treatment or prevention, the route of administration of the compound, the health and condition of a patient, and the judgment of a prescribing physician. The proportion or concentration of the compound of the present application in a pharmaceutical composition may not be constant and depends on a variety of factors including dose, chemical properties (e.g., hydrophobicity), and route of administration. For example, the compound of the present application may be provided for parenteral administration by a physiological buffered aqueous solution containing about 0.1-10% w/v of the compound. Some typical dose ranges are about 0.001 mg/kg body weight/day to about 1000 mg/kg body weight/day. The dose is likely to depend on such variables as the type and degree of progression of the disease or disorder, the general health condition of a particular patient, the relative biological potency of the compound selected, the excipient formulation, and its route of administration. Effective doses can be extrapolated from dose-response curves derived from in vitro or animal model test systems.

The word "comprise" and variations thereof such as "comprises" or "comprising" will be understood in an open, non-exclusive sense, i.e., "including but not limited to".

The term "pharmaceutical composition" refers to a composition comprising one or more of the compound, the isomer thereof, or the pharmaceutically acceptable salt thereof disclosed herein, as well as other components such as a physiologically/pharmaceutically acceptable carrier and excipient. The pharmaceutical composition is intended to promote the administration to organisms, facilitate the absorption of the active ingredients and thus exert biological activity.

The pharmaceutical composition of the present application may be prepared by combining the compound of the present application with a suitable pharmaceutically acceptable excipient.

In some embodiments, the pharmaceutical composition is in an oral form. For oral administration, the pharmaceutical composition can be formulated by mixing the active compounds with pharmaceutically acceptable excipients well known in the art.

The compounds of the present application can be prepared using a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples of the present application.

The chemical reactions of the specific embodiments of the present application are conducted in a proper solvent that must be suitable for the chemical changes in the present application and the reagents and materials required. In order to obtain the compounds of the present application, it is sometimes necessary for those skilled in the art to modify or select a synthesis procedure or a reaction process based on the existing embodiments.

The starting materials or intermediates used in the embodiments of the present application may be obtained commercially or prepared by methods known in the art.

An important consideration in synthetic route planning in the art is the selection of suitable protective groups for reactive functional groups (e.g., amino in the present application). For example, reference may be made to Greene's Protective Groups in Organic Synthesis (4th Ed.) Hoboken, New Jersey: John Wiley & Sons, Inc.

In some embodiments, some of the compounds of the present application can be prepared by those skilled in the art of organic synthesis according to the following routes:

Route 1

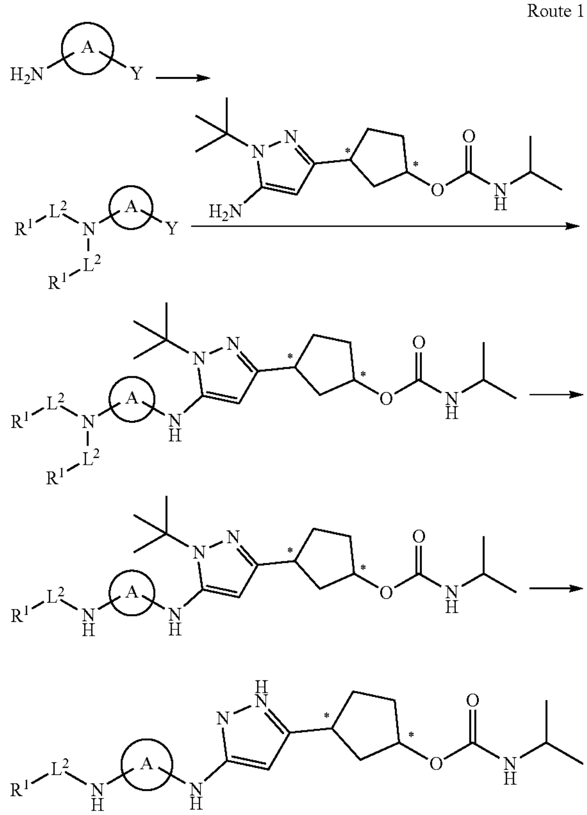

wherein, $R^1$, $L^2$, and ring A are as defined above;

Y is selected from halogen (e.g., bromine).

Route 2

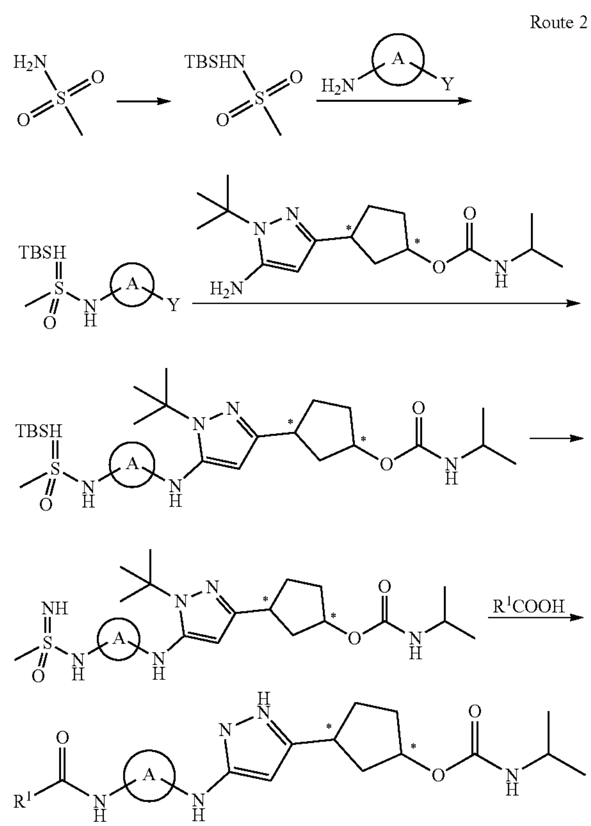

wherein, $R^1$ and ring A are as defined above;

Y is selected from halogen (e.g., bromine).

For clarity, the present application is further described with the following examples, which are, however, not intended to limit the scope of the present application. All reagents used in the present application are commercially available and can be used without further purification.

DETAILED DESCRIPTION

The present application is described in detail below by way of examples. However, this is by no means disadvantageously limiting the scope of the present application. Although the present application has been described in detail herein and specific examples have also been disclosed, it will be apparent to those skilled in the art that various changes and modifications can be made to the specific examples without departing from the spirit and scope of the present application.

Example 1: Preparation of Compound 1

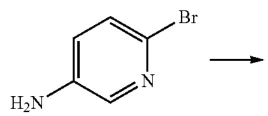

-continued

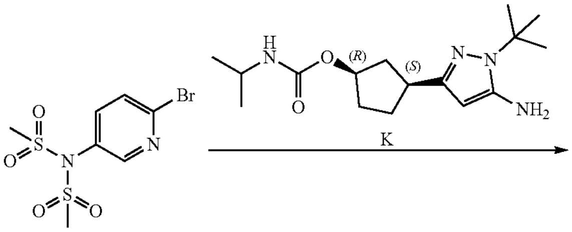

1A

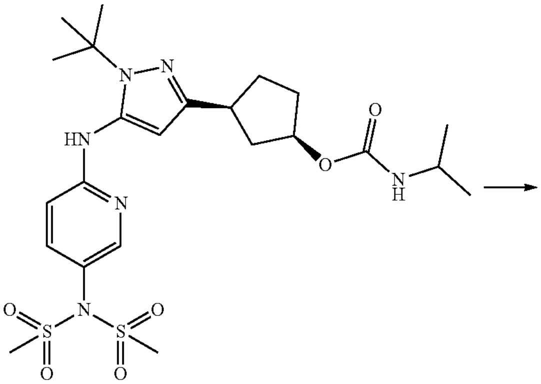

1B

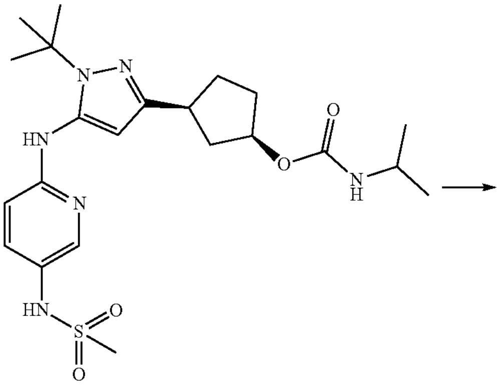

1C

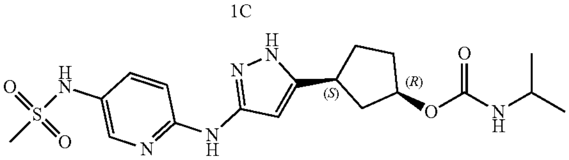

1

6-Bromopyridine-3-amine (0.50 g), diisopropylethylamine (0.49 g), and methanesulfonic anhydride (1.01 g) were added to dichloromethane (5 mL), and the mixture was stirred at room temperature. After the reaction was completed, the reaction solution was concentrated by evaporation under reduced pressure to remove the solvent, and separated by column chromatography (developing solvents: petroleum ether/ethyl acetate) to give intermediate 1A (0.43 g). MS (ESI): m/z 329.0 $[M+H]^+$.

Intermediate 1A (200 mg), intermediate K (256 mg), chloro(2-dicyclohexylphosphino-2',4',6'-triisopropyl-1,1'-biphenyl)[2-(2'-amino-1,1'-biphenyl)]palladium (II) (25 mg), and potassium phosphate (203 mg) were added to dioxane (10 mL), and the mixture was reacted at 120° C. under microwave under nitrogen atmosphere. After the reaction was completed, the reaction solution was filtered and concentrated to give intermediate 1B (365 mg). MS (ESI): m/z 557.3 $[M+H]^+$.

Intermediate 1B (365 mg) and potassium carbonate (100 mg) were added to 1,4-dioxane (5 mL) and water (1 mL), and the mixture was stirred at 100° C. After the reaction was completed, the reaction solution was concentrated by evaporation under reduced pressure to remove the solvent, and separated by column chromatography (developing solvents: dichloromethane/methanol) to give intermediate 1C (95 mg). MS (ESI): m/z 479.3 $[M+H]^+$.

Intermediate 1C (95 mg) was added to formic acid (5 mL), and the mixture was stirred at 70° C. After the reaction was completed, the reaction solution was concentrated by evaporation under reduced pressure to remove the solvent. An aqueous sodium bicarbonate solution was added to the residue to adjust the pH to alkalinity. A solid was precipitated, the mixture was filtered, and the filter cake was slurried with methanol to give compound 1 (47 mg) of Example 1. MS (ESI): m/z 423.2 $[M+H]^+$.

$^1H$ NMR (500 MHz, DMSO-$d_6$) δ 11.80 (s, 1H), 9.21 (s, 1H), 9.14 (s, 1H), 7.98 (d, J=2.7 Hz, 1H), 7.42 (dd, J=8.9, 2.7 Hz, 1H), 7.27 (s, 1H), 6.94 (d, J=7.8 Hz, 1H), 6.08 (s, 1H), 5.11-4.93 (m, 1H), 3.61-3.54 (m, 1H), 3.07-3.00 (m, 1H), 2.90 (s, 3H), 2.48-2.43 (m, 1H), 2.04-1.97 (m, 1H), 1.94-1.85 (m, 1H), 1.76-1.68 (m, 2H), 1.64-1.57 (m, 1H), 1.03 (d, J=6.7 Hz, 6H).

Example 2: Preparation of Compound 2

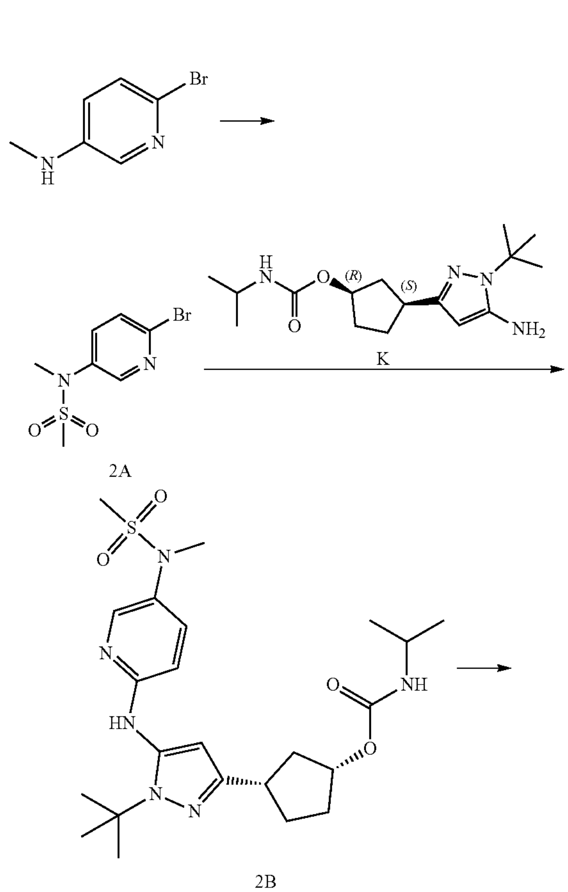

2A

2B

-continued

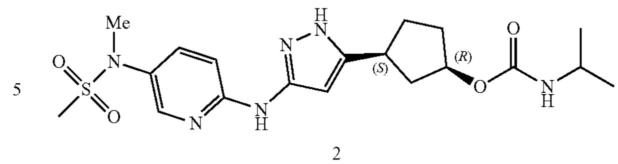

2

A crude product of compound 2 was obtained by reference to the preparation method for the compound of Example 1, with 6-bromopyridine-3-amine being replaced by 6-bromo-N-methylpyridine-3-amine.

The crude product of compound 2 was purified by medium and low pressure preparative liquid phase chromatography (silica gel column, dichloromethane/methanol (30/1)) to give compound 2 (13 mg). MS (ESI): m/z 437.2 $[M+H]^+$.

$^1H$ NMR (500 MHz, DMSO-$d_6$) δ 11.85 (s, 1H), 9.28 (s, 1H), 8.12 (d, J=2.7 Hz, 1H), 7.59 (dd, J=9.0, 2.8 Hz, 1H), 7.28 (s, 1H), 6.95 (d, J=7.8 Hz, 1H), 6.12 (s, 1H), 4.99 (s, 1H), 3.61-3.54 (m, 1H), 3.19 (s, 3H), 3.07-3.00 (m, 1H), 2.95 (s, 3H), 2.48-2.45 (m, 1H), 2.05-1.97 (m, 1H), 1.95-1.84 (m, 1H), 1.76-1.67 (m, 2H), 1.64-1.56 (m, 1H), 1.03 (d, J=6.2 Hz, 6H).

Example 3: Preparation of Compound 3

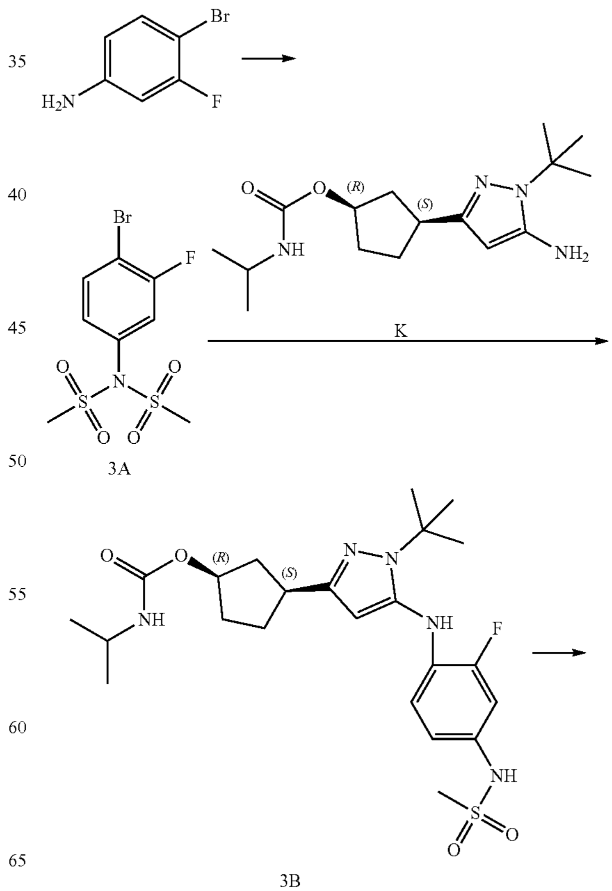

3A

3B

-continued

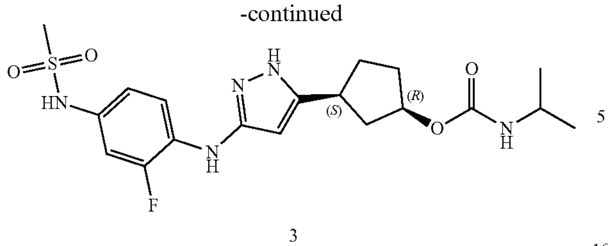

3

A crude product of compound 3 was obtained by reference to the preparation method for the compound of Example 1, with 6-bromopyridine-3-amine being replaced by 4-bromo-3-fluoroaniline. The crude product of compound 3 was purified by medium and low pressure preparative liquid phase chromatography (C18 column, acetonitrile/water (30/70), the eluent contained one thousandth of ammonium hydroxide) to give compound 3 (10 mg). MS (ESI): m/z 440.2 $[M+H]^+$.

$^1H$ NMR (500 MHz, DMSO-$d_6$) δ 11.73 (s, 1H), 9.37 (s, 1H), 8.00 (brs, 1H), 7.96 (s, 1H), 6.99 (d, J=13.0, 1H), 6.94-6.90 (m, 2H), 5.71 (s, 1H), 4.99 (s, 1H), 3.67-3.49 (m, 1H), 3.06-2.99 (m, 1H), 2.91 (s, 3H), 2.48-2.42 (m, 1H), 2.03-1.96 (m, 1H), 1.93-1.85 (m, 1H), 1.76-1.65 (m, 2H), 1.62-1.54 (m, 1H), 1.03 (d, J=5.35 Hz, 6H).

Example 4: Preparation of Compound 4

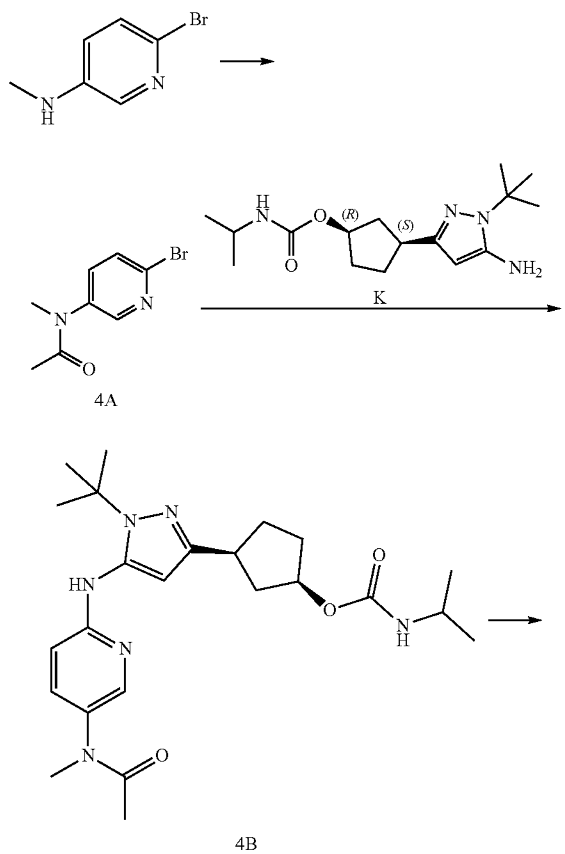

4A

4B

-continued

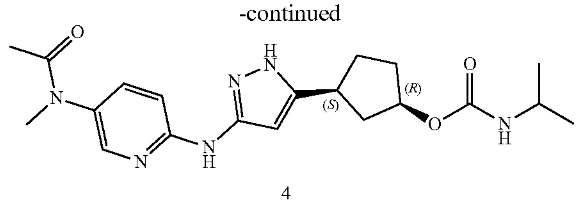

4

6-Bromo-N-methylpyridine-3-amine (500 mg), triethylamine (580 mg), and acetic anhydride (468 mg) were added to dichloromethane (5 mL), and the mixture was stirred at room temperature. After the reaction was completed, the reaction solution was concentrated by evaporation under reduced pressure to remove the solvent, and separated by column chromatography (developing solvents: petroleum ether/ethyl acetate) to give intermediate 4A (396 mg). MS (ESI): m/z 229.0 $[M+H]^+$.

A crude product of compound 4 was obtained by reference to the preparation method for the compound of Example 2, with intermediate 2A being replaced by intermediate 4A.

The crude product of compound 4 was purified by medium and low pressure preparative liquid phase chromatography (silica gel column, dichloromethane/methanol (30/1)) to give compound 4 (28 mg). MS (ESI): m/z 401.2 $[M+H]^+$.

$^1H$ NMR (500 MHz, DMSO-$d_6$) δ 11.85 (s, 1H), 9.29 (s, 1H), 8.06 (d, J=2.6 Hz, 1H), 7.52 (dd, J=9.1, 2.7 Hz, 1H), 7.29 (d, J=7.9 Hz, 1H), 6.95 (d, J=7.8 Hz, 1H), 6.15 (s, 1H), 5.13-4.92 (m, 1H), 3.58 (h, J=6.7 Hz, 1H), 3.09 (s, 3H), 3.08-3.03 (m, 1H), 2.49-2.44 (m, 1H), 2.06-1.98 (m, 1H), 1.94-1.88 (m, 1H), 1.76 (s, 3H), 1.75-1.67 (m, 2H), 1.64-1.56 (m, 1H), 1.03 (dd, J=6.7, 2.6 Hz, 6H).

Example 5: Preparation of Compound 5

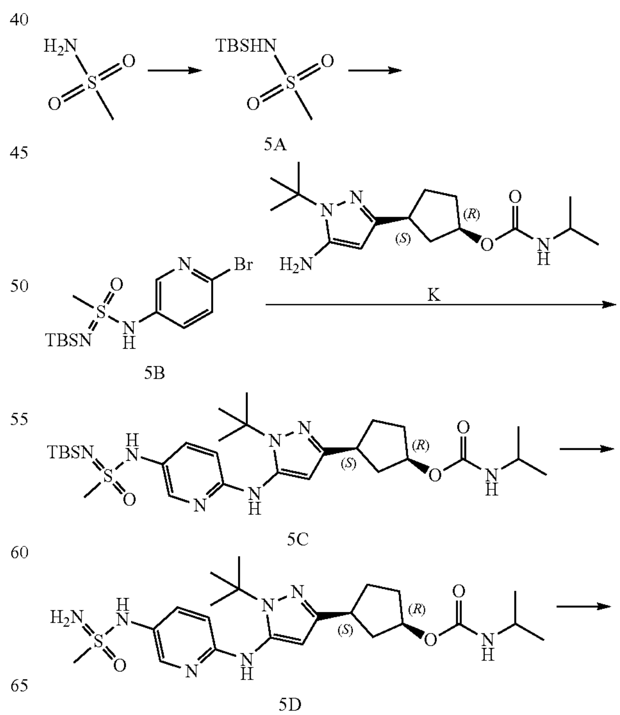

5A

5B

5C

5D

-continued

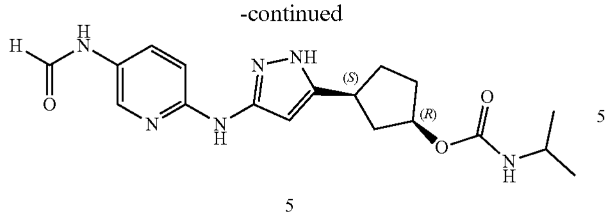

5

Methylsulfonamide (20.00 g) and tert-butyldimethylsilyl chloride (41.20 g) were added to chloroform (350 mL) at 0° C. under nitrogen atmosphere, triethylamine (42.60 g) was added, and the mixture was stirred at room temperature. After the reaction was completed, the reaction solution was concentrated by evaporation under reduced pressure to remove the solvent, water and ethyl acetate were added to the residue, and liquid separation was performed. The organic phase was washed with water, dried over anhydrous sodium sulfate, filtered, and concentrated to give intermediate 5A (43.00 g), which was used in the next reaction without further purification.

Triphenylphosphine (18.19 g) and hexachloroethane (16.42 g) were added to chloroform (90 mL), and the mixture was stirred at 73° C. for 6 h under nitrogen atmosphere. The mixture was cooled to room temperature, triethylamine (10.50 g) was added, and the mixture was stirred at room temperature for 15 min. The mixture was cooled to 0° C., a solution of intermediate 5A (12.10 g) in chloroform (10 mL) was added, and the mixture was stirred at 0° C. for 0.5 h. A solution of 6-bromopyridine-3-amine (2.00 g) and triethylamine (11.70 g) in tetrahydrofuran (10 mL) was added, and the mixture was stirred at 0° C. After the reaction was completed, the reaction solution was concentrated by evaporation under reduced pressure to remove the solvent, water and dichloromethane were added to the residue, and liquid separation was performed. The organic phase was dried over anhydrous sodium sulfate, filtered, concentrated, and separated by column chromatography (developing solvents: petroleum ether/ethyl acetate) to give intermediate 5B (1.60 g).

Intermediate 5C (0.07 g) was obtained by reference to the preparation method for intermediate 1B of Example 1, with intermediate 1A being replaced by intermediate 5B. MS (ESI): m/z 592.4 $[M+H]^+$. Intermediate 5C (0.07 g) and a solution of hydrochloric acid in 1,4-dioxane (0.6 mL, 4 mol/L) were added to dichloromethane (10 mL), and the mixture was stirred at room temperature. After the reaction was completed, a saturated aqueous sodium bicarbonate solution was added to adjust the pH to 9-10, and liquid separation was performed. The organic phase was dried over anhydrous magnesium sulfate, filtered, and concentrated to give intermediate 5D (0.05 g), which was used in the next reaction without further purification.

Intermediate 5D (0.05 g) was added to formic acid (20 mL), and the mixture was stirred at 70° C. After the reaction was completed, the reaction solution was concentrated by evaporation under reduced pressure to remove the solvent and separated by medium and low pressure preparative liquid phase chromatography (C18 column, acetonitrile/water (25/75), the eluent contained one thousandth of ammonium hydroxide) to give compound 5 (6 mg). MS (ESI): m/z 373.2 $[M+H]^+$.

$^1$H NMR (500 MHz, DMSO) δ 11.77 (s, 1H), 10.03 (9.85) (s, 1H), 8.99 (8.56) (s, 1H), 8.32 (8.48) (s, 1H), 8.21 (7.98) (s, 1H), 7.74-7.72 (7.43-7.42) (m, 1H), 7.29 (s, 1H), 6.94 (s, 1H), 6.03 (s, 1H), 4.99 (s, 1H), 3.62-3.51 (m, 1H), 3.09-2.98 (m, 1H), 2.48-2.40 (m, 1H), 2.05-1.95 (m, 1H), 1.94-1.84 (m, 1H), 1.79-1.66 (m, 2H), 1.65-1.55 (m, 1H), 1.03 (d, 6H).

Example 6: Preparation of Compound 6

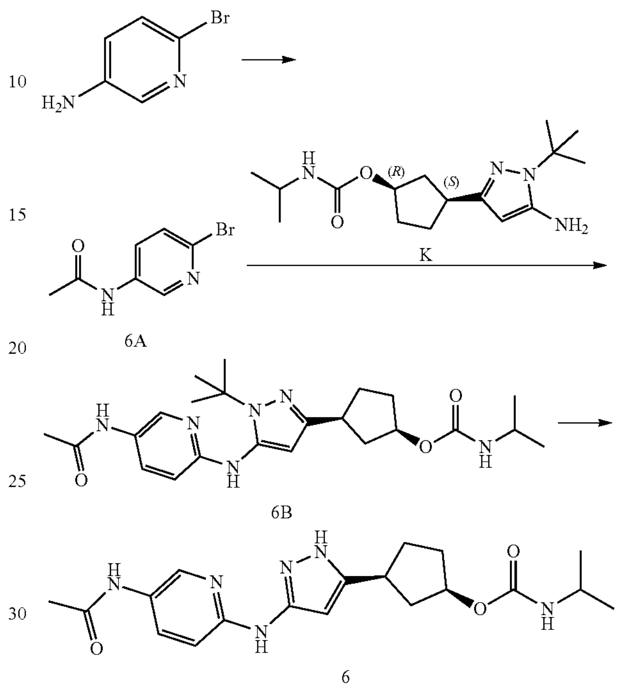

6A

6B

6

6-Bromopyridine-3-amine (500 mg), triethylamine (731 mg), and acetic anhydride (590 mg) were added to dichloromethane (5 mL), and the mixture was stirred at room temperature. After the reaction was completed, the reaction solution was concentrated by evaporation under reduced pressure to remove the solvent, and separated by column chromatography (developing solvents: petroleum ether/ethyl acetate) to give compound 6A (0.528 g). MS (ESI): m/z 214.85 $[M+H]^+$.

A crude product of compound 6 was obtained by reference to the preparation method for the compound 2 of Example 2, with intermediate 2A being replaced by intermediate 6A.

The crude product of compound 6 was slurried with methanol to give compound 6 (46 mg). MS (ESI): m/z 387.2144 $[M+H]^+$.

$^1$H NMR (500 MHz, DMSO-$d_6$) δ 11.74 (s, 1H), 9.76 (s, 1H), 8.93 (s, 1H), 8.27 (s, 1H), 7.70 (d, J=8.20 Hz, 1H), 7.26 (s, 1H), 6.95 (d, J=7.10 Hz, 1H), 6.03 (s, 1H), 5.13-4.90 (m, 1H), 3.56-3.60 (m, 1H), 3.01-3.04 (m, 1H), 2.44-2.47 (m, 1H), 2.01 (s, 3H), 1.99-1.96 (m, 1H), 1.92-1.84 (m, 1H), 1.76-1.68 (m, 2H), 1.64-1.56 (m, 1H), 1.03 (d, J=6.40 Hz, 6H).

Example 7: Preparation of Compound 7

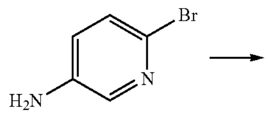

-continued

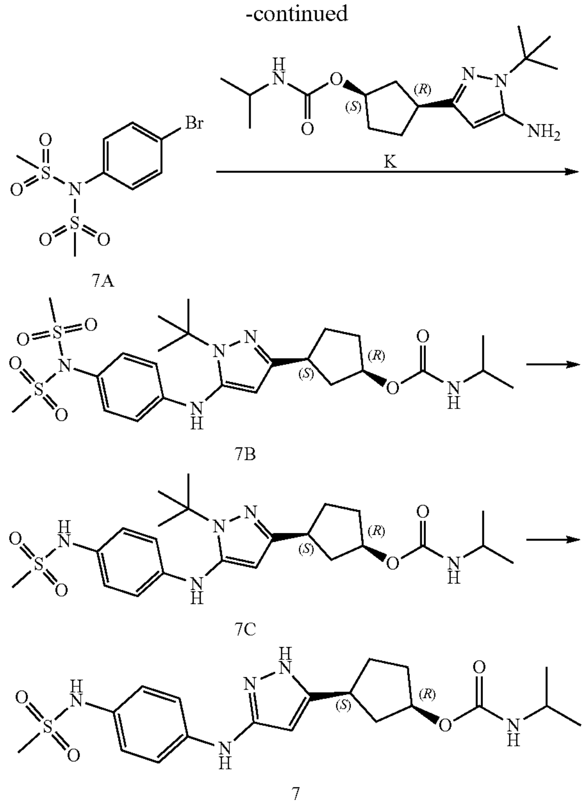

7A

7B

7C

7

4-Bromoaniline (1.00 g), diisopropylethylamine (3.00 g), and methanesulfonic anhydride (4.10 g) were added to dichloromethane (15 mL), and the mixture was stirred at room temperature. After the reaction was completed, the reaction solution was concentrated by evaporation under reduced pressure to remove the solvent, and separated by column chromatography (developing solvents: petroleum ether/ethyl acetate) to give intermediate 7A (0.66 g). MS (ESI): m/z 325.0 $[M-H]^-$.

Intermediate 7A (200 mg), intermediate K (125 mg), chloro(2-dicyclohexylphosphino-2',4',6'-triisopropyl-1,1'-biphenyl)[2-(2'-amino-1,1'-biphenyl)]palladium (II) (95 mg), potassium phosphate (283 mg), and diatomite (480 mg) were added to toluene/tert-butanol (10 mL, 5:1 (v/v)), and the mixture was reacted at 120° C. in an oil bath under nitrogen atmosphere. After the reaction was completed, the reaction solution was filtered, concentrated, and separated by column chromatography (developing solvents: dichloromethane/methanol) to give intermediate 7B (208 mg). MS (ESI): m/z 556.3 $[M+H]^+$.

Intermediate 7B (208 mg) and potassium carbonate (100 mg) were added to 1,4-dioxane (5 mL) and water (5 mL), and the mixture was stirred at 100° C. After the reaction was completed, the reaction solution was concentrated by evaporation under reduced pressure to remove the solvent, and separated by column chromatography (developing solvents: dichloromethane/methanol) to give intermediate 7C (130 mg). MS (ESI): m/z 478.3 $[M+H]^+$.

A crude product of compound 7 was obtained by reference to the preparation method for compound 1 of Example 1, with intermediate 1C being replaced by intermediate 7C.

The crude product of compound 7 was purified by medium and low pressure preparative liquid phase chromatography (C18 column, acetonitrile/water (30/70), the eluent contained one thousandth of ammonium hydroxide) to give compound 7 (40 mg). MS (ESI): m/z 442.2 $[M+H]^+$.

$^1$H NMR (500 MHz, DMSO-$d_6$) δ 11.67 (s, 1H), 9.10 (s, 1H), 8.27 (s, 1H), 7.28 (d, J=8.30 Hz, 2H), 7.11-6.99 (m, 2H), 6.95 (d, J=7.8 Hz, 1H), 5.60 (s, 1H), 4.99 (m, 1H), 3.59-2.55 (m, 1H), 3.05-2.98 (m, 1H), 2.85 (s, 3H), 2.47-2.42 (m, 1H), 2.02-1.98 (m, 1H), 1.95-1.83 (m, 1H), 1.74-1.67 (m, 2H), 1.63-1.56 (m, 1H), 1.03 (d, J=6.60 Hz, 6H).

Example 8: Preparation of Compound 8

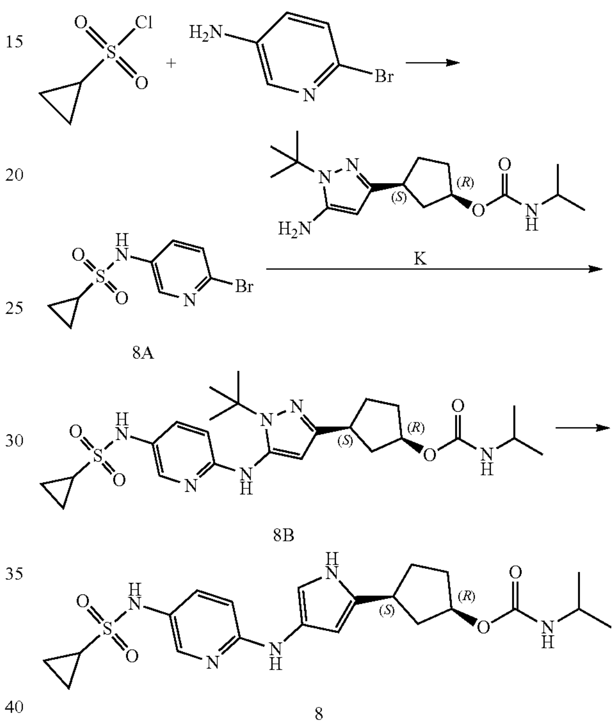

8A

8B

8

3-Amino-6-bromopyridine (500 mg), pyridine (700 mg), and cyclopropanesulfonyl chloride (800 mg) were added to dichloromethane (20 mL), and the mixture was stirred at 50° C. After the reaction was completed, the reaction solution was concentrated by evaporation under reduced pressure to remove the solvent, and separated by column chromatography (developing solvents: petroleum ether/ethyl acetate) to give intermediate 8A (758 mg). MS (ESI): m/z 276.9 $[M+H]^+$.

$^1$H NMR (500 MHz, DMSO-$d_6$): δ 10.17 (s, 1H), 8.25-8.24 (m, 1H), 7.62-7.61 (m, 2H), 2.77-2.72 (m, 1H), 1.00-0.92 (m, 4H).

Intermediate 8A (216 mg), intermediate K (120 mg), 2-(dicyclohexylphosphino)-3,6-dimethoxy-2',4',6'-triisopropyl-1,1'-biphenyl (65 mg), (2-dicyclohexylphosphino-3,6-dimethoxy-2',4',6'-triisopropyl-1,1'-biphenyl)[2-(2-amino-ethylphenyl)]palladium (II) chloride (100 mg), and potassium phosphate (330 mg) were added to 1,4-dioxane (50 mL), and the mixture was reacted at 110° C. in an oil bath under nitrogen atmosphere. After the reaction was completed, the reaction solution was concentrated by evaporation under reduced pressure to remove the solvent, and the residue 8B was directly fed for the next reaction without further purification.

A crude product of compound 8 was obtained by reference to the preparation method for compound 1 of Example 1, with intermediate 1C being replaced by intermediate 8B.

The crude product of compound 8 was first purified by column chromatography (developing solvents: dichloromethane/methanol), and then purified by medium and low pressure preparative liquid phase chromatography (C18 column, acetonitrile/water (40/60), the eluent contained one thousandth of ammonium hydroxide) to give compound 8 (10 mg). MS (ESI): m/z 449.1965 $[M+H]^+$.

$^1$H NMR (500 MHz, DMSO-$d_6$): δ 11.81 (s, 1H), 9.13 (brs, 1H), 9.13 (s, 1H), 7.99 (s, 1H), 7.43 (d, J=7.60 Hz, 1H), 7.26 (s, 1H), 6.94 (d, J=7.05 Hz, 1H), 6.08 (s, 1H), 4.99 (s, 1H), 3.61-3.52 (m, 1H), 3.10-2.98 (m, 1H), 2.48-2.41 (m, 1H), 2.06-1.95 (m, 1H), 1.94-1.85 (m, 1H), 1.80-1.66 (m, 2H), 1.64-1.55 (m, 1H), 1.03 (d, J=6.25 Hz, 6H), 0.96-1.80 (m, 5H).

Example 9: Preparation of Compound 9

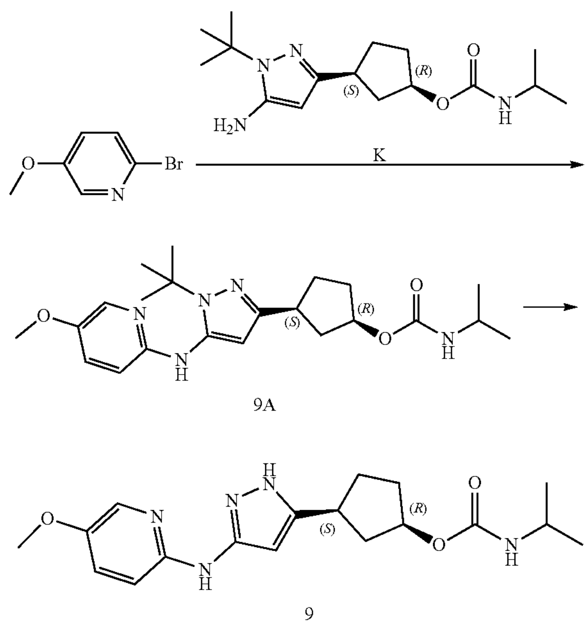

9A

9

A crude product of compound 9 was obtained by reference to the preparation method for compound 1 of Example 1, with intermediate 1A being replaced by 2-bromo-5-methoxypyridine.

The crude product of compound 9 was purified by medium and low pressure preparative liquid phase chromatography (C18 column, acetonitrile/water (30/70), the eluent contained one thousandth of ammonium hydroxide) to give compound 9 (18 mg). MS (ESI): m/z 360.2031 $[M+H]^+$.

$^1$H NMR (500 MHz, DMSO-$d_6$) δ 11.68 (s, 1H), 8.76 (s, 1H), 7.84 (s, 1H), 7.27 (d, J=12.5 Hz, 2H), 6.95 (d, J=7.0 Hz, 1H), 6.03 (s, 1H), 4.99 (s, 1H), 3.73 (s, 3H), 3.58 (dd, J=13.3, 6.4 Hz, 1H), 3.02 (s, 1H), 2.47-2.44 (m, 1H), 2.02-1.97 (m, 1H), 1.93-1.85 (m, 1H), 1.74-1.67 (m, 2H), 1.62-1.56 (m, 1H), 1.03 (d, J=6.4 Hz, 6H).

Example 10: Preparation of Compound 10

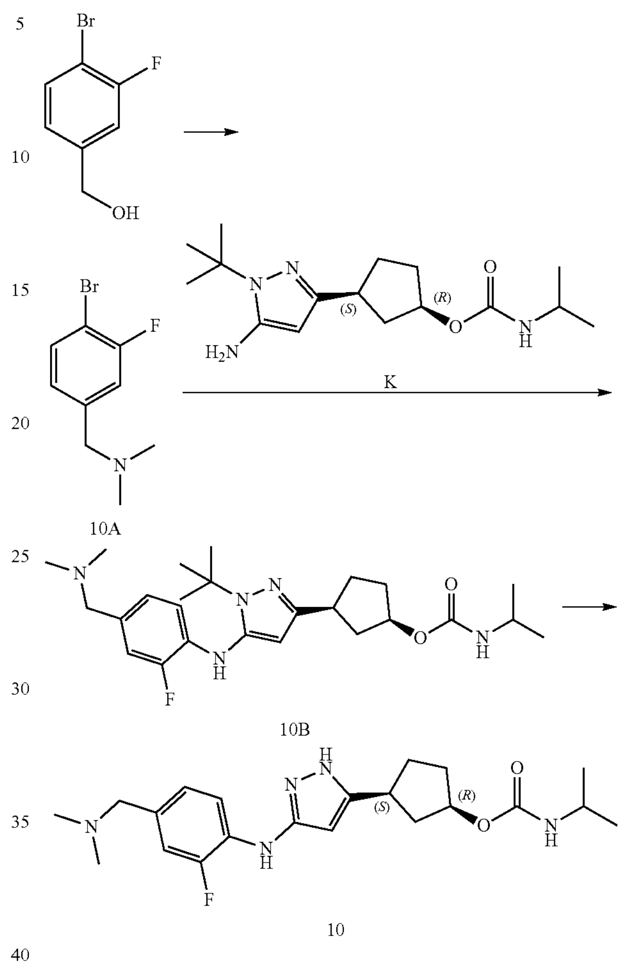

10A

10B

10

4-Bromo-3-fluorobenzyl alcohol (2.0 g), triethylamine (2.0 g), and methanesulfonic anhydride (2.7 g) were added to dichloromethane (20 mL) at 0° C. under nitrogen atmosphere, and the mixture was stirred at 0° C. After the reaction was completed, dimethylamine (1.3 g) was added, and the mixture was stirred. After the reaction was completed, the reaction solution was concentrated by evaporation under reduced pressure to remove the solvent, and separated by column chromatography (developing solvents: dichloromethane/methanol) to give intermediate 10A (1.9 g).

A crude product of compound 10 was obtained by reference to the preparation method for compound 1 of Example 1, with intermediate 1A being replaced by intermediate 10A.

The crude product of compound 10 was purified by medium and low pressure preparative liquid phase chromatography (C18 column, acetonitrile/water (25/75), the eluent contained one thousandth of ammonium hydroxide) to give compound 10 (60 mg). MS (ESI): m/z 404.2458 $[M+H]^+$.

$^1$H NMR (500 MHz, DMSO-$d_6$) δ 11.73 (s, 1H), 7.96-7.91 (m, 2H), 6.99 (dd, J=12.8, 1.2 Hz, 1H), 6.95-6.91 (m, 2H), 5.73 (s, 1H), 4.99 (s, 1H), 3.60-3.54 (m, 1H), 3.27 (s, 2H), 3.06-3.01 (m, 1H), 2.49-2.41 (m, 1H), 2.11 (s, 6H), 2.04-1.97 (m, 1H), 1.94-1.85 (m, 1H), 1.74-1.64 (m, 2H), 1.61-1.56 (m, 1H), 1.03 (d, J=6.3 Hz, 6H).

Example 11: Preparation of Compound 11

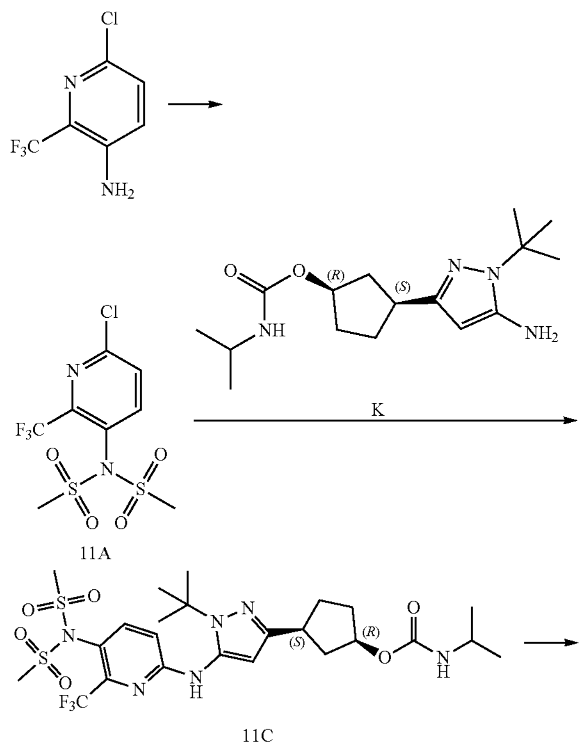

11A

11C

-continued

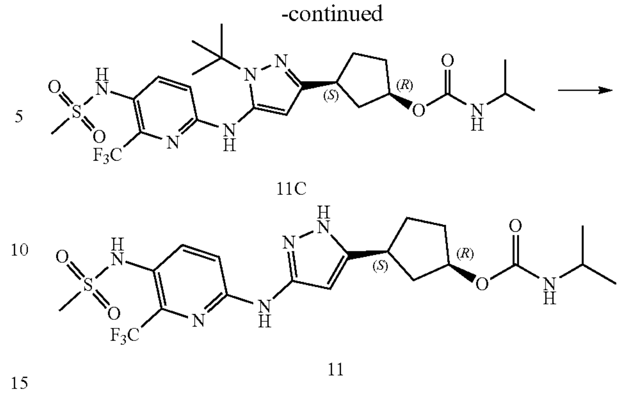

11C

11

A crude product of compound 11 was obtained by reference to the preparation method for compound 1 of Example 1, with 6-bromopyridine-3-amine being replaced by 6-chloro-2-(trifluoromethyl)pyridine-3-amine.

The crude product of compound 11 was purified by column chromatography (developing solvents: dichloromethane/methanol (96/4)) to give compound 11 (40 mg). MS (ESI): m/z 491.1687 $[M+H]^+$.

$^1$H NMR (500 MHz, DMSO-$d_6$) δ 11.97 (s, 1H), 9.75 (s, 1H), 9.26 (s, 1H), 7.70 (d, J=8.9 Hz, 1H), 7.48 (d, J=9.1 Hz, 1H), 6.92 (d, J=7.8 Hz, 1H), 6.22 (s, 1H), 5.00 (s, 1H), 3.60-3.53 (m, 1H), 3.11-3.04 (m, 1H), 3.02 (s, 3H), 2.48-2.44 (m, 1H), 2.05-1.88 (m, 2H), 1.76-1.56 (m, 3H), 1.03 (d, J=5.7 Hz, 6H).

Example 12: Preparation of Compound 12

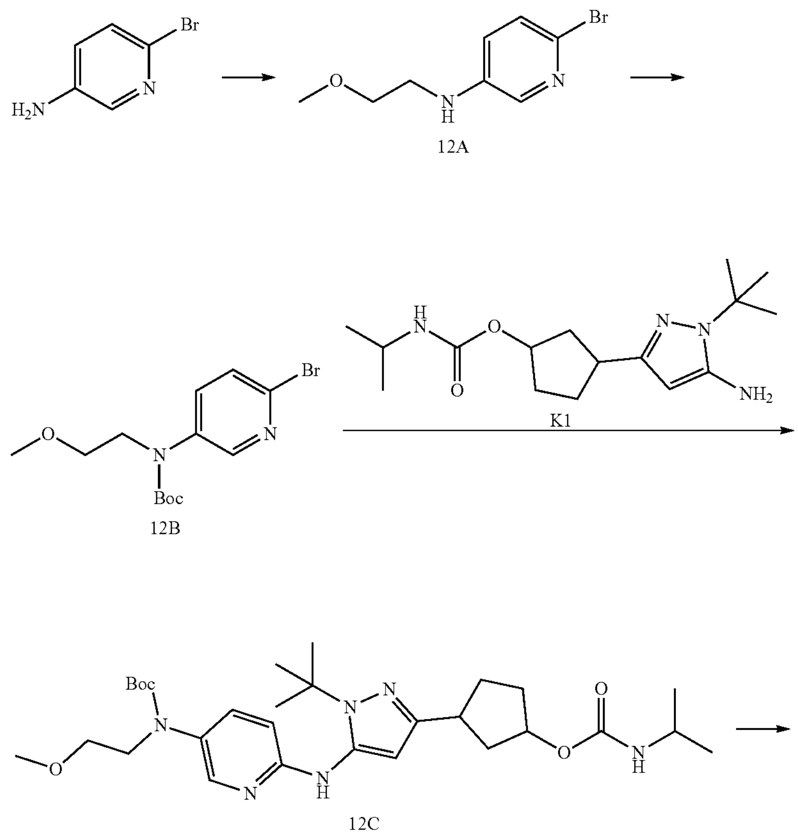

12A

12B

12C

-continued

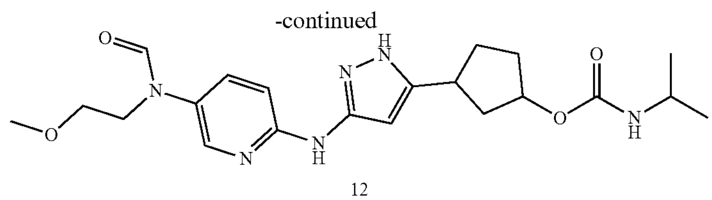

12

6-Bromopyridine-3-amine (1000 mg), sodium tert-butoxide (1666 mg), and 1-bromo-2-methoxyethane (1606 mg) were added to acetonitrile (10 mL), and the mixture was stirred at 80° C. After the reaction was completed, the reaction solution was concentrated by evaporation under reduced pressure to remove the solvent, and separated by column chromatography (developing solvents: petroleum ether/ethyl acetate) to give intermediate 12A (486 mg). MS (ESI): m/z 231.0 $[M+H]^+$.

Intermediate 12A (486 mg), N,N-dimethylaminopyridine (52 mg) and di-tert-butyl carbonate (660 mg) were added to dichloromethane (5 mL), and the mixture was stirred at room temperature. After the reaction was completed, the reaction solution was concentrated by evaporation under reduced pressure to remove the solvent, and separated by column chromatography (developing solvents: petroleum ether/ethyl acetate) to give intermediate 12B (0.36 g). MS (ESI): m/z 331.0 $[M+H]^+$.

Intermediate K1 (200 mg), intermediate 12B (240 mg), chloro(2-dicyclohexylphosphino-2',4',6'-triisopropyl-1,1'-biphenyl)[2-(2'-amino-1,1'-biphenyl)]palladium (II) (120 mg), 2-dicyclohexylphosphino-2',4',6'-triisopropylbiphenyl (160 mg), cesium carbonate (2400 mg), and diatomite (800 mg) were added to toluene/tert-butanol (35 mL, 5:1 (v/v)). After the addition was completed, the mixture was stirred at 120° C. After the reaction was completed, the reaction solution was filtered, and the filtrate was concentrated by evaporation under reduced pressure to remove the solvent, and separated by column chromatography (developing solvents: dichloromethane/methanol) to give intermediate 12C (224 mg). MS (ESI): m/z 559.58 $[M+H]^+$.

Intermediate 12C (224 mg) was added to formic acid (10 mL), and the mixture was stirred at 70° C. After the reaction was completed, the reaction solution was concentrated, and the pH of the residue was adjusted to alkalinity with a saturated aqueous sodium bicarbonate solution. The mixture was extracted with dichloromethane, dried over anhydrous sodium sulfate, and filtered. The filtrate was concentrated by evaporation under reduced pressure to remove the solvent and purified by medium and low pressure preparative liquid phase chromatography (C18 column, acetonitrile/water (30/70), the eluent contained one thousandth of ammonium hydroxide) to give compound 12 (105 mg). MS (ESI): m/z 434.2403 $[M+H]^+$.

$^1$H NMR (500 MHz, DMSO-$d_6$) δ 11.85 (s, 1H), 9.27 (s, 1H), 8.22 (s, 1H), 8.04-8.03 (m, 1H), 7.57-7.55 (m, 1H), 7.29 (s, 1H), 6.95 (d, J=7.4 Hz, 1H), 6.12 (s, 1H), 5.00-4.99 (m, 1H), 3.81-3.76 (m, 2H), 3.61-3.54 (m, 1H), 3.41-3.39 (m, 2H), 3.19 (s, 3H), 3.08-3.00 (m, 1H), 2.48-2.44 (m, 1H), 2.03-1.99 (m, 1H), 1.93-1.85 (m, 1H), 1.76-1.68 (m, 2H), 1.63-1.57 (m, 1H), 1.03 (d, J=6.5 Hz, 6H).

Example 13: Preparation of Compound 13

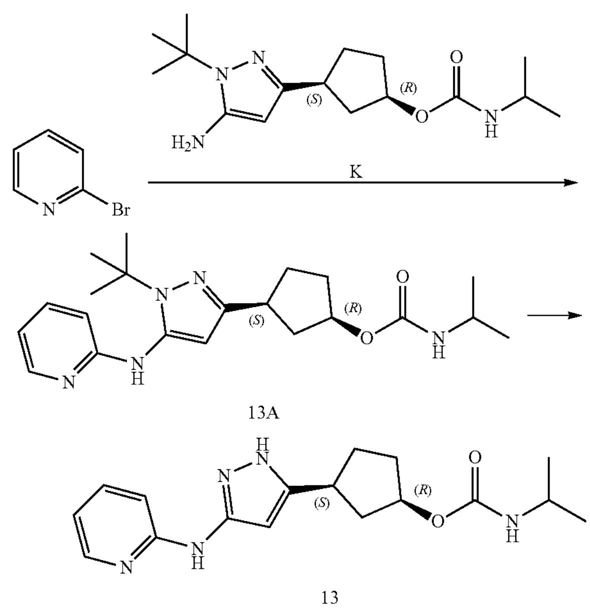

13A

13

A crude product of compound 13 was obtained by reference to the preparation method for compound 12 of Example 12, with intermediate 12B being replaced by 2-bromopyridine and intermediate K1 being replaced by intermediate K.

The crude product of compound 13 was purified by medium and low pressure preparative liquid phase chromatography (C18 column, acetonitrile/water (28/72), the eluent contained one thousandth of ammonium hydroxide) to give compound 13 (50 mg). MS (ESI): m/z 330.1927 $[M+H]^+$.

$^1$H NMR (500 MHz, DMSO-$d_6$): δ 11.79 (s, 1H), 9.04 (s, 1H), 8.09 (d, J=3.95 Hz, 1H), 7.51 (t, J=7.50 Hz, 1H), 7.24 (s, 1H), 6.95 (d, J=7.25 Hz, 1H), 6.66 (t, J=5.40 Hz, 1H), 6.10 (s, 1H), 5.00 (s, 1H), 3.60-3.56 (m, 1H), 3.05-3.02 (m, 1H), 2.47-2.43 (m, 1H), 2.01-1.98 (m, 1H), 1.93-1.85 (m, 1H), 1.76-1.66 (m, 2H), 1.64-1.58 (m, 1H), 1.03 (d, J=6.30 Hz, 6H).

Example 14: Preparation of Compound 14

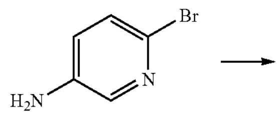

-continued

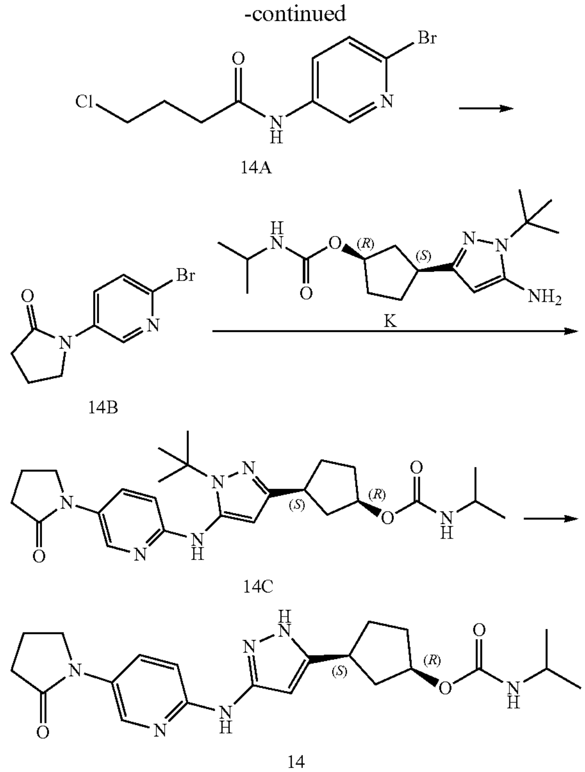

14A

14B

14C

14

6-Bromo-N-methylpyridine-3-amine (500 mg), 4-chlorobutyryl chloride (530 mg), and N,N-diisopropylethylamine (1121 mg) were added to dichloromethane (10 mL). After the addition, the mixture was stirred at room temperature. After the reaction was completed, the reaction solution was concentrated by evaporation under reduced pressure to remove the solvent, and separated by column chromatography (developing solvents: petroleum ether/ethyl acetate) to give intermediate 14A (800 mg). MS (ESI): m/z 276.9 $[M+H]^+$.

Intermediate 14A (800 mg) and potassium tert-butoxide (485 mg) were added to acetonitrile (10 mL), and the mixture was stirred at 80° C. After the reaction was completed, the reaction solution was concentrated by evaporation under reduced pressure to remove the solvent, and separated by column chromatography (developing solvents: petroleum ether/ethyl acetate) to give intermediate 14B (572 mg). MS (ESI): m/z 241.0 $[M+H]^+$.

A crude product of compound 14 was obtained by reference to the preparation method for compound 12 of Example 12, with intermediate 12B being replaced by intermediate 14B and intermediate K1 being replaced by intermediate K.

The crude product of compound 14 was purified by column chromatography (developing solvents: dichloromethane/methanol=5/1) to give compound 14 (30 mg). MS (ESI): m/z 413.2303 $[M+H]^+$.

$^1$H NMR (500 MHz, DMSO-$d_6$) δ 11.79 (s, 1H), 9.08 (s, 1H), 8.30 (d, J=2.7 Hz, 1H), 7.86-7.85 (m, 1H), 7.30 (s, 1H), 6.95 (d, J=7.7 Hz, 1H), 6.06 (s, 1H), 4.99 (m, 1H), 3.78 (t, J=7.0 Hz, 2H), 3.61-3.54 (m, 1H), 3.08-2.97 (m, 1H), 2.47 (d, J=7.2 Hz, 1H), 2.46-2.43 (m, 2H), 2.09-2.03 (m, 2H), 2.02-1.98 (m, 1H), 1.93-1.85 (m, 1H), 1.75-1.68 (m, 2H), 1.63-1.56 (m, 1H), 1.03 (d, J=6.4 Hz, 6H).

Example 15: Preparation of Compound 15

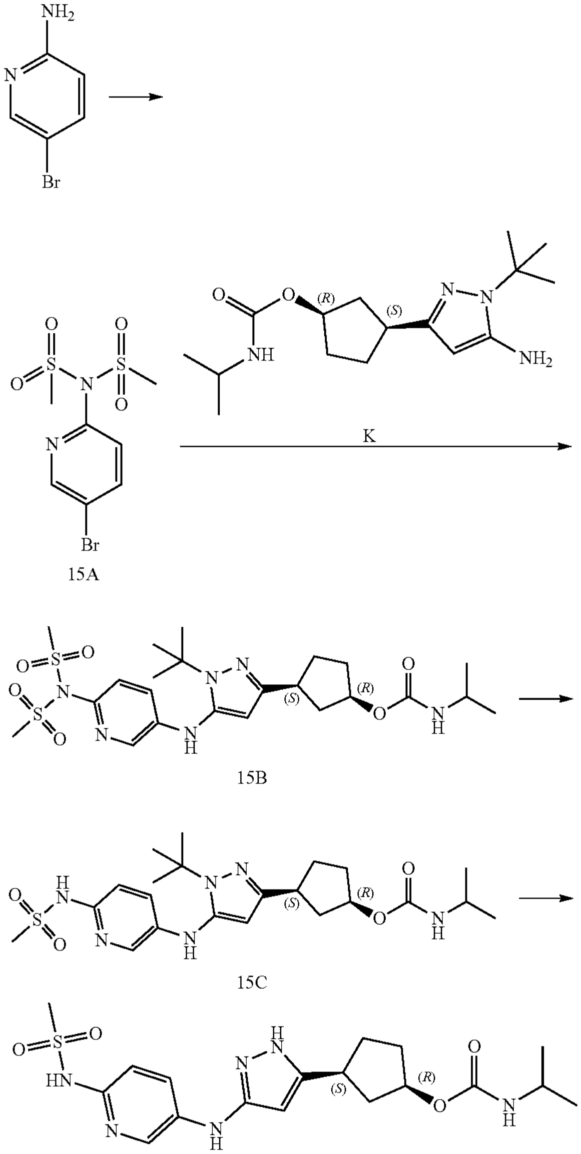

15A

15B

15C

15

A crude product of compound 15 was obtained by reference to the preparation method for compound 1 of Example 1, with 6-bromopyridine-3-amine being replaced by 2-amino-5-bromopyridine.

The crude product of compound 15 was purified by medium and low pressure preparative liquid phase chromatography (C18 column, acetonitrile/water (22/78), the eluent contained one thousandth of ammonium hydroxide) to give compound 15 (13 mg). MS (ESI): m/z 423.1810 $[M+H]^+$.

$^1$H NMR (500 MHz, DMSO-$d_6$) δ 8.05 (d, J=2.9 Hz, 1H), 7.83 (s, 1H), 7.49-7.37 (m, 1H), 6.96 (d, J=7.8 Hz, 1H), 6.53 (d, J=8.8 Hz, 1H), 5.50 (s, 1H), 4.98-4.97 (m, 1H), 3.59-3.55 (m, 1H), 3.02-2.96 (m, 1H), 2.83 (s, 3H), 2.46-2.40 (m, 1H), 2.02-1.96 (m, 1H), 1.92-1.83 (m, 1H), 1.75-1.66 (m, 2H), 1.59-1.55 (m, 1H), 1.03 (d, J=6.5 Hz, 6H).

Example 16: Preparation of Compound 16

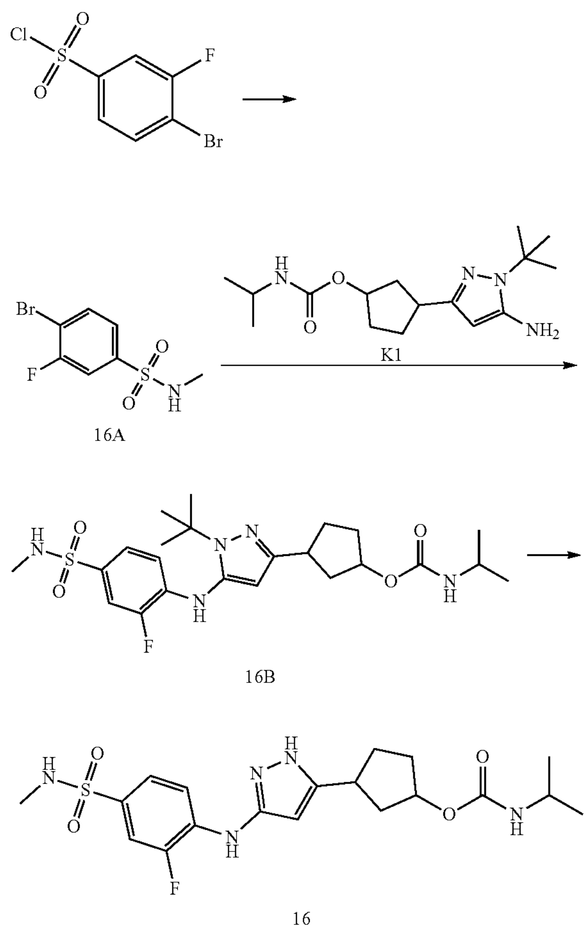

16A

16B

16

Methylamine hydrochloride (1000 mg), sodium hydroxide (285 mg), and 4-bromo-3-fluorobenzenesulfonyl chloride (1000 mg) were added to acetonitrile (20 mL), and the mixture was stirred at room temperature. After the reaction was completed, the reaction solution was concentrated by evaporation under reduced pressure to remove the solvent, and separated by column chromatography (developing solvents: petroleum ether/ethyl acetate) to give intermediate 16A (800 mg). MS (ESI): m/z 268.04 $[M-H]^-$.

A crude product of compound 16 was obtained by reference to the preparation method for compound 1 of Example 1, with intermediate 1A being replaced by intermediate 16A and intermediate K being replaced by intermediate K1.

The crude product of compound 16 was purified by medium and low pressure preparative liquid phase chromatography (C18 column, acetonitrile/water (30/70), the eluent contained one thousandth of ammonium hydroxide) to give compound 16 (60 mg). MS (ESI): m/z 440.5 $[M+H]^+$.

$^1$H NMR (500 MHz, DMSO-$d_6$) δ 12.00 (s, 1H), 8.70 (s, 1H), 8.20 (m, 1H), 7.46-7.44 (m, 2H), 7.23-7.20 (m, 1H), 6.95 (d, J=7.8 Hz, 1H), 5.83 (s, 1H), 5.00 (m, 1H), 3.59-3.55 (m, 1H), 3.09-3.03 (m, 1H), 2.48-2.44 (s, 1H), 2.39 (d, J=4.1 Hz, 3H), 2.04-2.00 (m, 1H), 1.96-1.86 (m, 1H), 1.76-1.67 (m, 2H), 1.64-1.56 (m, 1H), 1.03 (d, J=6.6 Hz, 6H).

Example 17: Preparation of Compound 17

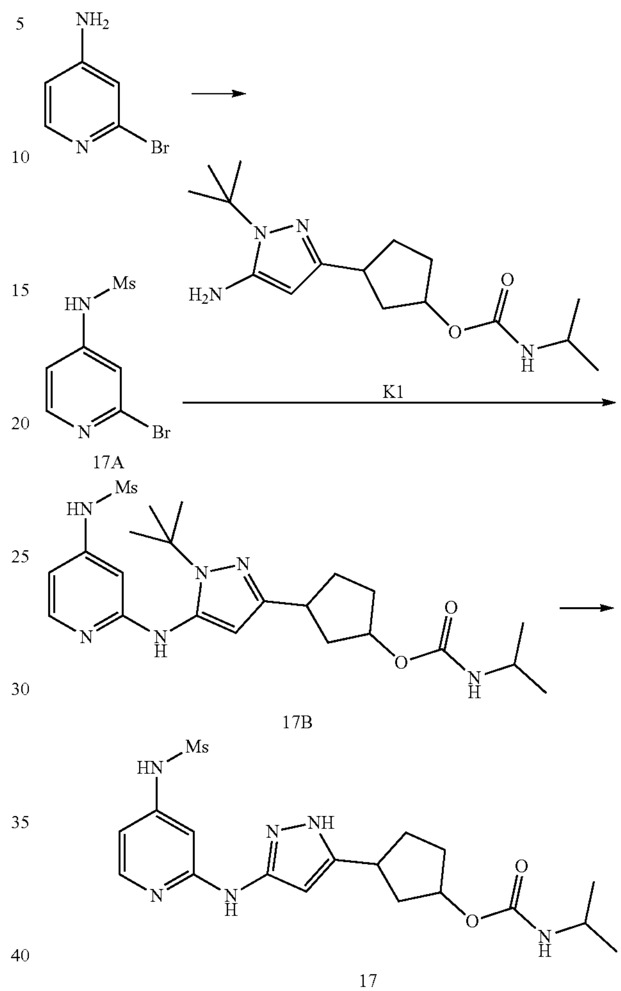

17A

17B

17

2-Bromo-4-aminopyridine (500 mg), methanesulfonic anhydride (503 mg), and N,N-diisopropylethylamine (747 mg) were added to dichloromethane (30 mL), and the mixture was stirred at room temperature. After the reaction was completed, the reaction solution was concentrated by evaporation under reduced pressure to remove the solvent, and separated by column chromatography (developing solvents: dichloromethane/methanol) to give intermediate 17A (200 mg). MS (ESI): m/z 251.02$[M+H]^+$.

A crude product of compound 17 was obtained by reference to the preparation method for compound 12 of Example 12, with intermediate 12B being replaced by intermediate 17A.

The crude product of compound 17 was purified by medium and low pressure preparative liquid phase chromatography (C18 column, acetonitrile/water (40/60), the eluent contained one thousandth of ammonium hydroxide) to give compound 17 (30 mg). MS (ESI): m/z 423.1813 $[M+H]^+$.

$^1$H NMR (500 MHz, DMSO-$d_6$): δ 8.78 (s, 1H), 7.66 (d, J=8.85 Hz, 1H), 6.95 (d, J=7.40 Hz, 1H), 6.58 (s, 1H), 6.24 (dd, J=1.50, 5.80 Hz, 1H), 5.81 (s, 1H), 4.99 (s, 1H), 3.61-3.54 (m, 1H), 3.00-2.95 (m, 1H), 2.73 (s, 3H), 2.45-2.40 (m, 1H), 1.99-1.95 (m, 1H), 1.91-1.85 (m, 1H), 1.71-1.68 (m, 2H), 1.64-1.59 (m, 1H), 1.03 (d, J=6.50 Hz, 6H).

Example 18: Preparation of Compound 18

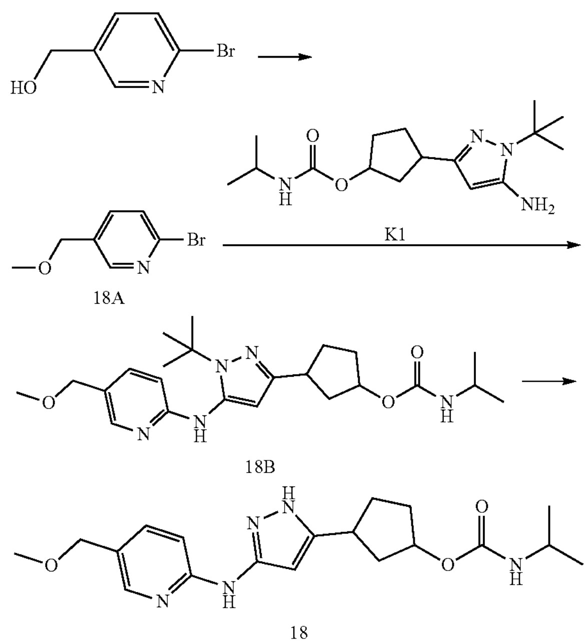

18A

18B

18

Sodium hydride (1.3 g) and 6-bromo-3-pyridinemethanol (2.0 g) were added to N,N-dimethylformamide (20 mL) at 0° C. under nitrogen atmosphere, and the mixture was stirred at 0° C. for half an hour. Iodomethane (2.3 g) was added, and the mixture was stirred at 0° C. After the reaction was completed, water was added to quench the reaction, and the mixture was extracted with ethyl acetate. The organic phase was separated, dried over anhydrous sodium sulfate, and filtered, and the filtrate was concentrated by evaporation under reduced pressure to remove the solvent, and separated by column chromatography (developing solvents: petroleum ether/ethyl acetate) to give intermediate 18A (1.6 g). MS (ESI): m/z 202.0 $[M+H]^+$.

A crude product of compound 18 was obtained by reference to the preparation method for compound 1 of Example 1, with intermediate 1A being replaced by intermediate 18A and intermediate K being replaced by intermediate K1.

The crude product of compound 18 was purified by medium and low pressure preparative liquid phase chromatography (C18 column, acetonitrile/water (35/65), the eluent contained one thousandth of ammonium hydroxide) to give compound 18 (19 mg). MS (ESI): m/z 374.2188 $[M+H]^+$.

$^1$H NMR (500 MHz, DMSO-$d_6$) δ 11.79 (s, 1H), 9.09 (s, 1H), 8.04 (s, 1H), 7.49 (d, J=8.1 Hz, 1H), 7.26 (d, J=7.3 Hz, 1H), 6.95 (d, J=6.9 Hz, 1H), 6.10 (s, 1H), 5.00 (s, 1H), 4.26 (s, 2H), 3.58 (dd, J=13.3, 6.7 Hz, 1H), 3.23 (s, 3H), 3.05-3.04 (m, 1H), 2.47-2.45 (m, 1H), 2.08-1.99 (m, 1H), 1.93-1.85 (m, 1H), 1.72-1.68 (m, 2H), 1.63-1.57 (m, 1H), 1.03 (d, J=6.4 Hz, 6H).

Example 19: Preparation of Compound 19

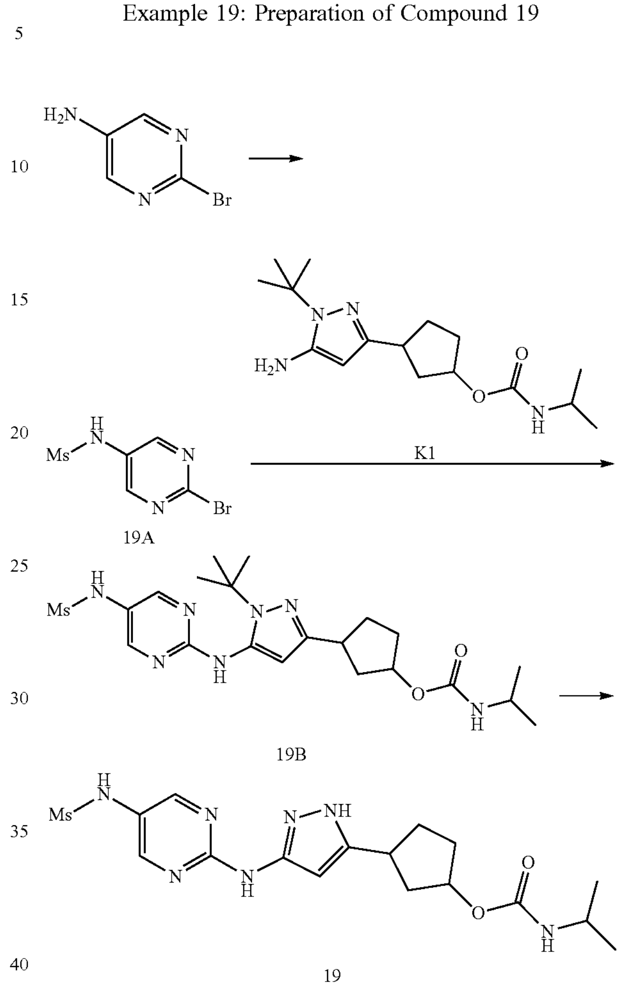

19A

19B

19

A crude product of compound 19 was obtained by reference to the preparation method for compound 17 of Example 17, with 2-bromo-4-aminopyridine being replaced by 5-amino-2-bromopyrimidine. The crude product of compound 19 was purified by medium and low pressure preparative liquid phase chromatography (C18 column, acetonitrile/water (40/60), the eluent contained one thousandth of ammonium hydroxide) to give compound 19 (32 mg). MS (ESI): m/z 424.1760 $[M+H]^+$.

$^1$H NMR (500 MHz, DMSO-$d_6$): δ 9.37 (s, 1H), 8.17 (s, 2H), 6.95 (d, J=7.45 Hz, 1H), 6.20 (s, 1H), 4.99 (s, 1H), 3.61-3.53 (m, 1H), 3.04-3.00 (m, 1H), 2.79 (s, 3H), 2.48-2.42 (m, 1H), 2.02-1.97 (m, 1H), 1.92-1.84 (m, 1H), 1.75-1.69 (m, 2H), 1.65-1.60 (m, 1H), 1.03 (d, J=6.50 Hz, 6H).

Example 20: Preparation of Compound 20

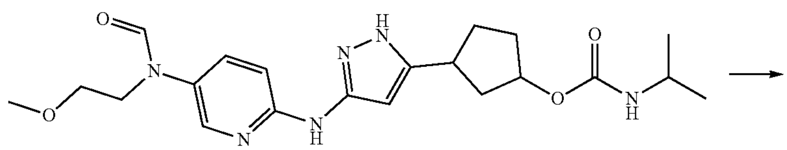

12

-continued

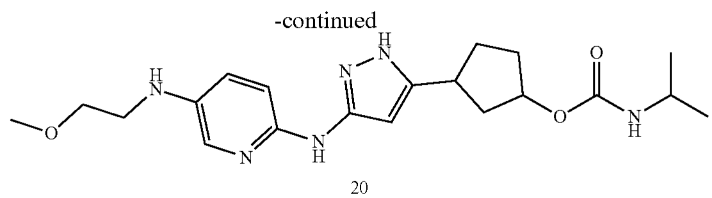

20

Compound 12 (80 mg) of Example 12 was added to diluted hydrochloric acid (1 M, 5 mL), and the mixture was stirred at 50° C. After the reaction was completed, the reaction solution was concentrated by evaporation under reduced pressure to remove the solvent, and the pH of the residue was adjusted to alkalinity with a saturated aqueous sodium bicarbonate solution. The mixture was extracted with dichloromethane, dried over anhydrous sodium sulfate, and filtered. The filtrate was concentrated by evaporation under reduced pressure to remove the solvent and purified by medium and low pressure preparative liquid phase chromatography (C18 column, acetonitrile/water (30/70), the eluent contained one thousandth of ammonium hydroxide) to give compound 20 (25 mg). MS (ESI): m/z 403.2455 $[M+H]^+$.

$^1$H NMR (500 MHz, DMSO-$d_6$) δ 11.60 (s, 1H), 8.43 (s, 1H), 7.57 (d, J=2.9 Hz, 1H), 7.11 (s, 1H), 6.98-6.94 (m, 2H), 5.90 (s, 1H), 5.11-4.84 (m, 2H), 3.59-3.56 (m, 1H), 3.48 (t, J=5.6 Hz, 2H), 3.28 (s, 3H), 3.13 (m, 2H), 3.04-2.95 (m, 1H), 2.46-2.39 (m, 1H), 2.00-1.96 (m, 1H), 1.94-1.83 (m, 1H), 1.73-1.67 (m, 2H), 1.63-1.56 (s, 1H), 1.03 (d, J=6.6 Hz, 6H).

Example 21: Preparation of Compound 21

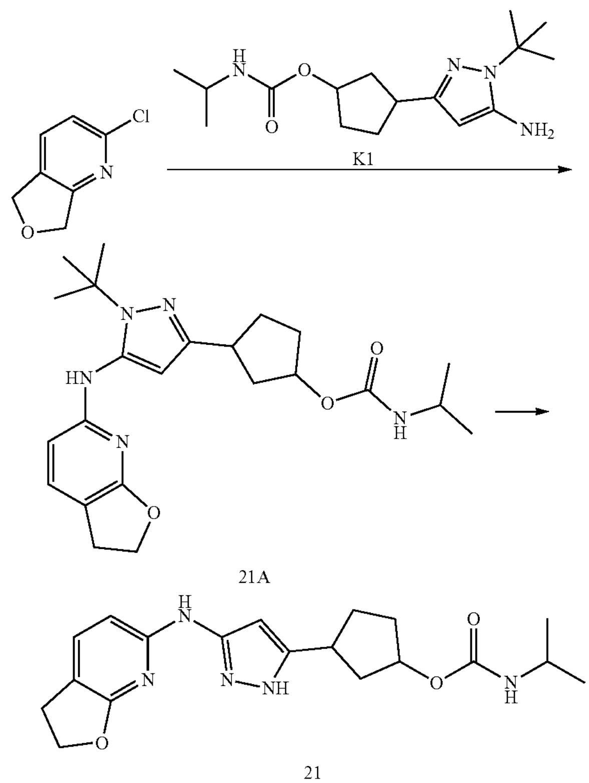

21A

21

Intermediate K1 (200 mg), 6-chloro-2,3-dihydrofuran[2,3-b]pyridine (120 mg), chloro(2-dicyclohexylphosphino-2',4',6'-triisopropyl-1,1'-biphenyl)[2-(2'-amino-1,1'-biphenyl)] palladium (II) (120 mg), 2-dicyclohexylphosphino-2',4',6'-triisopropylbiphenyl (160 mg), cesium carbonate (2400 mg), and diatomite (800 mg) were added to toluene/tert-butanol (35 mL, 5:1 (v/v)). The mixture was stirred at 120° C. under nitrogen atmosphere. After the reaction was completed, the reaction solution was filtered, concentrated by evaporation under reduced pressure to remove the solvent, and separated by column chromatography (developing solvents: dichloromethane/methanol) to give intermediate 21A (108 mg). MS (ESI): m/z 428.51 $[M+H]^+$.

Intermediate 21A (108 mg) was added to formic acid (5 mL), and the mixture was stirred at 70° C. After the reaction was completed, the reaction solution was concentrated by evaporation under reduced pressure to remove the solvent. The pH of the residue was adjusted to alkalinity with a saturated aqueous sodium bicarbonate solution. A solid was precipitated, the mixture was filtered, and the filter cake was slurried with methanol to give compound 21 (49 mg). MS (ESI): m/z 372.2036 $[M+H]^+$.

$^1$H NMR (500 MHz, DMSO-$d_6$) δ 11.74 (s, 1H), 8.89 (s, 1H), 7.37 (d, J=8.0 Hz, 1H), 6.94 (d, J=7.9 Hz, 1H), 6.79 (d, J=7.9 Hz, 1H), 6.01 (s, 1H), 5.00 (s, 1H), 4.49 (t, J=8.4 Hz, 2H), 3.58-3.57 (m, 1H), 3.08-3.02 (m, 3H), 2.48-2.40 (m, 1H), 2.07-1.95 (m, 1H), 1.92-1.84 (m, 1H), 1.77-1.65 (m, 2H), 1.63-1.54 (m, 1H), 1.03 (d, J=6.6 Hz, 6H).

Example 22: Preparation of Compound 22

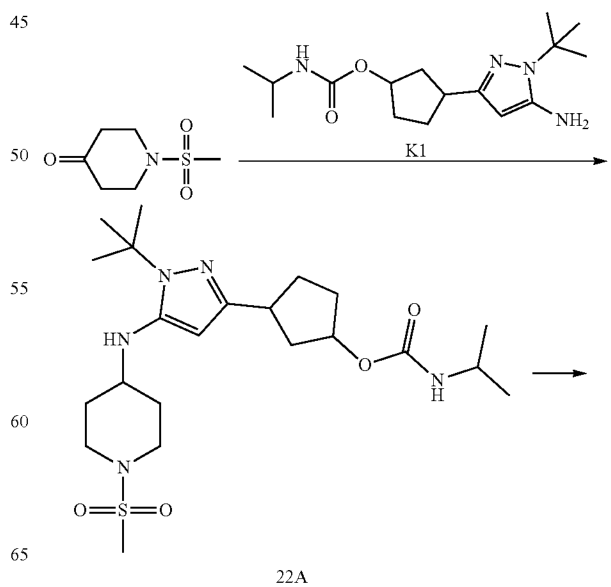

22A

-continued

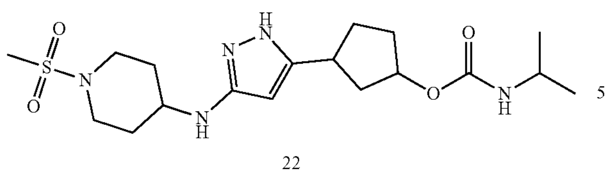

22

1-N-Methanesulfonyl-4-piperidone (264 mg), intermediate K1 (200 mg), and acetic acid (42.8 mg) were added to 1,2-dichloroethane (15 mL), and the mixture was stirred at room temperature under nitrogen atmosphere. After the reaction was completed, sodium triacetoxyborohydride (550 mg) was added, and the mixture was stirred at room temperature. After the reaction was completed, the reaction solution was concentrated by evaporation under reduced pressure to remove the solvent, and separated by column chromatography (developing solvents: dichloromethane/methanol) to give intermediate 22A (300 mg). MS (ESI): m/z 470.6 $[M+H]^+$.

Intermediate 22A (200 mg) was added to formic acid (10 mL), and the mixture was stirred at 110° C. After the reaction was completed, the reaction solution was concentrated by evaporation under reduced pressure to remove the solvent, and triethylamine was added to the residue to adjust the pH to alkalinity. The reaction solution was concentrated by evaporation under reduced pressure to remove the solvent. The crude product of compound 22 was purified by medium and low pressure preparative liquid phase chromatography (C18 column, acetonitrile/water (30/70), the eluent contained one thousandth of ammonium hydroxide) to give compound 22 (37 mg). MS (ESI): m/z 414.5 $[M+H]^+$.

$^1$H NMR (500 MHz, DMSO-$d_6$) δ 11.17 (s, 1H), 6.94 (d, J=7.8 Hz, 1H), 5.25 (s, 1H), 5.04-4.84 (m, 2H), 3.60-3.54 (m, 1H), 3.48-3.44 (m, 2H), 3.26 (s, 1H), 2.98-2.89 (m, 1H), 2.89-2.77 (m, 5H), 2.41-2.35 (m, 1H), 2.03-1.91 (m, 3H), 1.88-1.84 (m, 1H), 1.71-1.62 (m, 2H), 1.57-1.52 (m, 1H), 1.46-1.39 (m, 2H), 1.03 (d, J=6.5 Hz, 6H).

Example 23: Preparation of Compound 23

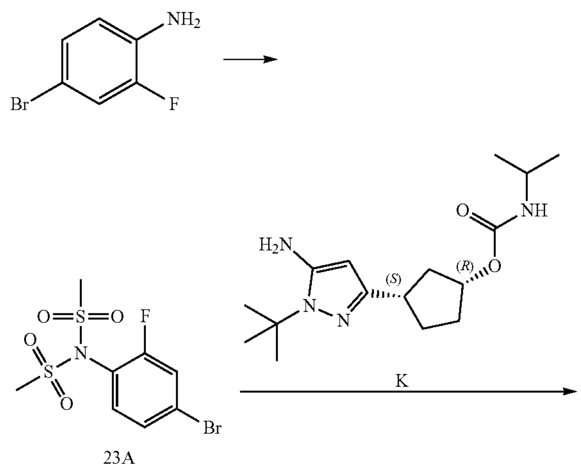

23A

-continued

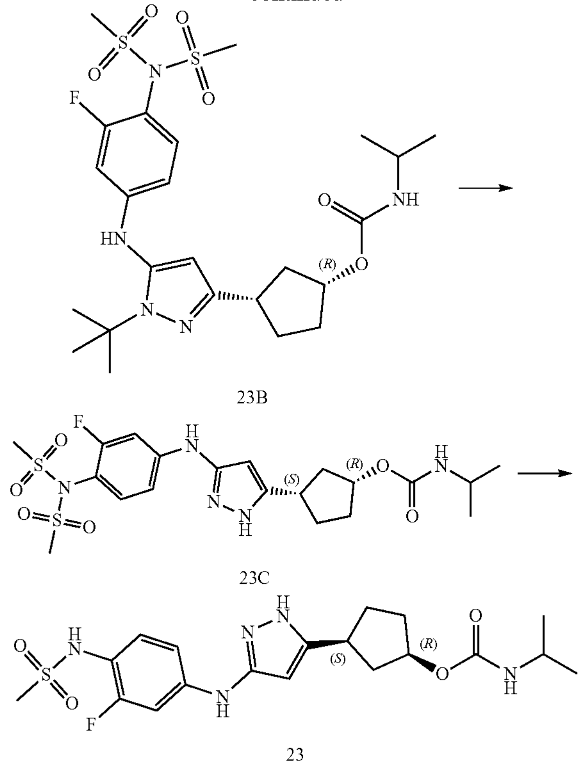

23B

23C

23

4-bromo-2-fluoroaniline (3.00 g), N,N-diisopropylethyl amine (10.20 g), and methanesulfonic anhydride (8.25 g) were added to dichloromethane (85 mL), and the mixture was stirred at room temperature under nitrogen atmosphere. After the reaction was completed, the reaction solution was concentrated by evaporation under reduced pressure to remove the solvent, and dichloromethane and a saturated aqueous ammonium chloride solution were added to the residue. The organic phase was separated, dried, and filtered, and the filtrate was concentrated by evaporation under reduced pressure to remove the solvent to give intermediate 23A (3.80 g).

Intermediate K (0.60 g), intermediate 23A (1.00 g), chloro (2-dicyclohexylphosphino-2',4',6'-triisopropyl-1,1'-biphenyl)[2-(2'-amino-1,1'-biphenyl)]palladium (II) (0.46 g), dicyclohexyl(2',4',6'-triisopropyl-[1,1'-biphenyl]-2-yl)phosphine (0.28 g), tripotassium phosphate (1.40 g), and diatomite (2.4 g) were added to toluene/tert-butanol (30 mL, 5:1 (v/v)), and the mixture was stirred at 120° C. under nitrogen atmosphere. After the reaction was completed, the reaction solution was filtered, and the filtrate was concentrated by evaporation under reduced pressure to remove the solvent, and separated by column chromatography (developing solvents: dichloromethane/methanol) to give intermediate 23B (1.00 g).

Intermediate 23B (0.12 g) was added to formic acid (20 mL), and the mixture was stirred at 70° C. After the reaction was completed, the reaction solution was concentrated by evaporation under reduced pressure to remove the solvent, and the residue was intermediate 23C, which was directly fed for the next reaction without further purification.

Intermediate 23C and sodium carbonate (0.74 g) were added to methanol (25 mL) and water (5 mL), and the mixture was stirred at 70° C. After the reaction was completed, the reaction solution was concentrated by evaporation under reduced pressure to remove the solvent, and dichloromethane and water were added to the residue. The organic phase was separated, concentrated by evaporation under reduced pressure to remove the solvent, and purified by column chromatography (developing solvents: dichloromethane/methanol (40/1)) to give compound 23 (0.30 g). HRMS (ESI, $[M+H]^+$) m/z: 440.1841.

$^1H$ NMR (500 MHz, DMSO-$d_6$) δ 11.80 (s, 1H), 9.06 (s, 1H), 8.67 (s, 1H), 7.43 (d, J=12.4 Hz, 1H), 7.11 (t, J=8.9 Hz, 1H), 6.96-6.95 (m, 2H), 5.62 (s, 1H), 4.99 (s, 1H), 3.62-3.54 (m, 1H), 3.09-3.00 (m, 1H), 2.91 (s, 3H), 2.49-2.43 (m, 1H), 2.03-1.99 (m, 1H), 1.94-1.85 (m, 1H), 1.74-1.66 (m, 2H), 1.62-1.56 (m, 1H), 1.03 (d, J=6.3 Hz, 6H).

Example 24: Preparation of Compound 24

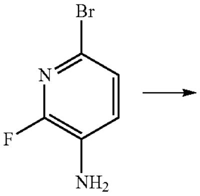

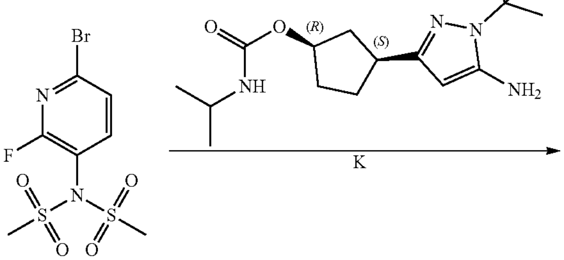

24A

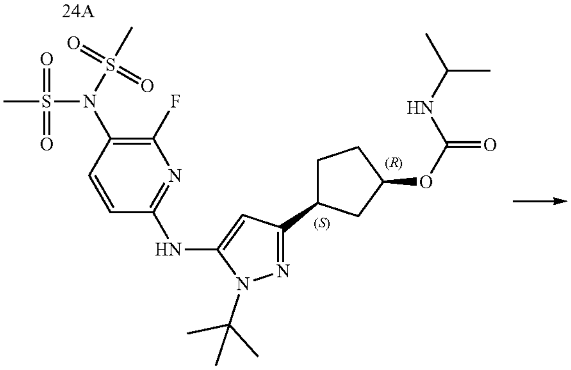

24B

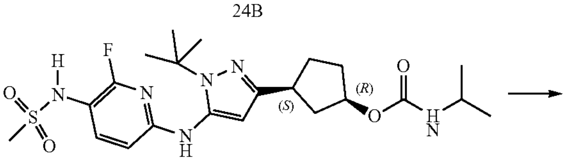

24C

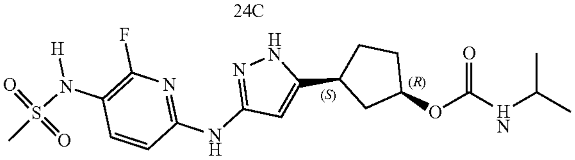

24

A crude product of compound 24 was obtained by reference to the preparation method for compound 1 of Example 1, with 2-bromo-4-aminopyridine being replaced by 2-fluoro-6-bromo-3-aminopyridine.

The crude product of compound 24 was purified by column chromatography (developing solvents: dichloromethane/methanol (96/4)) to give compound 24 (106 mg). MS (ESI): m/z 441.1722 $[M+H]^+$.

$^1H$ NMR (500 MHz, DMSO-$d_6$) δ 11.95 (s, 1H), 9.52 (s, 1H), 9.19 (s, 1H), 7.58 (dd, J=10.3, 8.5 Hz, 1H), 7.21-7.08 (m, 1H), 6.94 (d, J=7.8 Hz, 1H), 6.06 (s, 1H), 5.04-4.96 (m, 1H), 3.61-3.54 (m, 1H), 3.08-3.03 (m, 1H), 2.95 (s, 3H), 2.48-2.44 (m, 1H), 2.05-1.99 (m, 1H), 1.94-1.85 (m, 1H), 1.76-1.67 (m, 2H), 1.64-1.54 (m, 1H), 1.03 (dd, J=6.6, 2.4 Hz, 6H).

Example 25: Preparation of Compound 25

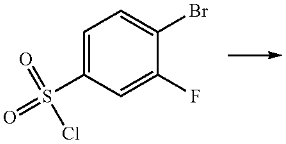

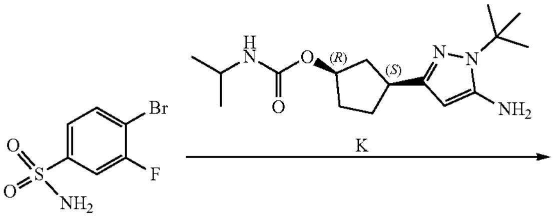

25A

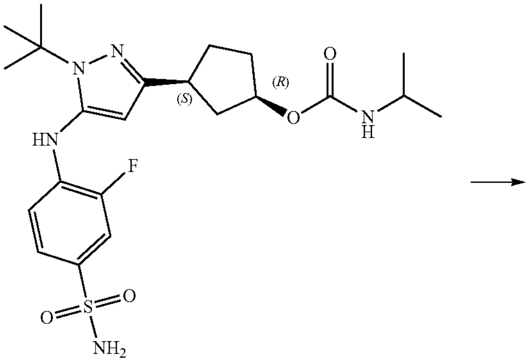

25B

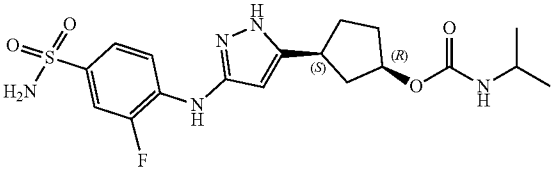

25

Compound 25A was obtained by reference to the preparation method for compound 16A of Example 16, with methylamine hydrochloride being replaced by ammonium hydroxide.

A crude product of compound 25 was obtained by reference to the preparation method for compound 16 of Example 16, with intermediate 16A being replaced by intermediate 25A and intermediate K1 being replaced by intermediate K.

The crude product of compound 25 was purified by medium and low pressure preparative liquid phase chromatography (C18 column, acetonitrile/water (30/70), the eluent contained one thousandth of ammonium hydroxide) to give compound 25 (50 mg). MS (ESI): m/z 426.5 $[M+H]^+$.

$^1$H NMR (500 MHz, DMSO-$d_6$) δ 11.96 (s, 1H), 8.62 (s, 1H), 8.19 (t, J=8.5 Hz, 1H), 7.50 (d, J=9.9 Hz, 2H), 7.17 (s, 2H), 6.94 (d, J=7.8 Hz, 1H), 5.82 (s, 1H), 5.00 (s, 1H), 3.68-3.48 (m, 1H), 3.09-3.02 (m, 1H), 2.48-2.44 (m, 1H), 2.04-2.00 (m, 1H), 1.95-1.89 (m, 1H), 1.75-1.67 (m, 2H), 1.62-1.56 (m, 1H), 1.03 (d, J=6.5 Hz, 6H).

Example 26: Preparation of Compound 26

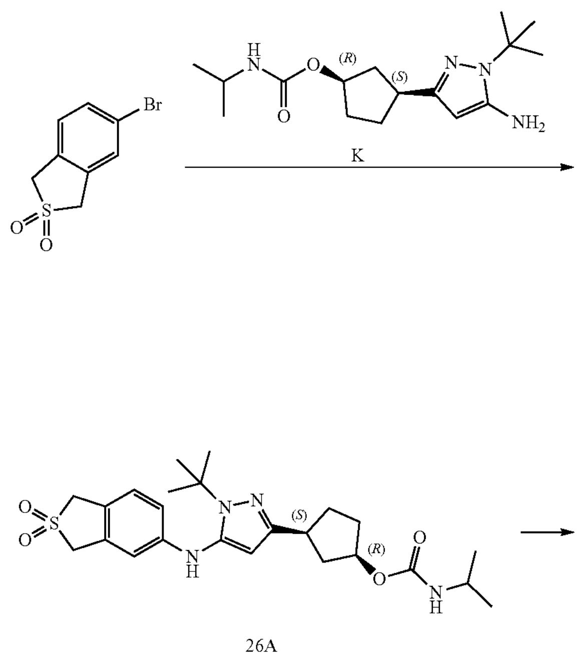

26A

-continued

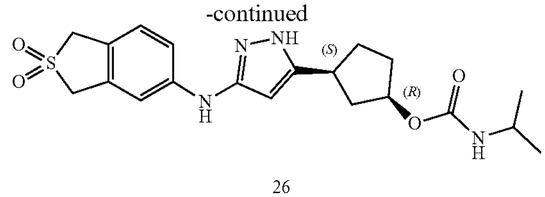

26

Intermediate K (450 mg), 5-bromo-1,3-dihydrobenzo[c]thiophene-2,2-dioxide (241 mg), chloro(2-dicyclohexylphosphino-2',4',6'-triisopropyl-1,1'-biphenyl)[2-(2'-amino-1,1'-biphenyl)]palladium (II) (230 mg), 2-dicyclohexylphosphino-2',4',6'-triisopropylbiphenyl (139 mg), and potassium phosphate (960 mg) were added to N,N-dimethylformamide (20 mL). After the addition, the mixture was stirred at 110° C. After the reaction was completed, the reaction solution was filtered, and the filtrate was concentrated by evaporation under reduced pressure to remove the solvent, and separated by column chromatography (developing solvents: dichloromethane/methanol) to give intermediate 26A (655 mg). MS (ESI): m/z 475.33 $[M+H]^+$.

Intermediate 26A (108 mg) was added to formic acid (10 mL), and the mixture was stirred at 70° C. After the reaction was completed, the reaction solution was concentrated by evaporation under reduced pressure to remove the solvent, and the pH of the residue was adjusted to alkalinity with a saturated aqueous sodium bicarbonate solution. The mixture was extracted with dichloromethane, dried over anhydrous sodium sulfate, and filtered. The filtrate was concentrated by evaporation under reduced pressure to remove the solvent and purified by medium and low pressure preparative liquid phase chromatography (C18 column, acetonitrile/water (30/70), the eluent contained one thousandth of ammonium hydroxide) to give compound 26 (140 mg). MS (ESI): m/z 419.1753 $[M+H]^+$.

1H NMR (500 MHz, DMSO-$d_6$) δ 11.73 (s, 1H), 8.48 (s, 1H), 7.41 (s, 1H), 7.22 (d, J=8.4 Hz, 1H), 7.14 (d, J=8.4 Hz, 1H), 6.95 (d, J=7.9 Hz, 1H), 5.63 (s, 1H), 4.99 (m, 1H), 4.41 (s, 2H), 4.32 (s, 2H), 3.60-3.56 (m, 1H), 3.08-3.00 (m, 1H), 2.48-2.42 (m, 1H), 2.03-1.98 (m, 1H), 1.93-1.85 (m, 1H), 1.73-1.68 (m, 2H), 1.62-1.56 (m, 1H), 1.04-1.02 (m, 6H).

Example 27: Preparation of Compound 27

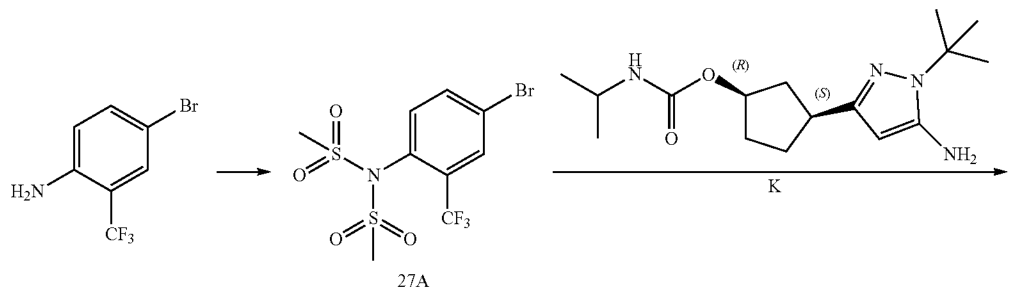

27A

-continued

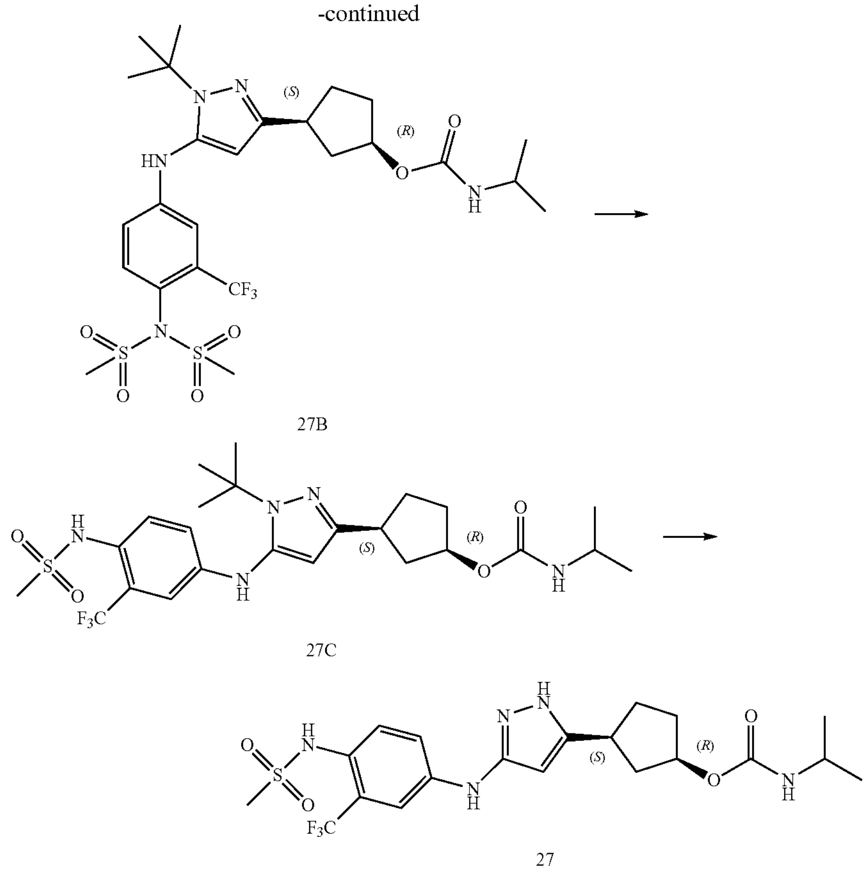

27B

27C

27

Compound 27A was obtained by reference to the preparation method for compound 1A of Example 1, with 6-bromopyridine-3-amine being replaced by 2-amino-5-bromotrifluorotoluene.

A crude product of compound 27 was obtained by reference to the preparation method for compound 1 of Example 1, with compound 1A being replaced by compound 27A.

The crude product of compound 27 was purified by medium and low pressure preparative liquid phase chromatography (C18 column, acetonitrile/water (30/70), the eluent contained one thousandth of ammonium hydroxide) to give compound 27 (60 mg). MS (ESI): m/z 490.3 $[M+H]^+$.

$^1$H NMR (500 MHz, DMSO-$d_6$) δ 11.87 (s, 1H), 9.04 (s, 1H), 8.80 (s, 1H), 7.90 (s, 1H), 7.46-7.45 (m, 1H), 7.34 (d, J=8.7 Hz, 1H), 6.95 (d, J=7.9 Hz, 1H), 5.62 (s, 1H), 5.01-4.97 (m, 1H), 3.61-3.54 (m, 1H), 3.05-2.98 (m, 1H), 2.99 (s, 3H), 2.48-2.40 (m, 1H), 2.04-1.98 (m, 1H), 1.95-1.84 (m, 1H), 1.75-1.67 (m, 2H), 1.62-1.59 (m, 1H), 1.03 (d, J=6.1 Hz, 6H).

Example 28: Preparation of Compound 28

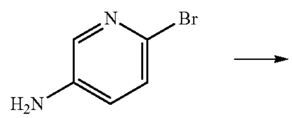

-continued

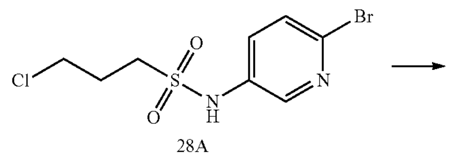

28A

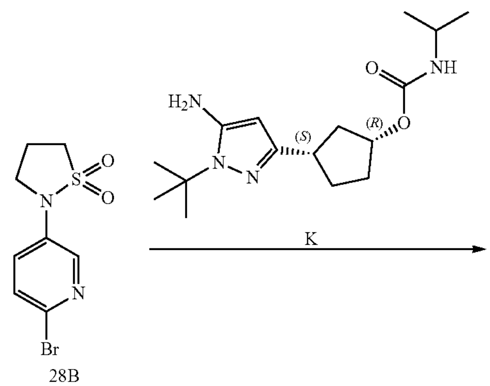

28B

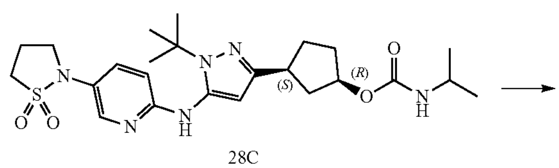

28C

-continued

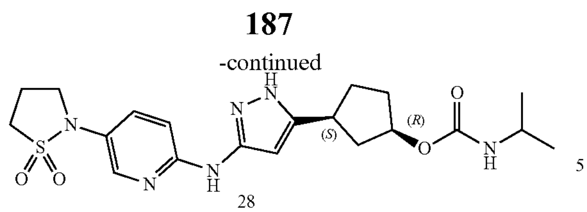

28

Compound 28A was obtained by reference to the preparation method for compound 14A of Example 14, with 4-chlorobutyryl chloride being replaced by 3-chloropropanesulfonyl chloride.

Compound 28B was obtained by reference to the preparation method for compound 14B of Example 14, with intermediate 14A being replaced by compound 28A.

A crude product of compound 28 was obtained by reference to the preparation method for compound 14 of Example 14, with intermediate 14B being replaced by compound 28B.

The crude product of compound 28 was purified by medium and low pressure preparative liquid phase chromatography (C18 column, acetonitrile/water (25/75), the eluent contained one thousandth of ammonium hydroxide) to give compound 28 (25 mg). MS (ESI): m/z 449.1964 $[M+H]^+$.

$^1H$ NMR (500 MHz, DMSO-$d_6$) δ 11.81 (s, 1H), 9.17 (s, 1H), 8.02 (d, J=2.1 Hz, 1H), 7.55-7.47 (m, 1H), 7.33 (s, 1H), 6.93 (d, J=6.8 Hz, 1H), 6.08 (s, 1H), 5.00 (s, 1H), 3.66 (t, J=6.6 Hz, 2H), 3.62-3.54 (m, 1H), 3.43 (t, J=7.6 Hz, 2H), 3.07-3.00 (m, 1H), 2.48-2.42 (m, 1H), 2.41-2.35 (m, 2H), 2.03-1.99 (m, 1H), 1.93-1.84 (m, 1H), 1.76-1.68 (m, 2H), 1.63-1.56 (s, 1H), 1.03 (d, J=6.4 Hz, 6H).

Example 29: Preparation of Compound 29

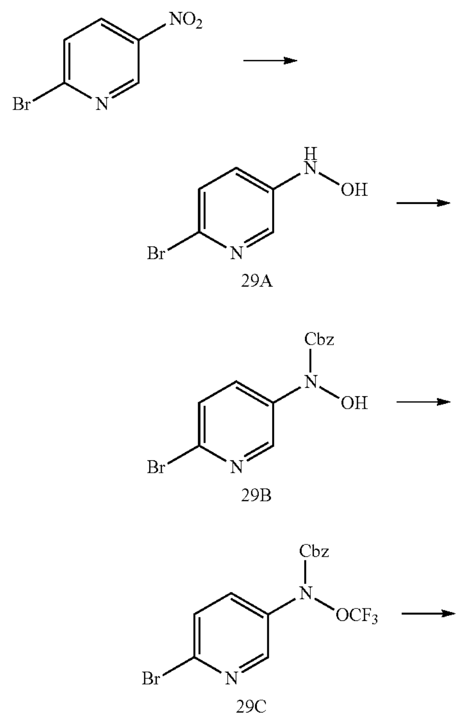

29A

29B

29C

-continued

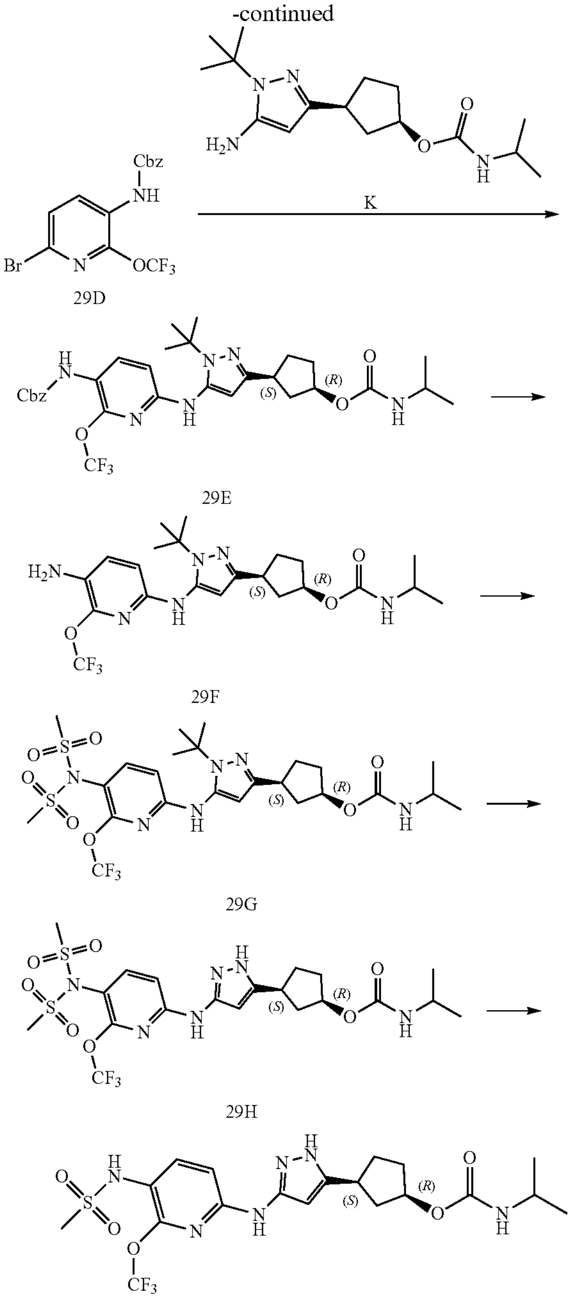

29D

29E

29F

29G

29H

29

2-Bromo-5-nitropyridine (5.00 g), hydrazine hydrate (1.48 g), and rhodium on carbon (485 mg) were added to tetrahydrofuran (150 mL), and the mixture was stirred at room temperature. After the reaction was completed, the reaction solution was filtered, and the filtrate was concentrated by evaporation under reduced pressure to remove the solvent to give intermediate 29A (4.20 g). MS (ESI): m/z 189.0 $[M+H]^+$.

Intermediate 29A (4.20 g), sodium bicarbonate (2.10 g), and benzyl chloroformate (4.17 g) were added to 1,4-dioxane (200 mL), and the mixture was stirred at room temperature. After the reaction was completed, the reaction solution was filtered, and the filtrate was concentrated by evaporation under reduced pressure to remove the solvent, and separated by column chromatography (developing solvents: dichloromethane/methanol) to give intermediate 29B (3.63 g). MS (ESI): m/z 323.16 [M+H]$^+$.

Intermediate 29B (3.63 g), 3,3-dimethyl-1-(trifluoromethyl)-1,2-benziodoxole (4.17 g) were added to dichloromethane (100 mL), and the mixture was stirred at room temperature. After the reaction was completed, the reaction solution was concentrated by evaporation under reduced pressure to remove the solvent to give intermediate 29C (4.00 g). MS (ESI): m/z 391.25 [M+H]$^+$.

Intermediate 29C (4.00 g) was added to nitromethane (50 mL), and the mixture was stirred at 120° C. After the reaction was completed, the reaction solution was concentrated by evaporation under reduced pressure to remove the solvent, and separated by column chromatography (developing solvents: petroleum ether/ethyl acetate) to give intermediate 29D (930 mg). MS (ESI): m/z 391.25 [M+H]$^+$.

Intermediate K (200 mg), intermediate 29D (300 mg), chloro(2-dicyclohexylphosphino-2',4',6'-triisopropyl-1,1'-biphenyl)[2-(2'-amino-1,1'-biphenyl)]palladium (II) (120 mg), 2-dicyclohexylphosphino-2',4',6'-triisopropylbiphenyl (160 mg), cesium carbonate (2400 mg), and diatomite (800 mg) were added to toluene/tert-butanol (35 mL, 5:1 (v/v)), and the mixture was stirred at 120° C. under nitrogen atmosphere. After the reaction was completed, the reaction solution was filtered, and the filtrate was concentrated by evaporation under reduced pressure to remove the solvent, and separated by column chromatography (developing solvents: dichloromethane/methanol) to give intermediate 29E (120 mg). MS (ESI): m/z 619.49 [M+H]$^+$.

Intermediate 29E (120 mg) and palladium on carbon (30 mg, 50% (w/w)) were added to tetrahydrofuran (5 mL), and the mixture was stirred at room temperature under hydrogen atmosphere. After the reaction was completed, the reaction solution was filtered, and the filtrate was concentrated by evaporation under reduced pressure to remove the solvent to give intermediate 29F (70 mg). MS (ESI): m/z 485.31 [M+H]$^+$.

Intermediate 29F (70 mg), methanesulfonic anhydride (83 mg), and N,N-diisopropylethylamine (42 mg) were added to dichloromethane (5 mL), and the mixture was stirred at room temperature. After the reaction was completed, the reaction solution was concentrated by evaporation under reduced pressure to remove the solvent to give compound 29G (90 mg). MS (ESI): m/z 641.31 [M+H]$^+$.

Intermediate 29G (90 mg) was added to formic acid (5 mL), and the mixture was stirred at 90° C. After the reaction was completed, the reaction solution was concentrated by evaporation under reduced pressure to remove the solvent, and the pH of the residue was adjusted to alkalinity with a saturated aqueous sodium bicarbonate solution. The mixture was extracted with dichloromethane, dried over anhydrous sodium sulfate, and filtered. The filtrate was concentrated by evaporation under reduced pressure to remove the solvent to give intermediate 29H (70 mg). MS (ESI): m/z 585.18 [M+H]$^+$.

Intermediate 29H (70 mg) and sodium carbonate (70 mg) were added to methanol (5 mL) and water (1 mL), and the mixture was stirred at 70° C. After the reaction was completed, the reaction solution was concentrated by evaporation under reduced pressure to remove methanol, and the residue was extracted with dichloromethane, dried over anhydrous sodium sulfate, and filtered. The filtrate was concentrated by evaporation under reduced pressure to remove the solvent and purified by medium and low pressure preparative liquid phase chromatography (C18 column, acetonitrile/water (30/70), the eluent contained one thousandth of ammonium hydroxide) to give compound 29 (20 mg). MS (ESI): m/z 507.1638 [M+H]$^+$.

$^1$H NMR (500 MHz, DMSO-$d_6$) δ 11.92 (s, 1H), 9.62 (s, 1H), 9.26 (s, 1H), 7.58 (d, J=8.6 Hz, 1H), 6.97 (d, J=8.6 Hz, 1H), 6.90 (d, J=7.9 Hz, 1H), 6.31 (s, 1H), 4.99 (s, 1H), 3.62-3.55 (m, 1H), 3.07-3.01 (m, 1H), 2.92 (s, 3H), 2.48-2.44 (m, 1H), 2.05-1.99 (m, 1H), 1.96-1.85 (m, 1H), 1.75-1.65 (m, 2H), 1.61-1.55 (m, 1H), 1.03 (d, J=6.7 Hz, 6H).

Example 30: Preparation of Compound 30

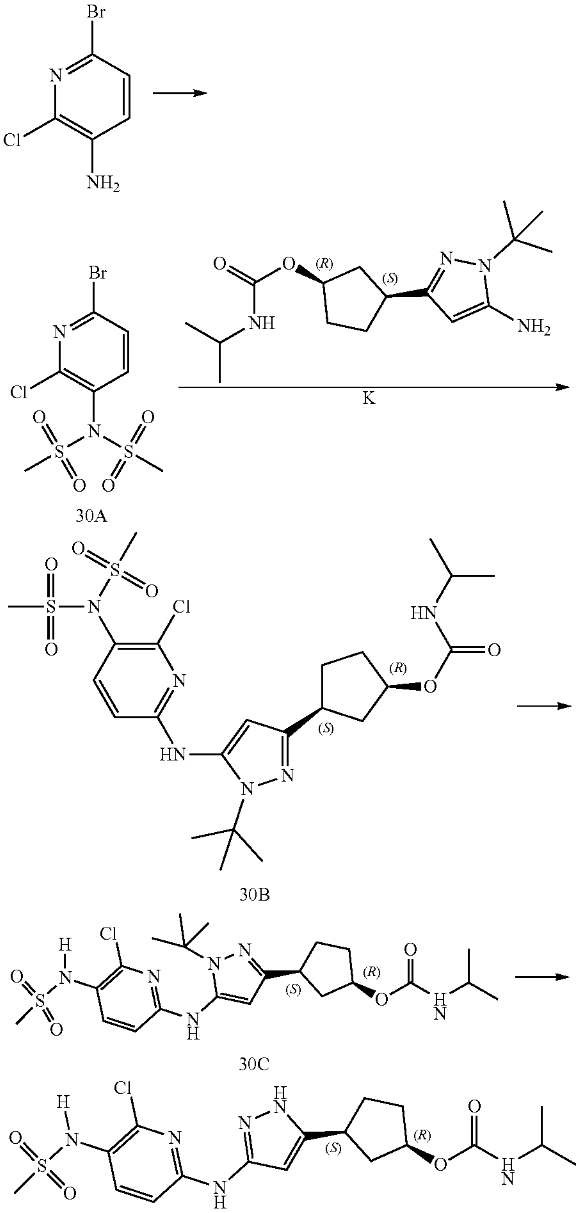

30A

30B

30C

30

Compound 30A was obtained by reference to the preparation method for compound 1A of Example 1, with 2-bromo-4-aminopyridine being replaced by 2-chloro-3-amino-6-bromopyridine.

A crude product of compound 30 was obtained by reference to the preparation method for compound 1 of Example 1, with intermediate 1A being replaced by intermediate 30A.

The crude product of compound 30 was purified by medium and low pressure preparative liquid phase chromatography (C18 column, acetonitrile/water (18/82), the eluent contained one thousandth of ammonium hydroxide) to give compound 30 (30 mg). MS (ESI): m/z 457.1422 $[M+H]^+$.

$^1$H NMR (500 MHz, DMSO-$d_6$) δ 11.94 (s, 1H), 9.59 (s, 1H), 9.26 (s, 1H), 7.57 (d, J=8.6 Hz, 1H), 7.30 (s, 1H), 6.93 (d, J=8.8 Hz, 1H), 6.04 (s, 1H), 5.00 (s, 1H), 3.62-3.53 (m, 1H), 3.12-3.02 (m, 1H), 2.99 (s, 3H), 2.48-2.44 (m, 1H), 2.05-1.99 (m, 1H), 1.94-1.85 (m, 1H), 1.76-1.67 (m, 2H), 1.64-1.54 (m, 1H), 1.03 (d, J=4.8 Hz, 6H).

Example 31: Preparation of Compound 31

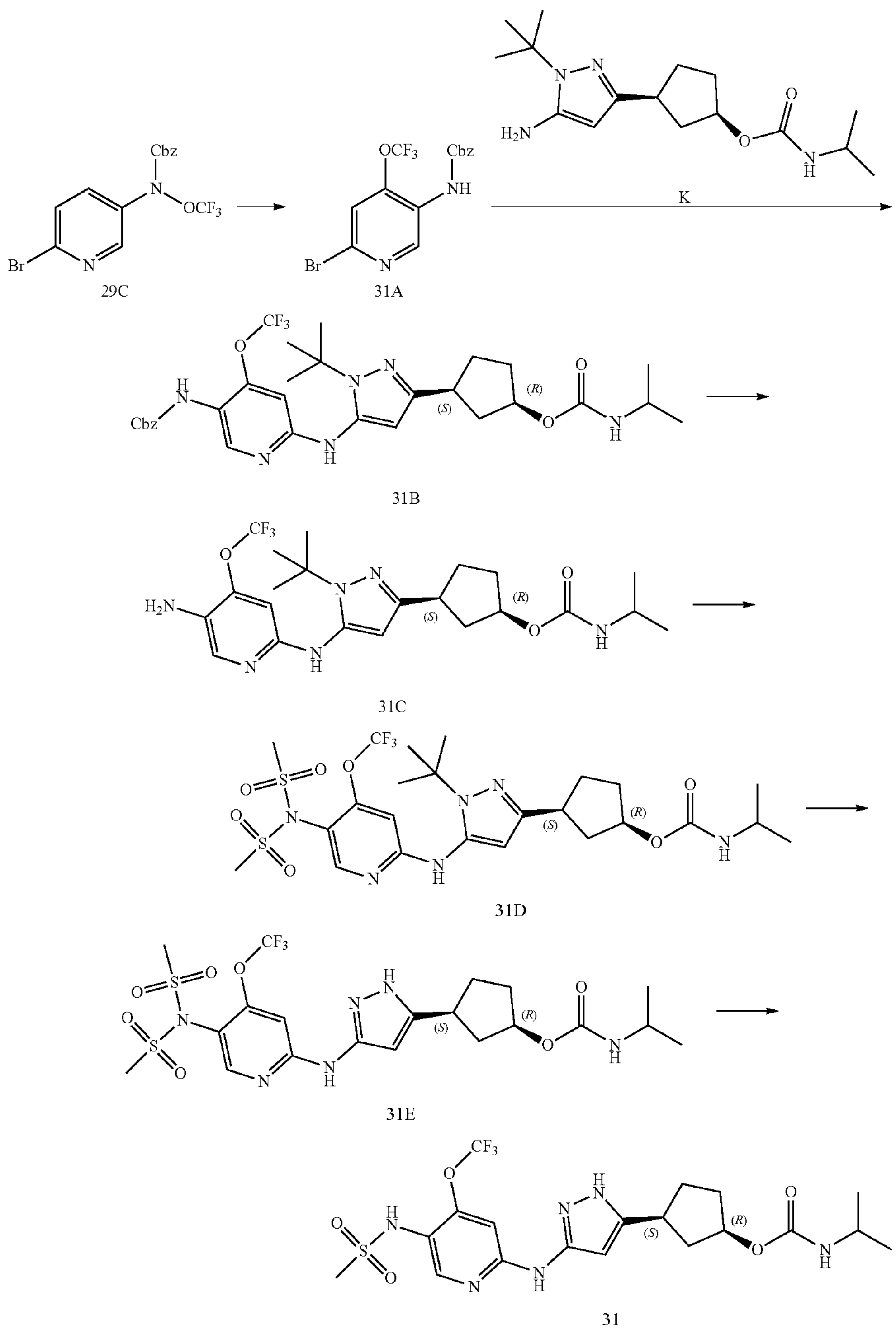

29C

31A

31B

31C

31D

31E

31

Intermediate 29C was reacted in nitromethane and subjected to column chromatography to give intermediate 31A by reference to the preparation method for compound 29D of Example 29.

A crude product of compound 31 was obtained by reference to the preparation method for compound 29 of Example 29, with intermediate 29D being replaced by intermediate 31A.

The crude product of compound 31 was purified by medium and low pressure preparative liquid phase chromatography (C18 column, acetonitrile/water (30/70), the eluent contained one thousandth of ammonium hydroxide) to give compound 31 (13 mg). MS (ESI): m/z 507.1638 $[M+H]^+$.

$^1H$ NMR (500 MHz, DMSO-$d_6$) δ 11.99 (s, 1H), 9.60 (s, 1H), 9.28 (s, 1H), 8.12 (s, 1H), 7.64 (s, 1H), 6.93 (d, J=7.2 Hz, 1H), 5.99 (s, 1H), 4.99 (s, 1H), 3.64-3.54 (m, 1H), 3.06-3.01 (m, 1H), 2.98 (s, 3H), 2.49-2.43 (m, 1H), 2.07-1.97 (m, 1H), 1.96-1.84 (m, 1H), 1.75-1.67 (m, 2H), 1.62-1.56 (m, 1H), 1.03 (d, J=6.3 Hz, 6H).

Example 32: Preparation of Compound 32

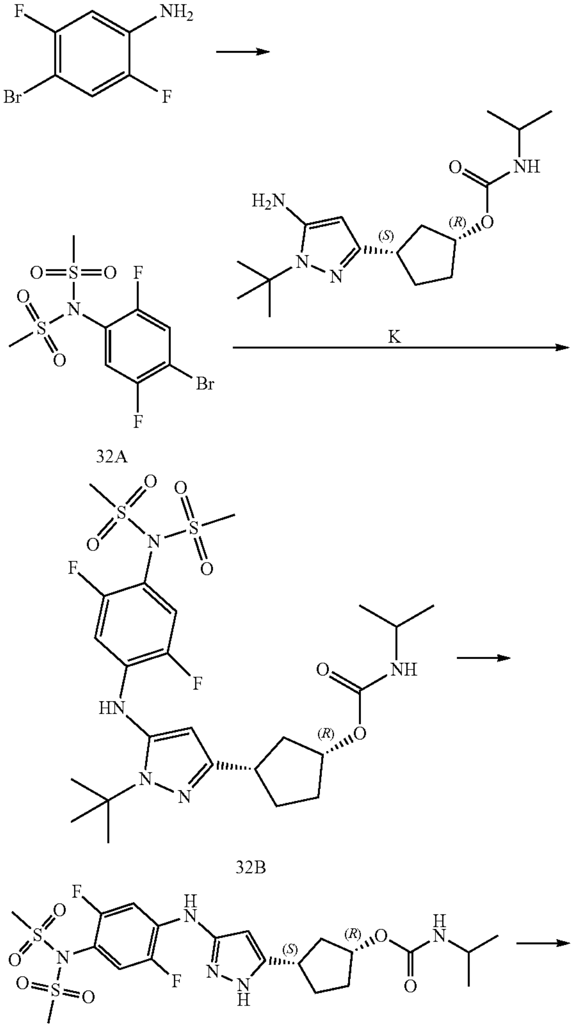

32A

32B

32C

-continued

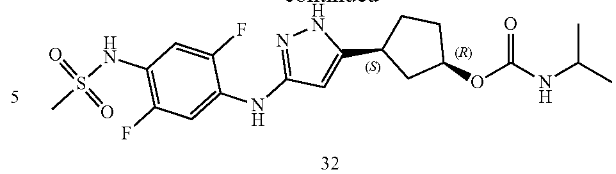

32

Compound 32A was obtained by reference to the preparation method for compound 23A of Example 23, with 4-bromo-2-fluoroaniline being replaced by 4-bromo-2,5-difluoroaniline.

A crude product of compound 32 was obtained by reference to the preparation method for compound 23 of Example 23, with intermediate 23A being replaced by compound 32A.

The crude product of compound 32 was purified by medium and low pressure preparative liquid phase chromatography (C18 column, acetonitrile/water (24/76), the eluent contained one thousandth of ammonium hydroxide) to give compound 32 (25 mg). MS (ESI): m/z 458.1670 $[M+H]^+$.

$^1H$ NMR (500 MHz, DMSO-$d_6$) δ 11.87 (s, 1H), 9.29 (s, 1H), 8.47 (s, 1H), 8.13-8.09 (m, 1H), 7.14-7.10 (m, 1H), 6.93 (d, J=7.1 Hz, 1H), 5.77 (s, 1H), 5.00 (s, 1H), 3.61-3.55 (m, 1H), 3.08-3.01 (m, 1H), 2.96 (s, 3H), 2.47-2.43 (m, 1H), 2.05-1.99 (m, 1H), 1.94-1.87 (m, 1H), 1.75-1.65 (m, 2H), 1.61-1.55 (m, 1H), 1.03 (d, J=6.3 Hz, 6H).

Example 33: Preparation of Compound 33

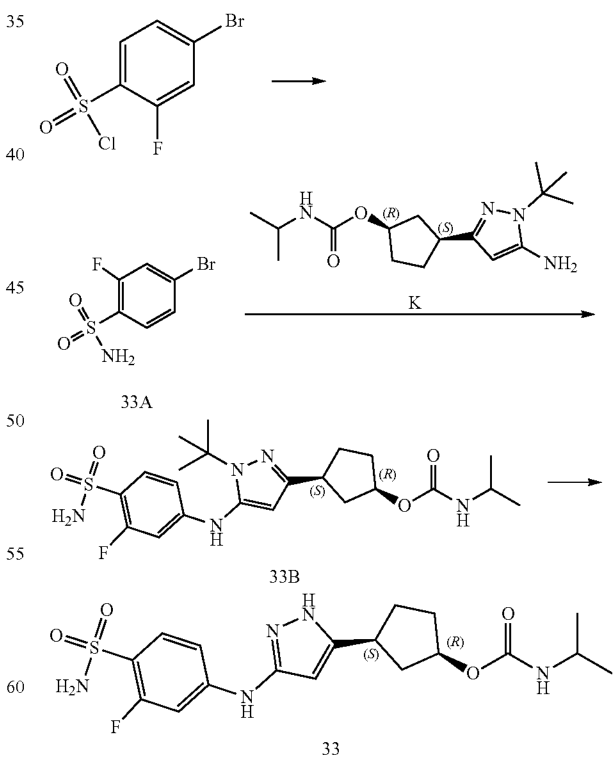

33A

33B

33

Compound 33A was prepared by reference to the preparation method for compound 16A of Example 16, with methylamine hydrochloride being replaced by ammonium hydroxide and 4-bromo-3-fluorobenzenesulfonyl chloride being replaced by 4-bromo-2-fluorobenzenesulfonyl chloride.

A crude product of compound 33 was obtained by reference to the preparation method for compound 16 of Example 16, with intermediate K1 being replaced by intermediate K.

The crude product of compound 33 was purified by medium and low pressure preparative liquid phase chromatography (C18 column, acetonitrile/water (30/70), the eluent contained one thousandth of ammonium hydroxide) to give compound 33 (40 mg). MS (ESI): m/z 426.3 $[M+H]^+$.

$^1$H NMR (500 MHz, DMSO-$d_6$) δ 11.96 (s, 1H), 9.15 (s, 1H), 7.54 (t, J=8.7 Hz, 1H), 7.43 (dd, J=13.9, 2.1 Hz, 1H), 7.27 (s, 2H), 7.03 (dd, J=8.8, 2.1 Hz, 1H), 6.94 (d, J=7.8 Hz, 1H), 5.69 (d, J=2.2 Hz, 1H), 5.00 (s, 1H), 3.66-3.54 (m, 1H), 3.10-3.02 (m, 1H), 2.48-2.44 (m, 1H), 2.07-1.97 (m, 1H), 1.95-1.83 (m, 1H), 1.75-1.66 (m, 2H), 1.63-1.56 (s, 1H), 1.03 (d, J=6.8 Hz, 6H).

Example 34: Preparation of Compound 34

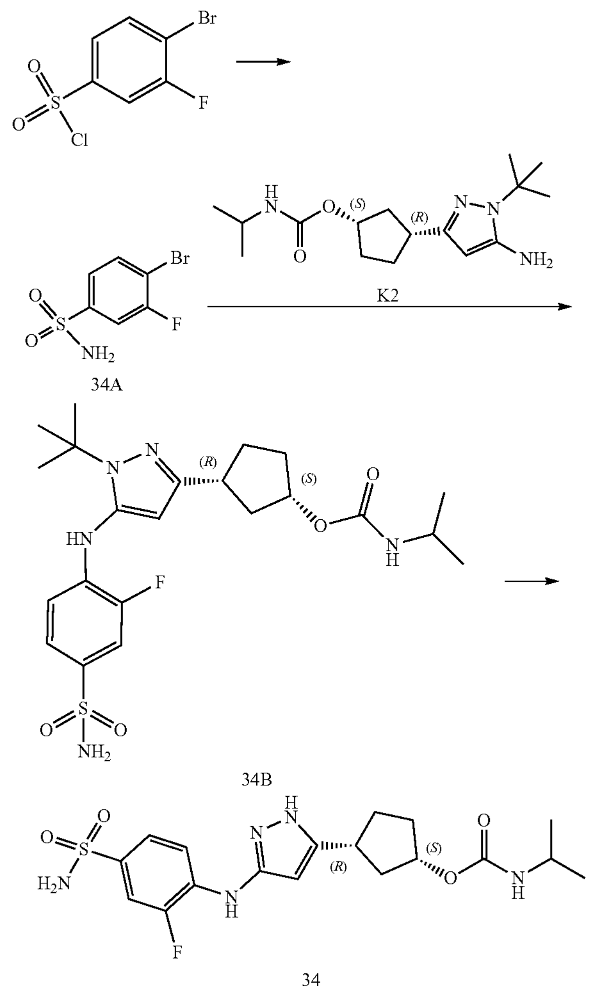

34A

34B

34

Compound 34A was prepared by reference to the preparation method for compound 16A of Example 16, with methylamine hydrochloride being replaced by ammonium hydroxide and 4-bromo-3-fluorobenzenesulfonyl chloride being replaced by 4-bromo-2-fluorobenzenesulfonyl chloride.

A crude product of compound 34 was obtained by reference to the preparation method for compound 16 of Example 16, with intermediate K1 being replaced by intermediate K2.

The crude product of compound 34 was purified by medium and low pressure preparative liquid phase chromatography (C18 column, acetonitrile/water (30/70), the eluent contained one thousandth of ammonium hydroxide) to give compound 34 (25 mg). MS (ESI): m/z 426.3 $[M+H]^+$.

$^1$H NMR (500 MHz, DMSO-$d_6$) δ 11.96 (s, 1H), 8.61 (s, 1H), 8.18 (t, J=8.4 Hz, 1H), 7.57-7.45 (m, 2H), 7.16 (s, 2H), 6.93 (d, J=7.9 Hz, 1H), 5.82 (s, 1H), 5.00 (s, 1H), 3.65-3.50 (m, 1H), 3.16-2.97 (m, 1H), 2.50-2.42 (m, 1H), 2.08-1.97 (m, 1H), 1.96-1.85 (m, 1H), 1.79-1.61 (m, 2H), 1.63-1.54 (m, 1H), 1.03 (d, J=6.9, 6H).

Example 35: Preparation of Compound 35

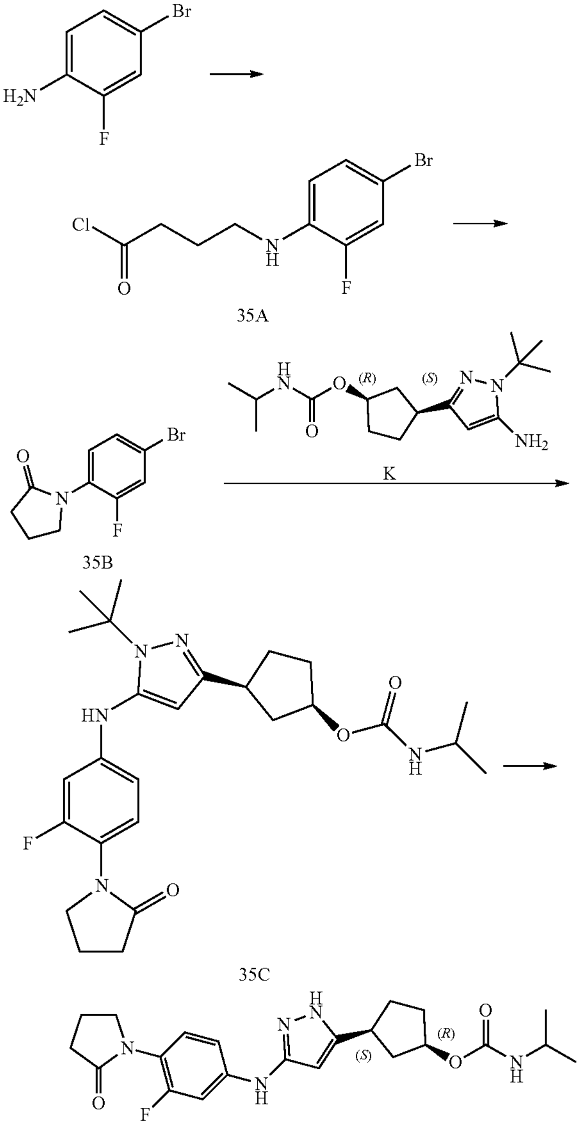

35A

35B

35C

35

A crude product of compound 35 was obtained by reference to the preparation method for compound 14 of Example 14, with 6-bromo-N-methylpyridine-3-amine being replaced by 4-bromo-2-fluoroaniline.

The crude product of compound 35 was purified by medium and low pressure preparative liquid phase chromatography (C18 column, acetonitrile/water (30/70), the eluent contained one thousandth of ammonium hydroxide) to give compound 35 (30 mg). MS (ESI): m/z 430.2246 $[M+H]^+$.

$^1$H NMR (500 MHz, DMSO-$d_6$) δ 11.79 (s, 1H), 8.66 (s, 1H), 7.41 (d, J=13.9 Hz, 1H), 7.13 (t, J=8.8 Hz, 1H), 7.03-6.88 (m, 2H), 5.62 (s, 1H), 4.99 (s, 1H), 3.65 (t, J=7.0 Hz, 2H), 3.60-3.56 (m, 1H), 3.07-3.00 (m, 1H), 2.49-2.426 (m, 1H), 2.38 (t, J=8.0 Hz, 2H), 2.11-2.06 (m, 2H), 2.04-1.97 (m, 1H), 1.94-1.84 (m, 1H), 1.74-1.68 (m, 2H), 1.62-1.56 (m, 1H), 1.03 (d, J=6.5 Hz, 6H).

Example 36: Preparation of Compound 36

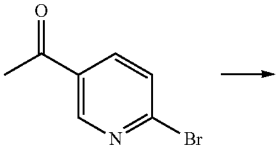

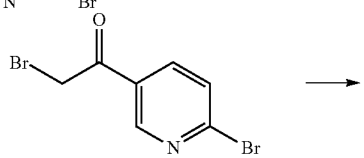

36A

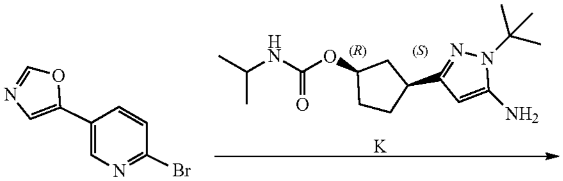

36B

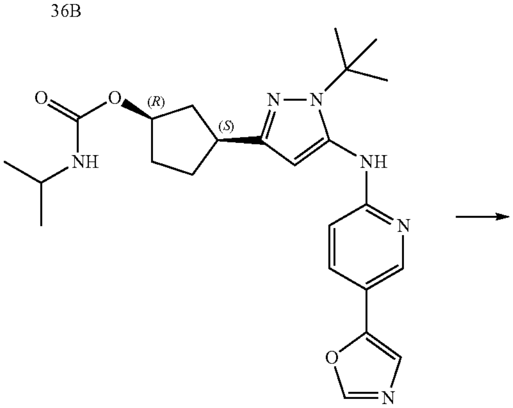

36C

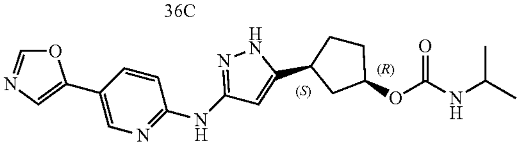

36

1-(6-Bromopyridin-3-yl)ethane-1-one (3.00 g) and liquid bromine (0.90 mL) were added to hydrobromic acid (45 mL), and the mixture was stirred at 70° C. under nitrogen atmosphere. After the reaction was completed, diethyl ether was added. The mixture was stirred for 30 min and filtered, and the filter cake was dried to give intermediate 36A (4.00 g). MS (ESI): m/z 277.88 $[M+H]^+$.

Intermediate 36A (3.00 g) was added to formamide (20 mL), and the mixture was reacted at 150° C. under microwave. After the reaction was completed, the reaction solution was poured into water, extracted with dichloromethane, dried over anhydrous sodium sulfate, filtered, concentrated, and separated by column chromatography (developing solvents: dichloromethane/methanol) to give intermediate 36B (0.45 g). MS (ESI): m/z 225.0 $[M+H]^+$.

A crude product of compound 36 was obtained by reference to the preparation method for compound 12 of Example 12, with intermediate 12B being replaced by intermediate 36B.

The crude product of compound 36 was slurried with methanol and purified to give compound 36 (28 mg). MS (ESI): m/z 397.1988 $[M+H]^+$.

$^1$H NMR (500 MHz, DMSO-$d_6$) δ 11.84 (s, 1H), 9.27 (s, 1H), 8.55 (s, 1H), 8.48 (s, 1H), 8.43 (s, 1H), 7.89 (d, J=8.2 Hz, 1H), 7.35 (s, 1H), 6.94 (d, J=6.8 Hz, 1H), 6.12 (s, 1H), 5.00 (s, 1H), 3.60-3.56 (m, 1H), 3.08-3.02 (m, 1H), 2.53-2.50 (m, 1H), 2.05-1.98 (m, 1H), 1.94-1.86 (m, 1H), 1.78-1.68 (m, 2H), 1.66-1.57 (m, 1H), 1.03 (d, J=5.9 Hz, 6H).

Example 37: Preparation of Compound 37

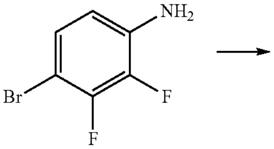

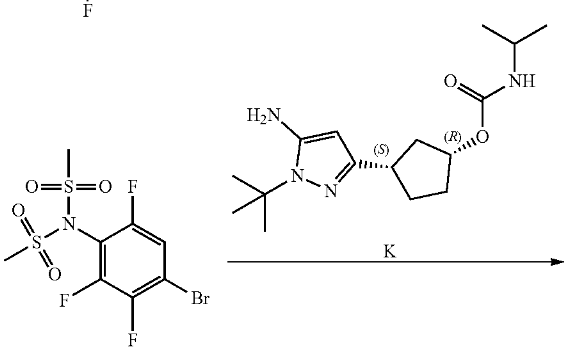

37A

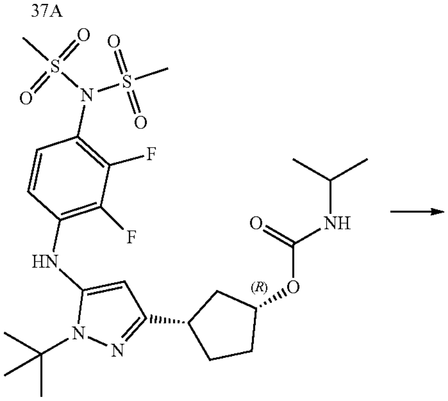

37B

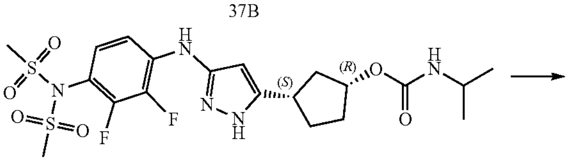

37C

-continued

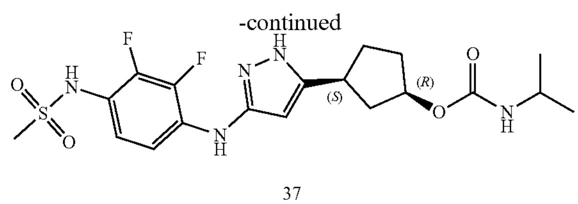

37

A crude product of compound 37 was obtained by reference to the preparation method for compound 23 of Example 23, with 4-bromo-2-fluoroaniline being replaced by 4-bromo-2,3-difluoroaniline.

The crude product of compound 37 was purified by medium and low pressure preparative liquid phase chromatography (C18 column, acetonitrile/water (28/72), the eluent contained one thousandth of ammonium hydroxide) to give compound 37 (156 mg). MS (ESI): m/z 458.1674 $[M+H]^+$.

$^1H$ NMR (500 MHz, DMSO-$d_6$) δ 11.84 (s, 1H), 9.31 (s, 1H), 8.31 (s, 1H), 7.80-7.76 (m, 1H), 7.02-6.98 (m, 1H), 6.93 (d, J=7.1 Hz, 1H), 5.75 (s, 1H), 5.00 (s, 1H), 3.60-3.56 (m, 1H), 3.08-3.02 (m, 1H), 2.96 (s, 3H), 2.47-2.43 (m, 1H), 2.05-1.99 (m, 1H), 1.94-1.86 (m, 1H), 1.75-1.65 (m, 2H), 1.61-1.55 (m, 1H), 1.03 (d, J=6.4 Hz, 6H).

Example 38: Preparation of Compound 38

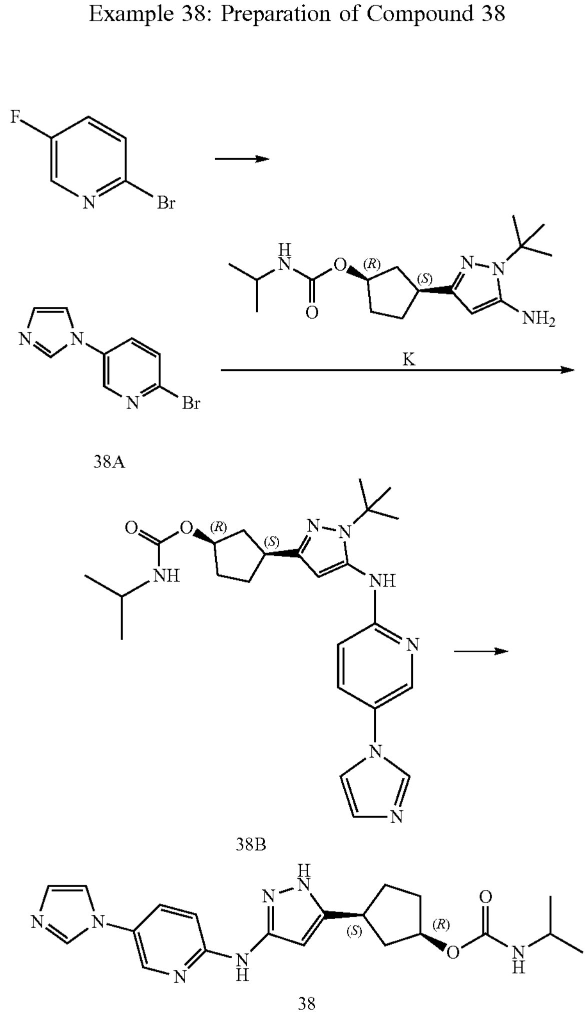

38A

38B

38

2-Bromo-5-fluoropyridine (2.00 g), 1H-imidazole (0.90 g), and potassium carbonate (3.10 g) were added to N,N-dimethylformamide (20 mL), and the mixture was stirred at 100° C. After the reaction was completed, the reaction solution was poured into water, extracted with ethyl acetate, dried over anhydrous sodium sulfate, and filtered. The filtrate was concentrated and separated by column chromatography (developing solvents: dichloromethane/methanol) to give intermediate 38A (0.50 g).

A crude product of compound 38 was obtained by reference to the preparation method for compound 12 of Example 12, with intermediate 12B being replaced by intermediate 38A.

The crude product of compound 38 was slurried with acetonitrile and purified to give compound 38 (100 mg). MS (ESI): m/z 396.2147 $[M+H]^+$.

$^1H$ NMR (500 MHz, DMSO-$d_6$) δ 11.86 (s, 1H), 9.42 (s, 1H), 8.38 (d, J=2.6 Hz, 1H), 8.09 (s, 1H), 7.81 (dd, J=9.0, 2.8 Hz, 1H), 7.61 (s, 1H), 7.36 (d, J=8.9 Hz, 1H), 7.09 (s, 1H), 6.94 (d, J=7.2 Hz, 1H), 6.13 (s, 1H), 5.01 (s, 1H), 3.62-3.55 (m, 1H), 3.09-3.02 (m, 1H), 2.49-2.45 (m, 1H), 2.06-2.00 (m, 1H), 1.94-1.86 (m, 1H), 1.79-1.67 (m, 2H), 1.64-1.58 (m, 1H), 1.03 (d, J=6.4 Hz, 6H).

Example 39: Preparation of Compound 39

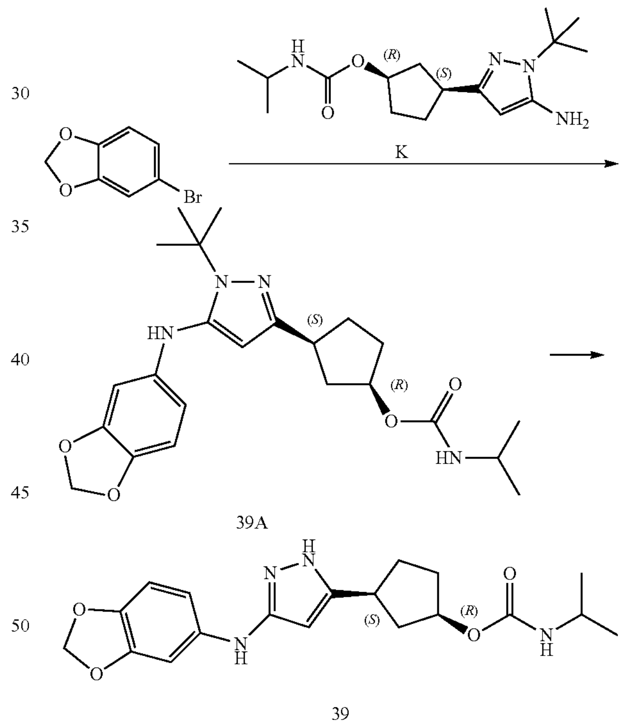

39A

39

A crude product of compound 39 was obtained by reference to the preparation method for compound 26 of Example 26, with 5-bromo-1,3-dihydrobenzo[c]thiophene-2,2-dioxide being replaced by 4-bromo-1,2-methylenedioxybenzene.

The crude product of compound 39 was purified by medium and low pressure preparative liquid phase chromatography (C18 column, nitrile/water (30/70), the eluent contained one thousandth of ammonium hydroxide) to give compound 39 (28 mg). MS (ESI): m/z 373.1869 $[M+H]^+$.

$^1H$ NMR (500 MHz, DMSO-$d_6$) δ 11.60 (s, 1H), 8.09 (s, 1H), 7.09 (s, 1H), 6.93 (d, J=7.2 Hz, 1H), 6.72-6.69 (m, 2H), 5.87 (s, 2H), 5.54 (s, 1H), 4.99 (s, 1H), 3.61-3.54 (m, 1H), 3.04-2.98 (m, 1H), 2.47-2.41 (m, 1H), 2.03-1.97 (m, 1H), 1.93-1.85 (m, 1H), 1.75-1.65 (m, 2H), 1.61-1.55 (m, 1H), 1.03 (d, J=6.4 Hz, 6H).

Example 40: Preparation of Compound 40

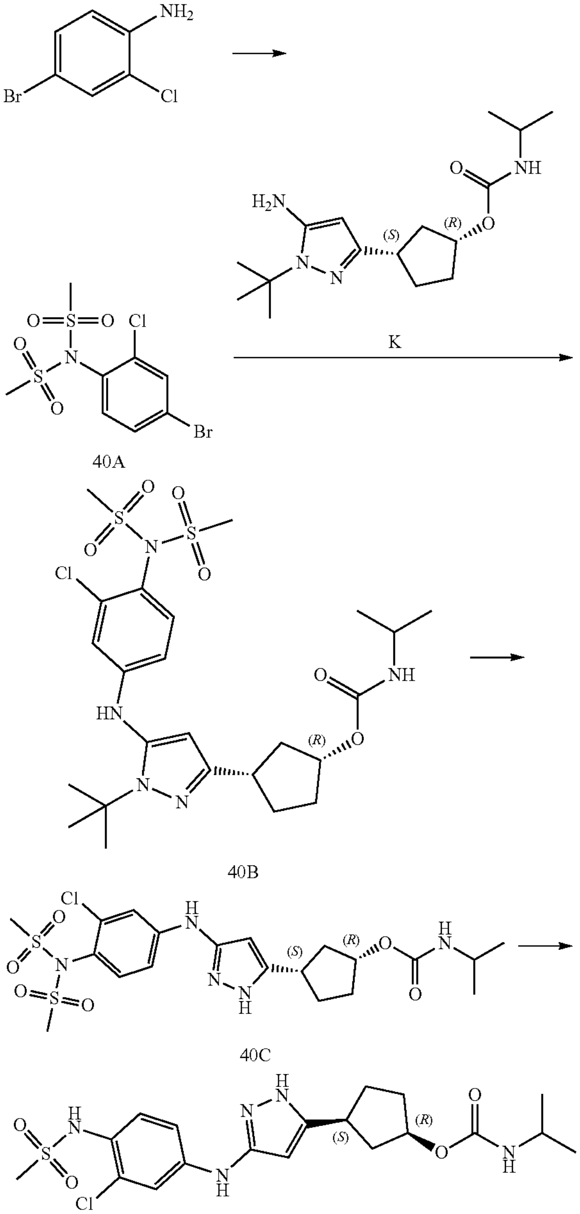

40A

40B

40C

40

A crude product of compound 40 was obtained by reference to the preparation method for compound 23 of Example 23, with 4-bromo-2-fluoroaniline being replaced by 4-bromo-2-chloroaniline.

The crude product of compound 40 was purified by medium and low pressure preparative liquid phase chromatography (C18 column, acetonitrile/water (30/70), the eluent contained one thousandth of ammonium hydroxide) to give compound 40 (70 mg). MS (ESI): m/z 456.1470 $[M+H]^+$.

$^1$H NMR (500 MHz, DMSO-$d_6$) δ 11.80 (s, 1H), 9.08 (s, 1H), 8.64 (s, 1H), 7.68 (s, 1H), 7.19 (d, J=8.7 Hz, 1H), 7.13 (d, J=8.1 Hz, 1H), 6.94 (d, J=8.2 Hz, 1H), 5.61 (s, 1H), 4.99 (s, 1H), 3.61-3.54 (m, 1H), 3.07-3.00 (m, 1H), 2.93 (s, 3H), 2.48-2.42 (m, 1H), 2.04-1.99 (m, 1H), 1.94-1.86 (m, 1H), 1.75-1.67 (m, 2H), 1.62-1.56 (m, 1H), 1.03 (d, J=6.4 Hz, 6H).

Example 41: Preparation of Compound 41

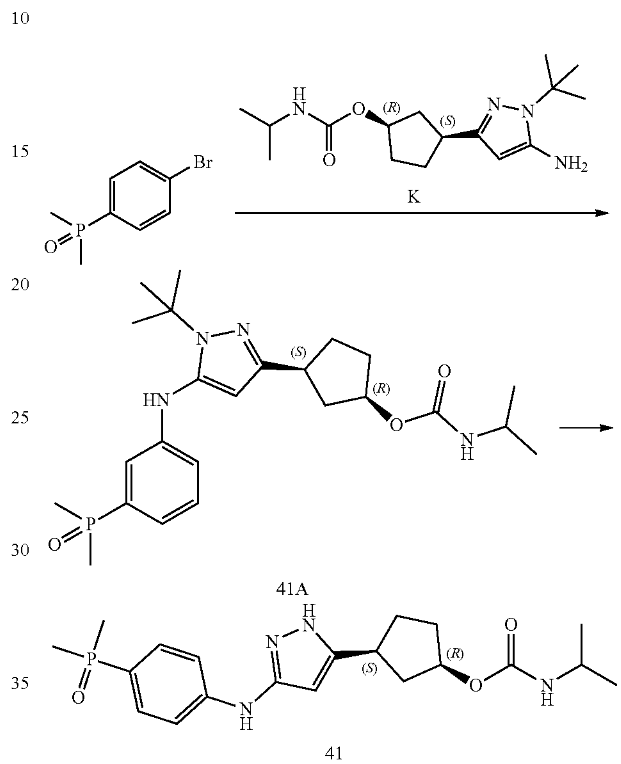

41A

41

A crude product of compound 41 was obtained by reference to the preparation method for compound 26 of Example 26, with 5-bromo-1,3-dihydrobenzo[c]thiophene-2,2-dioxide being replaced by 4-bromophenyldimethylphosphine oxide.

The crude product of compound 41 was purified by medium and low pressure preparative liquid phase chromatography (C18 column, acetonitrile/water (30/70), the eluent contained one thousandth of ammonium hydroxide) to give compound 41 (120 mg). MS (ESI): m/z 405.2055 $[M+H]^+$.

$^1$H NMR (500 MHz, DMSO-$d_6$) δ 11.83 (s, 1H), 8.68 (s, 1H), 7.53-7.49 (m, 2H), 7.39-7.37 (m, 2H), 6.94 (d, J=7.9 Hz, 1H), 5.67 (s, 1H), 5.04-4.95 (m, 1H), 3.61-3.55 (m, 1H), 3.08-3.01 (m, 1H), 2.47-2.43 (m, 1H), 2.04-1.99 (m, 1H), 1.96-1.86 (m, 1H), 1.76-1.69 (m, 2H), 1.63-1.54 (m, 1H), 1.58 (s, 3H), 1.55 (s, 3H), 1.03 (d, J=6.7 Hz, 6H).

Example 42: Preparation of Compound 42

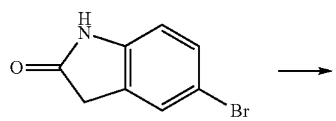

-continued

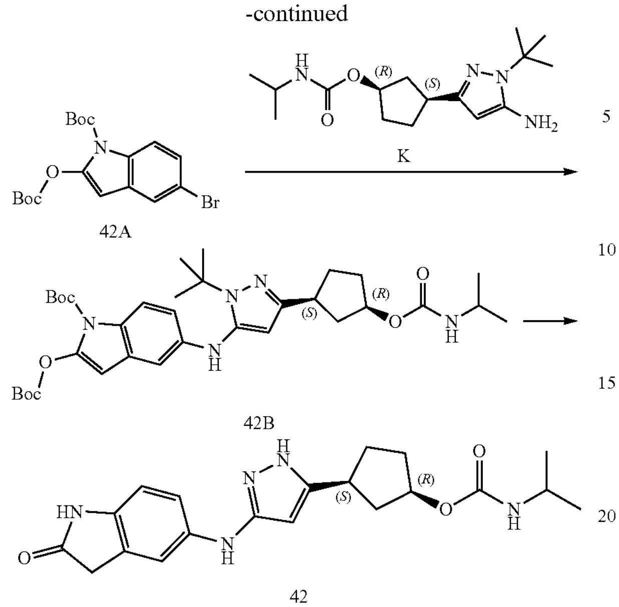

42A

42B

42

4-Bromoindoline-2-one (4.60 g), sodium carbonate (18.39 g), di-tert-butyl dicarbonate (9.47 g) were added to tetrahydrofuran (150 mL), and the mixture was stirred at 65° C. After the reaction was completed, the reaction solution was filtered, concentrated, and separated by evaporation under reduced pressure to remove the solvent, and separated by column chromatography (developing solvents: petroleum ether/ethyl acetate) to give intermediate 42A (3.25 g). MS (ESI): m/z: 412.21 $[M+H]^+$.

A crude product of compound 42 was obtained by reference to the preparation method for compound 1 of Example 11, with intermediate 1A being replaced by intermediate 42A.

The crude product of compound 42 was purified by medium and low pressure preparative liquid phase chromatography (C18 column, acetonitrile/water (30/70), the eluent contained one thousandth of ammonium hydroxide) to give compound 42 (10 mg). MS (ESI): m/z 384.20 $[M+H]^+$.

$^1H$ NMR (500 MHz, DMSO-$d_6$) δ 11.51 (s, 1H), 10.04 (s, 1H), 7.97 (s, 1H), 7.26 (s, 1H), 7.10-7.08 (m, 1H), 6.94 (d, J=7.9 Hz, 1H), 6.62 (d, J=8.3 Hz, 1H), 5.55 (s, 1H), 4.99 (s, 1H), 3.60-3.55 (m, 1H), 3.39 (s, 2H), 3.05-2.98 (m, 1H), 2.47-2.41 (m, 1H), 2.03-1.97 (m, 1H), 1.95-1.84 (m, 1H), 1.76-1.65 (m, 2H), 1.61-1.55 (m, 1H), 1.03-1.02 (m, 6H).

Example 43: Preparation of Compound 43

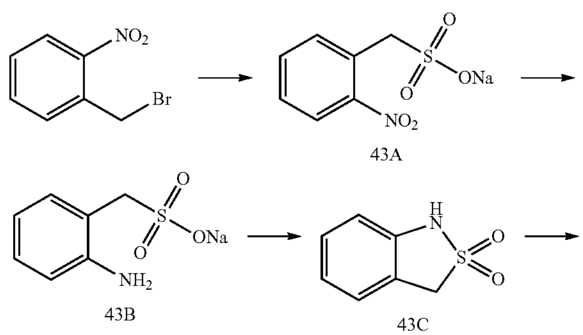

43A

43B

43C

-continued

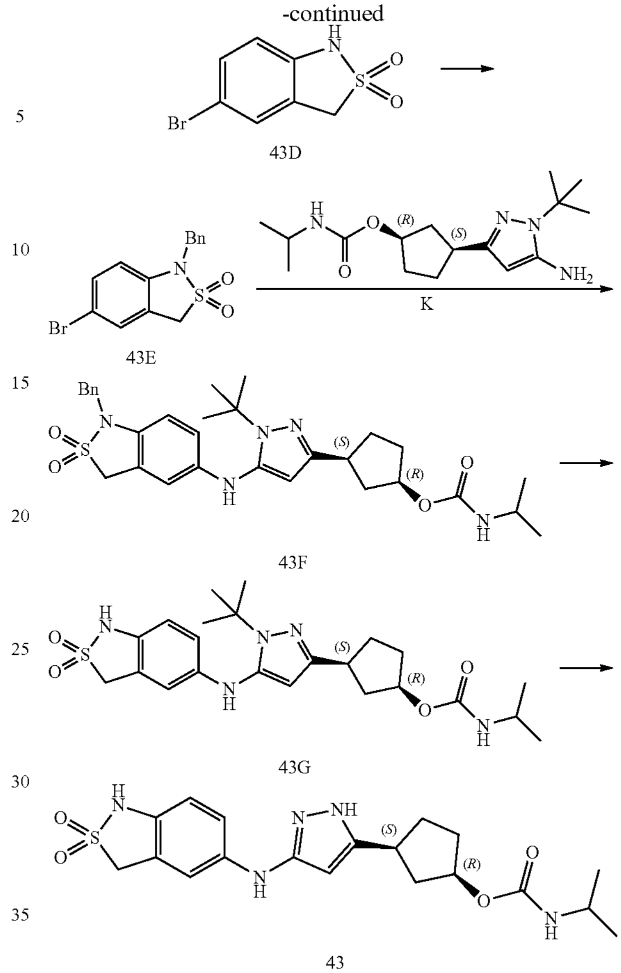

43D

43E

43F

43G

43

2-Nitrobenzyl bromide (10.00 g), anhydrous sodium sulfite (7.58 g), and tetrabutylammonium iodide (171 mg) were added to water (80 mL), and the mixture was stirred at 90° C. After the reaction was completed, the reaction solution was concentrated by evaporation under reduced pressure to remove the solvent to give intermediate 43A (10.00 g).

Intermediate 43A (10.00 g) and palladium on carbon (palladium content 5%, water content 50% (w/w), 1.90 g) were added to methanol (50 mL), and the mixture was purged with hydrogen and stirred at room temperature. After the reaction was completed, the reaction solution was filtered and concentrated to give intermediate 43B (5.00 g).

Intermediate 43B (5.00 g) was added to phosphorus oxychloride (100 mL), and the mixture was stirred at 115° C. under nitrogen atmosphere. After the reaction was completed, the reaction solution was concentrated by evaporation under reduced pressure to remove the solvent, and then the pH was adjusted to alkalinity with an aqueous sodium hydroxide solution (1 mol/L). The mixture was extracted with ethyl acetate, and then the pH of the organic phase was adjusted to acidity with diluted hydrochloric acid (2 N). The mixture was extracted with dichloromethane, dried over anhydrous sodium sulfate, filtered, concentrated, and separated by column chromatography (developing solvents: dichloromethane/methanol) to give intermediate 43C (670 mg). MS (ESI): m/z 168.1 $[M-H]^-$.

Intermediate 43C (0.63 g) and bromine (0.46 g) were added to acetic acid (8 mL), and the mixture was stirred at room temperature. After the reaction was completed, the reaction solution was concentrated by evaporation under reduced pressure to remove the solvent, and separated by column chromatography (developing solvents: petroleum ether/ethyl acetate) to give intermediate 43D (0.75 g). MS (ESI): m/z 246.0 $[M-H]^-$.

Intermediate 43D (0.75 g), potassium carbonate (0.83 g), and benzyl bromide (0.54 g) were added to DMF (10 mL), and the mixture was stirred at room temperature. After the reaction was completed, the reaction solution was concentrated by evaporation under reduced pressure to remove the solvent, and separated by column chromatography (developing solvents: petroleum ether/ethyl acetate) to give intermediate 43E (800 mg). MS (ESI): m/z 335.95 $[M-H]^-$.

Intermediate K (425 mg), intermediate 43E (680 mg), chloro(2-dicyclohexylphosphino-2',4',6'-triisopropyl-1,1'-biphenyl)[2-(2'-amino-1,1'-biphenyl)]palladium (II) (217 mg), 2-dicyclohexylphosphino-2',4',6'-triisopropylbiphenyl (131 mg), and potassium phosphate (877 mg) were added to N,N-dimethylformamide (20 mL), and the mixture was stirred at 110° C. under nitrogen atmosphere. After the reaction was completed, the reaction solution was filtered, concentrated, and separated by column chromatography (developing solvents: dichloromethane/methanol) to give intermediate 43F (223 mg). MS (ESI): m/z 566.41 $[M+H]^+$.

Intermediate 43F (223 mg) and palladium on carbon (palladium content 5%, water content 50% (w/w), 83 mg) were added to methanol (20 mL), and the mixture was purged with hydrogen and stirred at room temperature. After the reaction was completed, the reaction solution was filtered, concentrated, and separated by column chromatography (developing solvents: dichloromethane/methanol) to give intermediate 43G (127 mg). MS (ESI): m/z 476.32 $[M+H]^+$.

Intermediate 43G (127 mg) was added to ethanol (1 mL) and diluted hydrochloric acid (1 N, 20 mL), and the mixture was reacted at 100° C. under microwave. After the reaction was completed, the reaction solution was concentrated by evaporation under reduced pressure to remove the solvent, and the pH of the residue was adjusted to alkalinity with a saturated aqueous sodium bicarbonate solution.

The mixture was extracted with dichloromethane, dried over anhydrous sodium sulfate, and filtered. The filtrate was concentrated by evaporation under reduced pressure to remove the solvent and purified by medium and low pressure preparative liquid phase chromatography (C18 column, acetonitrile/water (30/70), the eluent contained one thousandth of ammonium hydroxide) to give compound 43 (9 mg). MS (ESI): m/z 420.1701 $[M+H]^+$.

$^1$H NMR (500 MHz, DMSO-$d_6$) δ 11.61 (s, 1H), 9.74 (s, 1H), 8.18 (s, 1H), 7.37 (s, 1H), 7.15 (d, J=8.6 Hz, 1H), 6.94 (d, J=7.7 Hz, 1H), 6.71 (d, J=8.6 Hz, 1H), 5.57 (s, 1H), 4.99 (s, 1H), 4.43 (s, 2H), 3.61-3.55 (m, 1H), 3.03 (q, J=8.7 Hz, 1H), 2.44 (dt, J=14.3, 7.4 Hz, 1H), 2.04-1.97 (m, 1H), 1.94-1.85 (m, 1H), 1.76-1.67 (m, 2H), 1.63-1.55 (m, 1H), 1.03 (dd, J=6.7, 2.3 Hz, 6H).

Example 44: Preparation of Compound 44

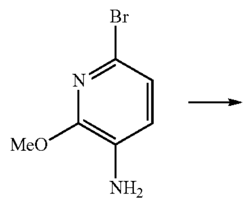

-continued

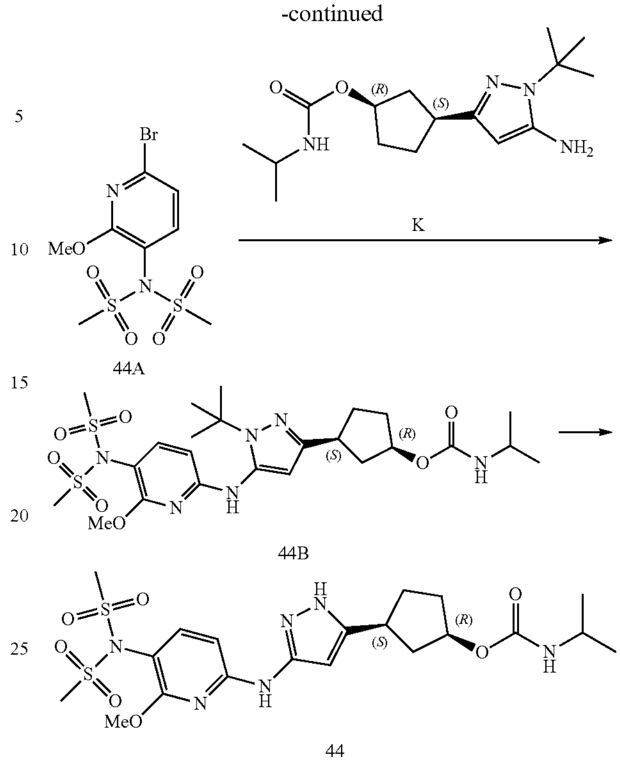

44A

44B

44

A crude product of intermediate 44B was obtained by reference to the preparation method for compound 1B of Example 1, with 6-bromopyridine-3-amine being replaced by 3-amino-2-methoxy-6-bromopyridine.

A crude product of compound 44 was obtained by reference to the preparation method for compound 1 of Example 1, with intermediate 1C being replaced by intermediate 44B.

The crude product of compound 44 was purified by column chromatography (developing solvents: dichloromethane/methanol (90/10)) to give compound 44 (39 mg). MS (ESI): m/z 531.27 $[M+H]^+$.

$^1$H NMR (500 MHz, DMSO-d6) δ 12.17 (s, 1H), 9.12 (s, 1H), 9.00 (s, 1H), 7.78 (s, 1H), 6.91 (d, J=7.8 Hz, 1H), 6.54 (s, 1H), 5.00 (d, J=8.6 Hz, 1H), 4.01 (s, 3H), 3.64-3.48 (m, 1H), 3.26 (s, 3H), 3.11 (q, J=8.7 Hz, 1H), 2.97 (s, 3H), 2.49-2.42 (m, 1H), 2.09-1.99 (m, 1H), 1.98-1.85 (m, 1H), 1.79-1.67 (m, 2H), 1.64-1.60 (m, 1H), 1.02 (d, J=6.2 Hz, 6H).

Example 45: Preparation of Compound 45

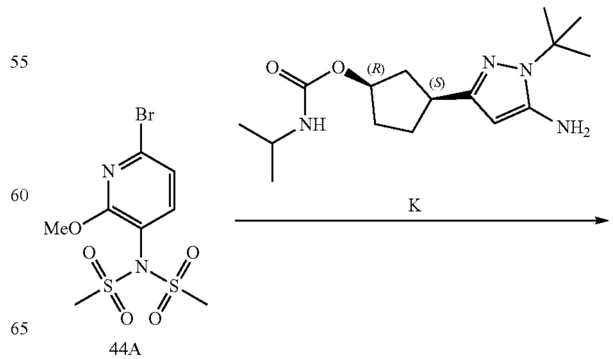

44A

-continued

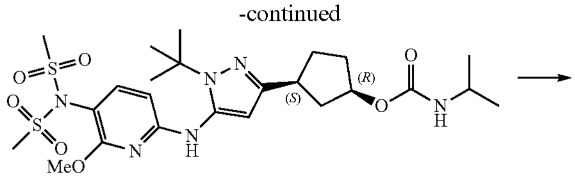

45A

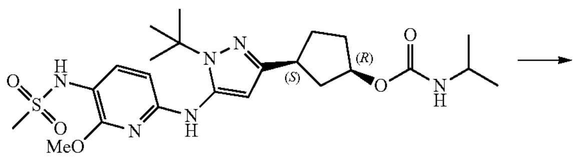

45B

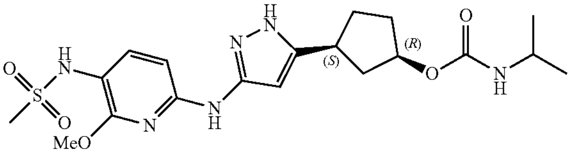

45

A crude product of compound 45 was obtained by reference to the preparation method for compound 1 of Example 1, with intermediate 1A being replaced by intermediate 44A.

The crude product of compound 45 was purified by column chromatography (developing solvents: dichloromethane/methanol (90/10)) to give compound 45 (55 mg). MS (ESI): m/z 453.29 $[M+H]^+$.

$^1$H NMR (500 MHz, DMSO-d6) δ 11.84 (s, 1H), 9.18 (s, 1H), 8.72 (s, 1H), 7.33 (d, J=8.3 Hz, 1H), 6.92 (d, J=7.9 Hz, 1H), 6.79-6.62 (m, 1H), 6.23 (s, 1H), 5.00 (d, J=7.8 Hz, 1H), 3.90 (s, 3H), 3.58 (dt, J=13.8, 7.0 Hz, 1H), 3.08-3.02 (m, 1H), 2.88 (s, 3H), 2.48-2.40 (m, 1H), 2.05-1.96 (m, 1H), 1.95-1.84 (m, 1H), 1.80-1.66 (m, 2H), 1.64-1.60 (m, 1H), 1.02 (d, J=6.6 Hz, 6H).

Example 46: Preparation of Compound 46

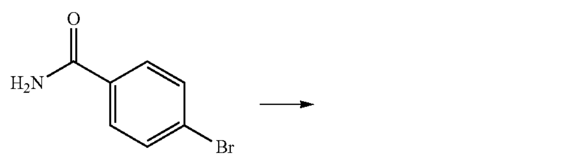

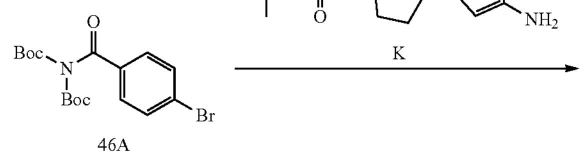

46A

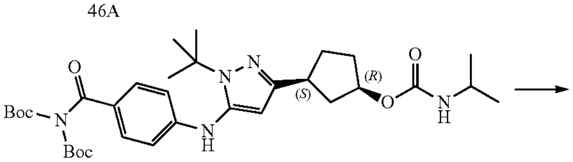

46B

-continued

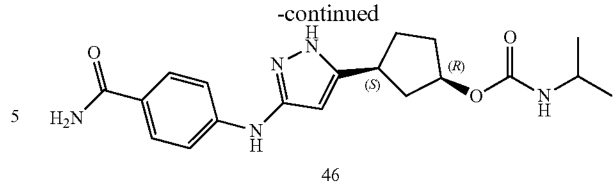

46 p-Bromobenzamide (1.00 g), 4-dimethylaminopyridine (0.06 g), N,N-diisopropylethylamine (2.58 g), and di-tert-butyl dicarbonate (3.27 g) were added to dichloromethane (50 mL), and the mixture was stirred at room temperature. After the reaction was completed, the reaction solution was concentrated by evaporation under reduced pressure to remove the solvent, and separated by column chromatography (developing solvents: petroleum ether/ethyl acetate) to give intermediate 46A (0.37 g). MS (ESI): m/z: 422.1 $[M+Na]^+$.

$^1$H NMR (500 MHz, DMSO-$d_6$) δ 7.81-7.83 (m, 2H), 7.71-7.68 (m, 2H), 1.36 (s, 18H).

A crude product of compound 46 was obtained by reference to the preparation method for compound 23 of Example 23, with 23A being replaced by 46A and formic acid being replaced by ethanol/1 N diluted hydrochloric acid (1/5).

The crude product of compound 46 was purified by medium and low pressure preparative liquid phase chromatography (C18 column, acetonitrile/water (30/70), the eluent contained one thousandth of ammonium hydroxide) to give compound 46 (13 mg). MS (ESI): m/z 372.2035 $[M+H]^+$.

$^1$H NMR (500 MHz, DMSO-$d_6$) δ 11.51 (s, 1H), 10.04 (s, 1H), 7.97 (s, 1H), 7.26 (s, 1H), 7.10-7.08 (m, 1H), 6.94 (d, J=7.9 Hz, 1H), 6.62 (d, J=8.3 Hz, 1H), 5.55 (s, 1H), 4.99 (s, 1H), 3.60-3.55 (m, 1H), 3.39 (s, 2H), 3.05-2.98 (m, 1H), 2.47-2.41 (m, 1H), 2.03-1.97 (m, 1H), 1.95-1.84 (m, 1H), 1.76-1.65 (m, 2H), 1.61-1.55 (m, 1H), 1.03-1.02 (m, 6H).

Example 47: Preparation of Compound 47

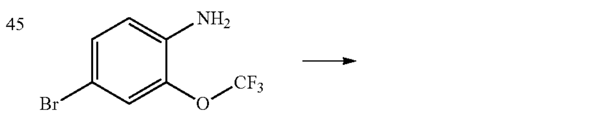

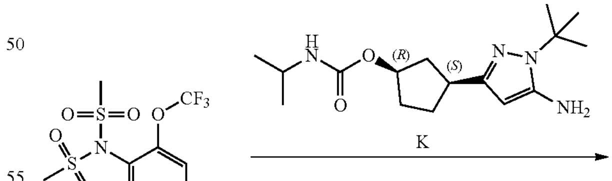

47A

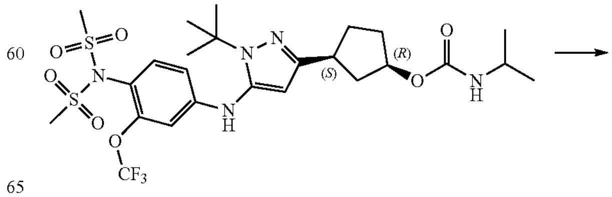

47B

-continued

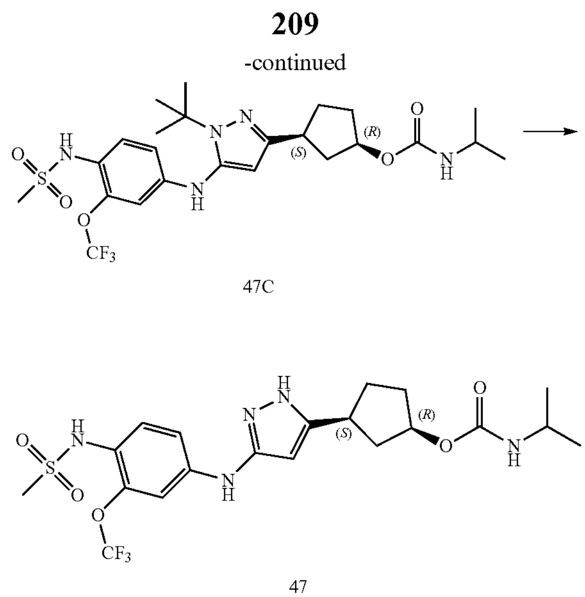

47C

47

Intermediate 47C (146 mg) was obtained by reference to the preparation method for compound 7 of Example 7, with 4-bromoaniline being replaced by 4-bromo-2-trifluoromethoxyaniline. MS (ESI): m/z 562.14 $[M+H]^+$.

Intermediate 47C (145 mg) was added to ethanol (2 mL) and diluted hydrochloric acid (1 N, 20 mL), and the mixture was reacted at 100° C. under microwave. After the reaction was completed, the reaction solution was concentrated by evaporation under reduced pressure to remove the solvent, and the pH of the residue was adjusted to alkalinity with a saturated aqueous sodium bicarbonate solution. The mixture was extracted with dichloromethane, dried over anhydrous sodium sulfate, filtered, concentrated, and purified by medium and low pressure preparative liquid phase chromatography (C18 column, acetonitrile/water (30/70), the eluent contained one thousandth of ammonium hydroxide) to give compound 47 (30 mg). MS (ESI): m/z 506.1693 $[M+H]^+$.

$^1$H NMR (500 MHz, DMSO-d6) δ 11.86 (s, 1H), 9.12 (s, 1H), 8.75 (s, 1H), 7.70 (s, 1H), 7.22 (d, J=8.8 Hz, 1H), 7.14-7.12 (m, 1H), 6.93 (d, J=7.8 Hz, 1H), 5.60 (d, J=2.2 Hz, 1H), 4.99 (s, 1H), 3.60-3.55 (m, 1H), 3.09-2.98 (m, 1H), 2.93 (s, 3H), 2.49-2.42 (m, 1H), 2.03-1.98 (m, 1H), 1.92-1.87 (m, 1H), 1.77-1.66 (m, 2H), 1.63-1.55 (m, 1H), 1.03 (d, J=6.5 Hz, 6H).

Example 48: Preparation of Compound 48

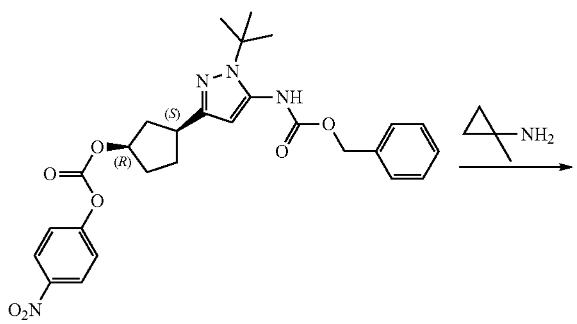

-continued

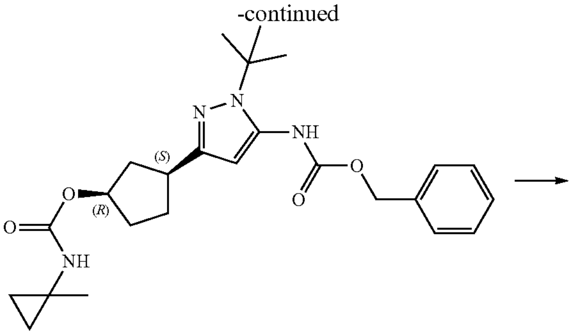

48A

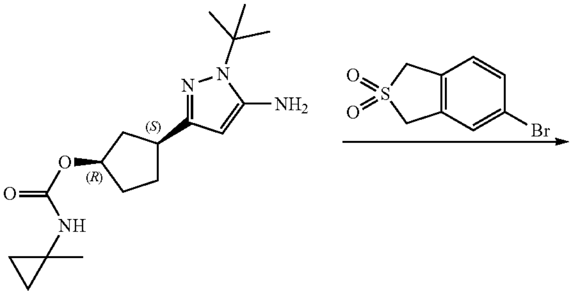

48B

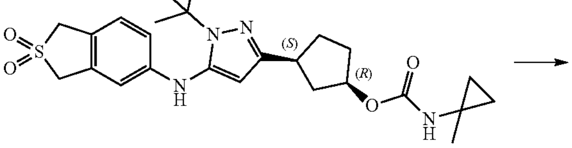

48C

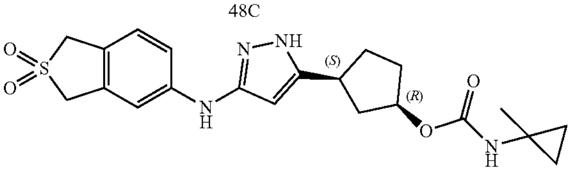

48

Benzyl (1-(tert-butyl)-3-((1S,3R)-3-(4-nitrophenoxy)carbonyl)oxy)cyclopentyl)-1H-pyrazol-5-yl)carbamate (0.50 g), N,N-diisopropylethylamine (0.50 g), and 1-methylcyclopropane-1-amine hydrochloride (0.15 g) were added to tetrahydrofuran (20 mL), and the mixture was stirred at 60° C. After the reaction was completed, the reaction solution was concentrated by evaporation under reduced pressure to remove the solvent, and ethyl acetate was added to the residue. The mixture was washed with an aqueous sodium hydroxide solution (1 N) and saturated brine, dried over anhydrous sodium sulfate, filtered, and concentrated to give intermediate 48A (0.40 g). MS (ESI): m/z 455.35 $[M+H]^+$.

Intermediate 48A (0.40 g) and palladium on carbon (palladium content 5%, water content 50% (w/w), 0.30 g) were added to tetrahydrofuran (5 mL) and ethyl acetate (5 mL), and the mixture was stirred at room temperature under hydrogen atmosphere. After the reaction was completed, the reaction solution was filtered and concentrated to give intermediate 48B (0.25 g). MS (ESI): m/z 321.30 $[M+H]^+$.

Intermediate 48B (0.23 g), 5-bromo-1,3-dihydrobenzo[c]thiophene-2,2-dioxide (0.27 g), chloro(2-dicyclohexylphosphino-2',4',6'-triisopropyl-1,1'-biphenyl)[2-(2'-amino-1,1'-biphenyl)]palladium (II) (0.11 g), 2-dicyclohexylphosphino-2',4',6'-triisopropylbiphenyl (0.10 g), and potassium phosphate (0.46 g) were added to N,N-dimethylformamide (10 mL). After the addition was completed, the mixture was stirred at 110° C. under nitrogen atmosphere. After the reaction was completed, the reaction solution was filtered, concentrated, and separated by column chromatography (developing solvents: dichloromethane/methanol) to give intermediate 48C (0.20 g). MS (ESI): m/z 487.29 [M+H]$^+$.

Intermediate 48C (0.20 g) was added to ethanol (2 mL) and diluted hydrochloric acid (1 N, 20 mL), and the mixture was stirred at 100° C. under microwave. After the reaction was completed, the reaction solution was concentrated by evaporation under reduced pressure to remove the solvent, and the pH of the residue was adjusted to alkalinity with a saturated aqueous sodium bicarbonate solution. The mixture was extracted with dichloromethane, dried over anhydrous sodium sulfate, filtered, concentrated, and purified by medium and low pressure preparative liquid phase chromatography (C18 column, acetonitrile/water (20/80), the eluent contained one thousandth of ammonium hydroxide) to give compound 48 (15 mg). MS (ESI): m/z 431.1745 [M+H]$^+$.

$^1$H NMR (500 MHz, DMSO) δ 11.69 (s, 1H), 8.46 (s, 1H), 7.36 (d, J=22.0 Hz, 2H), 7.20 (d, J=8.1 Hz, 1H), 7.13 (d, J=8.4 Hz, 1H), 5.62 (s, 1H), 4.98 (s, 1H), 4.40 (s, 2H), 4.32 (s, 2H), 3.03 (s, 1H), 2.48-2.41 (m, 1H), 2.05-1.84 (m, 2H), 1.75-1.52 (m, 3H), 1.23 (s, 3H), 0.63-0.44 (m, 4H).

Example 49: Preparation of Compound 49

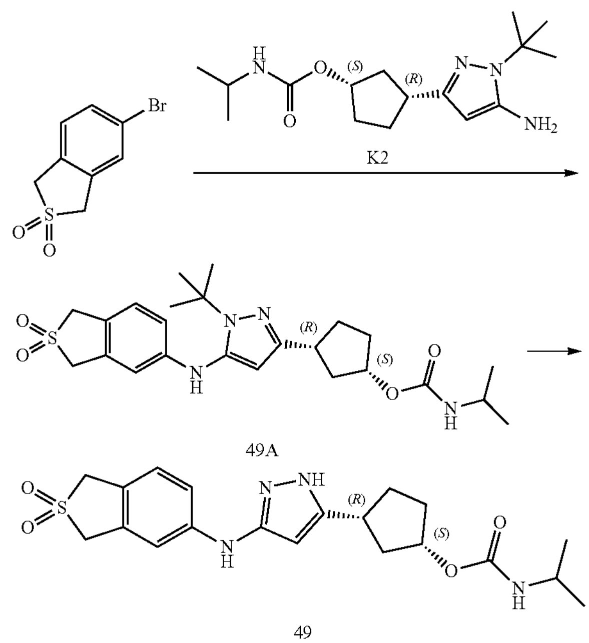

49A

49

Intermediate 49A (120 mg) was obtained by reference to the preparation method for intermediate 26A of Example 26, with intermediate K being replaced by intermediate K2. MS (ESI): m/z 475.50 [M+H]$^+$.

Compound 49 (40 mg) was obtained by reference to the preparation method for the compound 47 of Example 47, with intermediate 47C being replaced by intermediate 49A. MS (ESI): m/z 419.1756 [M+H]$^+$.

$^1$H NMR (500 MHz, DMSO-$d_6$) δ 11.73 (s, 1H), 8.46 (s, 1H), 7.41 (s, 1H), 7.22-7.21 (m, 1H), 7.14-7.13 (m, 1H), 6.94 (d, J=7.05 Hz, 1H), 5.63 (s, 1H), 4.99 (s, 1H), 4.40 (s, 2H), 4.32 (s, 2H), 3.60-3.56 (m, 1H), 3.05-3.02 (m, 1H), 2.48-2.42 (m, 1H), 2.03-1.99 (m, 1H), 1.92-1.88 (m, 1H), 1.75-1.68 (m, 2H), 1.62-1.56 (m, 1H), 1.03 (d, J=6.35 Hz, 6H).

Example 50: Preparation of Compound 50

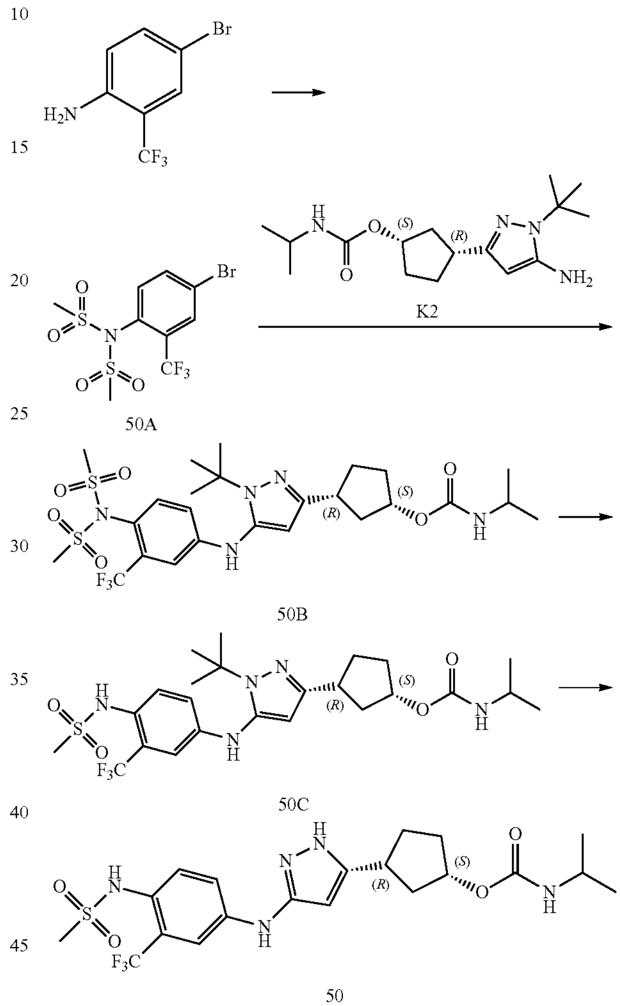

50A

50B

50C

50

A crude product of compound 50 was obtained by reference to the preparation method for the compound 47 of Example 47, with 4-bromo-2-trifluoromethoxyaniline being replaced by 4-bromo-2-trifluoromethylaniline and intermediate K being replaced by intermediate K2.

The crude product of compound 50 was purified by medium and low pressure preparative liquid phase chromatography (C18 column, acetonitrile/water (30/70), the eluent contained one thousandth of ammonium hydroxide) to give compound 50 (20 mg). MS (ESI): m/z 490.1742 [M+H]$^+$.

$^1$H NMR (500 MHz, DMSO-$d_6$) δ 11.86 (s, 1H), 9.04 (s, 1H), 8.77 (s, 1H), 7.89 (s, 1H), 7.46-7.45 (m, 1H), 7.34 (d, J=8.7 Hz, 1H), 6.92 (d, J=7.9 Hz, 1H), 5.62 (s, 1H), 5.01-4.97 (m, 1H), 3.58-3.56 (m, 1H), 3.05-2.98 (m, 1H), 2.98 (s, 3H), 2.48-2.40 (m, 1H), 2.04-1.98 (m, 1H), 1.95-1.84 (m, 1H), 1.75-1.67 (m, 2H), 1.62-1.59 (m, 1H), 1.03 (d, J=6.1 Hz, 6H).

Example 51: Preparation of Compound 51

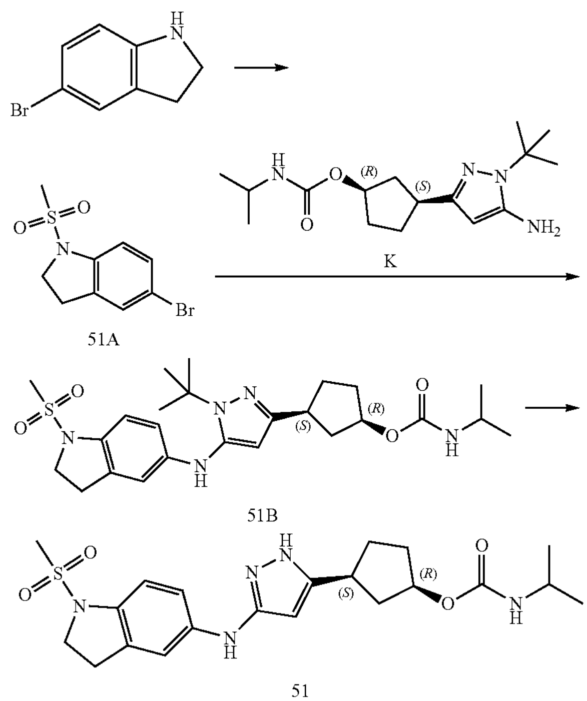

51A

51B

51

5-Bromoindoline (1.00 g), triethylamine (1.02 g), and methanesulfonic anhydride (1.05 g) were added to dichloromethane (30 mL), and the mixture was stirred at room temperature overnight. After the reaction was completed, the reaction solution was concentrated by evaporation under reduced pressure to remove the solvent, and separated by column chromatography (developing solvents: petroleum ether/ethyl acetate) to give intermediate 51A (1.05 g).

$^1$H NMR (500 MHz, DMSO-$d_6$) δ 7.47 (s, 1H), 7.38-7.36 (m, 1H), 7.18 (d, J=8.55 Hz, 1H), 3.94 (t, J=8.40 Hz, 2H), 3.12 (t, J=8.45 Hz, 2H), 3.01 (s, 3H).

Compound 51 (72 mg) was obtained by reference to the preparation method for the compound 47 of Example 47, with intermediate 47A being replaced by intermediate 51A. MS (ESI): m/z 448.2015 $[M+H]^+$.

$^1$H NMR (500 MHz, DMSO-$d_6$) δ 11.62 (s, 1H), 8.21 (s, 1H), 7.34 (s, 1H), 7.11-7.06 (m, 2H), 6.95 (d, J=7.35 Hz, 1H), 5.58 (s, 1H), 4.99 (s, 1H), 3.86 (t, J=8.35 Hz, 1H), 3.60-3.54 (m, 1H), 3.06-3.00 (s, 3H), 2.86 (s, 3H), 2.47-2.42 (m, 1H), 2.03-1.98 (m, 1H), 1.93-1.85 (m, 1H), 1.75-1.67 (m, 2H), 1.62-1.55 (m, 1H), 1.03 (d, J=6.40 Hz, 6H).

Example 52: Preparation of Compound 52

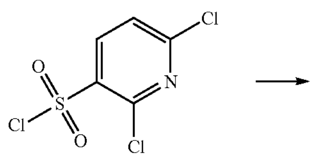

-continued

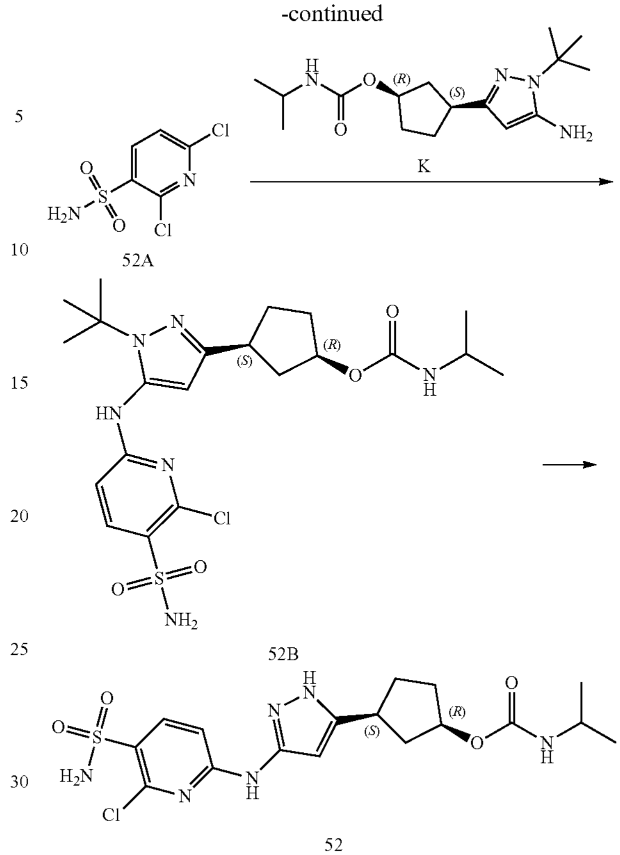

52A

52B

52

Intermediate 52B (210 mg) was obtained by reference to the preparation method for the compound 16 of Example 16, with methylamine hydrochloride being replaced by ammonium hydroxide and intermediate K1 being replaced by intermediate K. MS (ESI): m/z 499.48 $[M+H]^+$.

Compound 52 (60 mg) was obtained by reference to the preparation method for the compound 47 of Example 47, with intermediate 47C being replaced by intermediate 52B. MS (ESI): m/z 443.42 $[M+H]^+$.

$^1$H NMR (500 MHz, DMSO-d6) δ 12.10 (s, 1H), 10.10 (s, 1H), 8.04 (d, J=8.7 Hz, 1H), 7.43 (s, 2H), 7.34 (s, 1H), 6.94 (d, J=7.7 Hz, 1H), 6.08 (s, 1H), 5.08-4.93 (m, 1H), 3.65-3.52 (m, 1H), 3.14-2.98 (m, 1H), 2.49-2.42 (m, 1H), 2.09-1.98 (m, 1H), 1.97-1.85 (m, 1H), 1.79-1.66 (m, 2H), 1.65-1.54 (m, 1H), 1.03 (d, J=6.8 Hz, 6H).

Example 53: Preparation of Compound 53

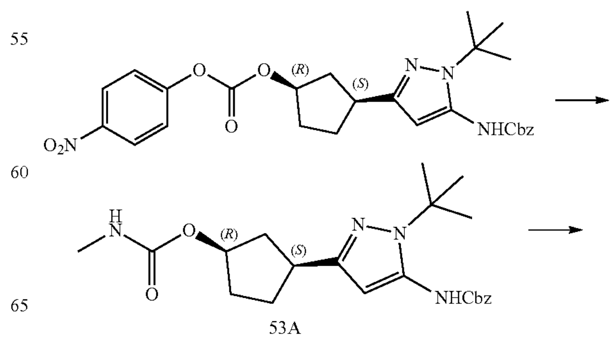

53A

-continued

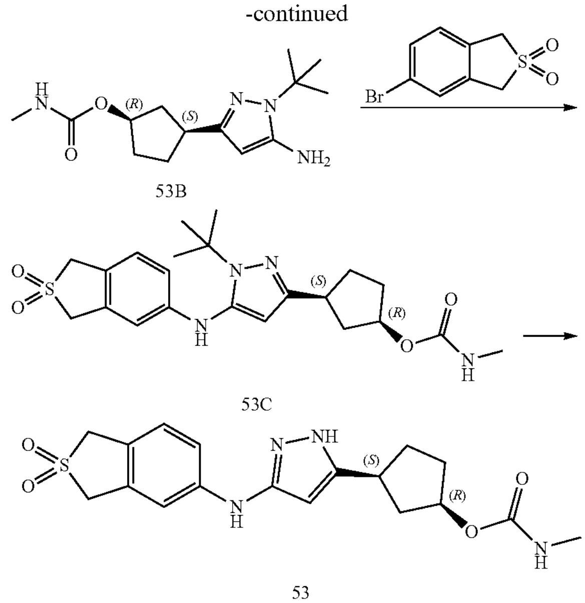

53B

53C

53

A crude product of compound 53 was obtained by reference to the preparation method for compound 48 of Example 48, with 1-methylcyclopropane-1-amine hydrochloride being replaced by methylamine hydrochloride.

The crude product of compound 53 was purified by medium and low pressure preparative liquid phase chromatography (C18 column, acetonitrile/water (30/70), the eluent contained one thousandth of ammonium hydroxide) to give compound 53 (55 mg). MS (ESI): m/z 391.46 $[M+H]^+$.

$^1$H NMR (500 MHz, DMSO-d6) δ 11.73 (s, 1H), 8.48 (s, 1H), 7.41 (s, 1H), 7.22-7.21 (m, 1H), 7.13 (d, J=8.4 Hz, 1H), 6.92 (d, J=5.3 Hz, 1H), 5.62 (d, J=2.2 Hz, 1H), 5.08-4.88 (m, 1H), 4.40 (s, 2H), 4.32 (s, 2H), 3.07-3.00 (m, 1H), 2.55 (d, J=4.6 Hz, 3H), 2.47-2.41 (m, 1H), 2.06-1.96 (m, 1H), 1.95-1.85 (m, 1H), 1.79-1.64 (m, 2H), 1.65-1.52 (m, 1H).

Example 54: Preparation of Compound 54

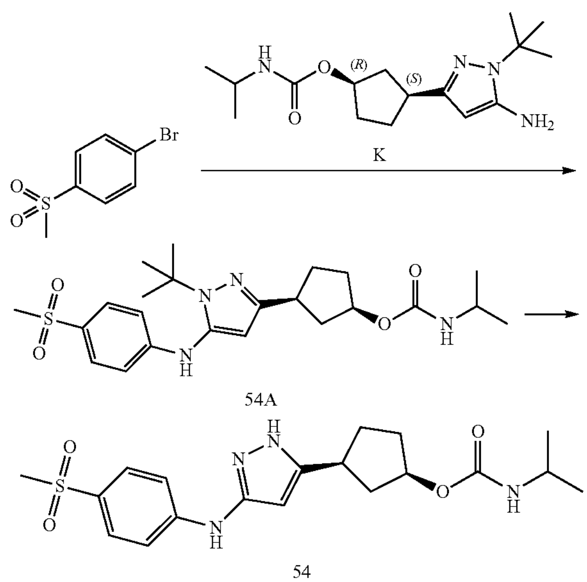

54A

54

A crude product of compound 54 was obtained by reference to the preparation method for compound 26 of Example 26, with 5-bromo-1,3-dihydrobenzo[c]thiophene-2,2-dioxide being replaced by 1-bromo-4-methylsulfonylbenzene.

The crude product of compound 54 was purified by medium and low pressure preparative liquid phase chromatography (C18 column, acetonitrile/water (30/70), the eluent contained one thousandth of ammonium hydroxide) to give compound 54 (20 mg). MS (ESI, $[M+H]^+$) m/z: 407.1748.

$^1$H NMR (500 MHz, DMSO-d6) δ 9.13 (s, 1H), 7.73-7.64 (m, 2H), 7.50-7.39 (m, 2H), 6.94 (d, J=7.2 Hz, 1H), 5.75 (s, 1H), 5.13-4.97 (m, 1H), 4.11 (s, 3H), 3.63-3.53 (m, 1H), 2.46 (m, 1H), 2.02 (m, 1H), 1.91 (m, 1H), 1.72 (m, 2H), 1.61 (m, 1H), 1.03 (m, 6H).

Example 55: Preparation of Compound 55

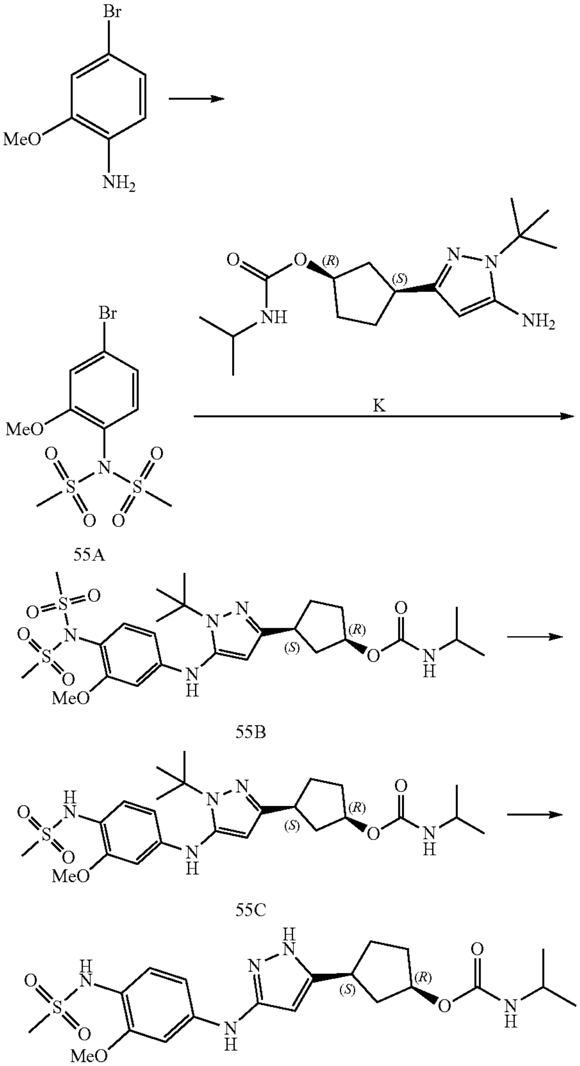

55A

55B

55C

55

A crude product of compound 55 was obtained by reference to the preparation method for compound 47 of Example 47, with 4-bromo-2-trifluoromethoxyaniline being replaced by 4-bromo-2-methoxyaniline.

The crude product of compound 55 was purified by column chromatography (developing solvents: dichloromethane/methanol (90/10)) to give compound 55 (44 mg). MS (ESI): m/z 452.28 $[M+H]^+$.

$^1$H NMR (500 MHz, DMSO-d6) δ 11.75 (s, 1H), 8.72-8.44 (m, 1H), 8.38 (s, 1H), 7.19 (s, 1H), 6.97 (d, J=8.6 Hz, 1H), 6.94 (d, J=7.9 Hz, 1H), 6.77 (d, J=8.6 Hz, 1H), 5.62 (s, 1H), 4.99 (s, 1H), 3.76 (s, 3H), 3.64-3.51 (m, 1H), 3.04-2.99 (m, 1H), 2.82 (s, 3H), 2.50-2.39 (m, 1H), 2.06-1.95 (m, 1H), 1.95-1.81 (m, 1H), 1.76-1.69 (m, 2H), 1.62-1.57 (m, 1H), 1.03 (d, J=6.3 Hz, 6H).

Example 56: Preparation of Compound 56

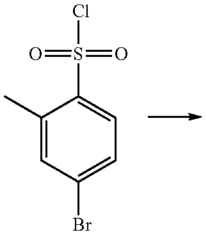

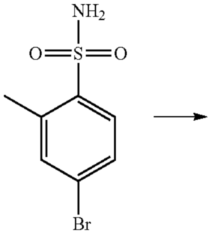

56A

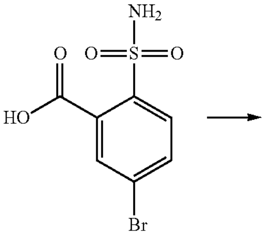

56B

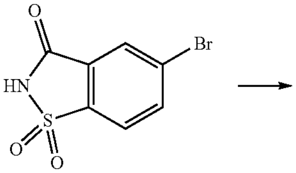

56C

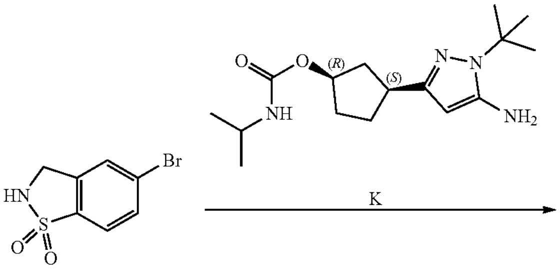

56D

-continued

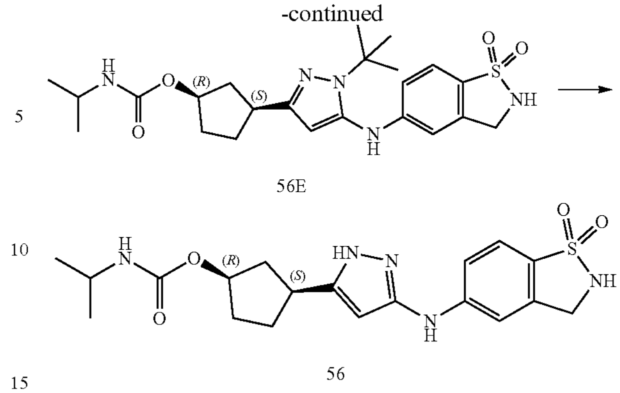

56E

56

4-Bromo-2-methylbenzene-1-sulfonyl chloride (5.0 g) and ammonium hydroxide (115.0 g) were added to dioxane (70 mL), and the mixture was stirred under an ice bath. After the reaction was completed, the reaction solution was concentrated by evaporation under reduced pressure to remove the solvent to give intermediate 56A (4.6 g).

Intermediate 56A (4.60 g), sodium hydroxide (3.34 g), and potassium permanganate (14.7 g) were added to water (50 mL), and the mixture was stirred at 40° C. After the reaction was completed, the reaction was quenched with a saturated aqueous sodium sulfite solution. The mixture was filtered, and the filtrate was adjusted to pH 2 and concentrated to give intermediate 56B (2.58 g).

Intermediate 56B (2.58 g) was dissolved in polyphosphoric acid (50 mL), and the mixture was stirred at 140° C. After the reaction was completed, the reaction solution was allowed to return to room temperature, and the reaction was quenched with ice water. The mixture was extracted with ethyl acetate, dried over anhydrous sodium sulfate, filtered, concentrated, and separated by column chromatography (developing solvents: dichloromethane/methanol) to give intermediate 56C (2.00 g). MS (ESI): m/z 260.0 $[M-H]^-$.

Intermediate 56C (2.00 g) and sodium borohydride (2.89 g) were dissolved in tetrahydrofuran (50 mL), boron trifluoride diethyl etherate (12.00 g) was added at −10° C., and the mixture was stirred at 80° C. After the reaction was completed, water was added to quench the reaction, and the mixture was extracted with ethyl acetate, dried over anhydrous sodium sulfate, filtered, concentrated, and separated by column chromatography (developing solvents: dichloromethane/methanol) to give intermediate 56D (1.72 g). MS (ESI): m/z 246.0 $[M-H]^-$.

Intermediate 56E (200 mg) was obtained by reference to the preparation method for compound 47 of Example 47, with intermediate 47A being replaced by intermediate 56D. MS (ESI): m/z 476.16 $[M+H]^+$.

A crude product of compound 56 was obtained by reference to the preparation method for compound 47 of Example 47, with intermediate 47C being replaced by intermediate 56E.

The crude product of compound 56 was purified by medium and low pressure preparative liquid phase chromatography (C18 column, acetonitrile/water (33/67), the eluent contained one thousandth of ammonium hydroxide) to give compound 56 (40 mg). MS (ESI): m/z 420.1693 $[M+H]^+$.

$^1$H NMR (500 MHz, DMSO-$d_6$) δ 11.90 (s, 1H), 8.99 (s, 1H), 7.58-7.38 (m, 3H), 7.30 (d, J=8.6 Hz, 1H), 6.94 (d, J=7.8 Hz, 1H), 5.71 (s, 1H), 4.99 (q, J=7.2, 6.1 Hz, 1H), 4.29 (s, 2H), 3.58 (h, J=7.0 Hz, 1H), 3.07 (q, J=8.7 Hz, 1H), 2.48-2.42 (m, 1H), 2.02 (m, 1H), 1.90 (m, 1H), 1.73 (m, 2H), 1.66-1.55 (m, 1H), 1.06-1.01 (m, 6H).

Example 57: Preparation of Compound 57

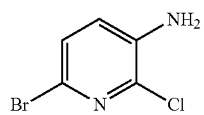

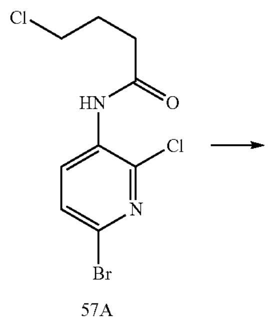

57A

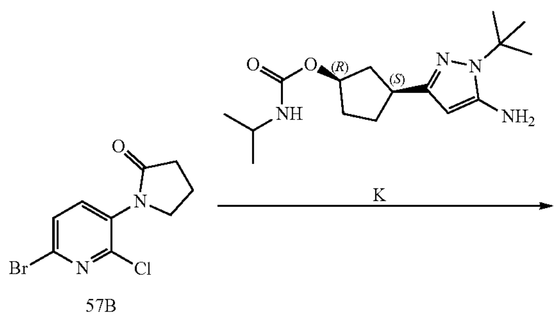

57B

-continued

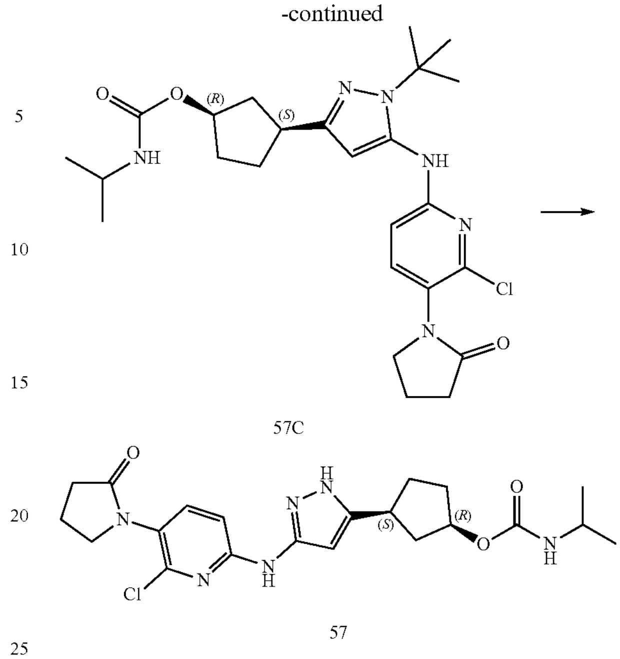

57C

57

A crude product of compound 57 was obtained by reference to the preparation method for compound 14 of Example 14, with the intermediate 6-bromo-N-methylpyridine-3-amine being replaced by 3-amino-6-bromo-2-chloropyridine.

The crude product of compound 57 was purified by medium and low pressure preparative liquid phase chromatography (C18 column, acetonitrile/water (32/68), the eluent contained one thousandth of ammonium hydroxide) to give compound 57 (9 mg). MS (ESI): m/z 447.1904 $[M+H]^+$.

$^1$H NMR (500 MHz, DMSO-$d_6$): δ 11.89 (s, 1H), 9.64 (s, 1H), 9.44 (s, 1H), 7.67 (d, J=8.7 Hz, 1H), 7.28 (d, J=8.7 Hz, 1H), 6.93 (d, J=7.7 Hz, 1H), 6.03 (s, 1H), 5.08-4.91 (m, 1H), 3.58 (h, J=6.8 Hz, 1H), 3.05 (p, J=8.7, 8.3 Hz, 1H), 2.46 (q, J=7.2 Hz, 1H), 2.02 (m, 1H), 1.89 (m, 2H), 1.78-1.55 (m, 3H), 1.03 (d, J=6.8 Hz, 6H), 0.78 (d, J=6.1 Hz, 4H).

Example 58: Preparation of Compound 58

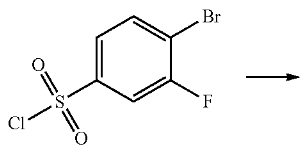

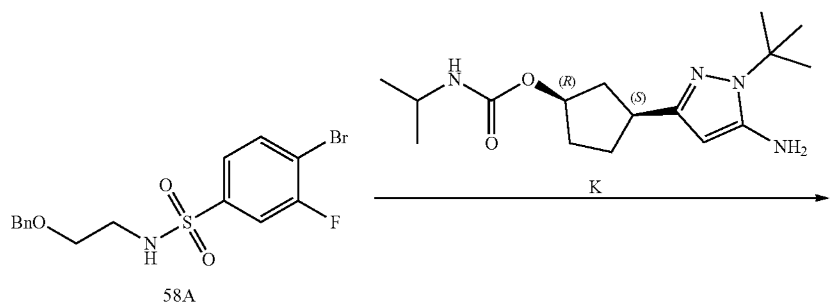

58A

-continued

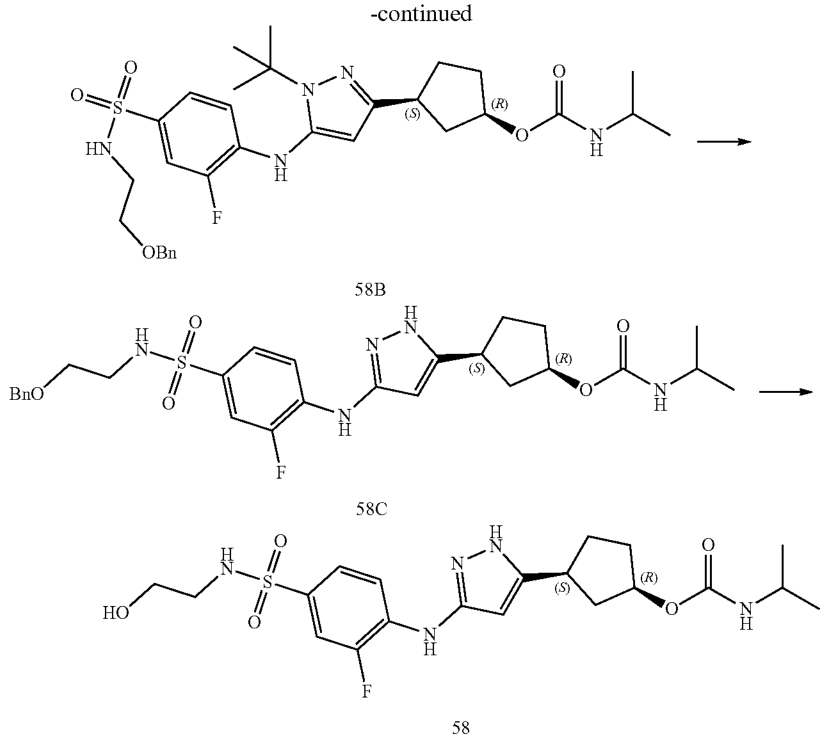

58B

58C

58

The crude product of intermediate 58C was obtained by reference to the preparation method for compound 16 of Example 16, with methylamine hydrochloride being replaced by 2-benzyl-1-ethylamine, 4-bromo-3-fluorobenzenesulfonyl chloride being replaced by 4-bromo-2-fluorobenzenesulfonyl chloride, and intermediate K1 being replaced by K.

The crude product of intermediate 58C was separated by column chromatography (developing solvents: dichloromethane/methanol) to give product 58C (150 mg). MS (ESI): m/z 560.29 $[M+H]^+$. Palladium on carbon (palladium content 5%, water content 50% (w/w), 70 mg) and intermediate 58C (150 mg) were added to methanol (10 mL) under hydrogen atmosphere, and the mixture was stirred at room temperature. After the reaction was completed, the reaction solution was filtered, concentrated, and purified by medium and low pressure preparative liquid phase chromatography (C18 column, acetonitrile/water (30/70), the eluent contained one thousandth of ammonium hydroxide) to give compound 58 (23 mg). MS (ESI): m/z 470.29 $[M+H]^+$.

$^1$H NMR (500 MHz, DMSO-d6) δ 11.98 (s, 1H), 8.67 (s, 1H), 8.17 (s, 1H), 7.59-7.38 (m, 2H), 7.35 (s, 1H), 6.93 (d, J=7.8 Hz, 1H), 5.83 (s, 1H), 5.00 (s, 1H), 4.66 (s, 1H), 3.58 (q, J=8.5, 7.7 Hz, 1H), 3.36 (t, J=6.4 Hz, 2H), 3.13-2.99 (m, 1H), 2.76 (t, J=6.3 Hz, 2H), 2.50-2.40 (m, 1H), 2.10-1.98 (m, 1H), 1.96-1.83 (m, 1H), 1.79-1.65 (m, 2H), 1.65-1.55 (m, 1H), 1.03 (d, J=6.6 Hz, 6H).

Example 59: Preparation of Compound 59

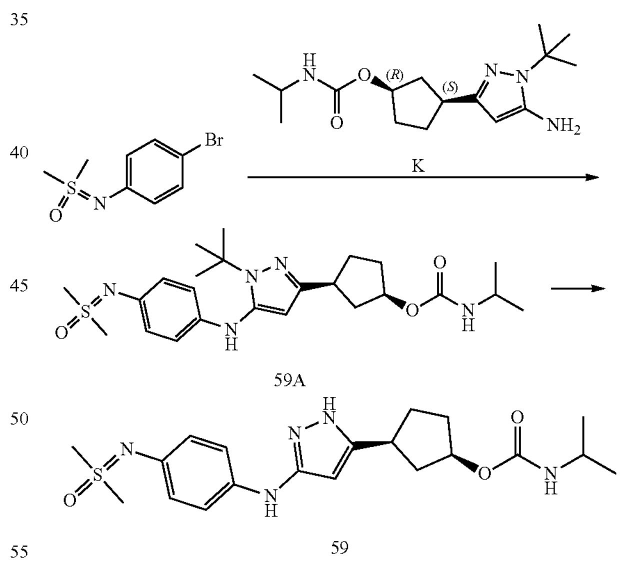

59A

59

A crude product of compound 59 was obtained by reference to the preparation method for compound 26 of Example 26, with 5-bromo-1,3-dihydrobenzo[c]thiophene-2,2-dioxide being replaced by ((4-bromophenyl)imino)dimethyl-$\lambda^6$-cyclic sulfone.

The crude product of compound 59 was purified by medium and low pressure preparative liquid phase chromatography (C18 column, acetonitrile/water (34/66), the eluent contained one thousandth of ammonium hydroxide) to give compound 59 (8 mg). MS (ESI, $[M+H]^+$) m/z: 420.2058.

$^1$H NMR (500 MHz, DMSO-d6) δ 11.56 (s, 1H), 7.92 (s, 1H), 7.14-7.13 (m, 2H), 6.95-6.94 (m, 1H), 6.77-6.75 (s, 2H), 5.56 (s, 1H), 4.99 (m, 1H), 3.61-3.53 (m, 1H), 3.11 (s, 6H), 3.04-2.97 (m, 1H), 2.47-2.41 (s, 1H), 2.02-1.96 (m, 1H), 1.91-1.85 (m, 1H), 1.76-1.65 (m, 2H), 1.61-1.55 (m, 1H), 1.03 (d, J=6.85 Hz, 6H).

Example 60: Preparation of Compound 60

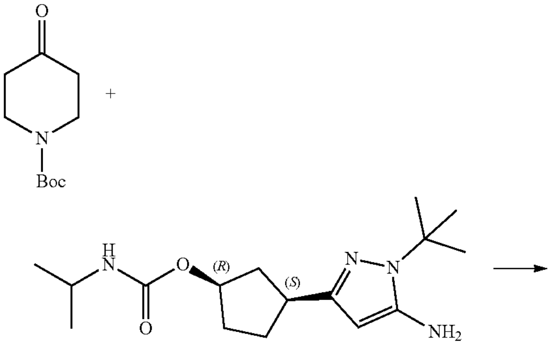

K

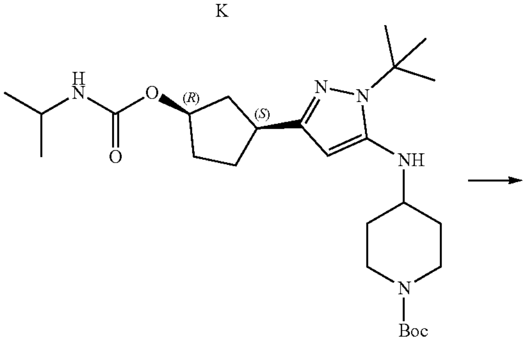

60A

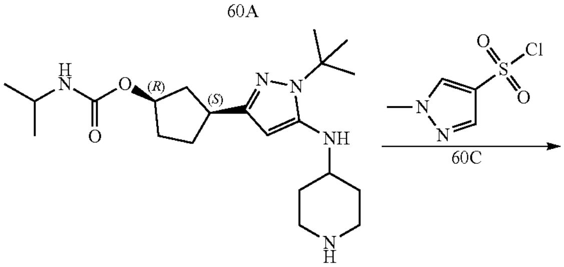

60B

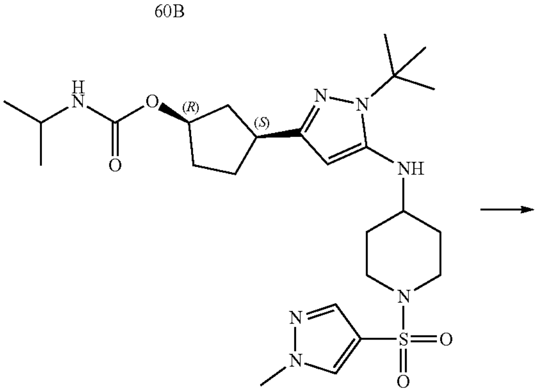

60D

-continued

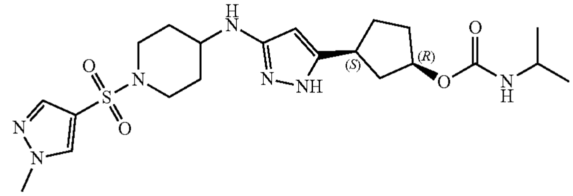

60

Intermediate 60A (203 mg) was obtained by reference to the preparation method for compound 22 of Example 22, with 1-N-methanesulfonyl-4-piperidone being replaced by 4-oxopiperidine-1-carboxylate. MS (ESI): m/z 492.39 $[M+H]^+$.

Intermediate 60A (200 mg) and a solution of hydrochloric acid in dioxane (4 M, 5 mL) were added to dichloromethane (20 mL), and the mixture was stirred at room temperature. After the reaction was completed, the reaction solution was concentrated by evaporation under reduced pressure to remove the solvent to give intermediate 60B (150 mg). MS (ESI): m/z 392.38 $[M+H]^+$.

Intermediate 60B (32 mg), intermediate 60C (22 mg), and N,N-diisopropylethylamine (53 mg) were added to dichloromethane (10 mL), and the mixture was stirred at room temperature. The reaction solution was concentrated by evaporation under reduced pressure to remove the solvent to give intermediate 60D (40 mg). MS (ESI): m/z 536.37 $[M+H]^+$.

A crude product of compound 60 was obtained by reference to the preparation method for compound 47 of Example 47, with intermediate 47C being replaced by intermediate 60D.

The crude product of compound 60 was purified by medium and low pressure preparative liquid phase chromatography (C18 column, acetonitrile/water (32/68), the eluent contained one thousandth of ammonium hydroxide) to give compound 60 (8 mg). MS (ESI, $[M+H]^+$) m/z: 480.2387.

$^1$H NMR (500 MHz, DMSO-$d_6$) δ 11.12 (s, 1H), 8.31 (s, 1H), 7.76 (s, 1H), 6.91 (d, J=7.6 Hz, 1H), 5.22 (s, 1H), 4.94 (m, 2H), 3.91 (s, 3H), 3.60-3.53 (m, 1H), 3.38-3.35 (m, 2H), 3.15-3.069 (m, 1H), 2.93-2.86 (m, 1H), 2.45-2.41 (m, 2H), 2.39-2.33 (m, 1H), 1.98-1.80 (m, 4H), 1.72-1.44 (m, 5H), 1.03-1.01 (m, 6H).

Example 61: Preparation of Compound 61

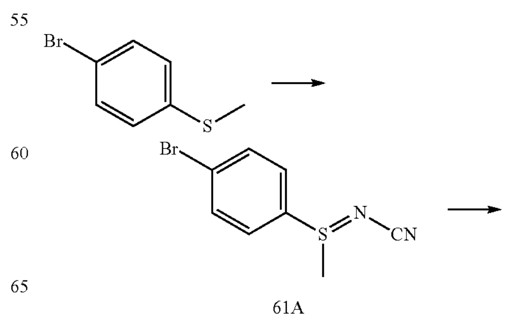

61A

-continued

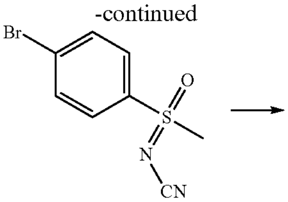

61B

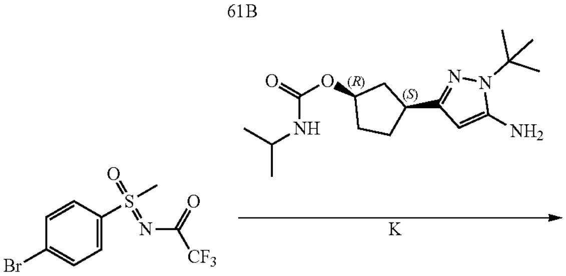

61C

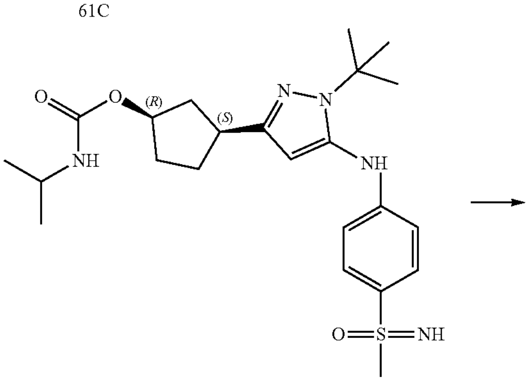

61D

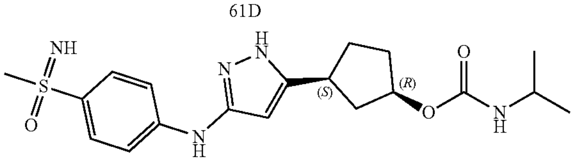

61

4-Bromothioanisole (1.0 g), (diacetoxyiodo)benzene (1.7 g), and cyanamide (0.4 g) were added to dichloromethane (30 mL), and the mixture was stirred at room temperature. After the reaction was completed, the reaction solution was concentrated by evaporation under reduced pressure to remove the solvent, and separated by column chromatography (developing solvents: petroleum ether/ethyl acetate) to give intermediate 61A (1.1 g). MS (ESI): m/z 243.03 [M+H]$^+$.

Potassium permanganate (1.6 g) was added to a solution of 61A (1.1 g) in acetone (30 mL), and the mixture was stirred at room temperature. After the reaction was completed, the reaction solution was filtered, concentrated, and separated by evaporation under reduced pressure to remove the solvent, and separated by column chromatography (developing solvents: petroleum ether/ethyl acetate) to give intermediate 61B (1.2 g). MS (ESI): m/z 258.91 [M+H]$^+$.

Trifluoroacetic anhydride (3.3 mL) was added to a solution of 61B (1.2 g) in dichloromethane (50 mL). After the addition was completed, the mixture was stirred at room temperature. After the reaction was completed, the reaction solution was concentrated by evaporation under reduced pressure to remove the solvent, and separated by column chromatography (developing solvents: petroleum ether/ethyl acetate) to give intermediate 61C (1.5 g). MS (ESI): m/z 329.99 [M−H]$^-$.

Intermediate 61C (241 mg), intermediate K (150 mg), chloro(2-dicyclohexylphosphino-2',4',6'-triisopropyl-1,1'-biphenyl)[2-(2'-amino-1,1'-biphenyl)]palladium (II) (114 mg), 2-dicyclohexylphosphino-2',4',6'-triisopropylbiphenyl (70 mg), and potassium phosphate (475 mg) were added to dioxane (40 mL), and the mixture was stirred at 100° C. under nitrogen atmosphere. After the reaction was completed, the reaction solution was filtered, concentrated, and separated by column chromatography (developing solvents: dichloromethane/methanol) to give intermediate 61D (200 mg). MS (ESI): m/z 462.32 [M+H]$^+$.

Intermediate 61D (200 mg) was added to a 1.0 M aqueous hydrochloric acid solution (10 mL), and the mixture was stirred at 100° C. After the reaction was completed, the pH of the reaction solution was adjusted to alkalinity with a saturated aqueous sodium bicarbonate solution. The mixture was extracted with dichloromethane, dried over anhydrous sodium sulfate, and filtered. The filtrate was concentrated by evaporation under reduced pressure to remove the solvent and purified by medium and low pressure preparative liquid phase chromatography (C18 column, acetonitrile/water (30/70), the eluent contained one thousandth of ammonium hydroxide) to give compound 61 (100 mg). MS (ESI): m/z 406.25 [M+H]$^+$.

$^1$H NMR (500 MHz, DMSO-d6) δ 11.90 (s, 1H), 8.92 (s, 1H), 7.74-7.63 (m, 2H), 7.42 (d, J=7.8 Hz, 2H), 6.94 (d, J=7.8 Hz, 1H), 5.70 (s, 1H), 5.00 (s, 1H), 3.81 (s, 1H), 3.65-3.50 (m, 1H), 3.12-3.01 (m, 1H), 2.97 (d, J=1.1 Hz, 3H), 2.48-2.43 (m, 1H), 2.05-1.99 (m, 1H), 1.96-1.84 (m, 1H), 1.75-1.69 (m, 2H), 1.64-1.60 (m, 1H), 1.03 (d, J=6.8 Hz, 6H).

Example 62: Preparation of Compound 62

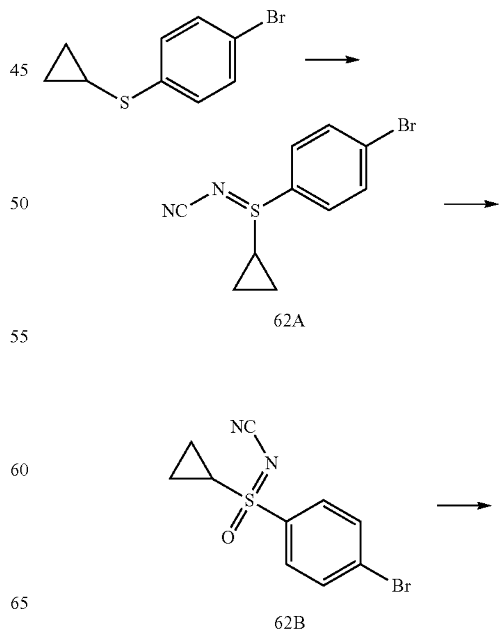

62A

62B

-continued

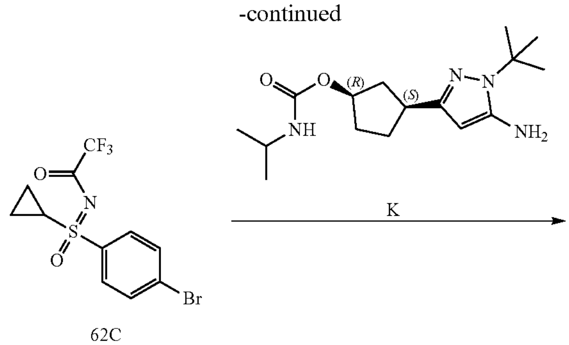

62C

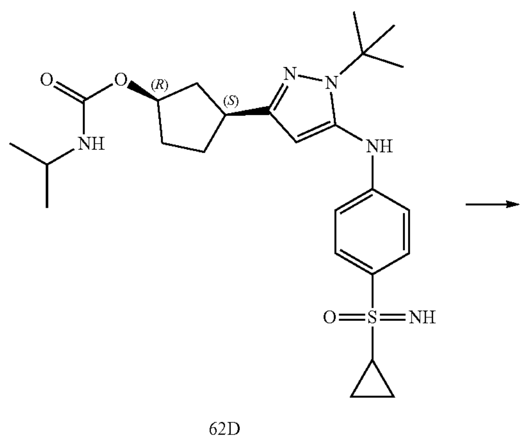

62D

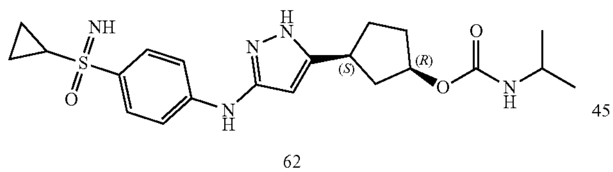

62

A crude product of compound 62 was obtained by reference to the preparation method for compound 61 of Example 61, with 4-bromothioanisole being replaced by 1-bromo-4-(cyclopropylthio)benzene. The crude product of compound 62 was purified by medium and low pressure preparative liquid phase chromatography (C18 column, acetonitrile/water (30/70), the eluent contained one thousandth of ammonium hydroxide) to give compound 62 (40 mg). MS (ESI): m/z 432.24 $[M+H]^+$.

$^1$H NMR (500 MHz, DMSO-d6) δ 11.89 (s, 1H), 8.91 (s, 1H), 7.64 (d, J=8.6 Hz, 2H), 7.41 (d, J=8.5 Hz, 2H), 6.94 (d, J=7.8 Hz, 1H), 5.70 (s, 1H), 5.00 (s, 1H), 3.76 (s, 1H), 3.60-3.56 (m, 1H), 3.36-3.33 (m, 1H), 3.13-2.99 (m, 1H), 2.59-2.50 (m, 1H), 2.48-2.41 (m, 1H), 2.08-1.97 (m, 1H), 1.95-1.83 (m, 1H), 1.79-1.66 (m, 2H), 1.64-1.56 (m, 1H), 1.03 (d, J=6.4 Hz, 6H), 0.94-0.88 (m, 1H), 0.88-0.77 (m, 2H).

Examples 63 and 64: Preparation of Compounds 63 and 64

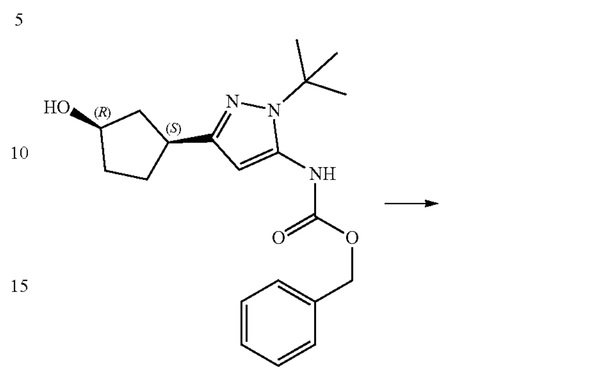

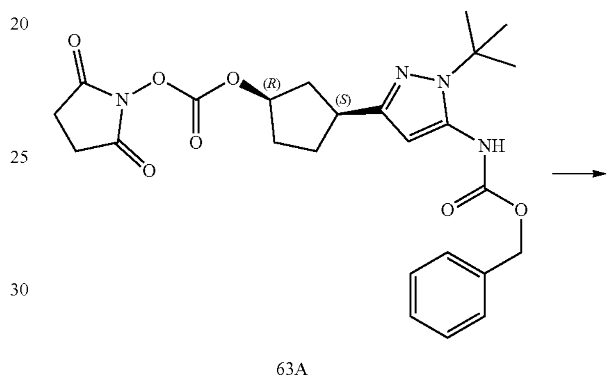

63A

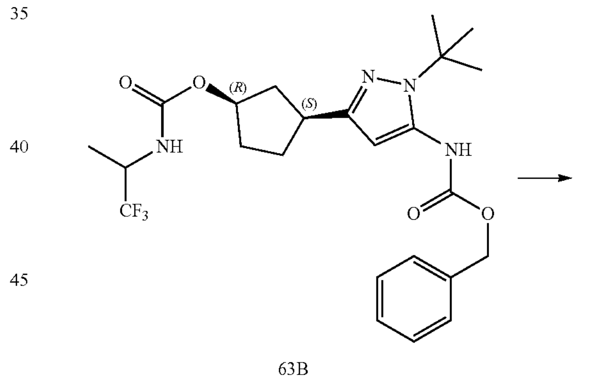

63B

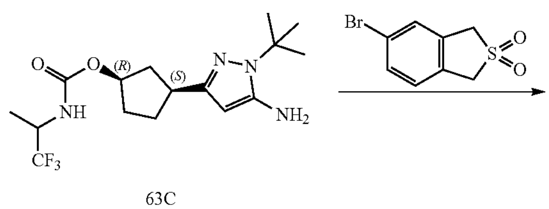

63C

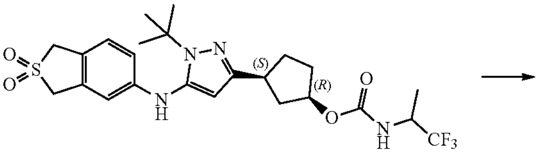

63D

-continued

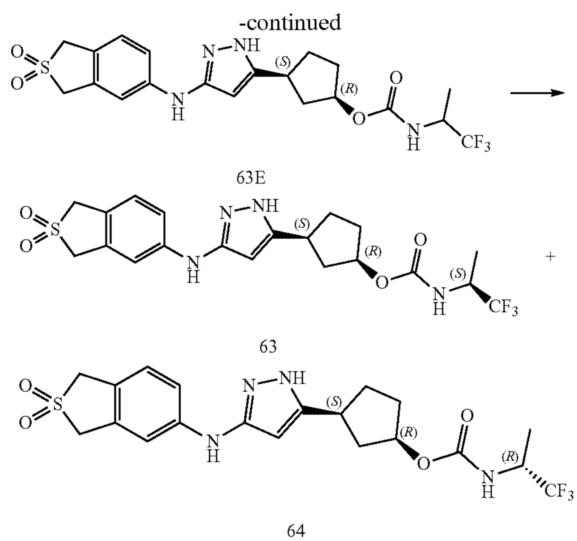

63E

63

64

Benzyl (1-(tert-butyl)-3-((1S,3R)-3-hydroxycyclopentyl)-1H-pyrazol-5-yl)carbamate (2.00 g), triethylamine (1.70 g), and bis(2,5-dioxopyrrolidin-1-yl)carbonate (4.30 g) were added to acetonitrile (20 mL), and the mixture was stirred at 40° C. After the reaction was completed, the reaction solution was concentrated by evaporation under reduced pressure to remove the solvent, and separated by column chromatography (developing solvents: petroleum ether/ethyl acetate) to give intermediate 63A (1.73 g). MS (ESI): m/z 499.32 [M+H]$^+$.

N,N-Diisopropylethylamine (1.02 g), 1,1,1-trifluoropropan-2-amine (0.36 g), and intermediate 63A (1.00 g) were added to dichloromethane (20 mL), and the mixture was stirred at 35° C. After the reaction was completed, the reaction solution was washed with a saturated aqueous sodium bicarbonate solution and brine in sequence, dried over anhydrous sodium sulfate, filtered, and concentrated to give intermediate 63B (0.80 g). MS (ESI): m/z 497.34 [M+H]$^+$.

Intermediate 63B (0.80 g) and palladium on carbon (palladium content 5%, water content 50% (w/w), 0.34 g) were added to tetrahydrofuran (8 mL) and ethyl acetate (8 mL), and the mixture was stirred at room temperature under hydrogen atmosphere. After the reaction was completed, the reaction solution was filtered and concentrated to give intermediate 63C (0.45 g). MS (ESI): m/z 363.27 [M+H]$^+$.

Intermediate 63C (0.25 g), 5-bromo-1,3-dihydrobenzo[c]thiophene-2,2-dioxide (0.26 g), chloro(2-dicyclohexylphosphino-2',4',6'-triisopropyl-1,1'-biphenyl)[2-(2'-amino-1,1'-biphenyl)]palladium (II) (0.11 g), 2-dicyclohexylphosphino-2',4',6'-triisopropylbiphenyl (0.10 g), and potassium phosphate (0.44 g) were added to N,N-dimethylformamide (10 mL). After the addition was completed, the mixture was stirred at 110° C. under nitrogen atmosphere. After the reaction was completed, the reaction solution was filtered, concentrated, and separated by column chromatography (developing solvents: dichloromethane/methanol) to give intermediate 63D (0.23 g). MS (ESI): m/z 529.28 [M+H]$^+$.

Intermediate 63D (0.23 g) was added to ethanol (2 mL) and diluted hydrochloric acid (1 N, 20 mL), and the mixture was stirred at 100° C. under microwave. After the reaction was completed, the reaction solution was concentrated by evaporation under reduced pressure to remove the solvent, and the pH of the residue was adjusted to alkalinity with a saturated aqueous sodium bicarbonate solution. The mixture was extracted with dichloromethane, dried over anhydrous sodium sulfate, filtered, concentrated, and separated by column chromatography (developing solvents: dichloromethane/methanol) to give intermediate 63E (70 mg). MS (ESI): m/z 473.14 [M+H]$^+$.

Intermediate 63E (70 mg) was subjected to SFC chiral preparation (CHIRALART Amylose-SA column (30×250 mm, 5 m), mobile phase: ethanol/n-hexane (0-60%)) to give compound 63 (35 mg). MS (ESI): m/z 473.1491 [M+H]$^+$. $^1$H NMR (500 MHz, DMSO-$d_6$) δ 11.75 (s, 1H), 8.47 (s, 1H), 7.82 (d, J=8.95 Hz, 1H), 7.40 (m, 1H), 7.22-7.20 (m, 1H), 7.14-7.13 (m, 1H), 5.64 (s, 1H), 5.18-4.94 (m, 1H), 4.40 (s, 2H), 4.32 (s, 2H), 4.30-4.23 (m, 1H), 3.08-3.02 (m, 1H), 2.05-2.00 (m, 1H), 1.97-1.90 (m, 1H), 1.77-1.69 (m, 2H), 1.68-1.54 (m, 1H), 1.23-1.22 (m, 3H).

Compound 64 (35 mg). MS (ESI): m/z 473.1485 [M+H]$^+$. $^1$H NMR (500 MHz, DMSO-$d_6$) δ 11.75 (s, 1H), 8.47 (s, 1H), 7.82 (d, J=8.95 Hz, 1H), 7.40 (m, 1H), 7.22-7.20 (m, 1H), 7.14-7.13 (m, 1H), 5.64 (s, 1H), 5.18-4.94 (m, 1H), 4.40 (s, 2H), 4.32 (s, 2H), 4.30-4.23 (m, 1H), 3.08-3.02 (m, 1H), 2.05-2.00 (m, 1H), 1.97-1.90 (m, 1H), 1.77-1.69 (m, 2H), 1.68-1.54 (m, 1H), 1.23-1.22 (m, 3H).

Example 65: Preparation of Compound 65

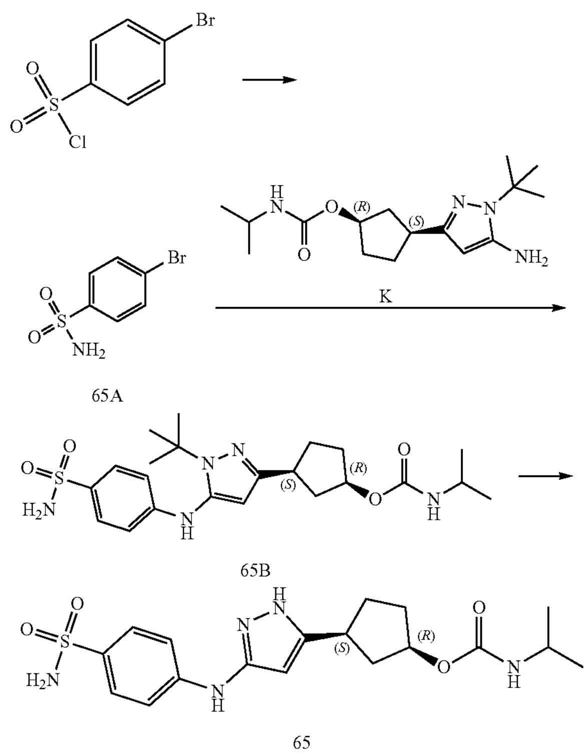

65A

65B

65

Compound 65 (35 mg) was prepared by reference to the preparation method for compound 33 of Example 33, with 4-bromo-2-fluorobenzenesulfonyl chloride being replaced by 4-bromobenzenesulfonyl chloride. MS (ESI): m/z 408.1709 [M+H]$^+$.

$^1$H NMR (500 MHz, DMSO-$d_6$) δ 11.86 (s, 1H), 8.85 (s, 1H), 7.61-7.59 (m, 2H), 7.39 (d, J=8.40 Hz, 2H), 7.00 (s, 2H), 6.95-6.93 (m, 1H), 5.68 (s, 1H), 5.09-4.92 (m, 1H), 3.61-3.55 (m, 1H), 3.09-3.02 (m, 1H), 2.49-2.42 (m, 1H), 2.04-2.00 (m, 1H), 1.94-1.86 (m, 1H), 1.75-1.69 (m, 2H), 1.63-1.57 (m, 1H), 1.03 (d, J=6.40 Hz, 6H).

Example 66: Preparation of Compound 66

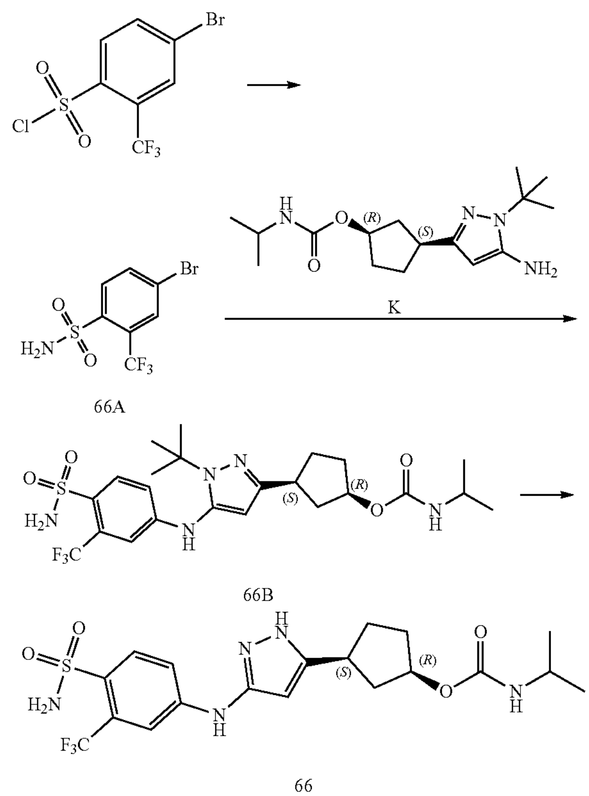

66A

66B

66

Compound 66 (35 mg) was prepared by reference to the preparation method for compound 33 of Example 33, with 4-bromo-2-fluorobenzenesulfonyl chloride being replaced by 4-bromo-2-trifluoromethylbenzenesulfonyl chloride. MS (ESI): m/z 476.1585 $[M+H]^+$.

$^1H$ NMR (500 MHz, DMSO-$d_6$) δ 12.03 (s, 1H), 9.28 (s, 1H), 8.00 (s, 1H), 7.93 (d, J=8.90 Hz, 1H), 7.58-7.57 (m, 1H), 7.30 (s, 2H), 6.93 (d, J=7.15 Hz, 1H), 5.69 (s, 1H), 4.99 (s, 1H), 3.60-3.56 (m, 1H), 3.08-3.03 (m, 1H), 2.49-2.42 (m, 1H), 2.05-2.00 (m, 1H), 1.94-1.88 (m, 1H), 1.75-1.69 (m, 2H), 1.64-1.54 (m, 1H), 1.03 (d, J=6.45 Hz, 6H).

Example 67: Preparation of Compound 67

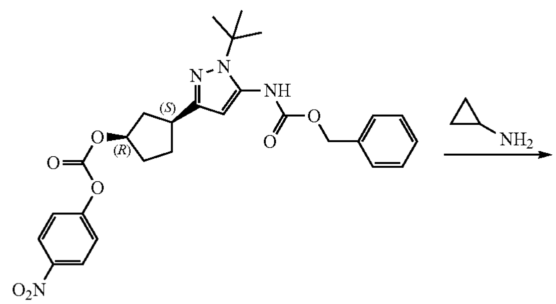

-continued

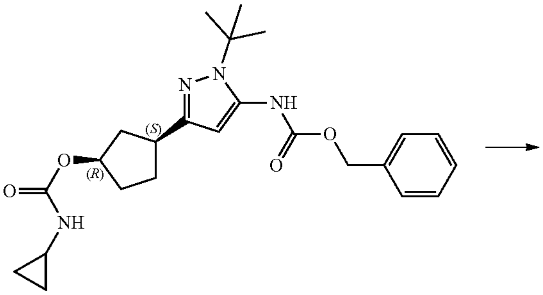

67A

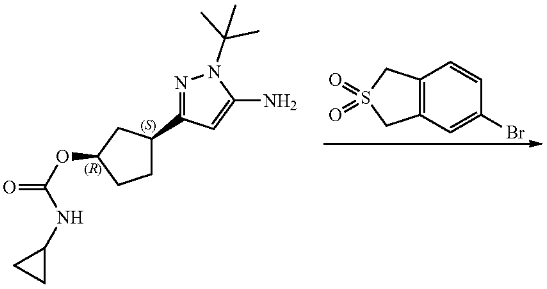

67B

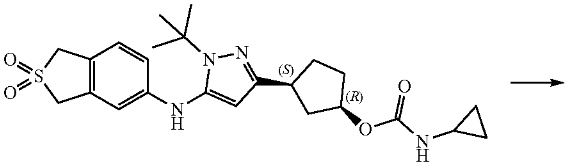

67C

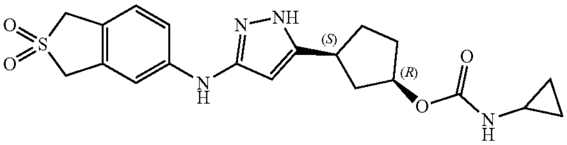

67

A crude product of compound 67 was obtained by reference to the preparation method for compound 48 of Example 48, with 1-methylcyclopropane-1-amine hydrochloride being replaced by cyclopropylamine.

The crude product of compound 67 was purified by medium and low pressure preparative liquid phase chromatography (C18 column, acetonitrile/water (30/70), the eluent contained one thousandth of ammonium hydroxide) to give compound 67 (20 mg). MS (ESI): m/z 417.1596 $[M+H]^+$.

$^1H$ NMR (500 MHz, DMSO-$d_6$) δ 11.72 (s, 1H), 8.46 (s, 1H), 7.40 (s, 1H), 7.21 (d, J=9.8 Hz, 2H), 7.13 (d, J=8.4 Hz, 1H), 5.63 (s, 1H), 5.00 (s, 1H), 4.40 (s, 2H), 4.32 (s, 2H), 3.05 (m, 1H), 2.45 (m, 2H), 2.03-1.98 (m, 1H), 1.94-1.86 (m, 1H), 1.78-1.67 (m, 2H), 1.63-1.56 (s, 1H), 0.55-0.53 (m, 2H), 0.39-0.35 (m, 2H).

Example 68: Preparation of Compound 68

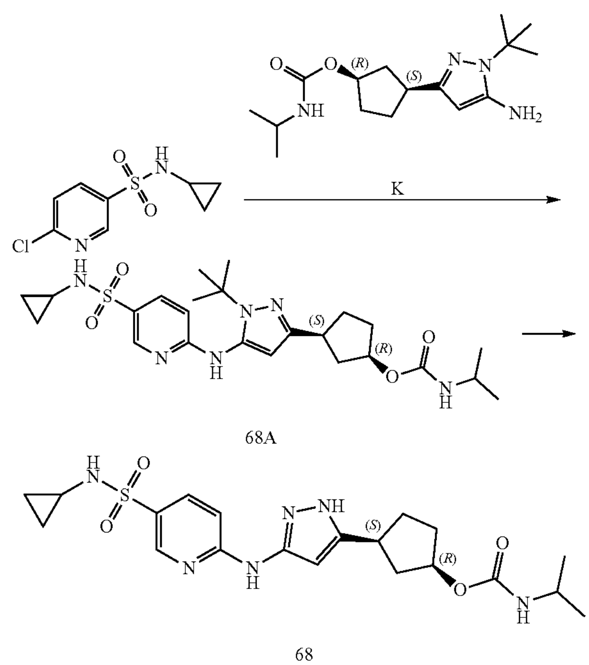

68A

68

A crude product of compound 68 of Example 68 was obtained by reference to the preparation method for compound 1 of Example 1, with 1A being replaced by 6-chloro-N-cyclopropylpyridine-3-sulfonamide.

The crude product of compound 68 was purified by column chromatography (developing solvents: dichloromethane/methanol (90/10)) to give compound 68 (70 mg). MS (ESI): m/z 449.1967 $[M+H]^+$.

$^1H$ NMR (500 MHz, DMSO-$d_6$) δ 12.02 (s, 1H), 9.85 (s, 1H), 8.46 (d, J=2.5 Hz, 1H), 7.83 (dd, J=8.9, 2.5 Hz, 1H), 7.70 (s, 1H), 7.34 (s, 1H), 6.93 (d, J=7.8 Hz, 1H), 6.18 (s, 1H), 5.00 (s, 1H), 3.60-3.54 (m, 1H), 3.17-2.98 (m, 1H), 2.49-2.44 (m, 1H), 2.15-2.12 (m, 1H), 2.05-2.00 (m, 1H), 1.95-1.83 (m, 1H), 1.80-1.67 (m, 2H), 1.64-1.58 (m, 1H), 1.03 (dd, J=6.9, 2.8 Hz, 6H), 0.57-0.42 (m, 2H), 0.38-0.35 (m, 2H).

Example 69: Preparation of Compound 69

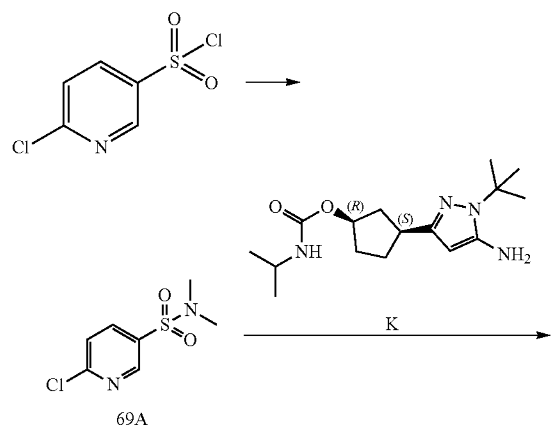

69A

-continued

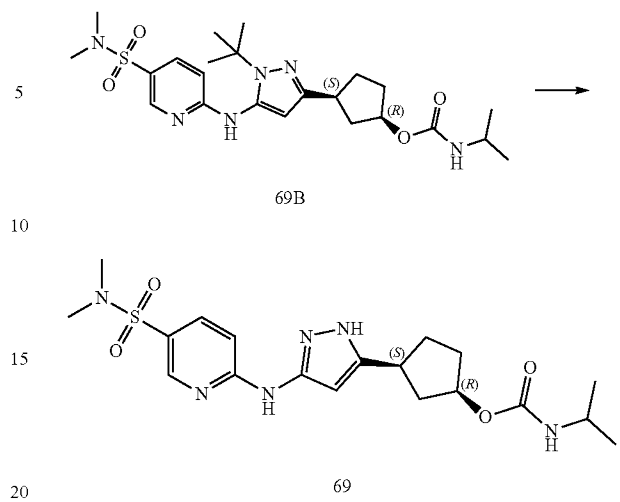

69B

69

Compound 69 (10 mg) was prepared by reference to the preparation method for compound 33 of Example 33, with 4-bromo-2-fluorobenzenesulfonyl chloride being replaced by 2-chloropyridine-5-sulfonyl chloride and ammonium hydroxide being replaced by dimethylamine. MS (ESI): m/z 437.1966 $[M+H]^+$.

$^1H$ NMR (500 MHz, DMSO-$d_6$) δ 12.05 (s, 1H), 9.93 (s, 1H), 8.41 (d, J=1.30 Hz, 1H), 7.82 (dd, J=2.15, 8.90 Hz, 1H), 7.35 (s, 1H), 6.93 (d, J=6.85 Hz, 1H), 6.22 (s, 1H), 5.11-4.90 (m, 1H), 3.61-3.54 (m, 1H), 3.14-3.02 (m, 1H), 2.60 (s, 6H), 2.49-2.35 (m, 1H), 2.06-2.00 (m, 1H), 1.94-1.86 (m, 1H), 1.78-1.67 (m, 2H), 1.65-1.58 (m, 1H), 1.03 (m, 6H).

Example 70: Preparation of Compound 70

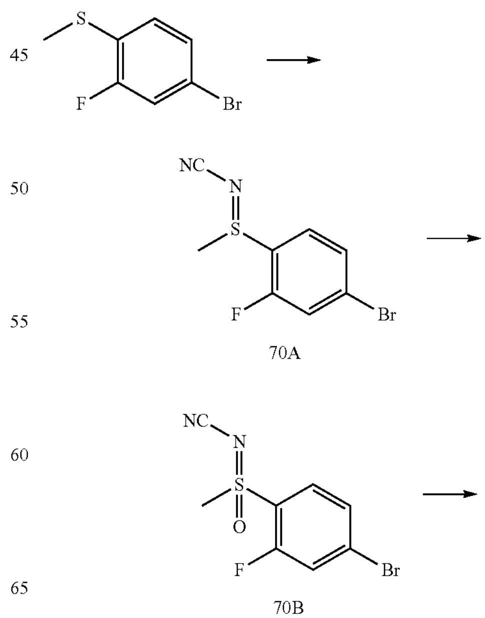

70A

70B

-continued

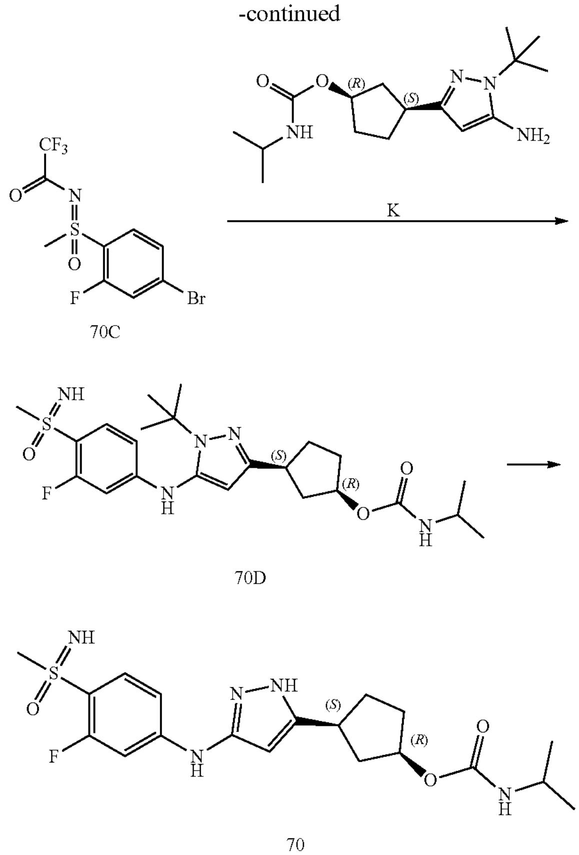

70C

70D

70

A crude product of compound 70 of Example 70 was obtained by reference to the preparation method for compound 61 of Example 61, with 4-bromothioanisole being replaced by 4-bromo-2-fluoro-1-methylthiobenzene.

The crude product of compound 70 was purified by medium and low pressure preparative liquid phase chromatography (C18 column, acetonitrile/water (30/70), the eluent contained one thousandth of ammonium hydroxide) to give compound 70 (80 mg) of Example 70. MS (ESI): m/z 424.23 $[M+H]^+$.

$^1$H NMR (500 MHz, DMSO-$d_6$) δ 11.98 (s, 1H), 9.20 (s, 1H), 7.61 (t, J=8.7 Hz, 1H), 7.44 (d, J=13.7 Hz, 1H), 7.07 (d, J=8.8 Hz, 1H), 6.94 (d, J=7.8 Hz, 1H), 5.70 (s, 1H), 4.99 (s, 1H), 4.27 (s, 1H), 3.68-3.49 (m, 1H), 3.10-3.04 (m, 4H), 2.49-2.41 (m, 1H), 2.09-1.97 (m, 1H), 1.96-1.85 (m, 1H), 1.75-1.68 (m, 2H), 1.63-1.59 (m, 1H), 1.15-0.94 (m, 6H).

Example 71: Preparation of Compound 71

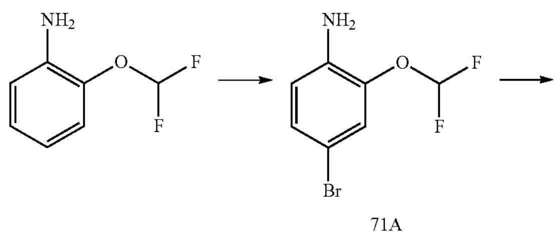

71A

-continued

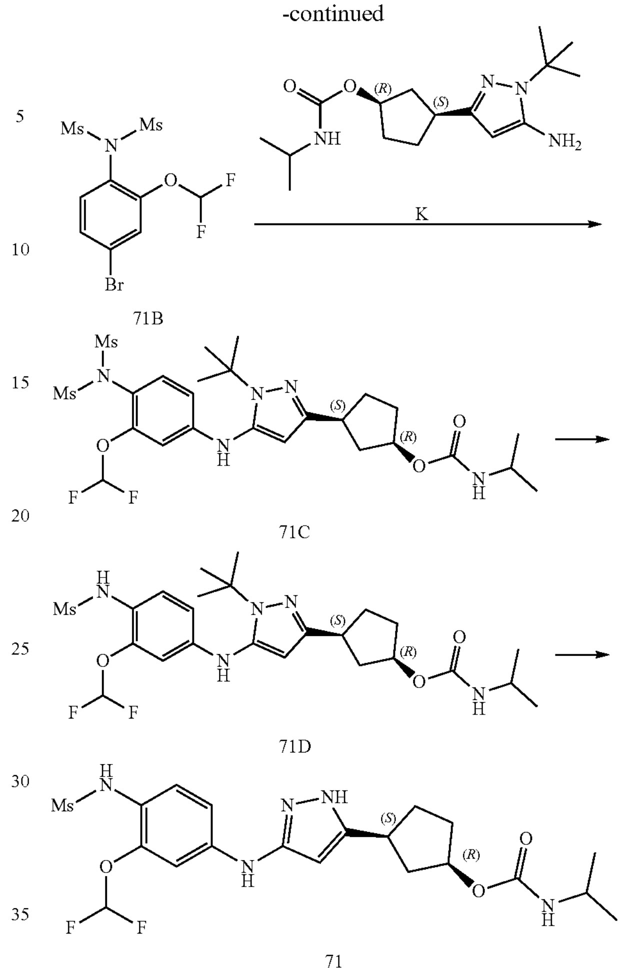

71B

71C

71D

71

N-Bromosuccinimide (2.46 g) and 2-(difluoromethoxy) aniline (2.00 g) were added to dichloromethane (20 mL), and the mixture was stirred under an ice bath. After the reaction was completed, the reaction solution was concentrated to give intermediate 71A (1.90 g).

Intermediate 71A (1.80 g), N,N-diisopropylethylamine (2.93 g), and methanesulfonic anhydride (3.95 g) were added to dichloromethane (20 mL), and the mixture was stirred at room temperature. After the reaction was completed, the reaction solution was concentrated and separated by evaporation under reduced pressure to remove the solvent, and separated by column chromatography (developing solvents: petroleum ether/ethyl acetate) to give intermediate 71B (2.0 g). MS (ESI): m/z 315.97$[M-H]^-$.

Intermediate 71B (0.46 g), intermediate K (0.3 g), methanesulfonato[9,9-dimethyl-4,5-bis(diphenylphosphino)xanthene][2'-amino-1,1'-biphenyl]palladium (II) dichloromethane adduct (0.18 g), and cesium carbonate (0.95 g) were added to dioxane (20 mL), and the mixture was stirred at 110° C. under nitrogen atmosphere. After the reaction was completed, the reaction solution was filtered, concentrated, and separated by column chromatography (developing solvents: dichloromethane/methanol) to give intermediate 71C (350 mg). MS (ESI): m/z 544.46$[M+H]^+$.

Intermediate 71C (0.35 g) and a saturated aqueous sodium carbonate solution (10 mL) were added to dioxane (20 mL). After the addition was completed, the mixture was stirred at 50° C. After the reaction was completed, the reaction solution was extracted with dichloromethane, washed with saturated brine, dried over anhydrous sodium sulfate, filtered, and concentrated to give intermediate 71D (300 mg).

Intermediate 71D (300 mg) was added to ethanol (1 mL) and diluted hydrochloric acid (1 N, 15 mL), and the mixture was stirred at 100° C. under microwave. After the reaction was completed, the reaction solution was concentrated by evaporation under reduced pressure to remove the solvent, and the pH of the residue was adjusted to alkalinity with a saturated aqueous sodium bicarbonate solution. The mixture was extracted with dichloromethane, dried over anhydrous sodium sulfate, filtered, concentrated, and separated by column chromatography (developing solvents: dichloromethane/methanol) to give intermediate 71 (100 mg). MS (ESI): m/z 488.1787 $[M+H]^+$.

$^1H$ NMR (500 MHz, DMSO-$d_6$) δ 11.83 (s, 1H), 8.93 (s, 1H), 8.64 (s, 1H), 7.44 (s, 1H), 7.23-7.02 (m, 3H), 6.95-6.90 (m, 1H), 5.61 (s, 1H), 4.99 (s, 1H), 3.61-3.54 (m, 1H), 3.06-2.98 (m, 1H), 2.91 (s, 3H), 2.48-2.42 (m, 1H), 2.03-1.98 (m, 1H), 1.93-1.86 (m, 1H), 1.76-1.65 (m, 2H), 1.62-1.55 (m, 1H), 1.03 (d, J=7.10 Hz, 6H).

Example 72: Preparation of Compound 72

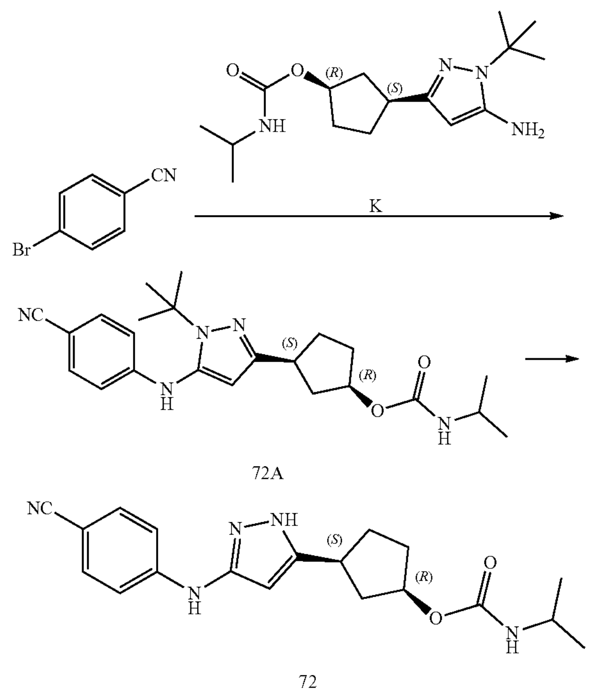

72A

72

Compound 72 (60 mg) was obtained by reference to the preparation method for compound 1 of Example 1, with 1A being replaced by 4-bromobenzonitrile. MS (ESI): m/z 354.1923 $[M+H]^+$.

$^1H$ NMR (500 MHz, DMSO-$d_6$) δ 11.96 (s, 1H), 9.07 (s, 1H), 7.57-7.55 (m, 2H), 7.42-7.40 (m, 2H), 7.70 (s, 1H), 6.94-6.93 (m, 1H), 5.71 (s, 1H), 5.00 (s, 1H), 3.60-3.56 (m, 1H), 3.08-3.04 (m, 1H), 2.48-2.44 (m, 1H), 2.05-2.00 (m, 1H), 1.94-1.86 (m, 1H), 1.76-1.67 (m, 2H), 1.64-1.58 (m, 1H), 1.04-1.02 (m, 6H).

Example 73: Preparation of Compound 73

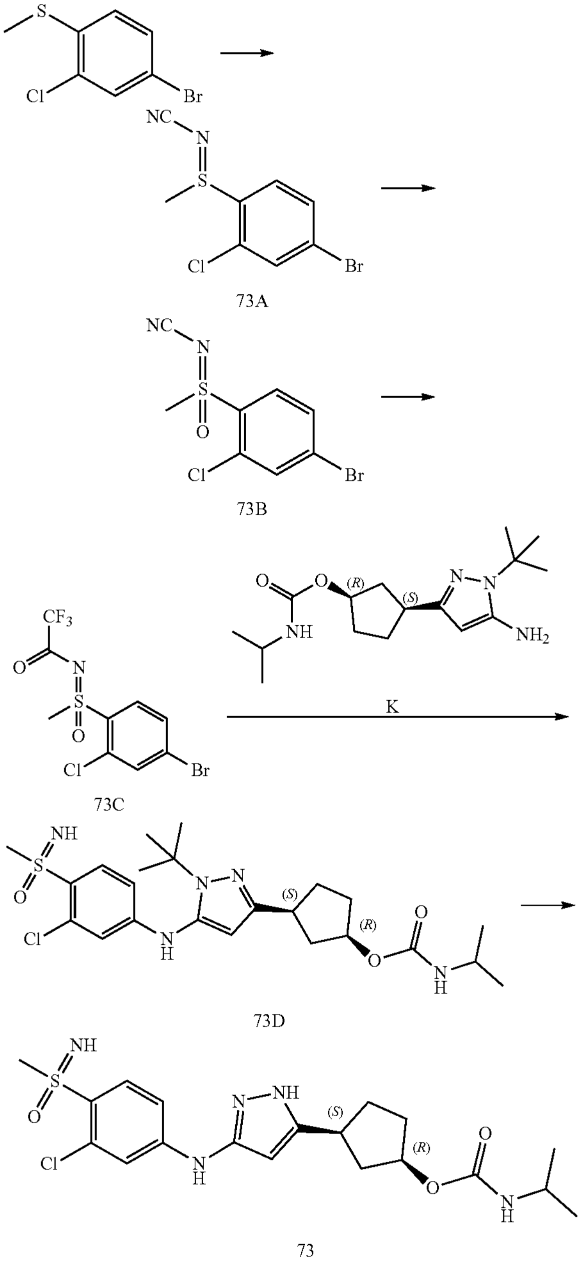

73A

73B

73C

73D

73

A crude product of compound 73 was obtained by reference to the preparation method for compound 61 of Example 61, with 4-bromothioanisole being replaced by 1-bromo-3-chloro-4-(methylthio)benzene.

The crude product of compound 73 was purified by medium and low pressure preparative liquid phase chromatography (C18 column, acetonitrile/water (30/70), the eluent contained one thousandth of ammonium hydroxide) to give compound 73 (50 mg) of Example 73. MS (ESI): m/z 440.15 $[M+H]^+$.

$^1H$ NMR (500 MHz, DMSO-$d_6$) δ 11.98 (s, 1H), 9.15 (s, 1H), 7.85 (d, J=8.8 Hz, 1H), 7.71 (s, 1H), 7.31-7.22 (m, 1H), 6.94 (d, J=7.8 Hz, 1H), 5.68 (s, 1H), 5.00 (s, 1H), 4.20 (s, 1H), 3.62-3.55 (m, 1H), 3.13 (d, J=1.2 Hz, 3H), 3.10-3.03

(m, 1H), 2.49-2.40 (m, 1H), 2.05-1.97 (m, 1H), 1.96-1.83 (m, 1H), 1.79-1.65 (m, 2H), 1.63-1.57 (m, 1H), 1.03 (dd, J=6.6, 2.2 Hz, 6H).

Example 74: Preparation of Compound 74

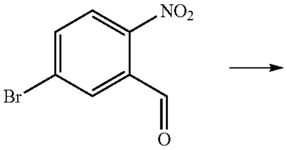

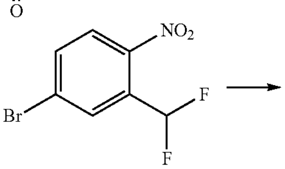

74A

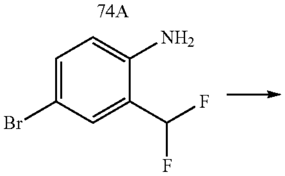

74B

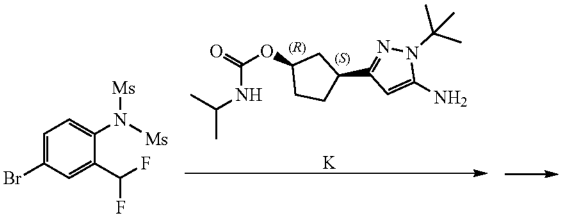

74C

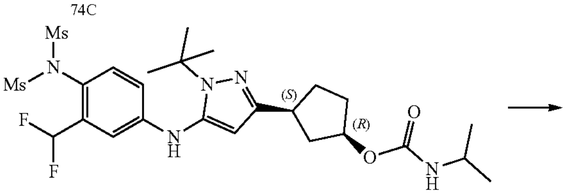

74D

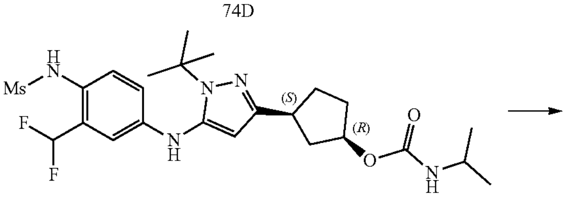

74E

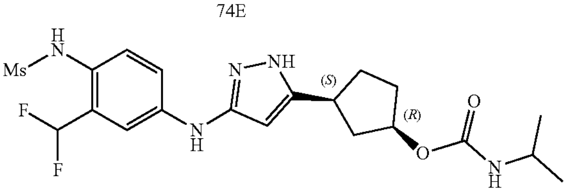

74

5-Bromo-2-nitrobenzaldehyde (3.00 g) and di ethyl aminosulfur trifluoride (3.15 g) were added to dichloromethane (20 mL), and the mixture was stirred under an ice bath. After the reaction was completed, the reaction solution was concentrated to give intermediate 74A (3.00 g).

Intermediate 74A (3.00 g), zine powder (3.89 g), and ammonium chloride (3.82 g) were added to methanol (30 mL). After the addition, the mixture was stirred at room temperature. After the reaction was completed, the reaction solution was filtered, concentrated, and separated by evaporation under reduced pressure to remove the solvent, and separated by column chromatography (developing solvents: petroleum ether/ethyl acetate) to give intermediate 74B (1.37 g).

Intermediate 74B (1.37 g), N,N-diisopropylethylamine (2.39 g), and methanesulfonic anhydride (3.22 g) were added to dichloromethane (20 mL). After the addition, the mixture was stirred at room temperature. After the reaction was completed, the reaction solution was concentrated and separated by evaporation under reduced pressure to remove the solvent, and separated by column chromatography (developing solvents: petroleum ether/ethyl acetate) to give intermediate 74C (0.90 g).

Intermediate 74C (0.36 g), intermediate K (0.20 g), chloro (2-dicyclohexylphosphino-2',4',6'-triisopropyl-1,1'-biphenyl)[2-(2'-amino-1,1'-biphenyl)]palladium (II) (0.10 g), 2-dicyclohexylphosphino-2',4',6'-triisopropylbiphenyl (0.06 g), and potassium phosphate (0.34 g) were added to dioxane (20 mL). After the addition was completed, the mixture was stirred at 100° C. under nitrogen atmosphere. After the reaction was completed, the reaction solution was filtered, concentrated, and separated by column chromatography (developing solvents: dichloromethane/methanol) to give intermediate 74D (0.30 g).

Intermediate 74D (0.3 g) and a saturated aqueous sodium carbonate solution (10 mL) were added to dioxane (20 mL), and the mixture was stirred at 50° C. After the reaction was completed, the reaction solution was extracted with dichloromethane, dried over anhydrous sodium sulfate, filtered, concentrated, and separated by column chromatography (developing solvents: dichloromethane/methanol) to give intermediate 74E (230 mg). MS (ESI): m/z 528.29[M+H]$^+$.

Intermediate 74E (100 mg) was added to ethanol (1 mL) and diluted hydrochloric acid (1 N, 15 mL), and the mixture was stirred at 100° C. under microwave. After the reaction was completed, the reaction solution was concentrated by evaporation under reduced pressure to remove the solvent, and the pH of the residue was adjusted to alkalinity with a saturated aqueous sodium bicarbonate solution. The mixture was extracted with dichloromethane, dried over anhydrous sodium sulfate, filtered, concentrated, and separated by column chromatography (developing solvents: dichloromethane/methanol) to give intermediate 74 (25 mg). MS (ESI): m/z 472.1821[M+H]$^+$.

$^1$H NMR (500 MHz, DMSO-d$_6$) δ 11.83 (s, 1H), 9.07 (s, 1H), 8.69 (s, 1H), 7.81 (s, 1H), 7.47-7.34 (m, 1H), 7.26-6.89 (m, 3H), 5.62 (s, 1H), 5.00 (s, 1H), 3.60-3.56 (m, 1H), 3.08-3.01 (m, 1H), 2.94 (s, 3H), 2.46-2.43 (m, 1H), 2.03-2.00 (m, 1H), 1.95-1.85 (m, 1H), 1.76-1.68 (m, 2H), 1.63-1.57 (m, 1H), 1.03 (d, J=6.25 Hz, 6H).

Example 75: Preparation of Compound 75

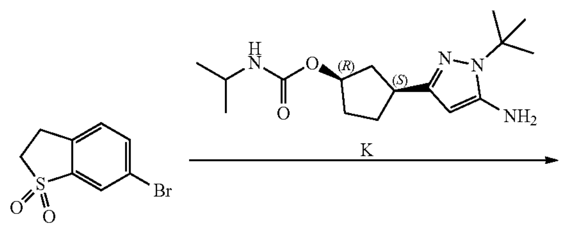

-continued

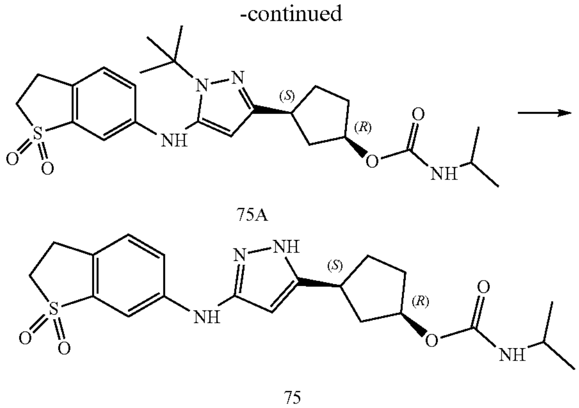

75A

75

A crude product of compound 75 was obtained by reference to the preparation method for compound 26 of Example 26, with 5-bromo-1,3-dihydrobenzo[c]thiophene-2,2-dioxide being replaced by 6-bromo-2,3-dihydrobenzo[b]thiophene-1,1-dioxide.

The crude product of compound 75 was purified by medium and low pressure preparative liquid phase chromatography (C18 column, acetonitrile/water (30/70), the eluent contained one thousandth of ammonium hydroxide) to give compound 75 (60 mg) of Example 75. MS (ESI): m/z 419.23 $[M+H]^+$.

$^1H$ NMR (500 MHz, DMSO-$d_6$) δ 11.82 (s, 1H), 8.82 (s, 1H), 7.93 (s, 1H), 7.38 (dd, J=8.5, 2.2 Hz, 1H), 7.29 (d, J=8.5 Hz, 1H), 6.95 (d, J=7.8 Hz, 1H), 5.61 (s, 1H), 5.10-4.80 (m, 1H), 3.64-3.54 (m, 1H), 3.52 (t, J=6.8 Hz, 2H), 3.20 (t, J=6.8 Hz, 2H), 3.12-2.96 (m, 1H), 2.49-2.40 (m, 1H), 2.06-1.97 (m, 1H), 1.95-1.85 (m, 1H), 1.78-1.64 (m, 2H), 1.65-1.53 (m, 1H), 1.03 (d, J=6.5 Hz, 6H).

Example 76: Preparation of Compound 76

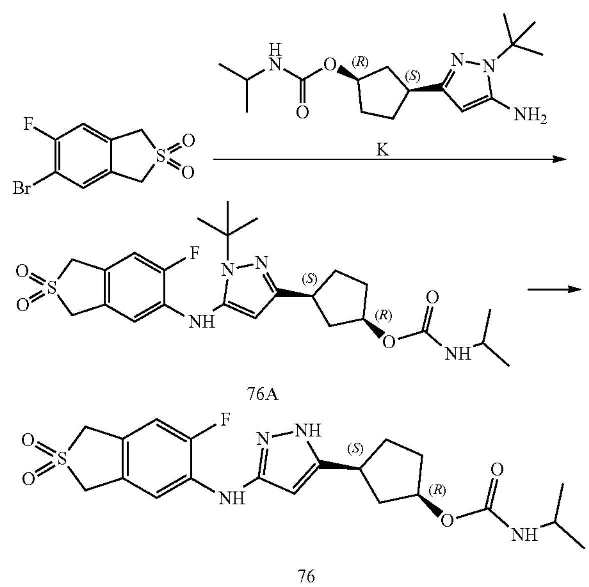

76A

76

A crude product of compound 76 was obtained by reference to the preparation method for compound 26 of Example 26, with 5-bromo-1,3-dihydrobenzo[c]thiophene-2,2-dioxide being replaced by 5-bromo-6-fluoro-1,3-dihydrobenzo[c]thiophene-2,2-dioxide.

The crude product of compound 76 was purified by medium and low pressure preparative liquid phase chromatography (C18 column, acetonitrile/water (30/70), the eluent contained one thousandth of ammonium hydroxide) to give compound 76 (110 mg) of Example 76. MS (ESI, $[M+H]^+$) m/z: 437.1662.

$^1H$ NMR (500 MHz, DMSO-$d_6$) δ 11.80 (s, 1H), 8.22 (s, 1H), 8.10 (d, J=8.10 Hz, 1H), 7.16 (d, J=11.70 Hz, 1H), 6.93 (d, J=7.80 Hz, 1H), 5.77 (s, 1H), 5.03-4.96 (m, 1H), 4.41 (s, 2H), 4.36 (s, 2H), 3.60-3.56 (m, 1H), 3.08-3.03 (m, 1H), 2.48-2.43 (m, 1H), 2.05-2.00 (m, 1H), 1.94-1.86 (m, 1H), 1.76-1.65 (m, 2H), 1.62-1.56 (m, 1H), 1.04-1.03 (m, 6H).

Example 77: Preparation of Compound 77

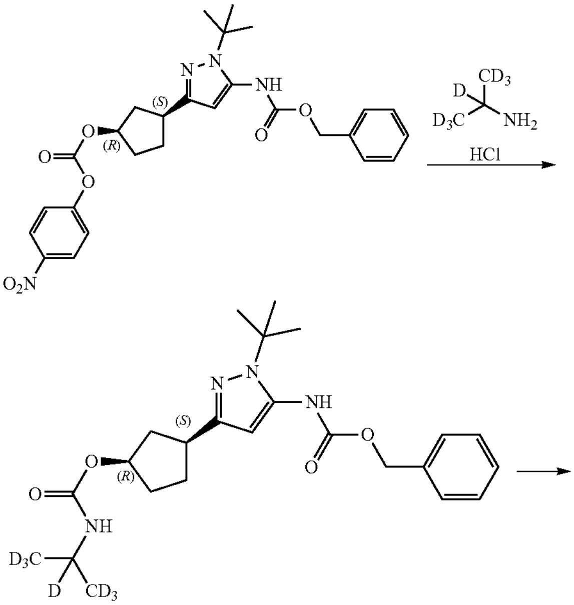

77A

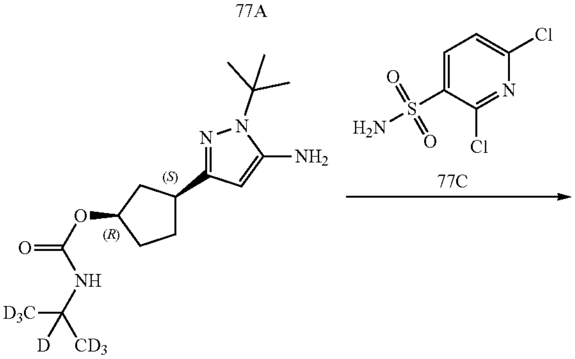

77B

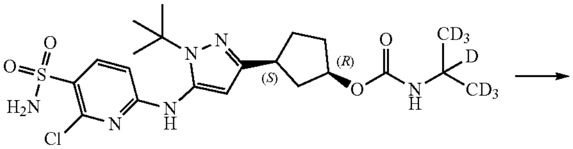

77D

-continued

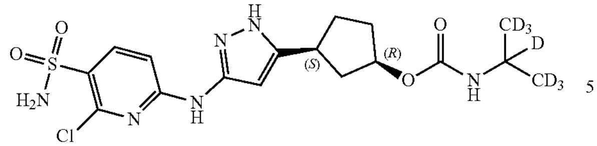

77

Intermediate 77B was obtained by reference to the preparation method for compound 48 of Example 48, with 1-methylcyclopropane-1-amine hydrochloride being replaced by isopropylamine hydrochloride-$d_7$.

Compound 77 (80 mg) was obtained by reference to the preparation method for the compound 52 of Example 52, with intermediate K being replaced by intermediate 77B. MS (ESI): m/z 450.1821 $[M+H]^+$.

$^1H$ NMR (500 MHz, DMSO-d6) δ 12.09 (s, 1H), 10.08 (s, 1H), 8.03 (d, J=8.75 Hz, 1H), 7.42 (s, 2H), 7.34 (s, 1H), 6.91 (s, 1H), 6.08 (s, 1H), 5.00 (m, 1H), 3.11-3.04 (m, 1H), 2.49-2.42 (m, 1H), 2.05-1.98 (m, 1H), 1.95-1.86 (m, 1H), 1.79-1.66 (m, 2H), 1.65-1.56 (m, 1H).

Example 78: Preparation of Compound 78

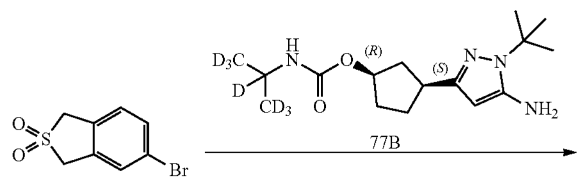

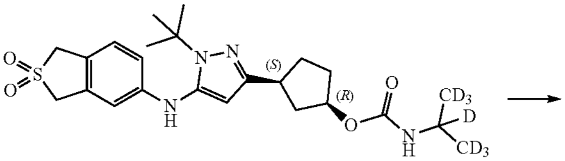

78A

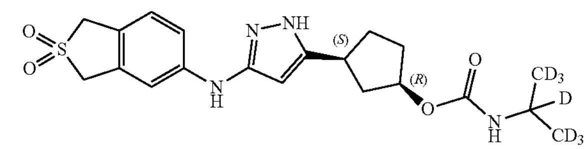

78

Compound 78 (40 mg) was obtained by reference to the preparation method for the compound 26 of Example 26, with intermediate K being replaced by intermediate 77B. MS (ESI): m/z 426.2284 $[M+H]^+$.

$^1H$ NMR (500 MHz, DMSO-$d_6$) δ 11.72 (s, 1H), 8.46 (s, 1H), 7.41 (s, 1H), 7.22 (d, J=7.95 Hz, 1H), 7.14 (d, J=8.40 Hz, 1H), 6.92 (d, J=7.95 Hz, 1H), 5.63 (s, 1H), 4.99 (m, 1H), 4.40 (s, 2H), 4.32 (s, 2H), 3.08-3.00 (m, 1H), 2.48-2.42 (m, 1H), 2.03-1.98 (m, 1H), 1.93-1.86 (m, 1H), 1.73-1.68 (m, 2H), 1.62-1.56 (m, 1H).

Example 79: Preparation of Compound 79

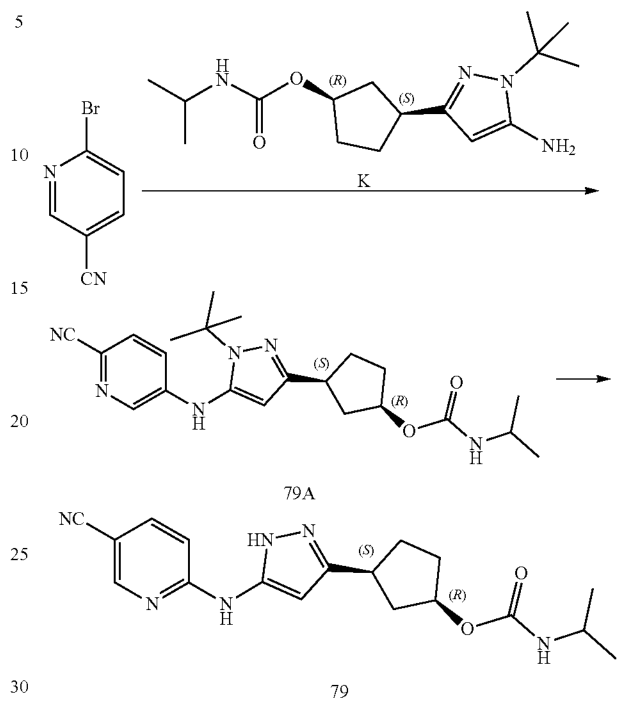

79A

79

Compound 79 (70 mg) of Example 79 was obtained by reference to the preparation method for compound 13 of Example 13, with the intermediate 2-bromopyridine being replaced by 5-bromo-2-cyanopyridine. MS (ESI): m/z 355.1880 $[M+H]^+$.

1H NMR (500 MHz, DMSO-d6) δ 12.15-12.01 (m, 1H), 9.42 (s, 1H), 8.58 (d, 1H), 7.96 (dd, 1H), 7.77 (d, 1H), 6.93 (d, 1H), 5.74 (d, 1H), 5.00 (s, 1H), 3.58 (dd, 1H), 3.13-3.01 (m, 1H), 2.49-2.41 (m, 1H), 2.07-1.98 (m, 1H), 1.96-1.86 (m, 1H), 1.80-1.67 (m, 2H), 1.09-0.98 (m, 6H).

Example 80: Preparation of Compound 80

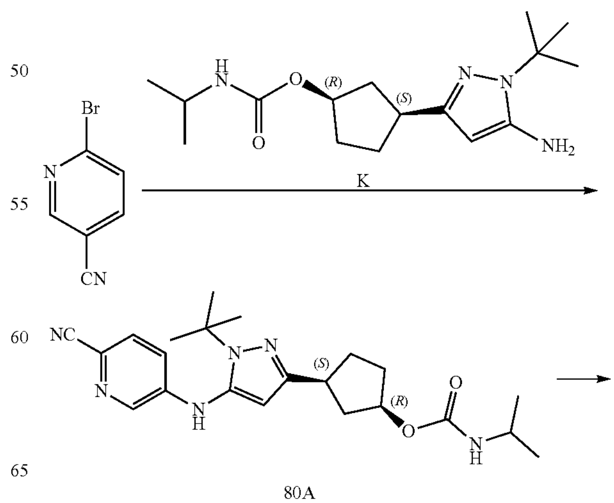

80A

-continued

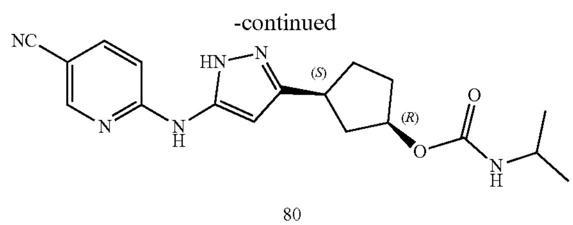

80

2-Bromo-5-cyanopyridine (178 mg), potassium tert-butoxide (0.146 g), and intermediate K (0.2 g) were added to THF (15 mL), and the mixture was reacted at 80° C. under an oil bath. After the reaction was completed, the reaction solution was concentrated by evaporation under reduced pressure to remove the solvent, and separated by column chromatography (developing solvents: dichloromethane/methanol) to give intermediate 80A (100 mg). MS (ESI): m/z 411.29 $[M+H]^+$.

Compound 80 (30 mg) of Example 80 was obtained by reference to the preparation method for the compound 79 of Example 79, with intermediate 79A being replaced by 80A. MS (ESI): m/z 355.1882 $[M+H]^+$.

1H NMR (500 MHz, DMSO-d6) δ 8.37 (d, 1H), 7.30-7.21 (m, 1H), 6.92 (d, 1H), 6.68 (d, 1H), 6.45 (s, 1H), 5.01 (t, 1H), 3.57 (h, 1H), 3.16 (p, 1H), 2.47 (dd, 1H), 2.13-2.02 (m, 1H), 1.94-1.89 (m, 1H), 1.81-1.71 (m, 2H), 1.65 (ddd, 4.7 Hz, 1H), 1.03 (t, 6H).

Experimental Example 1: In Vitro Inhibitory Activity Against Kinase

1.1 Determination of Inhibitory Activity Against CDK2/CycA2 Kinase

CDK2/CycA2 kinase solution (concentration: 0.078 ng/μL) was added to assay wells at 6 μL/well, and different compounds dissolved in DMSO were added to the assay wells separately using a nanoliter pipettor, such that the final concentrations of the compounds were 1000 nM to 0.244 nM. The wells were set in duplicate, and a control well was set. After incubation of the above system for 30 min, ATP (concentration: 50 μM or 5000 μM) was mixed with ULight-Myelin Basic Protein Peptide substrate (manufacturer: PerkinElmer, concentration: 0.25 μM) at a ratio of 1:1, and the mixture was added to the assay wells at 4 μL/well. The resulting mixture was left to react at room temperature for 2 h, and then 5 μL of EDTA was added to terminate the reaction, followed by addition of 5 μL of a detection antibody (manufacturer: PerkinElmer, concentration: 8 nM). The mixture was incubated at room temperature for 1 h. Assay was performed using a PerkinElmer Envision multi-functional microplate reader (excitation: 320 nm, emission: 615 nm/665 nm), and $IC_{50}$ was calculated by four-parameter fitting.

1.2 Determination of Inhibitory Activity Against CDK2 CycE1 Kinase

CDK2 CycE1 kinase solution (concentration: 0.015 ng/μL) was added to assay wells at 6 μL/well, and different compounds dissolved in DMSO were added to the assay wells separately using a nanoliter pipettor, such that the final concentrations of the compounds were 300 nM to 0.07 nM. The wells were set in duplicate, and a control well was set. After incubation of the above system for 30 min, ATP (concentration: 50 μM or 5000 μM) was mixed with ULight-Myelin Basic Protein Peptide substrate (manufacturer: PerkinElmer, concentration: 0.25 μM) at a ratio of 1:1, and the mixture was added to the assay wells at 4 μL/well. The resulting mixture was left to react at room temperature for 2 h, and then 5 μL of EDTA was added to terminate the reaction, followed by addition of 5 μL of a detection antibody (manufacturer: PerkinElmer, concentration: 8 nM). The mixture was incubated at room temperature for 1 h. Assay was performed using a PerkinElmer Envision multi-functional microplate reader (excitation: 320 nm, emission: 615 nm/665 nm), and $IC_{50}$ was calculated by four-parameter fitting.

The experimental results are shown in Table 1, wherein A represents: 0 nM<$IC_{50}$≤10 nM; B represents: 10 nM<$IC_{50}$≤50 nM; C represents: 50 nM<$IC_{50}$≤100 nM; D represents: 100 nM<$IC_{50}$≤1000 nM; E represents: 1000 nM<$IC_{50}$.

TABLE 1

Inhibitory activity of compound against CDK2 CycA2 and CDK2 CycE1 kinases

| Example | CDK2/CycA2 10 μM ATP (kinase) $IC_{50}$ (nM) | CDK2/CycE1 10 μM ATP (kinase) $IC_{50}$ (nM) |
|---|---|---|
| Example 1 | A | A |
| Example 2 | B | B |
| Example 3 | A | A |
| Example 4 | B | B |
| Example 5 | A | A |
| Example 6 | A | A |
| Example 7 | A | A |
| Example 8 | A | A |
| Example 9 | B | A |
| Example 10 | B | A |
| Example 11 | A | A |
| Example 12 | B | B |
| Example 13 | A | A |
| Example 14 | A | A |
| Example 15 | A | A |
| Example 16 | A | A |
| Example 18 | B | B |
| Example 19 | B | A |
| Example 20 | B | B |
| Example 21 | A | A |
| Example 22 | B | B |
| Example 23 | A | A |
| Example 24 | A | A |
| Example 25 | A | A |
| Example 26 | A | A |
| Example 27 | A | A |
| Example 28 | A | A |
| Example 29 | A | A |
| Example 30 | A | A |
| Example 31 | A | A |
| Example 32 | A | A |
| Example 33 | A | A |
| Example 34 | A | A |
| Example 35 | A | A |
| Example 36 | B | A |
| Example 37 | A | A |
| Example 38 | B | A |
| Example 39 | A | A |
| Example 40 | A | A |
| Example 41 | B | B |
| Example 42 | A | A |
| Example 43 | A | A |
| Example 45 | A | A |
| Example 46 | A | A |
| Example 47 | A | A |
| Example 48 | A | A |
| Example 49 | A | A |
| Example 50 | A | A |
| Example 51 | B | A |
| Example 52 | A | A |
| Example 53 | A | A |
| Example 54 | A | A |
| Example 55 | A | A |

TABLE 1-continued

| Inhibitory activity of compound against CDK2 CycA2 and CDK2 CycE1 kinases | | |
|---|---|---|
| Example | CDK2/CycA2 10 μM ATP (kinase) $IC_{50}$ (nM) | CDK2/CycE1 10 μM ATP (kinase) $IC_{50}$ (nM) |
| Example 56 | A | A |
| Example 57 | A | A |
| Example 58 | A | A |
| Example 59 | B | B |
| Example 60 | B | B |
| Example 61 | A | A |
| Example 62 | A | A |
| Example 63 | A | A |
| Example 64 | A | A |
| Example 65 | A | A |
| Example 66 | A | A |
| Example 67 | A | A |
| Example 68 | A | A |
| Example 69 | B | B |
| Example 70 | A | A |
| Example 71 | A | A |
| Example 72 | A | A |
| Example 73 | A | A |
| Example 74 | A | A |
| Example 75 | B | A |
| Example 77 | A | A |
| Example 78 | A | A |

The invention claimed is:

1. A compound of formula (II), or a pharmaceutically acceptable salt thereof, (II)

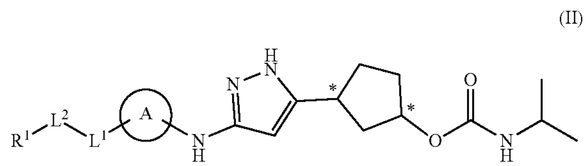

wherein, ring A is a benzene ring fused to a 5-6 membered heteroalkyl ring, wherein the benzene ring fused to the 5-6 membered heteroalkyl ring is optionally substituted with 1, 2 or 3 $R^a$;

$L^1$ and $L^2$ are each independently selected from the group consisting of a single bond;

$R^1$ is selected from the group consisting of H and $C_{1-3}$ alkyl; wherein the $C_{1-3}$ alkyl is optionally independently substituted with 1, 2 or 3 $R^d$;

$R^a$ is each independently selected from the group consisting of halogen, OH, CN, $NH_2$, =O, $C_{1-3}$ alkyl and $C_{1-3}$ alkoxy, and the $C_{1-3}$ alkyl or the $C_{1-3}$ alkoxy is optionally independently substituted with 1, 2 or 3 $R^x$;

$R^b$ is each independently selected from the group consisting of H and $C_{1-3}$ alkyl; the $C_{1-3}$ alkyl is optionally independently substituted with 1, 2 or 3 $R^x$;

$R^d$ is each independently selected from the group consisting of halogen, OH, CN, and $NH_2$;

$R^x$ is each independently selected from the group consisting of halogen, OH, CN, and $NH_2$;

m is selected from the group consisting of 1, 2, and 3; and the carbon atom with "*" is a chiral carbon atom present in a form of a single (R) or (S) enantiomer or in a form enriched with one enantiomer.

2. The compound of formula (II), the isomer thereof, or the pharmaceutically acceptable salt thereof according to claim 1, wherein ring A is a benzene ring fused to a 5 membered heteroalkyl ring, wherein the benzene ring fused to a 5 membered heteroalkyl ring is optionally substituted with 1, 2 or 3 $R^a$.

3. The compound of formula (II), or the pharmaceutically acceptable salt thereof according to claim 1, wherein $R^1$ is selected from the group consisting of H and methyl.

4. The compound of formula (II), or the pharmaceutically acceptable salt thereof according to claim 1, wherein $R^a$ is each independently selected from the group consisting of deuterium, F, Cl, Br, I, =O, $C_{1-3}$ alkyl, and $C_{1-3}$ alkoxy, and the $C_{1-3}$ alkyl or the $C_{1-3}$ alkoxy is optionally independently substituted with 1, 2 or 3 $R^x$.

5. The compound of formula (II), or the pharmaceutically acceptable salt thereof according to claim 1, wherein $R^b$ is each independently selected from the group consisting of H and methyl.

6. The compound of formula (II), or the pharmaceutically acceptable salt thereof according to claim 1, wherein $R^d$ is each independently selected from the group consisting of F, Cl, Br, I, and OH.

7. The compound of formula (II), or the pharmaceutically acceptable salt thereof according to claim 1, wherein the compound is selected from a compound of formula (II-1), (II-1)

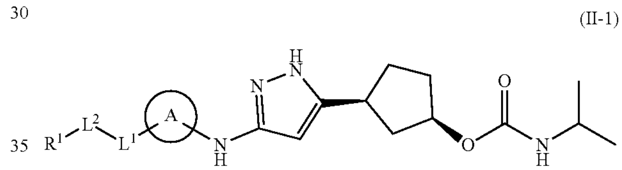

wherein, ring A, $R^1$, $L^1$ and $L^2$ are as defined in claim 1.

8. The compound of formula (II), or the pharmaceutically acceptable salt thereof according to claim 1, wherein the heteroalkyl ring of the ring A is a saturated cyclic group, wherein 1, 2 or 3 ring atoms are heteroatoms independently selected from the group consisting of S and N.

9. The compound of formula (II), or the pharmaceutically acceptable salt thereof according to claim 2, wherein ring A is selected from the group consisting of a benzene ring fused to a pyrrolidine ring, a benzene ring fused to a tetrahydrothiophene ring, and a benzene ring fused to an isothiazolidine ring, and ring A is optionally independently substituted with 1, 2 or 3 $R^a$.

10. The compound of formula (II), or the pharmaceutically acceptable salt thereof according to claim 3, wherein $R^1$ is H.

11. The compound of formula (II), or the pharmaceutically acceptable salt thereof according to claim 4, wherein $R^a$ is each independently selected from the group consisting of F, =O and methyl, and the methyl is optionally independently substituted with 1, 2 or 3 halogens.

12. The compound of formula (II), or the pharmaceutically acceptable salt thereof according to claim 11, wherein $R^a$ is each independently selected from the group consisting of F, =O, methyl, and trifluoromethyl.

13. The compound of formula (II), or the pharmaceutically acceptable salt thereof according to claim 6, wherein $R^d$ is each independently selected from the group consisting of F and OH.

14. The compound of formula (II), or the pharmaceutically acceptable salt thereof according to claim 1, wherein $R^x$ is a halogen.

15. The compound of formula (II), or a pharmaceutically acceptable salt thereof according to claim 1, wherein the compound has a formula selected from the group consisting of:

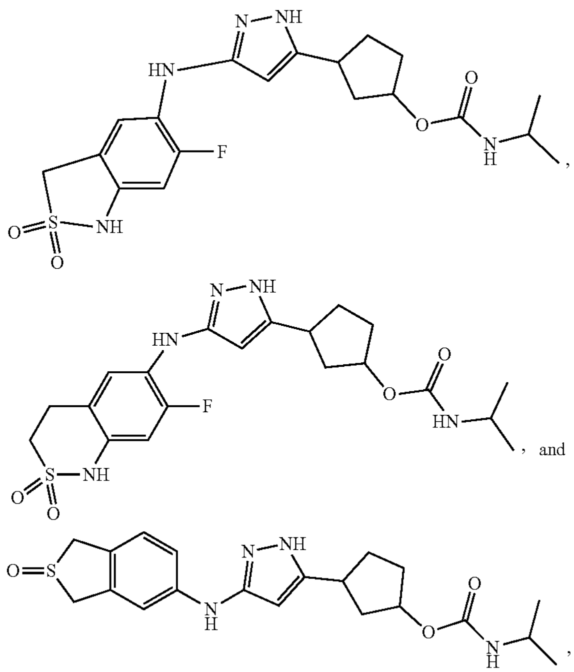

, , and , or a pharmaceutically acceptable salt thereof.

16. The compound of formula (II), or the pharmaceutically acceptable salt thereof according to claim 15, which is a compound of the formula below, or a pharmaceutically acceptable salt thereof,

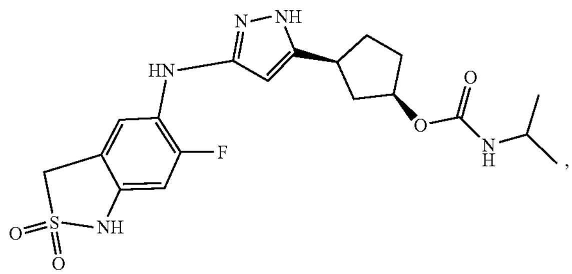

,

-continued

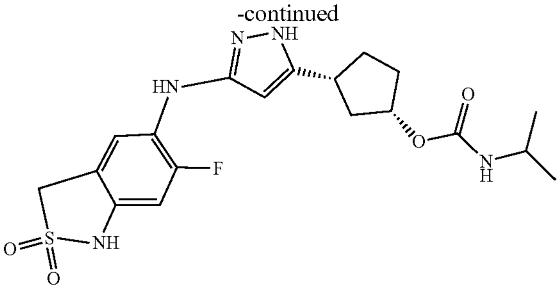

,

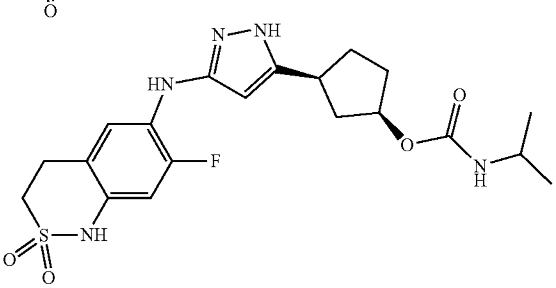

,

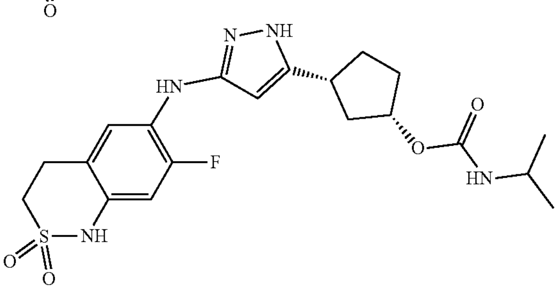

,

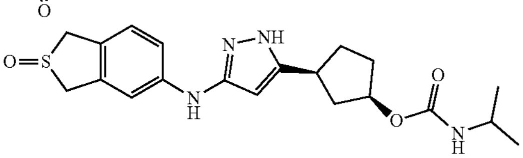

, or

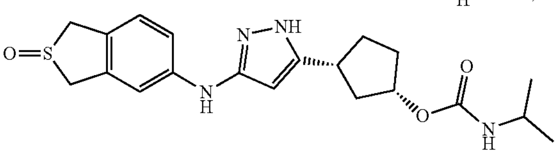

.

17. A pharmaceutical composition, comprising a therapeutically or prophylactically effective amount of the compound, or the pharmaceutically acceptable salt thereof according to claim 1 and optionally further comprising a pharmaceutically acceptable excipient.

18. A method for treating or preventing a CDK2-mediated disease, which comprises administering to a mammal in need of the treatment or the prevention a therapeutically or prophylactically effective amount of the compound, or the pharmaceutically acceptable salt thereof according to claim 1.

* * * * *